(12) United States Patent
DeBrabander et al.

(10) Patent No.: US 10,112,948 B2
(45) Date of Patent: Oct. 30, 2018

(54) BENZAMIDE OR BENZAMINE COMPOUNDS USEFUL AS ANTICANCER AGENTS FOR THE TREATMENT OF HUMAN CANCERS

(71) Applicant: THE BOARD OF REGENTS OF THE UNIVERSITY OF TEXAS SYSTEM, Austin, TX (US)

(72) Inventors: Jef DeBrabander, Flower Mound, TX (US); Luis Parada, New York, NY (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/194,825

(22) Filed: Jun. 28, 2016

(65) Prior Publication Data

US 2017/0114062 A1      Apr. 27, 2017

Related U.S. Application Data

(60) Provisional application No. 62/189,069, filed on Jul. 6, 2015.

(51) Int. Cl.

| | |
|---|---|
| *C07D 487/04* | (2006.01) |
| *C07D 213/16* | (2006.01) |
| *C07D 207/09* | (2006.01) |
| *C07C 323/22* | (2006.01) |
| *C07D 295/13* | (2006.01) |
| *C07D 401/12* | (2006.01) |
| *C07C 205/58* | (2006.01) |
| *C07D 213/70* | (2006.01) |
| *C07C 255/57* | (2006.01) |
| *C07D 307/14* | (2006.01) |
| *C07D 209/48* | (2006.01) |
| *C07C 235/50* | (2006.01) |
| *C07C 205/61* | (2006.01) |
| *C07D 211/14* | (2006.01) |
| *C07C 271/20* | (2006.01) |
| *C07C 323/62* | (2006.01) |

(52) U.S. Cl.
CPC .......... *C07D 487/04* (2013.01); *C07C 205/58* (2013.01); *C07C 205/61* (2013.01); *C07C 235/50* (2013.01); *C07C 255/57* (2013.01); *C07C 271/20* (2013.01); *C07C 323/22* (2013.01); *C07C 323/62* (2013.01); *C07D 207/09* (2013.01); *C07D 209/48* (2013.01); *C07D 211/14* (2013.01); *C07D 213/16* (2013.01); *C07D 213/70* (2013.01); *C07D 295/13* (2013.01); *C07D 307/14* (2013.01); *C07D 401/12* (2013.01)

(58) Field of Classification Search
CPC .. C07D 487/04; C07D 207/09; C07D 209/48; C07D 211/14; C07D 213/16; C07D 213/70; C07D 295/13; C07D 307/14; C07D 401/12; C07C 205/58; C07C 205/61; C07C 235/50; C07C 255/57; C07C 271/20; C07C 323/22; C07C 323/62
USPC ....................................................... 548/185
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 6,921,527 B2 | 7/2005 | Platz et al. | |
| 8,642,660 B2 * | 2/2014 | Goldfarb | A61K 31/122 514/18.9 |
| 2005/0256161 A1 | 11/2005 | Tempest et al. | |
| 2012/0004310 A1 | 1/2012 | Longo et al. | |

FOREIGN PATENT DOCUMENTS

| | | |
|---|---|---|
| WO | 9116038 A1 | 10/1991 |
| WO | 2010/037715 A1 | 4/2010 |
| WO | 2013/131018 A1 | 9/2013 |

OTHER PUBLICATIONS

Trifilenkov, A. S. et al., Liquid-phase parallel synthesis of 4-sulfanylbenzoic acid derivatives, Izvestiya Vysshikh Uchebnykh Zavedenii, Khimiya i Khimicheskaya Tekhnologiya (2005), 48(4), 101-112 (Year: 2005).*

English translation of Trifilenkov, A. S. et al., Liquid-phase parallel synthesis of 4-sulfanylbenzoic acid derivatives, Izvestiya Vysshikh Uchebnykh Zavedenii, Khimiya i Khimicheskaya Tekhnologiya (2005), 48(4), 101-112 (Year: 2005).*

Hartman IZ, et al., "Sterol-inducd dislocation of 3-hydroxy-3-methylglutaryl coenzyme A reductase from endoplasmic reticulum membranes into the cytosol through a subcellular compartment resembling lipi droplets," J. Biol. Chem. 285: 19288-98 (2010).

He, M, et al, "Mutations in the human SC4MOL gene encoding a methyl sterol oxidase cause psoriasifonn dermatitis, microcephaly, and developmental delay," J. Clin. Invest. 121: 976-984 (2011).

Hidaka, Y, et al, "Regulation of squalene epoxidase in HepG2 cells," 1. Lipid Res. 31: 2087-94 (1990).

Hiltunen, T P et al., Expression of LDL receptor, VLDL receptor, LDL receptor-related protein, and scavenger receptor in rabbit atherosclerotic lesions: Marked induction of scavenger receptor and VLDL receptor expression during lesion development, Circulation 97: 1079 (1998).

(Continued)

*Primary Examiner* — Kristin A Vajda

(74) *Attorney, Agent, or Firm* — Parker Highlander PLLC

(57) ABSTRACT

The described invention provides small molecule anti-cancer compounds for treating tumors that respond to cholesterol biosynthesis inhibition. The compounds selectively inhibit the cholesterol biosynthetic pathway in tumor-derived cancer cells, but do not affect normally dividing cells.

7 Claims, 27 Drawing Sheets

(56) References Cited

OTHER PUBLICATIONS

Hirsch, H.A. et al "A transcriptional signature and common gene networks link cancer with lipid metabolism and diverse human diseases," Cancer Cell. 17(4): 348-61 (2010).
Horton, J.D, et al., "SREBPs: activators of the complete program of cholesterol and fatty acid synthesis in the liver," J. Clin. Invest. 109: 1125-31 (2002).
Hua, X et al., "Sterol resistance in CHO cells traced to point mutation in SREBP cleavage-activating protein," Cell 87: 415-26 (1996).
Hussein, D and Mo, H, "d-8-tocotrienol-mediated suppression of the proliferation of human PANC-1, MIA PaCa2 and BxPC-3 pancreatic carcinoma cells," Pancreas 38: e124-e136 (2009).
Ilkanizadeh, et al., "Glial Progenitors as Targets for Transformation in Glioma," Adv. Cancer Res. 121: 1-65 (2014).
Inoue, S. et al, "Inhibition of degradation of 3- hydroxy-3-methylglutaryl-coenzyme A reductase in vivo by cysteine protease inhibitors," J. Biol. Chem. 266: 13311-17 (1991).
Ji, Y et al., "Scavenger receptor BI promotes high density lipoprotein-mediated cellular cholesterol efflux," J. Biol. Chem. 272: 20982-985 (1997).
Jian, B. et al., "Scavenger receptor class B type I as a mediator of cellular cholesterol efflux to lipoproteins and phospholipid acceptors," J. Biol. Chem. 273: 5599-5606 (1998).
Jiang W and Song, BL, "Ubiquitin ligases in cholesterol metabolism," Diabetes Metab. J. 38: 171-180 (2014).
Jo, Y et al, "Ancient ubiquitous protein-1 mediates sterol-induced ubiquitination of 3-hydroxy-3-methylglutaryl CoA reductase in lipid droplet-associated endoplasmic reticulum membranes", Mol. Biol. Cell 24: 169-83 (2013).
Jo, Y. and Debose-Boyd,R.A.,"Control of cholesterol synthesis through regulated ER-associated degradation of HMG CoA reductase," Crit. Rev. Biochem. Mol. Bio. 445: 185-198 (2010).
Kennedy, M A et al., "ABCG1 has a critical role in mediating cholesterol efflux to HDL and preventing cellular lipid accumulation," Cell Metab. 1: 121-31 (2005).
Khaidakov, M.,et al., "Oxidized LDL receptor 1 (OLR1) as a possible link between obesity, dyslipidemia and cancer," PLoS One 6(5): e20277 (2011).
Kim, J. et al, "Itraconazole, a commonly used antifungal that inhibits Hedgehog pathway activity and cancer growth," Cancer Cell. 17(4): 388-99 (2010).
Konstantinopoulos, P.A., et al, "Post translational modifications and regulation of the RAS superfamily of GTPases as anticancer targets," Nat. Rev. Drug Discov. 6: 541-55 (2007).
Krinbou, L. et al,"Biogenesis and speciation of nascent apo Al-containing particles in various cell lines," J. Lipid Res. 46: 1668 (2005).
Kuwabara, P.E, "The sterol-sensing domain: multiple families, a unique role," Trends Genet. 18: 193-201 (2002).
Labit-Le Bouteiller, C. et al., "Antiproliferative effects of SR31747A in animal cell lines are mediated by inhibition of cholesterol biosynthesis at the sterol isomerase step," Eur. J. Biochem. 256: 342-49 (1998).
Landry, YD, et al., "ATP-binding cassette transporter A1 expression disrupts raft membrane microdomains through its ATPase-related functions," J. Biol. Chem. 281: 36091-101 (2006).
Lange, Y. et al, "Effectors of rapid homeostatic responses of endoplasmic reticulum cholesterol and 3-hydroxy-3 methylglutarylCoA reductase," J. BioL. Chem. 283: 1445-55 (2008).
Langer, R., New Methods of Drug Delivery, Science 249, 1527-1533, 1990.
Lee, P.C. et al, "Isolation of sterol-resistant Chinese hamster ovary cells with genetic deficiencies in both Insig-1 and Insig-2," J. Biol. Chem. 280: 25242-249 (2005).
Lehmann, J M, et al., "Activation of the nuclear receptor LXR by oxysterols defines a new hormone response pathway," J. Biol. Chem. 272: 3137-40 (1997).

Leichner, G S, et al, "Metabolically regulated endoplasmic reticulum-associated degradation of 3-hydroxy-3-methylglutaryl-CoA reductase. Evidence for requirement of a geranylgeranylated protein," J. Biol. Chem. 286: 32150-61 (2011).
Liu, Y, and Tang, C., "Regulation of ABCA1 functions by signaling pathways", Biochim. Biophys. Acta, 1821: 522-29 (2012).
Llaguno SA et al., "Malignant Astrocytomas Originate from Neural Stem/Progenitor Cells in a Somatic Tumor Suppressor Mouse Model", Cancer Cell. Jan. 6, 2009; 15(1): 45-56.
Llaguno SA et al., "Neural and Cancer Stem Cells in Tumor Suppressor Mouse Models of Malignant Astrocytoma", Cold Spring Harb Symp Quant Biol. 2008; 73: 421-426.
Lo Sasso, G. et al., "Liver X receptors inhibit proliferation of human colorectal cancer cells and growth of intestinal tumors in mice," Gastroenterology 144(7): 1497-507 (2013).
Loberg, RD, et al., Enhanced Glycogen Synthase Kinase-3β Activity Mediates Hypoxia-induced Apoptosis of Vascular Smooth Muscle Cells and Is Prevented by Glucose Transport and Metabolism; J. Biol. Chem. 277 (44): 41667-673 (2002).
Louis DN, et al., "The 2007 WHO Classification of Tumours of the Central Nervous System" Acta Neuropathol, 2007, 114(2):97-109.
Mahley, R.W. and JI, Z.S., "Remnant lipoprotein metabolism: key pathways involving cell-surface heparin sulfate proteoglycans and apolipoprotein E," J. Lipid Res. 40: 1-16 (1999).
Maniar, A. et al, "Human gammadelta T lymphocytes induce robust NK cell-mediated antitumor cytotoxicity through CD137 engagement," Blood 116: 1726-33 (2010).
Mashima, T. et al, "De novo fatty-acid synthesis and related pathways as molecular targets for cancer therapy," Br. 1. Cancer 100 (9): 1369-72 (2009).
Mazein, A. et al., "A comprehensive machine-readable view of the mammalian cholesterol biosynthesis pathway," Biochemical Pharmacol. 86: 56-66 (2013).
McGee, T.P. et al., "Degradation of 3-hydroxy-3-methylglutaryl-CoA reductase in endoplasmic reticulum membranes is accelerated as a result of increased susceptibility to proteolysis," J. Biol. Chem. 271: 25630-638 (1996).
McNamara. M.G. et al., Emerging Biomarkers in Glioblastoma; Cancers, 2013, 5: 1103-1119.
Medina, M.W., et al, "Coordinately regulated alternative splicing of genes involved in cholesterol biosynthesis and uptake," PLosONE 6: e19420 (2011).
Menendez, JA and Lupu, R., Fatty acid synthase and the lipogenic phenotype in cancer pathogenesis, Nat. Rev. Cancer 7(10): 763-77 (2007).
Meyer, J M et al., "New developments in selective cholesteryl ester uptake," Curr.. Opin. Lipidol. 24: 386-92 (2013).
Mineo, C. and Shaul, P.W., "Regulation of signal transduction by HDL," J. Lipid Res. 54: 2315-24 (2013).
Mo H et al, Mevalonate-suppressive tocotrienols for cancer chemoprevention and adjuvant therapy, in Tocotrienols: Vitamin E beyond tocopherols, 2nd ed. (Boca Raton: CRC Press), 135-149 (2013).
Mo, H and Elson, CE, "Studies of the isopreoid-mediated inhibition of mevalonate synthesis applied to cancer chemotherapy and chemoprevention," Exp. Biol. Med. (Maywood) 229: 567-85 (2004).
Munz, C. et al, "Dendritic cell maturation by innate lymphocytes: coordinated stimulation of innate and adaptive immunity," J. Exptl Med. 202: 203-7 (2005).
Nagahashi, M. et al, "Sphingosine-1-phosphate produced by sphingosine kinase 1 promotes breast cancer progression by stimulating angiogenesis and lymphangiogenesis," Cancer Res. 72(3): 726-35 (2012).
Nakada, M., Etal., "Aberrant Signaling Pathways in Glioma"; Cancers; 2011, 3, 3242-3278; doi:10.3390/cancers3033242.
Nakanishi, M. et al., "Multivalent control of 3-hydroxy-3-methylglutaryl coenzyme A reductase. Mevalonate derived product inhibits translation of mRNA and accelerates degradation of enzyme", J. Biol. Chem. 263: 8929-37 (1988).
Acton, S. et al, "Identification of scavenger receptor SR-B 1 as a high density lipoprotein receptor," Science 271: 518-520 (1996).
Bach, T.J., "Some new aspects of isoprenoid biosynthesis in plants—a review," Lipids 30: 191-202 (1995).
Baranowski, M., "Biological role of liver X receptors," J. Physiol. Pharmacology. 59 Suppl. 7: 31-55 (2008).

(56) References Cited

OTHER PUBLICATIONS

Berthois, Y. et al., "SR31747A is a sigma receptor ligand exhibiting antitumoural activity both in vitro and in vivo," Br. J. Cancer 88: 438-46 (2003).
Bhatia, B. et al, "Mitogenic Sonic hedgehog signaling drives E2F1-dependent lipogenesis in progenitor cells and medulloblastoma ," Oncogene 30(4): 410-22 (2011).
Bjorkhem,I., "Do oxysterols control choleseterol homeostasis," J. Clin. Invest. 110: 725-30 (2002).
Bralten, LBC, et al., "IDH1 R132H decreases proliferation of glioma cell lines in vitro and in vivo," Annals Neurol. 69(3): 455-63 (2011)).
Brown M.L. et al, A macrophage receptor for apolipoprotein B48: cloning, expression and atherosclerosis, Proc. Natl Acad. Sci. 97: 7488-7493 (2000).
Brown, M.S. & Goldstein, J.L, "The SREBP pathway: regulation of cholesterol metabolism by proteolysis of a membrane-bound transcription factor," Cell 89: 331-40 (1997).
Brown, M.S. and Goldstein, J.L., "A proteolytic pathway that controls the cholesterol content of membranes, cells and blood," Proc. Natl Acad. Sci. USA 96: 11041-48 (1999).
Burg, J.S. and Espenshade, P. J.,"Regulation of HMG-CoA reductase in mammals and yeast", Prog. Lipid Res. 50: 403-410 (2011).
Chen,W. et al., "Preferential ATP-binding cassette transporter A1-mediated cholesterol efflux from late endosomes/lysosomes," J. Biol. Chem. 276: 43564-69 (2001).
Cruz, PMR, et al, "The role of cholesterol metabolism and cholesterol transport in carcinogenesis: a review of scientific findings, relevant to future cancer therapeutics" Frontiers in Pharmacol. 4:119, 2013.
Czarnecka, H. and Yokoyama, S., "Regulation of cellular cholesterol efflux by lecithin: cholesterol acyltransferase reaction through nonspecific lipid exchange," J. Biol. Chem. 271: 1023-27 (1996).
Daimiel, LA, et al, "Promoter analysis of the DHCR24 (3f3-hydroxysterol i124-reductase) gene: characterization of SREBP (sterol-regulatory element-binding-protein-mediated activation," Biosci. Rep. (2013) /art:e00006 / doi 10.1042/ BSR20120095.
Dang, H. et al., "Suppression of 2,3-oxidosqualene cyclase by high fat diet contributes to liver X receptor-a-mediated improvement of hepatic lipid profile," J. Biol. Chem. 284: 6218-26 (2009).
de la Llera-Moya, M. et al, "Scavenger receptor BI (SR-BI) mediates free cholesterol flux independently of HDL ethering to the cell surface," J. Lipid Res. 40: 575-80 (1999).
De La Grange, P., et al, "A new advance in alternative splicing databases: from catalogue to detailed analysis of regulation of expression and function of human alternative splicing variants", BMC Bioinformatics 8: 180 (2007).
De Man, F. H. et al., "Lipolysis of very low density lipoproteins by heparin sulfate proteoglycan-bound lipoprotein lipase," J. Lipid Res. 38: 2465-2472 (1997).
De Medina, P. et al, "Dendrogenin A arises from cholesterol and histamine metabolism and shows cell differentiation and anti-tumour properties," Nature Communications 4: 1840 (2013).
De Medina, P. et al, "Identification and pharmacological characterization of choleseterol-5,6-epoxide hydrolase as a target for tamoxifen and AEBS ligands," Proc. Natl. Acad. Sci. USA 107: 13520-5 (2010).
De Medina, P. et al, "Synthesis of new alkylaminooxysterols with potent cell differentiating activities: identification of leads for the treatment of cancer and neurodegenerative diseases," J. Med. Chem. 52: 7765-77 (2009).
Debose-Boyd, R. A. "Feedback Regulation of Cholesterol Synthesis: Sterol-accelerated ubiquitination and degradation of HMG CoA Reductase," Cell Res. 18 (6): 609-21 (2008).
Denis, M. et al, "ATP-binding cassette A1-mediated lipidation of apolipoprotein A-I occurs at the plasma membrane and not in the endocytic compaRtments," J. Biol. Chem.283: 16178-186 (2008).
Dictus, C. et al, "Comparative analysis of in vitro conditons for rat adult neural progenitor cells," J. Neurosci Methds. 161: 250-58 (2007).

Difato, F. et al, "Combined optical tweezers and laser dissector for controlled ablation of functional connections in neural networksnetworks," J. Biomed. Opt. 16: 051306 (2011).
Edwards, P.A. et al, "Purification and properties of rat liver 3-hydroxy-3-methylglutaryl coenzyme A reductase," Biochim. Biophys. Acta 574: 123-35 (1979).
Ehrlicher, A. et al., Guiding neuronal growth with light, Proc. Natl Acad. Sci. U.S.A. 99: 16024-8 (2002).
Elson, C.E. and Quereshi, A.A., "Coupling the cholesterol- and tumor-suppressive actions of palm oil to the impact of its minor constituents on 3-hydroxy-3-methylglutaryl coenzyme a reductase activity," Prostaglandins Leukot. Essent. Fatty Acids 52: 205-207 (1995).
Endo, A., "A historical perspective on the discovery of statins," Proc. Jpn Acad, Ser. B Phys. Biol. Sci 86(5): 484-93 (2010).
Faulkner, LE, et al., "An analysis of the role of a retroendocytosis pathway in ABCA1 mediated cholesterol efflux from macrophages," J. Lipid Res. 49: 1322-32 (2008).
Fernandez-Hernando, et al, "MicroRNAs in metabolic disease," Arterioscl. Thromb. Vasco Biol. 33: 178-85 (2013).
Freed-Pastor, W A, et al, "Mutant p53 disrupts mammary tissue architecture via the mevalonate pathway," Cell 148: 244-58 (2012).
Gabitova, L. et al., "Molecular Pathways: Sterols and receptor signaling in Cancer," Clin. Cancer Res. 19(23): 6344-50 (2013).
Garcia-Verdugo, JM et al, "Architecture and Cell types of the adlt subventricular zone: in search of the stem cells," J. Neurobiol. 36: 234-48 (1998).
Gaylor, JL, "Membrane bound enzymes of cholesterol synthesis from lanosterol", Biochem. Biophys. Res. Communic., 292: 1139-46 (2002).
Gill, S. et al., "Cholesterol-dependent degradation of squalene monooxygenase, a control point in cholesterol synthesis beyond HMG-CoA reductase," Cell Metab. 13: 260-73 (2011).
Gillotte, KL, et al, "Removal of cellular cholesterol by pre-f3-HDL involves plasma membrane microsolubilization," J. Lipid Res. 39: 1918-28 (1998).
Gong, Y. et al, "Sterol-regulated ubiquitination and degradation of Insig-1 creates a convergent mechanism for feedback control of cholesterol synthesis and uptake," Cell Metab. 3: 15-24 (2006).
Gonzalez, R. et al, "Two major regulatory steps in cholesterol synthesis by human renal cancer cells," Arch. Biochem. Biophys. 196: 574-80 (1979).
Gorin, A. et al., "Regulation of cholesterol biosynthesis and cancer signaling," Curr. Op. Phanncol. 12(6) 710-16 (2012).
Greenwood, J et al, Statin therapy and autoimmune disease: from protein prenylation to immunomodulation, Nat. Rev. Immunol. 6: 358-70 (2006).
Gruenbacher, G. et al., "CD56+ human blood dendritic cells effectively promote TH1-type gammadelta T cell responses," Blood 114: 4422-31 (2009).
Gruenbacher, G. et al., "IL-2 costimulation enables statin-mediated activation of human NK cells, preferentially through a mechanism involving CD56+ dendritic cells", Cancer Res. 70: 9611-20 (2010).
Gu, X et al., "Scavenger receptor class B, type I-mediated [3H]cholesterol efflux to high and low density lipoproteins is dependent on lipoprotein binding to the receptor," J. Biol. Chem. 275: 29993-30001 (2000).
Guo, D et al, "Targeting SREBP-1 driven lipid metabolism to treat cancer," Curr. Pharm Des. 20(15): 2619-26 (2014).
Guo et al, "EGFR signaling through an Akt-SREBP-I-dependent, rapamycin-resistant pathway sensitizes glioblastomas to anti-lipogenic therapy," Science Signaling 2: ra82 (2009).
H.S. Phillips, et al., "Molecular subclasses of high-grade glioma predict prognosis, delineate a pattern of disease progression, and resemble stages in neurogenesis," Cancer Cell. 9(3): 157-73, 2006.
Haas-Kogan,D.A. et al., Epidermal Growth Factor Receptor, Protein Kinase B/Akt, and Glioma Response to Erlotinib, J. Natl. Cancer Inst. 2005, 97, 880-887.
Hagiwara, et al, "Hepatic mTORC2 activates glycolysis and lipogenesis through Akt, glucokinase and SREBP1c," Cell Metab. 15: 725-38 (2012).
Nguyen, A.D. et al, "Hypoxia stimulates degradation of 3-hydroxy-3-methylglutaryl-coenzyme A reductase through accumulation of

(56) References Cited

OTHER PUBLICATIONS lanosterol and hypoxia-inducible factor-mediated induction of Insigs". Biol. Chem. 282: 27436-446 (2007).
Nguyen-Vu, T. et al, "Liver x receptor ligands disrupt breast cancer cell proliferation through an E2F-mediated mechanism," Breast Cancer Res. 15: R51 (2013).
Nimph, J, and Schneider, WJ, The VLDL receptor: an LDL receptor relative with eight ligand binding repeats, LR8. Atherosclerosis 141: 191-202 (1998).
Nohtmfft, A. et al., "Topology of SREBP cleavage-activating protein, a polytopic membrane protein with a sterol-sensing domain," J. Biol. Chem. 273: 17243-250 (1998).
Nohturfft, A. et al, "Recurrent G-to-A substitution in a single codon of SREBP cleavage-activating protein causes sterol resistance in three mutant Chinese hamster ovary cell lines", Proc. Natl Acad. Sci. USA 93: 13709-714 (1996).
Nohturfft, A. et al, "Sterols regulate processing of carbohydrate chains of wild-type SREBP cleavage-activating protein (SCAPa), but not sterolresistant mutants Y298C or D443N," Proc. Natl. Acad. Sci. USA 95: 12848-853 (1998).
Oliverase, G. et al, "Novel anti-fatty acid synthase compounds with anti-cancer activity in Her2+ breast cancer," Ann. N.Y. Acad. Sci. 1210: 86-92 (2010).
P.J. Noughton et al. "Antitumor Activity of Temozolomide Combined with Irinotecan IsPartly Independent ofO6-Methylguanine-DNA Methyltransferaseand Mismatch Repair Phenotypes in Xenograft Models1"; Clin. Cancer Res. (2000) 6:4110-4118.
Parker, N.R. et al., "Molecular heterogeneity in glioblastoma: potential clinical implications," Frontiers in Oncology 5, article 55 (Mar. 2015).
Paul, R. et al., "Both the immunosuppressant SR31747 and the antiestrogen tamoxifen bind to an emopamil-insensitive site of Mammalian il8-il7 sterol isomerase," J. Pharmacol. Exptl Thera. 285(3): 1296-1302 (1998).
Pehkonen, P. et al., "Genome-wide landscape of liver X receptor chromatin binding and gene regulation in human macrophages," BMC Genomics 13: 50 (2012).
Peterson T.R, et al, "mTOR complex I regulates lipin 1 localization to control the SREBP pathway," Cell 146: 408-20 (2011).
Peterson, T.R., et al, "mTOR complex 1 regulates lipin 1 localization to control the SREBP pathway," Cell 146: 408-20 (2011).
Phillips, M.C, "New insights into the determination of HDL structure by apolipoproteins," J. Lipid Res. 54: 2034-48 (2013).
Phillips, M.C., "Molecular Mechanisms of Cellular Cholesterol Efflux," J. Biol. Chem. 289 (35): 24020-29 (2014).
Piaskowski, S. et al. "Glioma acells showing IDH1 mutation cannot be propagated in standard cell culture conditions," Br. J. Cancer 104(6): 968-70 (2011).
Quazi, F and Molday, RS, "Differential phospholipid substrates and directional transport by ATP-binding cassette proteins ABCA1, ABCA 7, and ABCA4 and disease-causing mutants," J. Biol. Chem. 288: 34414-26 (2013).
Radhakrishnan, A. et al, "Sterol-regulated transport of SREBPs from endoplasmic reticulum to Golgi: Oxysterols block transport by binding to Insig," Proc. Natl Acad. Sci. USA 104: 6511-18 (2007).
Radhakrishnan, A., et al, "Direct binding of cholesterol to the purified membrane region of SCAP: Mechanism for a sterol-sensing domain," Mol. Cell 15: 259-68 (2004).
Ravid, T. et al, "The ubiquitin proteasome pathway mediates the regulated degradation of mammalian 3-hydroxy-3-methylglutaryl-Coenzyme A reductase," J. Biol. Chem. 275: 35840-47 (2000).
Reardon, D.A., et al., Phase II Study of Imatinib Mesylate Plus Hydroxyurea in Adults With Recurrent Glioblastoma Multiforme, J. Clin. Oncol. 2005,vol. 23,9359-9368.
Reardon, D.A., et al., Multicentre phase II studies evaluating imatinib plus hydroxyurea in patients with progressive glioblastoma, Br. J. Cancer 2009, 101, 1995-2004.
Rich, J.N., et al., N. Engl. J. Med. 2004, 351, 1260-1261.

Roitelman, J. and Simoni, R.D., "Distinct sterol and nonsterol signals for the regulated degradation of 3-hydroxy-3-methylglutaryl-CoA reductase," J. Biol. Chem. 267: 25264-273 (1992).
Rosenson, R S et al., "Cholesterol efflux and atheroprotection: advancing the concept of reverse cholesterol transport", Circulation 125: 1905-19 (2012).
Rothblat, G.H. and Phillips, M.C., "High-density lipoprotein heterogeneity and function in reverse cholesterol transport," Curr. Opin. Lipidol. 21: 229-38 (2010).
Russell, D.W., "Oxsterol biosynthetic enzymes," Biochim. Biophys. Acta-Molec. Cell Biol. Lipids 1529: 126-135 (2000).
Sabatini, D.M, "mTOR and cancer: insights into a complex relationship," Nat. Rev. Cancer 6: 729-34 (2006).
Sankaranarayanan, S. et al., "Effects of acceptor composition and mechanism of ABCG 1-mediated cellular free cholesterol efflux," J. Lipid Res. 50: 275-84 (2009).
Sasaki, M. et al, "D-2 hydroxyglutarate produced by mutant IDH1 perturbs collagen maturation and basement membrane function," Genes & Devel. 26(18): 2038-49 (2012).
Sawamura, T. et al., "An endothelial receptor for oxidized low-density lipoprotein," Nature 386: 73 (1997).
Sawhney et al., Bioerodible hydrogels based on photopolymerized poly(ethylene glycol)co-poly(alpha.-hydroxy acid) diacrylate macromers, Macromolecules (1993) 26,581-587.
Schroepfer, G.J., Jr., "Oxysterols: modulators of cholesterol metabolism and other processes," Physiol. Rev. 80: 361-554 (2000).
Serrano, M., et al., A new regulatory motif in cell-cycle control causing specific inhibition of cyclin D/CDK4; Nature, 1993, 366: 704-707.
Sever, N. et al, "Accelerated degradation of HMG CoA reductase mediated by binding of insig-I to its sterol-sensing domain," Mol. Cell 11: 25-33 (2003).
Sever, N. et al.,"Insig-dependent ubiquitination and degradation of mammalian 3 hydroxy-3-methylglutaryl-CoA reductase stimulated by sterols and geranylgeraniol," J. Biol. Chem. 278: 52479-90 (2003).
Sharpe, U and Brown, AJ, "Controlling cholesterol Synthesis beyond 3-hydroxy-3-methylglutaryl CoA reductase (HMOCR)," J. Biol. Chem. 288 (26): 18707-715 (2013).
Smith, B. and Land, H., "Anticancer activity of the cholesterol exporter ABCA1 gene," Cell Rep. 22(3): 580-90 (2012).
Smith, JD et al, "ABCA1 mediates concurrent cholesterol and phospholipid efflux to apolipoprotein AI," J. Lipid Res. 45: 635-44 (2004)).
Song, BL et al, "Gp78, a membrane-anchored ubiquitin ligase, associates with Insig-1 and couples sterol-regulated ubiquitination to degradation of HMG CoA reductase," Mol. Cell 19: 829-40 (2005).
Song, BL, et al, "Insig-mediated degradation of HMG CoA reductase stimulated by lanosterol, an intermediate in be synthesis of cholesterol," Cell Metab. 1: 179-89 (2005).
Spann, N J, et al, "Regulated accumulation of desmosterol integrates macrophage lipid metabolism and inflammatory responses," Cell 151: 138-52 (2012).
Spencer, T A, et al., "24(S),25-epoxycholesterol. Evidence consistent with a role in the regulation of hepatic cholestrogenesis," J. Biol. Chem. 260: 13391-94 (1985).
Steinman, R.M. and Banchereau, J., "Taking dendritic cells into medicine," Nature 449: 419-26 (2007).
Sturm, D. et al, "Hotspot mutations in H3F3A and IDH1 define distinct epigenetic and biological subgroups of glioblastoma," Cancer Cell 22(4): 425-37 (2012).
Sun LP et al, "Sterol-regulated transport of SREBPs from endoplasmic reticulum to Golgi: Insig renders sorting signal in Scap inaccessible to COPII proteins," Proc. Natl Acad. Sci. USA 104: 6519-26 (2007).
The Cancer Genome Atlas Research Network*; Comprehensive genomic characterization defines human glioblastoma genes and core pathways; Nature 455: 1061-1068 (2008).
Thuahnai, S.T., et al, "SR-BI-mediated cholesteryl ester selective uptake and efflux of unesterified cholesterol: influence of HDL size and structure," J. Biol. Chem. 279: 12448-455 (2004).

(56) References Cited

OTHER PUBLICATIONS

Thurnher, M., et al., "Novel aspects of mevalonate pathway inhibitors as antitumor agents", Clin. Cancer Res. 18: 3524-31 (2012).
Uddin, S. et al, "High prevalence of fatty acid synthase expression in colorectal cancers in Middle Eastern patients and its potential role as a therapeutic target," Am. J. Gastroenterol. 104(7): 1790-1801 (2009).
International Preliminary Report on Patentability for Application No. PCT/US16/039744 dated Jan. 9, 2018.
International Search Report and Written Opinion for Application No. PCT/US16/039744 dated Nov. 30, 2016.
Pubchem CID 2392976; Date created: Jul. 15, 2005, Date accessed: Nov. 1, 2016.
Chittur, S. V., et al; Histone deacetylase inhibitors: A new mode for inhibition of cholesterol metabolism; BMC Genomics, vol. 9, 1-14, Oct. 29, 2008.
Van Den Bent, M.J. et al., Randomized Phase II Trial of Erlotinib Versus Temozolomide or Carmustine in Recurrent Glioblastoma: EORTC Brain Tumor Group Study 26034., J. Clin. Oncol. 2009, vol. 27,1268-1274.
Vaughan, A.MM and Oram, J.F., "ABCG 1 redistributes cell cholesterol to domains removable by high density lipoprotein but not by lipid-depleted apolipoproteins," J. Biol. Chem. 280: 20150-57 (2005).
Veliz, I. et al., "Advances and challenges in the molecular biology and treatment of glioblastoma—is there any hope for the future?" Ann. Trans. Med. 3(1): 7. DOI:10.3978/j.issn.2305-5939.2014.10. 06. 2014.
Verhaak, RG, et al., Integrated Genomic Analysis Identifies Clinically Relevant Subtypes of Glioblastoma Characterized by Abnormalities in PDGFRA, IDH1, EGFR, and NF1, Cancer Cell, 17(1):98-110,2010.
Wang, L. et al., Interleukin-1f3 and transforming growth factor-f3 cooperate to induce neurosphere formation and increase tumorigenicity of adherent LN-229 glioma cells, Stem ell Res. & Therapy 3:5 (2012).
Wang, N. et al, "ATP-binding cassette transporters G1 and G4 mediate cellular cholesterol efflux to high-density lipoproteins," Proc. Natl Acad. Sci. USA 101: 9774-79 (2004).
Weiss, S. et al, "Multipotent CNS stem cells are present in the adult mammalian spinal cord and ventricular neuroaxis," J. Neurosci. 16(23): 7599-7609 (1996).
Williams, D. L, et al, "Scavenger receptor BI and cholesterol trafficking," Curr.. Opin. Lipidol. 10: 329-39 (1999).
Williams, DL et al., "Binding and cross-linking studies show that scavenger receptor B 1 interacts with multiple sites in apolipoprotein A-I and identify the class A amphipathic a helix as a recognition motif," J. Biol. Chem. 275: 18897-18904 (2000).
Williams, M.T., et al, "Investigation of the rate-determining microsomal reaction of cholesterol biosynthesis from lanosterol in Morris hepatomas and liver," Cancer Res. 37: 1377-83 (1977).
Willner, E. et al, Deficiency of acyl CoA:cholesterol aceyltransferase 2 prevents atherosclerosis in apolipoprotein E-deficient mice., Proc. Natl Acad. Sci. USA 100: 1262 (2003).
Wong, J. et al., "Endogenous 24(S),25-epoxycholesterol fine-tunes acute control of cellular cholesterol homeostasis," J. Biol. Chem. 283: 700-707 (2008).
Wong, WW et al, "HMG-CoA reductase inhibitors and the malignant cell: the statin family of drugs as triggers of tumor-specific apoptosis," Leukemia 16: 508-19 (2002).
Xu, J. et al, "Cholesterol trafficking is required for mTOR activation in endothelial cells," Proc. Natl Acad. Sci. USA 107(10): 4764-69 (2010).
Xu, Y. et al., Neurogenesis in the ependymal layer of the adultrat 3rd ventricle, Exptl Neurol. 192(2): 251-64 (2005).
Yabe, D. et al, "Insig-2, a second endoplasmic reticulum protein that binds SCAP and blocks export of sterol regulatory element-binding proteins," Proc. Natl. Acad. Sci. USA 99: 12753-758 (2002).
Yabe, D. et al., "Three mutations in sterol-sensing domain of SCAP block interaction with insig and render SREBP cleavage insensitive to sterols," Proc. Natl. Acad. Sci. USA 99: 16672-77 (2002).
Yancey, P.O., et al, "High density lipoprotein phospholipid compositon is a major determinant of the bi-directional lux and net movement of cellular free cholesterol mediated by scavenger receptor BI," J. Biol. Chern. 275: 36596-36604 (2000).
Yang, C. et al, "Sterol intermediates from cholesetterol biosynthetic pathway as liver X receptor ligands," J. Biol. Chern . 281: 27816-826 (2006).
Yang, T. et al, "Crucial step in cholesterol homeostasis: sterols promote binding of SCAP to INSIG-1, a membrane protein that facilitates retention of SREBPs in ER," Cell 110: 489-500 (2002).
Zannis, V. et al., "Role of apoA-I, ABCA1, LCAT and SR-BI in the biogenesis of HDL," J. Mol. Med. 84:276-94 (2006).
Zerenturk, E.J. et al, "The endogenous regulator 24(S),25-epoxycholesterol inhibits cholesterol synthesis at DHCR24 (Seladin-1)," Biochim. Biophys. Acta 1821: 1269-77 (2012).
Zerenturk, EJ, et al., "Sterols regulate 3f3-hydroxysterol 24-reductase (DHCR24) via dual sterol regulatory elements: cooperative induction of key enzymes in lipid synthesis by sterol regulatory element binding proteins," Biochim. Et Biophys. Acta 1821 (10): 1350-60 (2012).
Zhu, J. et al, "Effects of Fox04 overexpression on cholesterol biosynthesis, triacylglycerol accumulation, and glucose uptake," J. Lipid Res. 51: 1312-24 (2010).
Zhuang, L. et al, "Cholesterol targeting alters lipid raft composition and cell survival in prostate cancer cells and xenografts," J. Clin. Invest. 115: 959-68 (2005).

* cited by examiner

Microarray - Overrepresented pathways associated with treatment with 4C12

| Ingenuity Canonical Pathways | p | Ratio | Molecules |
|---|---|---|---|
| Superpathway of Cholesterol Biosynthesis | 6E-06 | 0.08 | MVD,FDPS,PMVK,Acat2/Acat3,HSD17B7,MSMO1,LSS |
| Superpathway of Geranylgeranyldiphosphate Biosynthesis I (via Mevalonate) | 1E-05 | 0.14 | MVD,FDPS,PMVK,Acat2/Acat3,FNTB |
| Mevalonate Pathway I | 0.0016 | 0.11 | MVD,PMVK,Acat2/Acat3 |
| Geranylgeranyldiphosphate Biosynthesis | 0.0019 | 0.25 | FDPS,FNTB |
| RhoA Signaling | 0.003 | 0.04 | PTK2,LPAR6,ARPC1B,GNA13,PIP4K2C |
| Cholesterol Biosynthesis I | 0.004 | 0.08 | HSD17B7,MSMO1,LSS |
| Cholesterol Biosynthesis II (via 24,25-dihydrolanosterol) | 0.004 | 0.08 | HSD17B7,MSMO1,LSS |
| Cholesterol Biosynthesis III (via Desmosterol) | 0.004 | 0.08 | HSD17B7,MSMO1,LSS |
| Wnt/β-catenin Signaling | 0.014 | 0.03 | SOX9,PPP2R1A,TGFB2,SOX5,FZD7 |
| Zymosterol Biosynthesis | 0.014 | 0.09 | HSD17B7,MSMO1 |
| Lipid Antigen Presentation by CD1 | 0.018 | 0.07 | AP1B1,AP2S1 |
| Lanosterol Biosynthesis | 0.025 | 0.33 | LSS |
| Cyclins and Cell Cycle Regulation | 0.028 | 0.03 | E2F6,PPP2R1A,TGFB2 |
| TWEAK Signaling | 0.031 | 0.05 | FADD,TNFRSF25 |
| Cell Cycle Regulation by BTG Family Proteins | 0.034 | 0.06 | E2F6,PPP2R1A |
| CTLA4 Signaling in Cytotoxic T Lymphocytes | 0.042 | 0.03 | PPP2R1A,AP1B1,AP2S1 |
| Tec Kinase Signaling | 0.043 | 0.02 | PTK2,FADD,TNFRSF25,GNA13 |
| Alanine Degradation III | 0.049 | 0.17 | GPT2 |
| Alanine Biosynthesis II | 0.049 | 0.17 | GPT2 |
| Netrin Signaling | 0.05 | 0.04 | NFAT5,ABLIM3 |
| Rac Signaling | 0.06 | 0.02 | PTK2,ARPC1B,PIP4K2C |
| Pancreatic Adenocarcinoma Signaling | 0.06 | 0.03 | E2F6,TGFB2,HBEGF |
| Tyrosine Biosynthesis IV | 0.06 | 0.13 | PCBD2 |
| Role of Tissue Factor in Cancer | 0.07 | 0.03 | CTGF,HBEGF,GNA13 |
| Molecular Mechanisms of Cancer | 0.07 | 0.02 | PTK2,FADD,E2F6,TGFB2,GNA13,FZD7 |
| GABA Receptor Signaling | 0.07 | 0.04 | AP1B1,AP2S1 |
| Axonal Guidance Signaling | 0.07 | 0.01 | PTK2,NFAT5,ARPC1B,ABLIM3,GNA13,FZD7,NTN3 |
| IL-8 Signaling | 0.07 | 0.02 | PTK2,ANGPT2,HBEGF,GNA13 |
| Gα12/13 Signaling | 0.08 | 0.02 | PTK2,LPAR6,GNA13 |
| Role of CHK Proteins in Cell Cycle Checkpoint Control | 0.08 | 0.04 | E2F6,PPP2R1A |
| Trans, trans-farnesyl Diphosphate Biosynthesis | 0.08 | 0.10 | FDPS |
| Death Receptor Signaling | 0.08 | 0.03 | FADD,TNFRSF25 |
| Cell Cycle: G1/S Checkpoint Regulation | 0.09 | 0.03 | E2F6,TGFB2 |
| Phenylalanine Degradation I (Aerobic) | 0.10 | 0.08 | PCBD2 |

(with Samuel Peña-Llopis)

➢ 4C12 deregulates cholesterol biosynthesis pathway ???

FIGURE 10

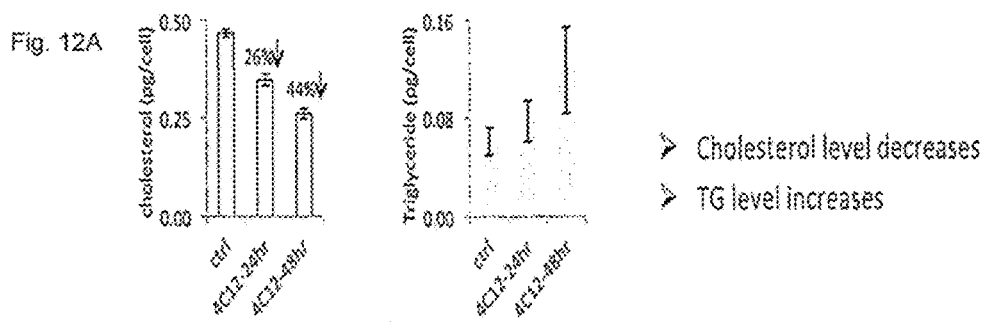
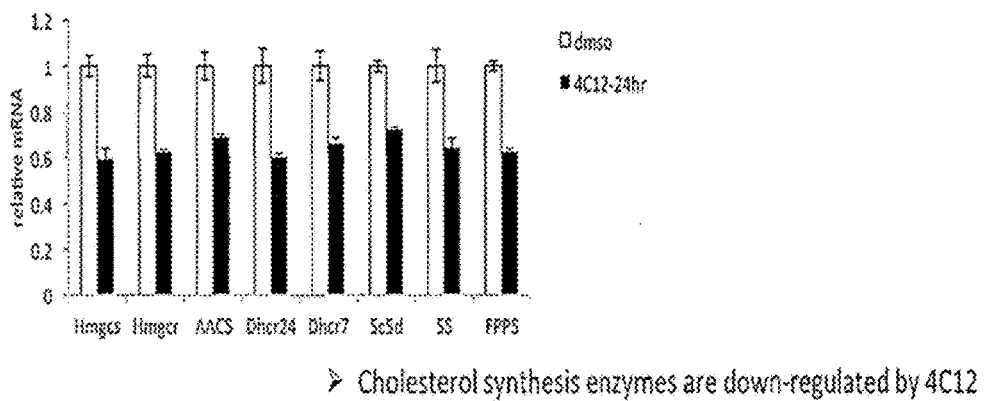
FIGURE 12

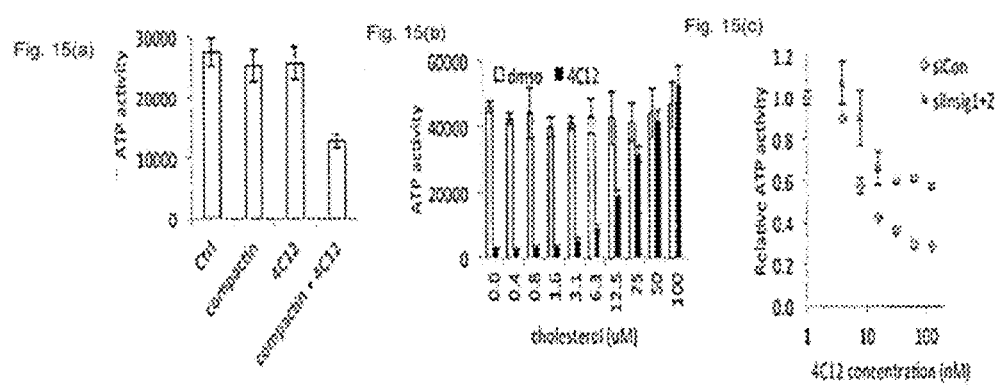
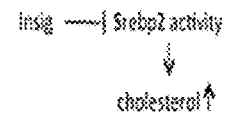
- Compactin (statin) and 4C12 make combination effect
- Addition of cholestrol inhibits 4C12-induced cell-death
- Activation of SREBP2 by knock-down of Insig1/Insig2 makes cells less sensitive to 4C12
FIGURE 15

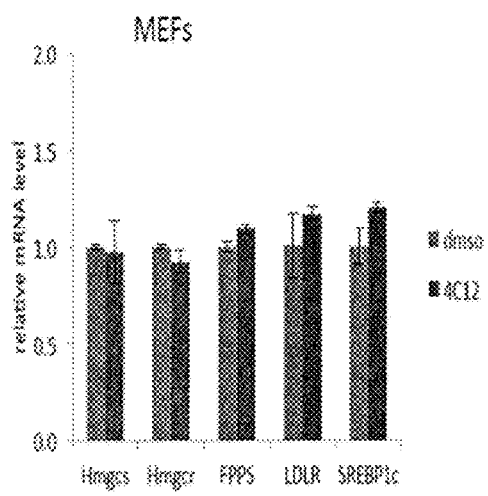
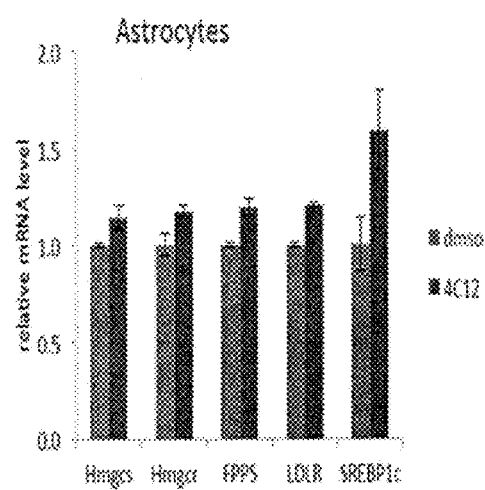
➢ Srebp2 targets genes were not decreased by 4C12 in MEFs and Astrocytes
FIGURE 16

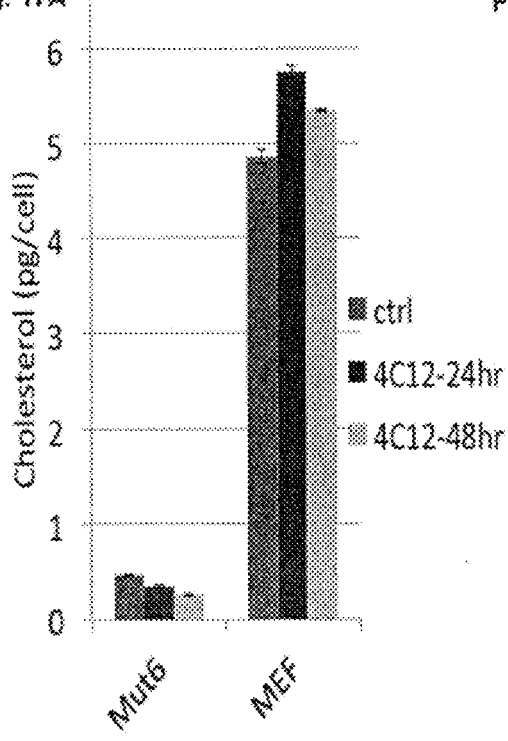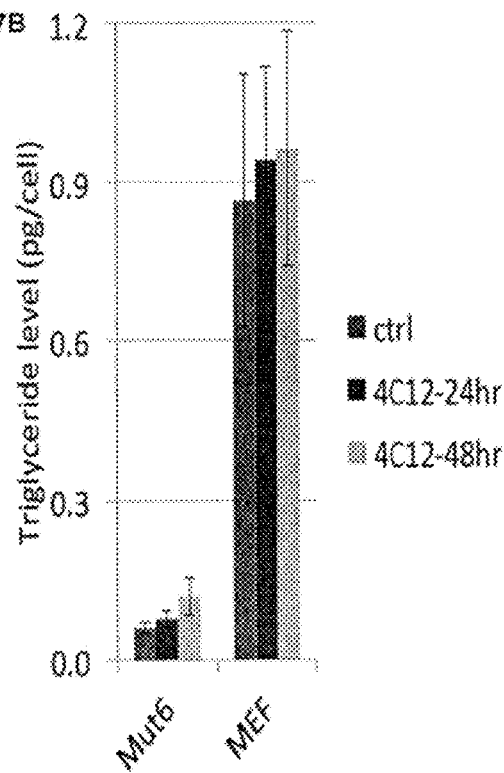
- Decrease of cholesterol by 4C12 is specific to Mut6 tumor cells
- Mut6 cells have much lower basal level of cholesterol and TG
FIGURE 17

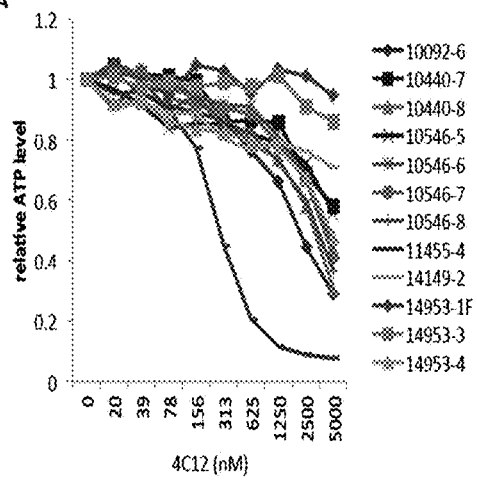
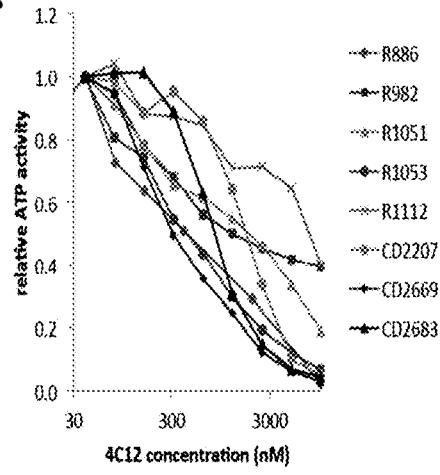
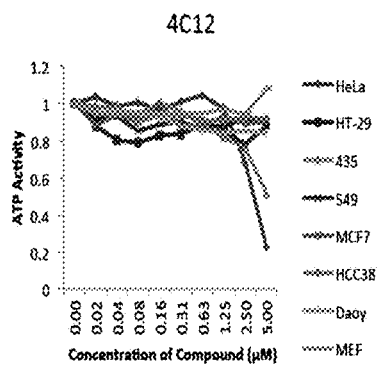
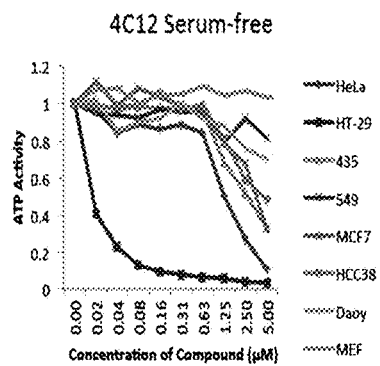
FIGURE 19

BENZAMIDE OR BENZAMINE COMPOUNDS USEFUL AS ANTICANCER AGENTS FOR THE TREATMENT OF HUMAN CANCERS

CROSS-REFERENCE TO RELATED APPLICATIONS

This application claims the benefit of priority to U.S. Provisional Application No. 62/189,069 filed on Jul. 6, 2015, the entire contents of which are incorporated by reference herein.

FIELD OF THE INVENTION

The described invention relates to small molecule anticancer therapeutics.

BACKGROUND OF THE INVENTION

Gliomas

Glial cells, the most abundant cell type in the central nervous system, are cells that surround neurons and provide support for and insulation between them. Unlike neurons, glial cells do not conduct electrical impulses. There are two major classes of glial cells in the central nervous system: astrocytes and oligodendrocytes (Kandel E R, et al., Principles of Neural Science, 4th Ed. McGraw-Hill New York (2000), Ch. 2, pp. 20-21).

Glial cells in the vertebrate nervous system are divided into two major classes: microglia and macroglia. Microglia are phagocytes that are mobilized after infection, injury or disease, which arise from macrophages outside the nervous system. Three types of macroglial cells predominate in the vertebrate nervous system: oligodendrocytes, Schwann cells, and astrocytes. Astrocytes, the most numerous of glial cells in the central nervous system characterized by their star-like shape and the broad end-feet on their processes, are thought to play a nutritive role, and help form an impermeable lining in the brains capillaries and venules—the blood brain barrier—that prevents toxic substances in the blood from entering the brain. Oligodendrocytes, small cells with relatively few processes, and Schwann cells produce the myelin used to insulate nerve cell axons.

The term "glioma" encompasses all tumors thought to originate in the glial cell linage. (Veliz, I. et al., "Advances and challenges in the molecular biology and treatment of glioblastoma—is there any hope for the future?" Ann. Trans. Med. 3(1): 7. Doi: 10.3978/j.issn.2305-5939.2014.10.06. The location of the tumor depends on the type of cells from which it originates.

Malignant gliomas exhibit properties that resemble astrocytes or oligodendrocytes, hence the designation as astrocytomas and oligodendrogliomas. These tumors are graded on a scale from I to IV, based on how normal or abnormal the cells look. Of numerous grading systems in use, the most common is the World Health Organization (WHO) grading system for glioma (Louis D N, et al., Acta Neuropathol, 2007, 114(2):97-109). Grade I tumors are slow-growing, nonmalignant, and associated with long-term survival. Grade II tumors are relatively slow-growing but sometimes recur as higher grade tumors. They can be nonmalignant or malignant. Grade III tumors are malignant and often recur as higher grade tumors. Grade IV tumors reproduce rapidly and are very aggressive malignant tumors.

Low grade astrocytomas usually are localized and grow slowly. High grade astrocytomas grow at a rapid pace and are infiltrative. Astrocytomas can appear in various parts of the brain and nervous system, including the cerebellum, the cerebrum, the central areas of the brain, the brainstem, and the spinal cord.

Pilocytic Astrocytoma (also called Juvenile Pilocytic Astrocytoma), are grade I astrocytomas, which typically stay in the area where they started and do not spread. They are considered the "most benign" (noncancerous) of all the astrocytomas. Two other, less well known grade I astrocytomas are cerebellar astrocytoma and desmoplastic infantile astrocytoma.

Diffuse Astrocytoma (also called Low-Grade or Astrocytoma Grade II) (e.g., Fibrillary, Gemistocytic, Protoplasmic Astrocytoma) tend to invade surrounding tissue and grow at a relatively slow pace.

An anaplastic astrocytoma is a grade III tumor. These rare tumors require more aggressive treatment than benign pilocytic astrocytoma.

Astrocytoma Grade IV (also called Glioblastoma, previously named "Glioblastoma Multiforme," "Grade IV Glioblastoma," and "GBM"). There are two types of astrocytoma grade IV—primary, or de novo, and secondary. Primary tumors are very aggressive and the most common form of astrocytoma grade IV. The secondary tumors are those which originate as a lower-grade tumor and evolve into a grade IV tumor.

Subependymal Giant Cell Astrocytoma—Subependymal giant cell astrocytomas are ventricular tumors associated with tuberous sclerosis.

Oligodendrogliomas can be found anywhere within the cerebral hemisphere of the brain, although the frontal and temporal lobes are the most common locations. Sometimes oligodendrogliomas are mixed with other cell types. These tumors may be graded using an "A to D" system, which is based on microscopic features of the individual tumor cells. The grade indicates how quickly the tumor cells reproduce and how aggressive the tumor is. About 4% of primary brain tumors are oligodendrogliomas, representing about 10-15% of the gliomas. Only 6% of these tumors are found in infants and children. Most oligodendrogliomas occur in adults ages 50-60, and are found in men more often than women.

Mixed glioma (or oligoastrocytoma) usually contain a high proportion of more than one type of cell, most often astrocytes and oligodendrocytes. Occasionally, ependymal cells are also found. The behavior of a mixed glioma appears to depend on the grade of the tumor. It is less clear whether their behavior is based on that of the most abundant cell type.

Ependymal cells line the ventricles of the brain and the center of the spinal cord. These tumors are divided into four major types: subependymomas (grade I), typically slow growing tumors; myxopapillary ependymomas (grade I), typically slow growing tumors; Ependymomas (grade II), the most common of the ependymal tumors, which can be further divided into the following subtypes, including cellular ependymomas, papillary ependymomas, clear cell ependymomas, and tancytic ependymomas; and anaplastic ependymomas (grade III), typically faster growing tumors. The various types of ependymomas appear in different locations within the brain and spinal column. Subependymomas usually appear near a ventricle. Myxopapillary ependymomas tend to occur in the lower part of the spinal column. Ependymomas are usually located along, within, or next to the ventricular system. Anaplastic ependymomas are most commonly found in the brain in adults and in the lower back part of the skull (posterior fossa) in children. They are rarely found in the spinal cord. Ependymomas are relatively rare tumors in adults, accounting for 2-3% of primary brain tumors. However, they are the sixth most common brain tumor in children. About 30% of pediatric ependymomas are diagnosed in children younger than 3 years of age.

Optic gliomas may involve any part of the optic pathway, and they have the potential to spread along these pathways. Most of these tumors occur in children under the age of 10. Grade I pilocytic astrocytoma and grade II fibrillary astrocytoma are the most common tumors affecting these structures. Higher-grade tumors may also arise in this location. Twenty percent of children with neurofibromatosis (NF-1) will develop an optic glioma. These gliomas are typically grade I, pilocytic astrocytomas. Children with optic glioma are usually screened for NF-1 for this reason. Adults with NF-1 typically do not develop optic gliomas.

Gliomatosis Cerebri is an uncommon brain tumor that is most frequently pediatric and features widespread glial tumor cells in the brain. This tumor is different from other gliomas because it is scattered and widespread, typically involving two or more lobes of the brain. It could be considered a "widespread low-grade glioma" because it does not have the malignant features seen in high-grade tumors.

Glioblastoma

Glioblastoma multiforme (GBM), a WHO grade IV malignant glioma, classification name "glioblastoma", is the most common and most aggressive primary brain tumor in adults. GBM accounts for 40%-60% of all diffuse astrocytic tumors and 10%-15% of all intracranial neoplastic lesions. The biological characteristics of this tumor are exemplified by prominent proliferation, active invasiveness, and rich angiogenesis. (Nakada, M. et al., Cancers, 2011, 3: 3242-3278). GBM is composed of poorly differentiated neoplastic astrocytes. The presence of microvascular proliferation and/or necrosis is essential for histopathological diagnosis of GBM.

GBM is one of the most aggressive human cancers and is very difficult to treat due to several complicating factors: the tumor cells are very resistant to conventional therapies; the brain is susceptible to damage by conventional therapy; the brain has a very limited capacity to repair itself; and many drugs cannot cross the blood-brain barrier to act on the tumor.

Although treatment can involve radiation, surgery and chemotherapy with temozolomide, which is an alkylating agent (P. J. Noughton et al. Clin. Cancer Res. (2000) 6:4110-4118), decades of surgical therapy, radiotherapy, and chemotherapy have failed to drastically change survival for GBM. The medium survival of patients with GBM in clinical trial populations treated with multimodal treatment approaches is approximately 12-15 months, with only 3%-5% of patients surviving longer than 36 months. (McNamara. M. G. et al., Cancers, 2013, 5: 1103-1119).

Glioblastoma multiforme has at least four distinct molecular subtypes. Tumor variants can be classified on the basis of somatic mutations in isocitrate dehydrogenase (IDH) ½ and TP53; transcriptional signature (classical, mesenchymal, neural or proneural), copy number variation, including co-deletion of chromosomes 1p and 19q; and amplification or mutation of the epidermal growth factor receptor (EGFR) and increased DNA hypermethylation of promoter-associated CpG islands. (Parker, N. R. et al., "Molecular heterogeneity in glioblastoma: potential clinical implications," Frontiers in Oncology 5, article 55 (March 2015)).

Classical GBM tumors are characterized by abnormally high levels of epidermal growth factor receptor (EGFR) which is a protein found on the surface of some cells that, when bound by epidermal growth factor, sends signals for the cell to keep growing in number (proliferation). The Cancer Genome Atlas (TCGA) Research Network, Nature 455: 1061-1068 (2008).

EGFR abnormalities occur at a much lower rate in the three other GBM subtypes. The TP53 gene codes for tumor protein p53 that normally suppresses tumor growth. TP53 is rarely mutated in classical GBM tumors subtype, but is the most frequently mutated gene in other subtypes of GBM.

Proneural GBM tumors are characterized by alterations of platelet derived growing factor receptor A (PDGFRA) and point mutations in IDH1, the gene that encodes isocitrate dehydrogenase 1. The gene IDH1, when mutated, codes for a protein that can contribute to abnormal cell growth. PDGFRA, which plays an important role in cell proliferation, cell migration, and angiogenesis, was also found to be mutated and expressed in abnormally high amounts. PDGFRA alteration only occurs in Proneural tumors and not in any other subtypes. When PDGFRA is altered, too much of its protein can be produced, leading to uncontrolled tumor growth. The patients of this subtype tend to be younger and to survive longer than in other subtypes.

The Mesenchymal subgroup contains the most frequent number of mutations in the neurofibromatosis type 1 (NF1) tumor suppressor gene. Frequent mutations in the PTEN (phosphatase and tensin homolog) and TP53 tumor suppressor genes also occur in the Mesenchymal subgroup. PTEN protein acts as a tumor suppressor, helping regulate the cycle of cell division.

While the Neural subgroup has mutations in many of the same genes as the other groups, the group does not stand out from the others as having significantly higher or lower rates of mutations. The Neural group is characterized by the expression of several markers that are also typical of the brain's normal, noncancerous nerve cells, or neurons, such as NEFL, GABRA1, SYT1 and SLC12A5.

While classical and mesenchymal GBMs express gene expression profiles reminiscent of NSCs, IDH-mutant gliomas display a proneural phenotype. (Ilkanizadeh, et al., "Glial Progenitors as Targets for Transformation in Glioma," Adv. Cancer Res. 121: 1-65 (2014)).

Based on clinical experience, two subgroups of otherwise histologically indistinguishable GBMs have been established: primary glioblastoma and secondary glioblastoma. Primary glioblastoma, which comprises more than 90% of biopsied or resected cases, arise de novo without antecedent history of low-grade disease, whereas secondary glioblastoma progresses from previously diagnosed low-grade gliomas. Primary glioblastomas display classical mesenchymal and neural phenotypes, whereas secondary glioblastomas tend to display a proneural phenotype that shifts toward a mesenchymal phenotype with recurrence. (Parker, N. R. et al., "Molecular heterogeneity in glioblastoma: potential clinical implications," Frontiers in Oncology 5, article 55 (March 2015)).

These molecular subtypes of glioblastoma multliforme appear to differ in their clinical courses and therapeutic responses. For example, the different subtypes show varying responses to aggressive chemotherapy and radiotherapy, with a difference of around 50% between the subtypes. It has been suggested that the pathology of each subtype might begin from different types of cells, which might explain the variation in response to therapy. The greatest benefit was seen in the Classical and Mesenchymal subtypes, where intensive therapy has significantly reduced mortality; and there was a suggestion of efficacy in the Neural subtype; but the Proneural subtype was less responsive to intensive therapy including conventional chemotherapy or chemo-radiation therapy. (Verhaak, R G, et al., Cancer Cell, 17(1): 98-110, 2010))

Major Glioma Signaling Pathways

Several major signaling pathways have been associated with Glioma (Nakada, M. et al., Cancers, 2011, 3: 3242-3278).

1. Receptor Tyrosine Kinase Pathway (RTK/PI3K/Akt/mTOR Pathway).

The RTK/PI3K/Akt pathway regulates various fundamental cellular processes such as proliferation, growth, apoptosis, and cytoskeletal rearrangement. The pathway involves receptor tyrosine kinases (RTKs), for example, epidermal growth factor receptor (EGFR), platelet derived growing factor receptor (PDGFR), and vascular endothelial growth factor receptor (VEGFR), etc., as well as tumor suppressor protein phosphatase, for example, phosphatase and tension homolog (PTEN), and protein kinases PI3K, Akt, and mTOR. The Receptor Tyrosine Kinase pathway (RTK/PI3K/Akt/mTOR Pathway) is shown in FIG. 1.

EGFR gene amplification is the most frequent alteration (approximately 40%) in GBM. EGFR is a transmembrane glycoprotein member of the ErbB receptor family. In GBM, EGFR is dysregulated through overexpression, which arises because of EGFR gene amplification or activating mutations such as EGFRvIII that lead to ligand-independent signaling. EGFR aberrations have been correlated with a classical subtype of GBM (TCGA Research Network, Nature 455: 1061-68; Verhaak, Roel G. W. et al., Cancer Cell, 2010, 17: 98-110). Although it has been suggested that alterations of EGFR may be correlated with increased aggressiveness of GBM (Nakada, M. et al., Cancers, 2011, 3: 3242-3278), EGFR inhibitors (e.g., Gefinitib, Erlotinib) have not elicited clinical responses in patients with GBMs in clinical trials (Rich, J. N., et al., N. Engl. J. Med. 2004, 351, 1260-1261; Haas-Kogan, D. A. et al., J. Natl. Cancer Inst. 2005, 97, 880-887; van den Bent, M. J. et al., J. Clin. Oncol. 2009, 27, 1268-1274).

Overexpression of platelet-derived growth factor receptor (PDGFR), especially PDGFR-α and platelet-derived growth factor (PDGF) have been observed in astrocytic tumors of all grades, and their association with malignant progression has been suggested (Nakada, M. et al., Cancers, 2011, 3: 3242-3278). PDGFRA amplification (14%), as well as IDH1 mutation, are major features of the Proneural subtype of GBM according to the TCGA classification (TCGA Research Network, Nature 455: 1061-68; Verhaak, R. G. et al., Cancer Cell, 2010, 17: 98-110). Despite deep association of this molecule with GBM, anti-PDGFR therapy using Imatinib yielded only limited clinical responses (Reardon, D. A., et al., J. Clin. Oncol. 2005, 23, 9359-9368; Reardon, D. A., et al., Br. J. Cancer 2009, 101, 1995-2004).

The PI3Ks are widely expressed lipid kinases that promote diverse biological functions. The binding of PI3Ks and RTKs results in activation of Akt through phosphatidylinositol 3,4,5-triphosphate (PiP3) and 3-phosphoinositide dependent protein kinase-1 (PDK1), which affects multiple fundamental cellular processes including cell survival, proliferation, and motility. According to the integrated genomic classification of GBM, PI3K mutations (15%) are associated with the Proneural subtype (TCGA Research Network, Nature, 2008, 455: 1061-68; Verhaak, R. G. et al., Cancer Cell, 2010, 17: 98-110).

Decreased PTEN activity can activate the RTKs/PI3K/Akt pathway since PTEN negatively regulates the pathway by antagonizing PI3K function. Homozygous deletion or mutation of PTEN is a common genetic feature in GBM (40%), resulting in constitutive activation of the RTKs/PI3K/Akt pathway. PTEN loss is associated with both classical and mesenchymal subtypes of GBM, according to the TCGA study (TCGA Research Network, Nature 455 (23): 1061-68).

Akt is an STK (Serine/threonine specific protein kinase) that regulates cell growth, proliferation, and apoptosis. Akt activation has been reported in approximately 80% of human GBMs and correlates with the fact that RTKs/PI3K/Akt signaling is altered in 88% of GBM (TCGA Research Network, Nature 455(23): 1061-68). Oncogenic Akt mutations have not been detected in GBM. Akt inhibitor perifosine is undergoing clinical evaluation in malignant gliomas (Nakada, M. et al., Cancers, 2011, 3: 3242-3278).

2. p14ARF/MDM2/p53 Pathway

The p53 gene encodes a protein that responds to diverse cellular stresses to regulate target genes that induce cell cycle arrest, cell death, cell differentiation, senescence, DNA repair, and neovascularization. Following DNA damage, p53 is activated and induces transcription of genes (such as p21Waf1/Cip1) that function as regulators of cell cycle progression at G1 phase. Mouse double minute 2 homolog (MDM2) oncogne inhibits p53 transcriptional activity by forming a tight complex with the p53 gene, and participates in the degradation of p53. The p14ARF gene codes a protein that directly binds to MDM2 and inhibits MDM2-mediated p53 degradation. In turn p14ARF expression is negatively regulated by p53. Thus, inactivation of p14ARF/MDM2/p53 is caused by altered expression of any of the p53, MDM2, or p14ARF genes. The p53 pathway plays a crucial role in the development of secondary GBMs. The p53 gene is the most commonly mutated p53 pathway gene in glioma; however, molecular abnormalities involving other genes in the pathway have also been described. (Nakada, M. et al., Cancers, 2011, 3: 3242-3278). The p14ARF/MDM2/p53 Pathway is shown in FIG. 2.

3. RB Pathway.

The RB (retinoblastoma tumor suppressor protein) pathway suppresses cell cycle entry and progression, as well as the p53 pathway. The 107-kDa RB1 protein encoded by RB1 (at 13q14) controls progression through G1 into the S-phase of the cell cycle (Serrano, M., et al., Nature, 1993, 366: 704-707). The CDKN2A protein (i.e. p16INK4a which is cyclin-dependent kinase inhibitor 2A) binds to cyclin-dependent kinases 4 (CDK4) and inhibits the CDK4/cyclin D1 complex, thus inhibiting cell cycle transition from G1 to S phase. Thus, alteration of RB1, CDK4, or CDKN2A can cause dysregulation of the G1-S phase transition. However, alteration of only the RB pathway is insufficient to induce tumor formation. EGFR amplification enhances the PI3K pro-growth pathway and is typically associated with CDKN2A deletions. CDKN2A loss is associated with the classical subtype of GBM, according to the TCGA study. (Nakada, M. et al., Cancers, 2011, 3: 3242-3278). The RB pathway is shown in FIG. 3.

4. Ras/MEK/MAPK Pathway.

RAS (Rat sarcoma) proteins act as on/off (RAS-GDP/RAS-GTP) switches controlled by RTKs and neurofibromatosis type 1 tumor suppressor gene (NF-1). Activated RAS (RAS-GTP) then activates serine/threonine kinase RAF. RAF activates mitogen-activated protein kinase kinase (MAPKK), also called MEK, which in turn activates MAPK. MAPK activation results in activation of various transcription factors, such as Elk1, c-myc, Ets, STAT1/3, and PPAR.

The NF-1 tumor suppressor gene encodes neurofibromin, which functions primarily as a RAS negative regulator and plays a role in adenylate cyclase- and Akt-mTOR-mediated pathways. There is increasing evidence that the NF-1 gene is involved in the tumorigenesis of not only NF-1-related, but also sporadically occurring, gliomas. In the TCGA pilot study, NF-1 mutation/homozygous deletions were identified in 18% of GBM. Mesenchymal GBMs, having frequent inactivation of the NF-1 (37%), p53 (32%), and PTEN genes, respond to aggressive chemo-radiation adjuvant therapies. (Nakada, M. et al., Cancers, 2011, 3: 3242-3278). The Ras/MAPK pathway is shown in FIG. 4. A global view of the signaling pathways mentioned above is shown in FIG. 4.

Other signaling pathways may play a role in GBM initiation, migration, and invasion.

Brain Stem Cells

Glial cells outnumber neurons by 10-fold in the human brain and are composed mainly of terminally differentiated cells and minor discrete precursor populations. (Ikanizadeh, S. et al., "Glial Progenitors as targets for transformation in glioma," Adv. Cancer Res. 121: 1-65 (2014)).

Two major germinal layers—the ventricular zone (VZ) and the subventricular zone (SVZ)— give rise to most neurons and glial cells in the forebrain. (Garcia-Verdugo, J M et al, "Architecture and Cell types of the adlt subventricular zone: in search of the stem cells," J. Neurobiol. 36: 234-48 (1998)). It was traditionally believed that the capacity of these germinal layers to generate neurons was restricted to the embryonic period; however, it is now known that new neurons continue to be added to certain regions of the adult vertebrate brain. In adult mammals, neuronal addition has been observed only in the olfactory bulb and the hippocampus. New neurons destined for the olfactory bulb are born in the SVZ of the lateral ventricles. A subpopulation of SVZ cells can proliferate in culture, giving rise to spherical clusters of cells (neurospheres), which have the capacity to generate neurons, astrocytes and oligodendrocytes. Based on their ability to self-renew and their potential to give rise to multiple cell types, these SVZ-derived cells are considered neural stem cells. Evidence also suggests that neural stem cells (NSCs) line the third and fourth ventricles (Ikanizadeh, S. et al., "Glial Progenitors as targets for transformation in glioma," Adv. Cancer Res. 121: 1-65 (2014), citing Weiss, S. et al, "Multipotent CNS stem cells are present in the adult mammalian spinal cord and ventricular neuroaxis," J. Neurosci. 16(23): 7599-7609 (1996); Xu, Y. et al., Neurogenesis in the ependymal layer of the adultrat $3^{rd}$ ventricle," Exptl Neurol. 192(2): 251-64 (2005)).

Modeling of glioma in mice has shown that cells at various differentiation stages throughout glial and neuronal lineages have the potential to generate glioma. Recent advances highlight the cellular heterogeneity in gliomas, the influence of the tumor microenvironment, and that treatment-resistant tumor cells display a high degree of stemness.

Transcriptomal profling of gliomas displaying a neuroepithelial origin, show that the mesenchymal phenotype is associated with stemness, invasiveness, and poor survival. Id. (citing H. S. Phillips, et al., "Molecular subclasses of high-grade glioma predict prognosis, delineate a pattern of disease progression, and resemble stages in neurogenesis," Cancer Cell. 9(3): 157-73 (2006); Sturm, D. et al, "Hotspot mutations in H3F3A and IDH1 define distinct epigenetic and biological subgroups of glioblastoma," Cancer Cell 22(4): 425-37 (2012); Verhaak, R G W, et al., "Integrated genomic analysis identifies clinically relevant subtypes of glioblastoma characterized by abnormalities in PDGFRA, IDH1, EGFR, and NF1," Cancer Cell. 17(1): 98-110 (2010)).

Cancer stem cells (CSCs) or tumor-initiating cells (TIC) are a subpopulation of tumor cells with the ability to undergo self-renewal and recapitulate the entire tumor population Wang, L. et al., Interleukin-1β and transforming growth factor-β cooperate to induce neurosphere formation and increase tumorigenicity of adherent LN-229 glioma cells," Stem ell Res. & Therapy 3:5 (2012). Glioma stem cells (GSC) have been identified from human glioma tissues and glioma cells lines. Id. GSCs are characterized by the ability of self-renewal to generate three-dimensional aggregates of cells in suspension termed "neurospheres" when cultured in serum-free conditions supplemented with epidermal growth factor (EGF) and basic fibroblast growth factor (bFGF). Id. These glioma neurospheres reflect biological and pathological characteristics of primary gliomas, display resistance to chemo- and radio-therapies, and have enhanced oncogenic potential, generating tumors that reproduce the characteristics of the original tumors after intracranial transplantation. (Id., citing Ehrlicher, A. et al., Guiding neuronal growth with light," Proc. Natl Acad. Sci. U.S.A. 99: 16024-8 (2002); Difato, F. et al, "combined optical tweezers and laser dissector for controlled ablation of functional connections in neural networks," J. Biomed. Opt. 16: 051306 (2011); Dictus, C. et al, "Comparative analysis of in vitro conditions for rat adult neural progenitor cells," J. Neurosci Methods. 161: 250-58 (2007))

Animal Models of Glioma

The study of IDH-mutant gliomas has been obstructed by the lack of models of IDH-mutant glioma-producing mice. Brain-specific IDH1$^{R132H}$ knock-in mice are embryonically lethal. Izanizadeh, S. et al, citing Sasaki, M. et al, "D-2 hydroxyglutarate produced by mutant IDH1 perturbs collagen maturation and basement membrane function," Genes & Devel. 26(18): 2038-49 (2012)). Cell lines with IDH1$^{R132H}$ mutation can only be maintained transiently in vitro, since the mutation does not persist in non-immortalized cells. Primary IDH-mutant gliomas from patient tumors do not grow well in vitro (Id., citing Piaskowski, S. et al., "Glioma acells showing IDH1 mutation cannot be propagated in standard cell culture conditions," Br. J. Cancer 104(6): 968-70 (2011)). In contrast to normal cells, introduction of IDH mutations into glioma cells decreases the proliferation rate, which may ultimately cause a selection pressure against cultured glioma cells harboring IDH mutations (Id., citing Bralten, L B C, et al., "IDH1 R132H decreases proliferation of glioma cell lines in vitro and in vivo," Annals Neurol. 69(3): 455-63 (2011)).

Spontaneous mouse models of GBM have been generated that are caused by mutation and therefore loss of three glioma relevant tumor suppressor genes: Pten, p53 and NFL These mice have tumors that exhibit histopathological and molecular similarity with human GBM and have provided a powerful platform for natural history studies, molecular studies and derivation of primary (Mut6) cells that can be maintained in low passage culture and reintroduced in allografts to produce GBM (Llaguno S A et al., "Malignant Astrocytomas Originate from Neural Stem/Progenitor Cells in a Somatic Tumor Suppressor Mouse Model", Cancer Cell. 2009 Jan. 6; 15(1): 45-56; Llaguno S A et al., "Neural and Cancer Stem Cells in Tumor Suppressor Mouse Models of Malignant Astrocytoma", Cold Spring Harb Symp Quant Biol. 2008; 73: 421-426).

SUMMARY OF THE INVENTION

According to one aspect, the described invention provides a small molecule anti-cancer compound of Formula I:

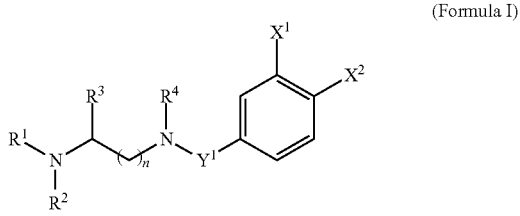

(Formula I)

wherein:
$X^1$ is selected from the group consisting of H, F, Cl, CN, $NH_2$, $NO_2$, $N_3$, $SO_2Me$, and $L^1$-$R^5$;

$X^2$ is selected from the group consisting of H, F, Cl, CN, $NH_2$, $NO_2$, $N_3$, $SO_2Me$, and $L^2$-$R^6$;

$Y^1$ is selected from the group consisting of C=O, $CH_2$, and $SO_2$;

n=1, 2, or 3;

$L^1$ is selected from the group consisting of S, O, NH, CHOH, C=O, —O($CH_2$)—, —S($CH_2$)—, —($CH_2$)O—, and —($CH_2$)S—;

$L^2$ is selected from the group consisting of S, O, NH, CHOH, C=O, —O($CH_2$)—, —S($CH_2$)—, —($CH_2$)O—, and —($CH_2$)S—;

$R^1$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —($CR^{10}R^{11}$)$_m$—, where m=2, 3, 4 or 5;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$ is selected from the group consisting of H, D, F, Me, and Et;

$R^4$ is selected from the group consisting of H, Me, $CD_3$, $CF_3$, Et, i-Pr, cyclopropyl, and $C_2$-$C_6$ alkynyl;

$R^5$ is selected from the group consisting of cycloalkyl, aryl, heteroaryl, heterocyclyl, benzyl, fused heteroarylaryl, fused arylheteroaryl, and fused arylaryl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, Et; and $R^{12}$ and $R^{13}$ are independently selected from the group consisting of H, D, F, Me, and Et;

such that all possible stereoisomers, including optically active isomers, are included whenever stereogenic centers are present;

or a pharmaceutically acceptable salt, prodrug, active metabolite, or solvate thereof.

According to another aspect, the described invention provides a small molecule anti-cancer compound of Formula I-a:

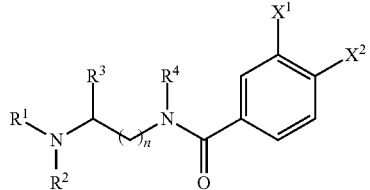

(Formula I-a)

wherein:
$X^1$ is selected from the group consisting of H, F, Cl, CN, $NH_2$, $NO_2$, $N_3$, $SO_2Me$, and $L^1$-$R^5$;

$X^2$ is selected from the group consisting of H, F, Cl, CN, $NH_2$, $NO_2$, $N_3$, $SO_2Me$, and $L^2$-$R^6$;

n=1, 2, or 3;

$L^1$ is selected from the group consisting of S, O, NH, CHOH, C=O, —O($CH_2$)—, —S($CH_2$)—, —($CH_2$)O—, and —($CH_2$)S—;

$L^2$ is selected from the group consisting of S, O, NH, CHOH, C=O, —O($CH_2$)—, —S($CH_2$)—, —($CH_2$)O—, and —($CH_2$)S—;

$R^1$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —($CR^{10}R^{11}$)$_m$—, where m=2, 3, 4 or 5;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$ is selected from the group consisting of H, D, F, Me, and Et;

$R^4$ is selected from the group consisting of H, Me, $CD_3$, $CF_3$, Et, i-Pr, cyclopropyl, and $C_2$-$C_6$ alkynyl;

$R^5$ is selected from the group consisting of cycloalkyl, aryl, heteroaryl, heterocyclyl, benzyl, fused heteroarylaryl, fused arylheteroaryl, and fused arylaryl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et; and $R^{12}$ and $R^{13}$ are independently selected from the group consisting of H, D, F, Me, and Et;

such that all possible stereoisomers, including optically active isomers, are included whenever stereogenic centers are present;

or a pharmaceutically acceptable salt, prodrug, active metabolite, or solvate thereof.

According to one embodiment, n=1 or 2; $R^3$=H; and $R^4$ is selected from the group consisting of H, Me, and propargyl. According to another embodiment, $R^1$ and $R^2$ are independently selected from the group consisting of H, $C_1$-$C_6$ alkyl, $C_2$-$C_6$ alkynyl, $C_1$-$C_6$ hydroxyalkyl, and acyloxyalkyl. According to another embodiment, $X^1$ is selected from the group consisting of H, F, Cl, CN, $NH_2$, $NO_2$, $N_3$, and $SO_2Me$; and $X^2$=$L^2$-$R^6$.

According to another aspect, the described invention provides a small molecule anti-cancer compound of Formula I-b:

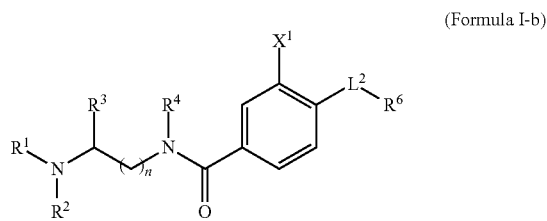

(Formula I-b)

wherein:

$X^1$ is selected from the group consisting of H, F, Cl, CN, $NH_2$, $NO_2$, $N_3$, and $SO_2Me$;

n=1, 2, or 3;

$L^2$ is selected from the group consisting of S, O, NH, CHOH, C=O, —O($CH_2$)—, —S($CH_2$)—, —($CH_2$)O—, and —($CH_2$)S—;

$R^1$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —($CR^{10}R^{11}$)$_m$—, where m=2, 3, 4 or 5;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$ is selected from the group consisting of H, D, F, Me, and Et;

$R^4$ is selected from the group consisting of H, Me, $CD_3$, $CF_3$, Et, i-Pr, cyclopropyl, and $C_2$-$C_6$ alkynyl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et; and $R^{12}$ and $R^{13}$ are independently selected from the group consisting of H, D, F, Me, and Et;

such that all possible stereoisomers, including optically active isomers, are included whenever stereogenic centers are present;

or a pharmaceutically acceptable salt, prodrug, active metabolite, or solvate thereof.

According to one embodiment, n=1 or 2; $R^1$ and $R^2$ are independently selected from the group consisting of H, $C_1$-$C_6$ alkyl, $C_2$-$C_6$ alkynyl, $C_1$-$C_6$ hydroxyalkyl, and acyloxyalkyl; $R^3$=H; and $R^4$ is selected from the group consisting of H, Me, and propargyl.

According to another aspect, the described invention provides a small molecule anti-proliferative compound of Formula I-c:

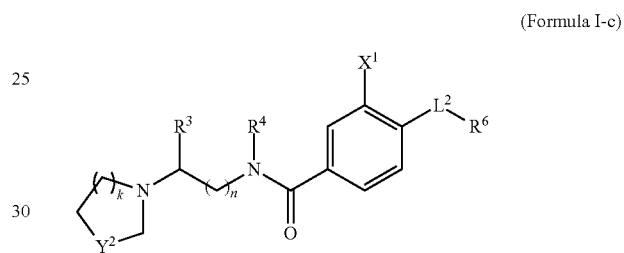

(Formula I-c)

wherein:

$X^1$ is selected from the group consisting of H, F, Cl, CN, $NH_2$, $NO_2$, $N_3$, and $SO_2Me$;

$Y^2$ is selected from the group consisting of CR'R", NR, O, and S. In the context of this paragraph, R, R', and R" are independently selected from the group consisting of H, F, Me, Et, i-Pr, and cyclopropyl;

k=0, 1, 2, or 3;

n=1, 2, or 3;

$L^2$ is selected from the group consisting of S, O, NH, CHOH, C=O, —O($CH_2$)—, —S($CH_2$)—, —($CH_2$)O—, and —($CH_2$)S—;

$R^3$ is selected from the group consisting of H, D, F, Me, and Et;

$R^4$ is selected from the group consisting of H, Me, $CD_3$, $CF_3$, Et, i-Pr, cyclopropyl, and $C_2$-$C_6$ alkynyl; and $R^6$ is selected from the group consisting of cycloalkyl, aryl, heteroaryl, heterocyclyl, benzyl, fused heteroarylaryl, fused arylheteroaryl, and fused arylaryl;

such that all possible stereoisomers, including optically active isomers, are included whenever stereogenic centers are present;

or a pharmaceutically acceptable salt, prodrug, active metabolite, or solvate thereof.

According to one embodiment, $Y^2$ is selected from the group consisting of $CH_2$, NR, O, and S. In the context of this paragraph, R is selected from the group consisting of H and Me; k=1 or 2; n=1 or 2; $L^2$ is selected from the group consisting of NH, O, S, CHOH, C=O, —S($CH_2$)—; and $R^3$=H; and $R^4$ is selected from the group consisting of H, Me, and propargyl. According to another embodiment, $L^2$ is selected from the group consisting of NH, O, and S; and $R^6$ is selected from the group consisting of aryl, and heteroaryl.

According to another aspect, the described invention provides a small molecule anti-cancer compound of Formula I-d:

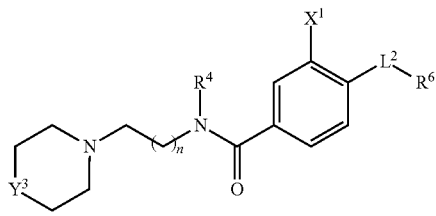

(Formula I-d)

wherein:

$X^1$ is selected from the group consisting of H, F, Cl, CN, $NH_2$, $NO_2$, $N_3$, and $SO_2Me$;

$Y^3$ is selected from the group consisting of $CH_2$, NR, O, and S. In the context of this paragraph, R is selected from the group consisting of H, Me, $CD_3$, $CF_3$, Et, isopropyl, and cyclopropyl.

n=1 or 2;

$L^2$ is selected from the group consisting of S, O, and NH;

$R^4$ is selected from the group consisting of H, Me, $CD_3$, $CF_3$, Et, and $C_2$-$C_6$ alkynyl; and $R^6$ is selected from the group consisting of aryl, heteroaryl, benzyl, fused heteroarylaryl, fused arylheteroaryl, and fused arylaryl;

such that all possible stereoisomers, including optically active isomers, are included whenever stereogenic centers are present;

or a pharmaceutically acceptable salt, prodrug, active metabolite, or solvate thereof.

According to one embodiment, $Y^3$ is selected from the group consisting of $CH_2$, NH, NMe, and O; $R^4$ is selected from the group consisting of H, Me, and propargyl; and $R^6$ is selected from the group consisting of aryl and heteroaryl.

According to another aspect, the described invention provides a small molecule anti-cancer compound of Formula I-e:

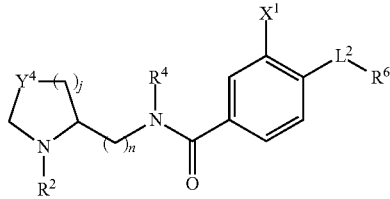

(Formula I-e)

wherein:

$X^1$ is selected from the group consisting of H, F, Cl, CN, $NH_2$, $NO_2$, $N_3$, and $SO_2Me$;

$Y^4$ is selected from the group consisting of CR'R", NR, O, and S. In the context of this paragraph, R, R', and R" are independently selected from the group consisting of H, F, Me, Et, isopropyl and cyclopropyl;

j=0, 1, 2, or 3;

n=1, 2, or 3;

$L^2$ is selected from the group consisting of S, O, NH, CHOH, C=O, —$O(CH_2)$—, —$S(CH_2)$—, —$(CH_2)O$—, and —$(CH_2)S$—;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^4$ is selected from the group consisting of H, Me, $CD_3$, $CF_3$, Et, i-Pr, cyclopropyl, and $C_2$-$C_6$ alkynyl; and $R^6$ is selected from the group consisting of cycloalkyl, aryl, heteroaryl, heterocyclyl, benzyl, fused heteroarylaryl, fused arylheteroaryl, and fused arylaryl;

such that all possible stereoisomers, including optically active isomers, are included whenever stereogenic centers are present;

or a pharmaceutically acceptable salt, prodrug, active metabolite, or solvate thereof.

According to one embodiment, $Y^4$=$CH_2$; j=1; n=1 or 2; $L^2$ is selected from the group consisting of S, O, NH, CHOH, C=O, and —$S(CH_2)$—; $R^2$ is selected from the group consisting of H, $C_1$-$C_3$ alkyl, propargyl, $C_1$-$C_3$ hydroxyalkyl, and acyloxyalkyl; and $R^4$ is selected from the group consisting of H, Me, and propargyl.

According to another aspect, the described invention provides a small molecule anti-cancer compound of Formula I-f:

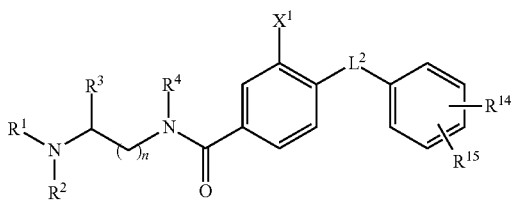

(Formula I-f)

wherein:

$X^1$ is selected from the group consisting of H, F, Cl, CN, $NH_2$, $NO_2$, $N_3$, and $SO_2Me$;

n=1, 2, or 3;

$L^2$ is selected from the group consisting of S, O, NH, CHOH, C=O, —$O(CH_2)$—, —$S(CH_2)$—, —$(CH_2)O$—, and —$(CH_2)S$—;

$R^1$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —($CR^{10}R^{11}$)$_m$—, where m=2, 3, 4 or 5;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$ is selected from the group consisting of H, D, F, Me, and Et;

$R^4$ is selected from the group consisting of H, Me, $CD_3$, $CF_3$, Et, i-Pr, cyclopropyl, and $C_2$-$C_6$ alkynyl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et; and $R^{14}$ and $R^{15}$ can be attached at any available position on the aromatic ring and are selected from the group consisting of H, D, F, Cl, Br, $CF_3$, $C_1$-$C_6$ alkyl, $C_2$-$C_6$ alkenyl, $C_2$-$C_6$ alkynyl, cycloalkyl, OR, $NR_2$, $NO_2$, $N_3$, CN, $CO_2R$, $CO_2NR_2$, SR, alkylacyl and arylacyl. In the context of this paragraph, R is independently selected from the group consisting of H, Me, Et, isopropyl, cyclopropyl, propargyl, and acyl;

such that all possible stereoisomers, including optically active isomers, are included whenever stereogenic centers are present;

or a pharmaceutically acceptable salt, prodrug, active metabolite, or solvate thereof.

According to one embodiment, n=1 or 2; $L^2$ is selected from the group consisting of NH, O, S, —S($CH_2$)—, C=O, and CHOH; $R^1$ and $R^2$ are independently selected from the group consisting of H, $C_1$-$C_3$ alkyl, propargyl, $C_1$-$C_3$ hydroxyalkyl, and acyloxyalkyl; $R^1$ and $R^2$ may optionally form a ring such that $R^1$-$R^2$ consists of a four or five subunit chain comprising subunits independently selected from the group consisting of $CH_2$, NH, NMe, and O; $R^1$ and $R^3$ may optionally form a ring such that $R^1$-$R^3$=—($CH_2$)$_3$—; $R^2$ and $R^4$ may optionally form a ring such that $R^2$-$R^4$ consists of a two subunit chain comprising subunits independently selected from the group consisting of $CH_2$ and CH-alkyl, and $R^2$ may simultaneously form a ring with $R^1$ as described above; $R^3$=H; $R^4$ is selected from the group consisting of H, Me, and propargyl; and $R^{14}$ and $R^{15}$ can be attached at any available position on the aromatic ring and are independently selected from the group consisting of H, F, Cl, Br, $CF_3$, $C_1$-$C_3$ alkyl, propargyl, OR, $NR_2$, $NO_2$, CN, $CO_2R$, and $CO_2NR_2$, SR. In the context of this paragraph, R is independently selected from the group consisting of H, Me, Et and propargyl.

According to another aspect, the described invention provides a compound selected from the group consisting of:

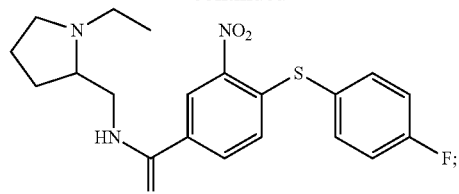

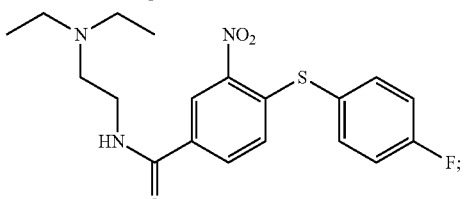

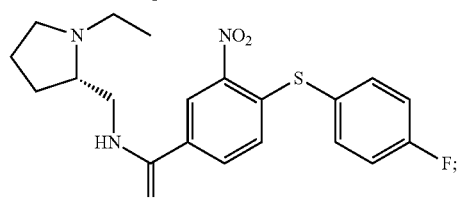

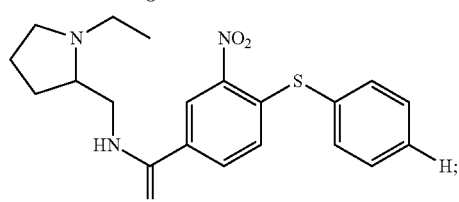

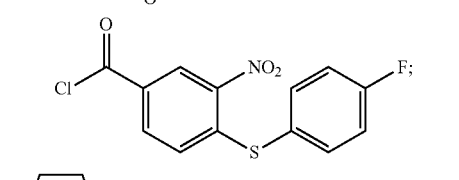

-continued

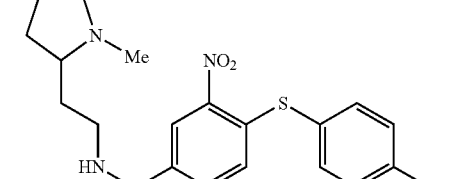

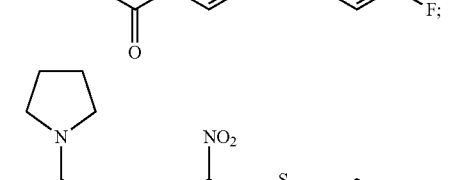

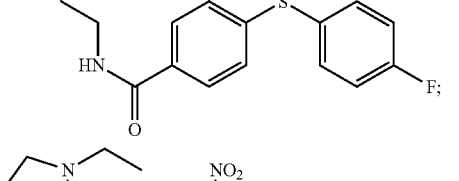

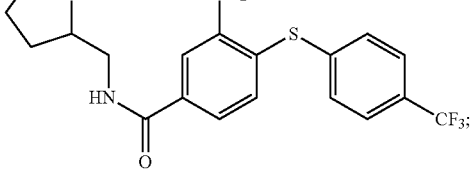

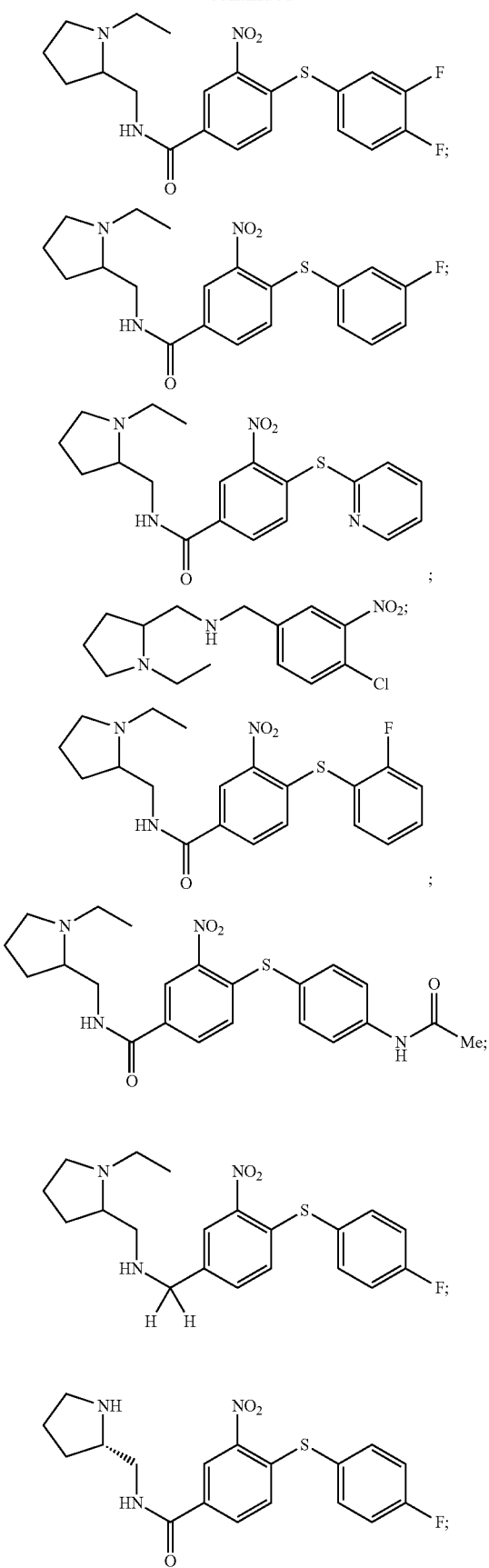

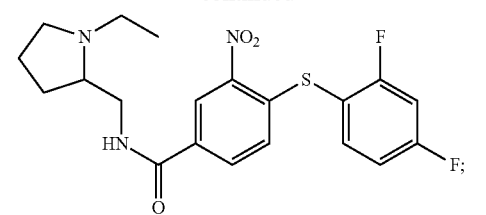
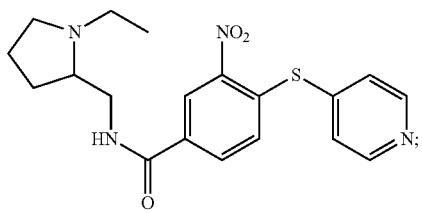
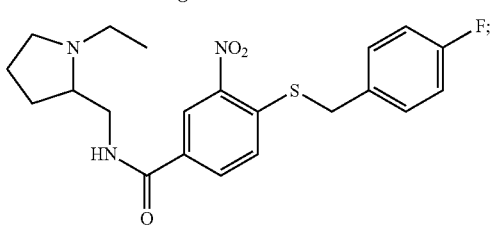
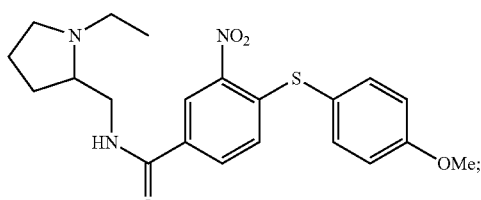
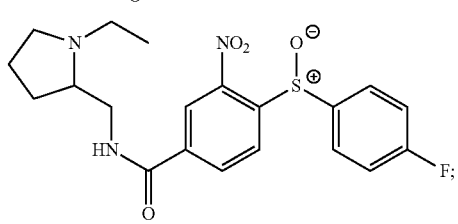
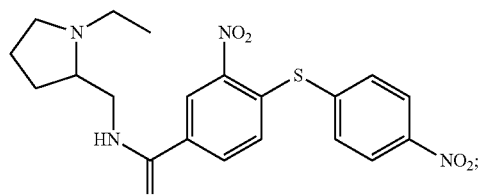
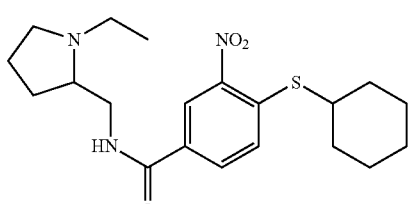
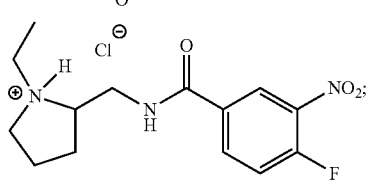
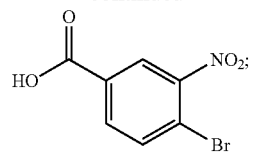
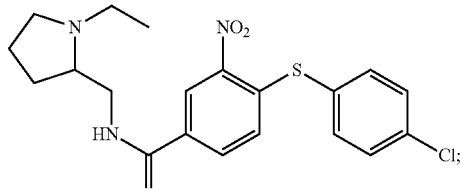
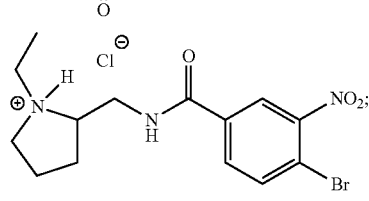
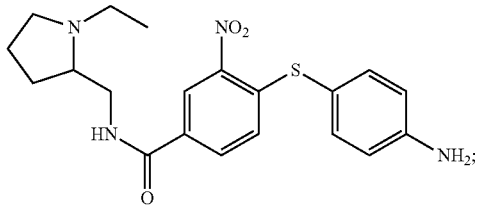
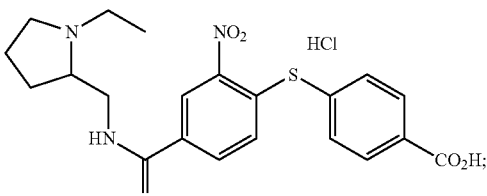
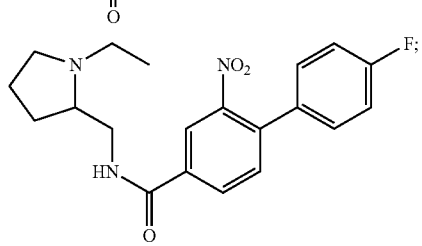
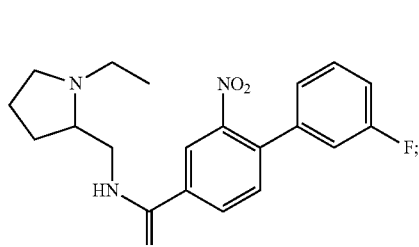
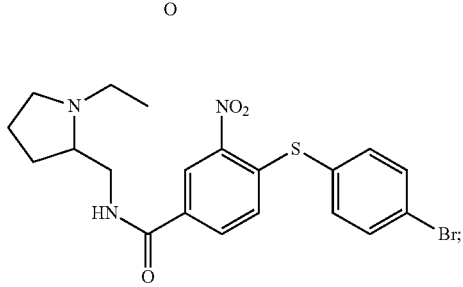

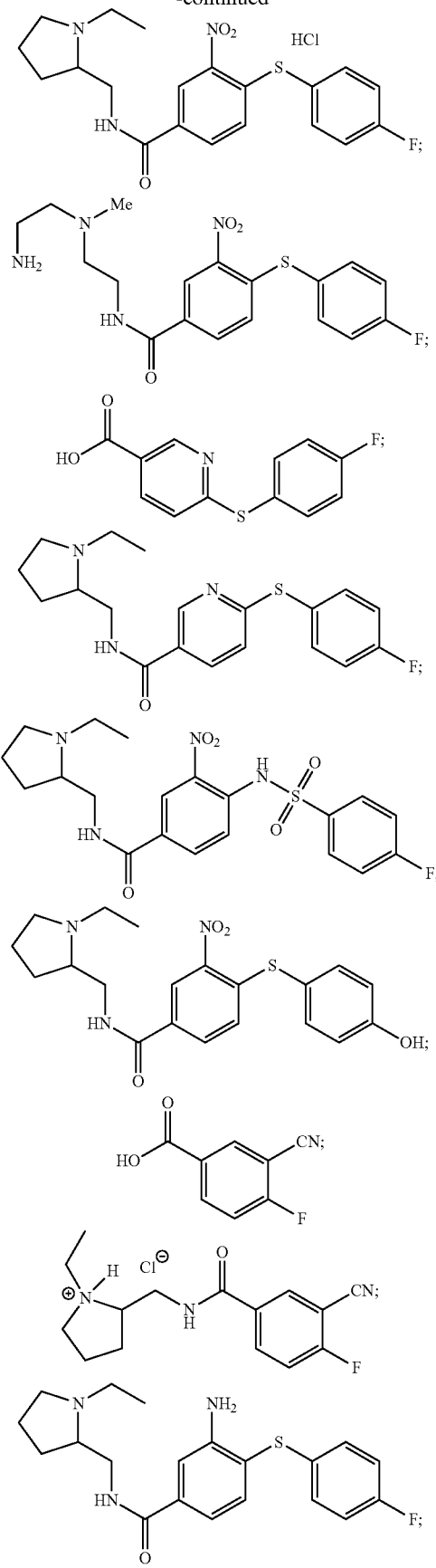
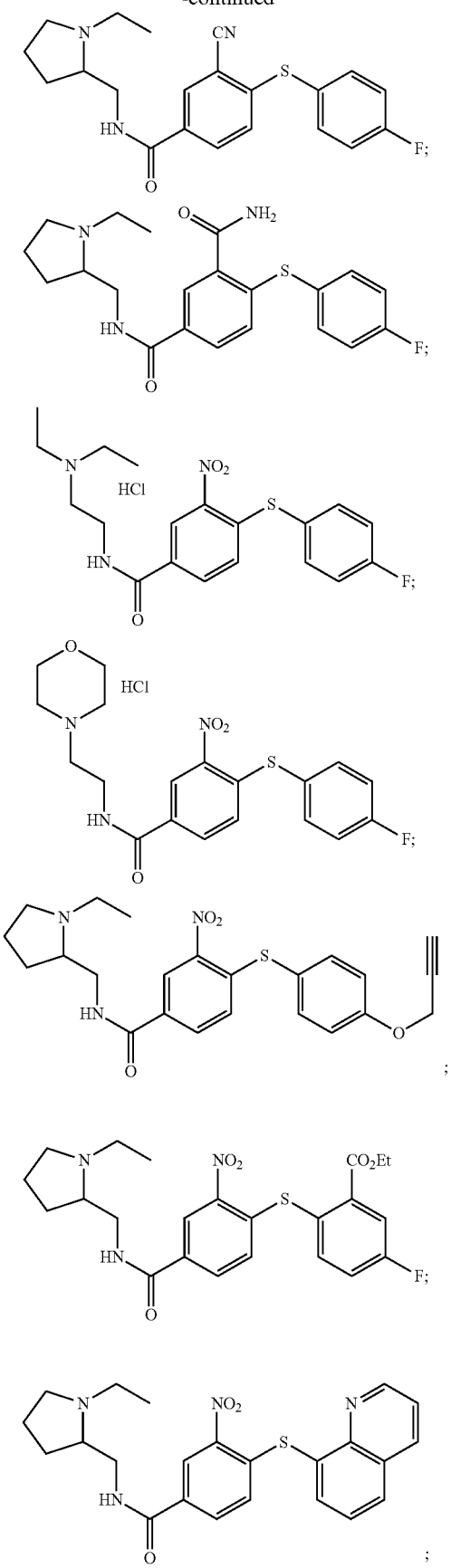

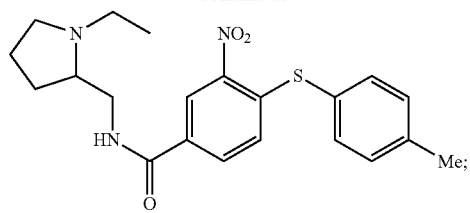
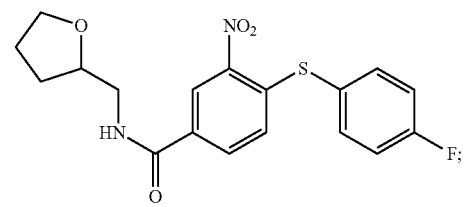
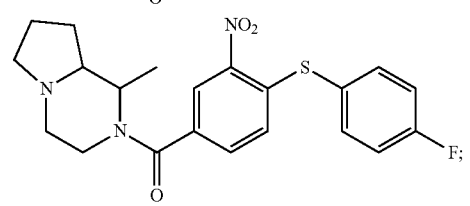
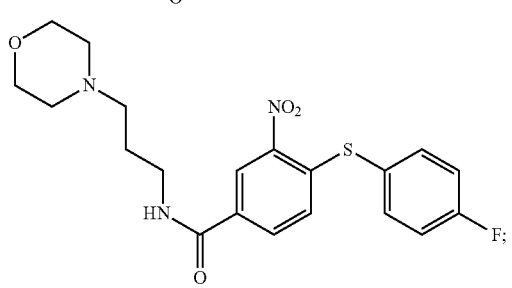
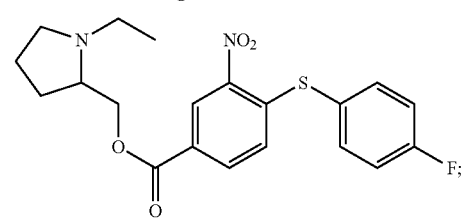
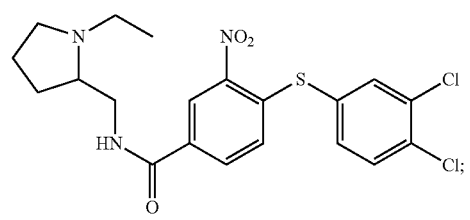
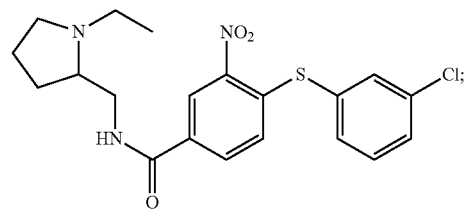
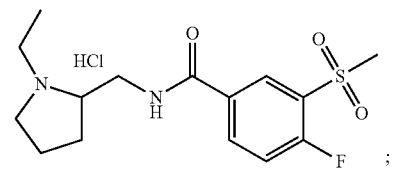
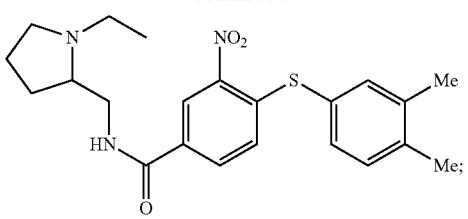
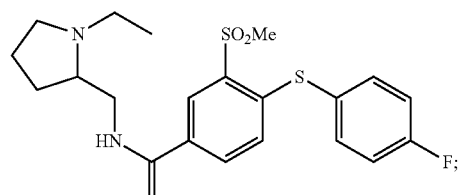
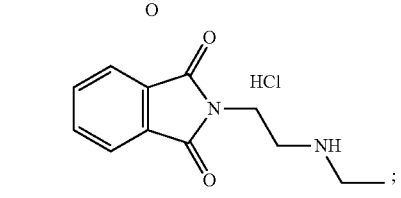
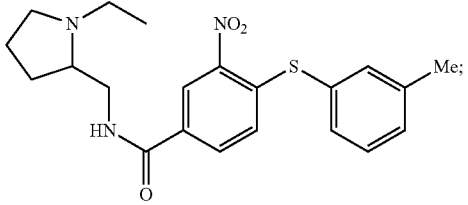
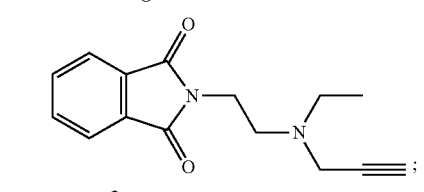
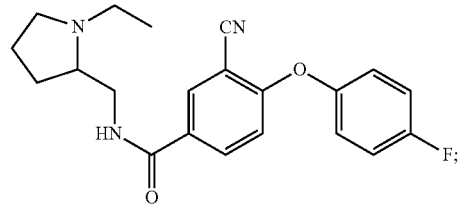
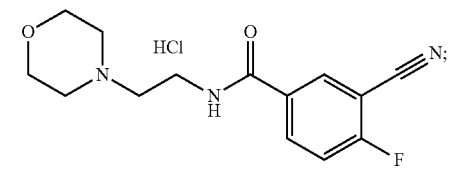
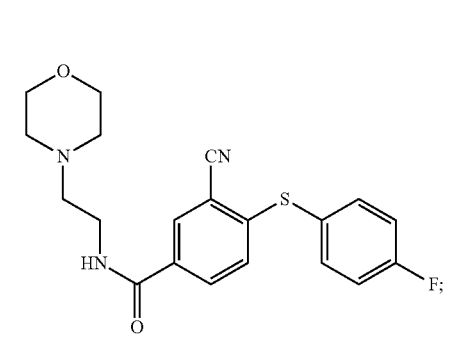

25
-continued
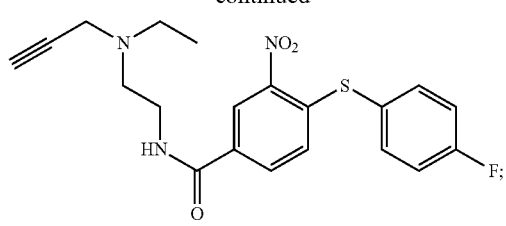
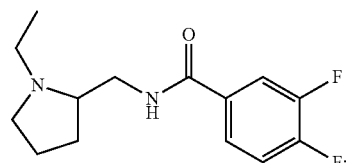
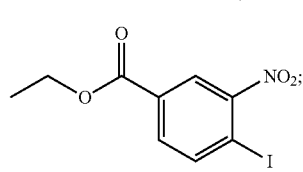
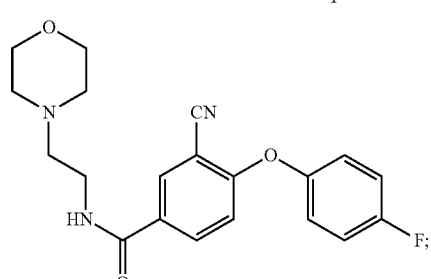
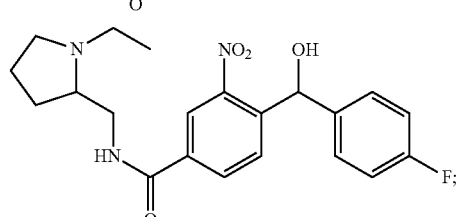
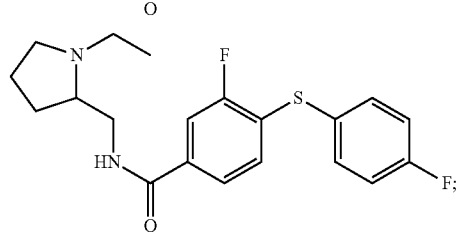
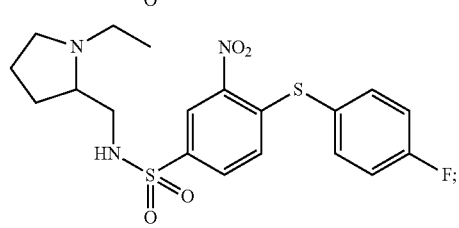
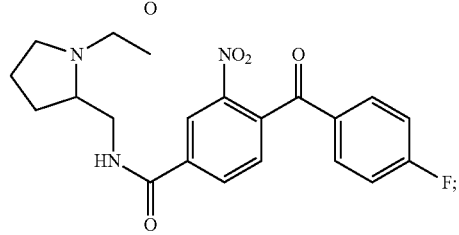
26
-continued

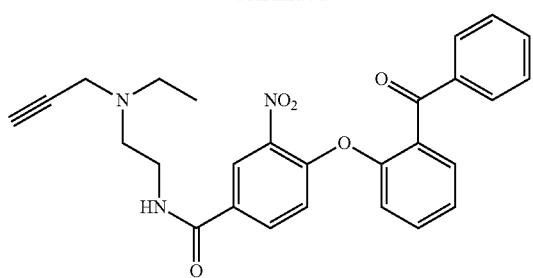
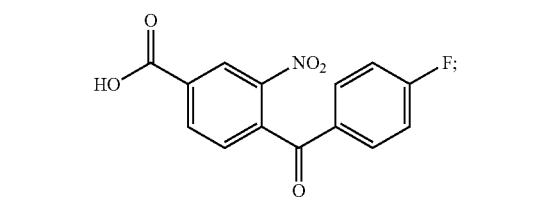
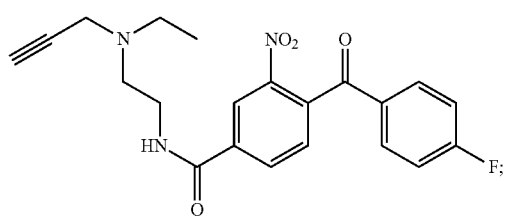
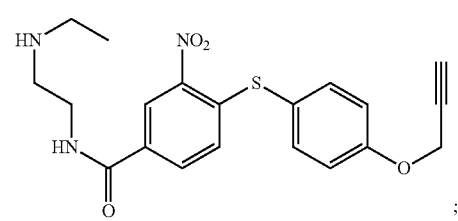
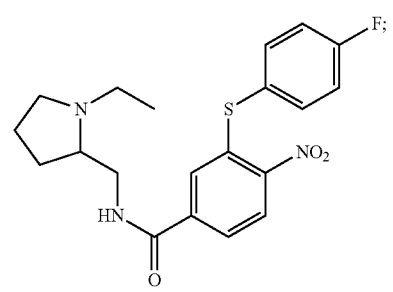
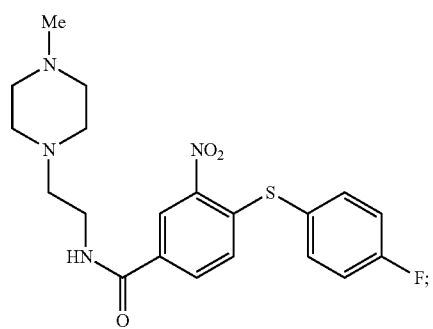
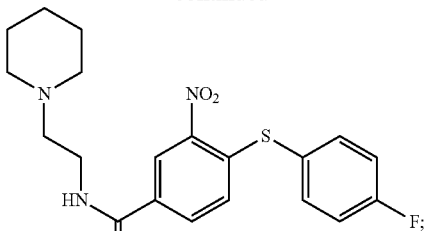
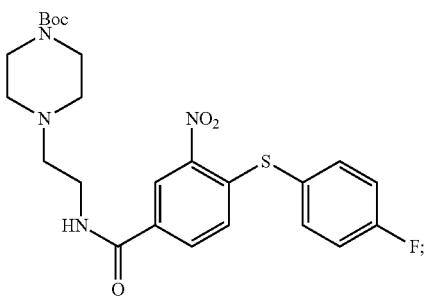
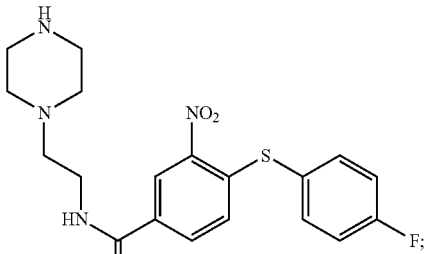
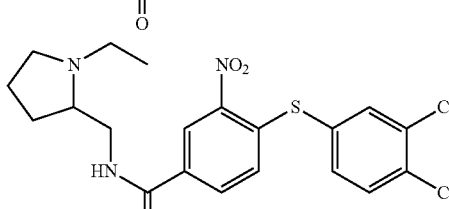
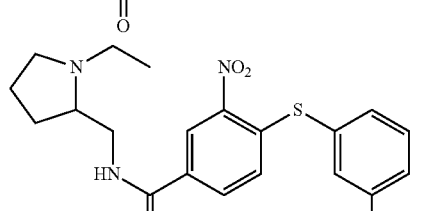
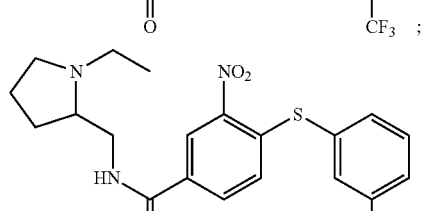
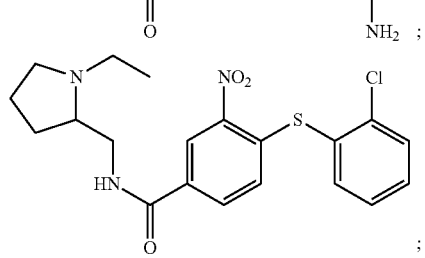

29
-continued
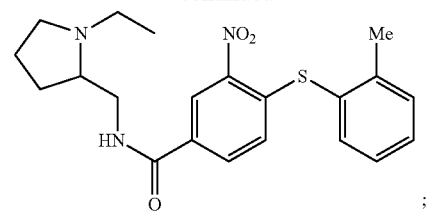
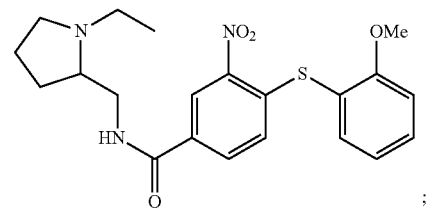
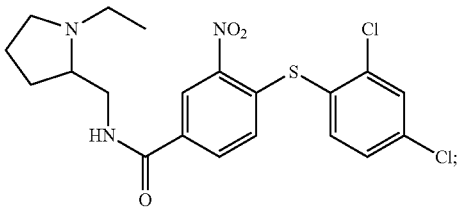
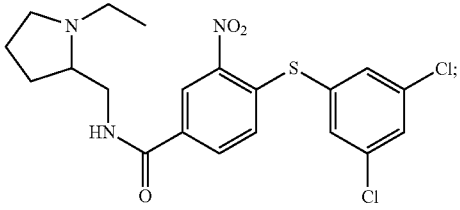
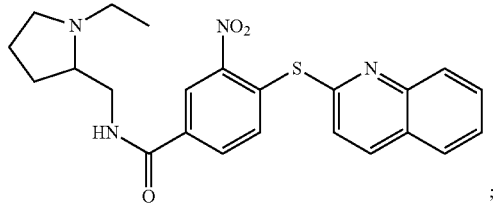
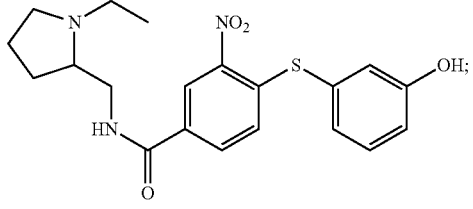
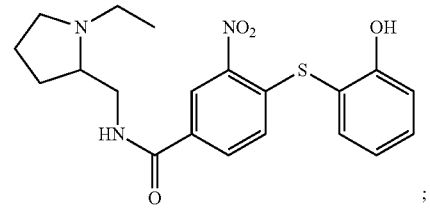
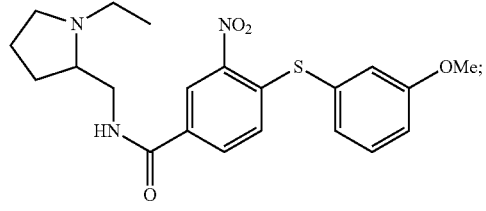
30
-continued
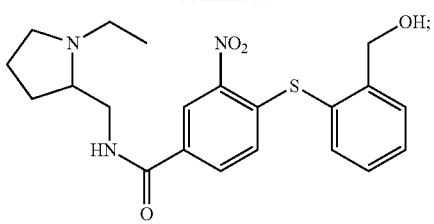
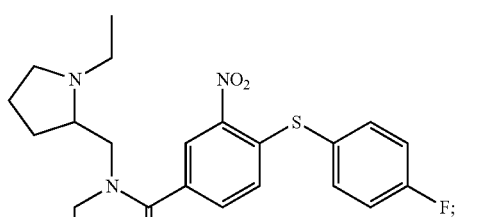
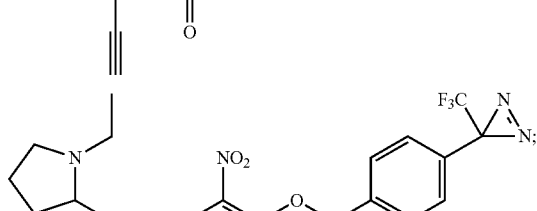
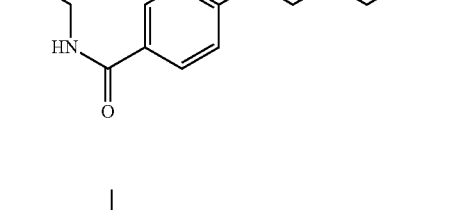
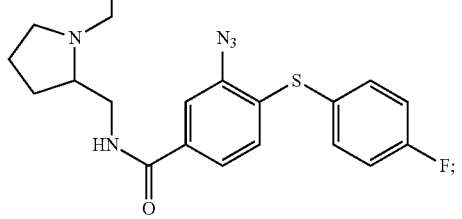
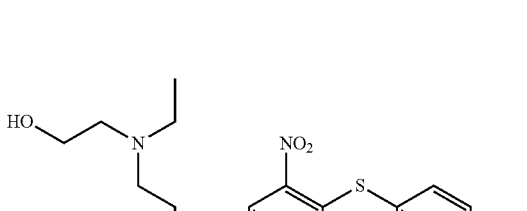
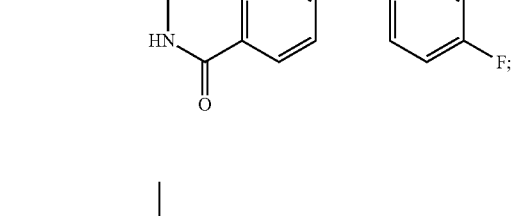
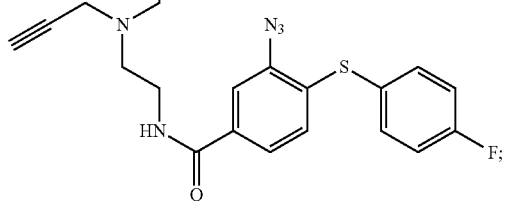

-continued

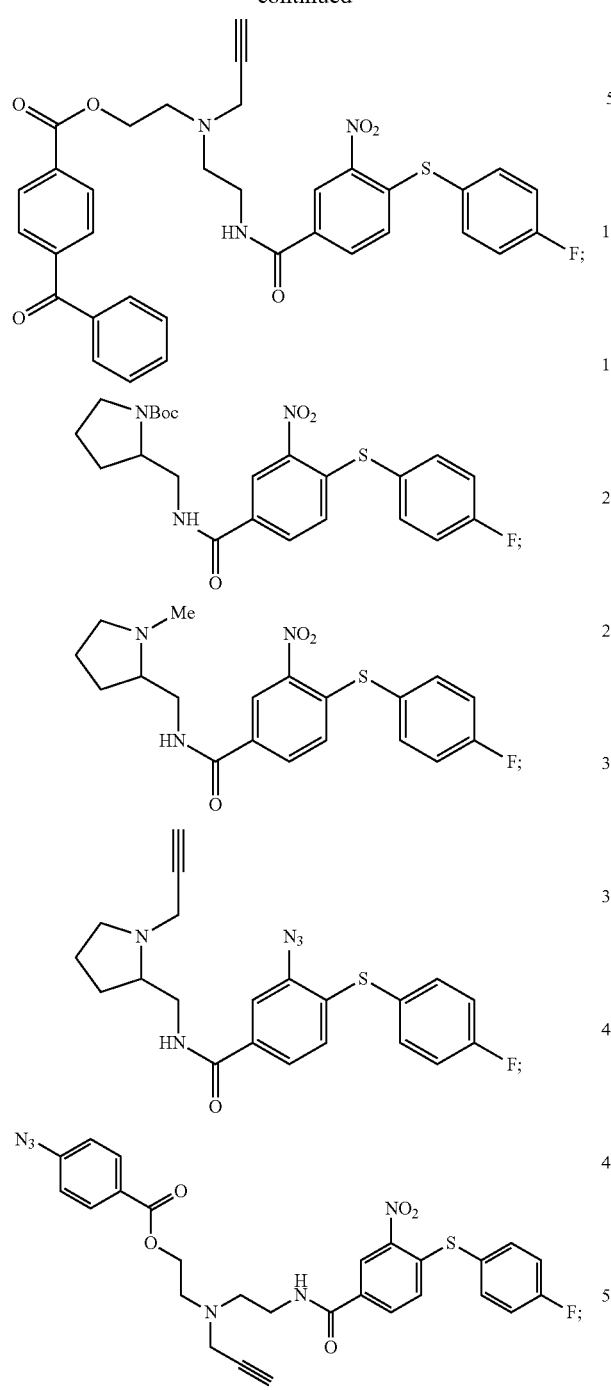

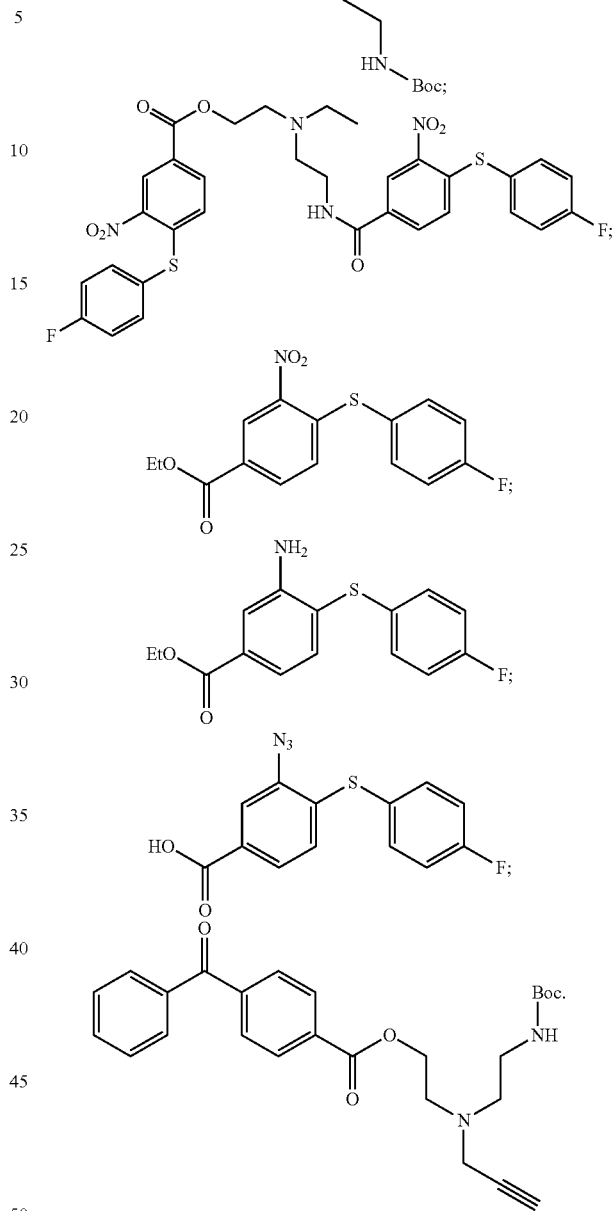

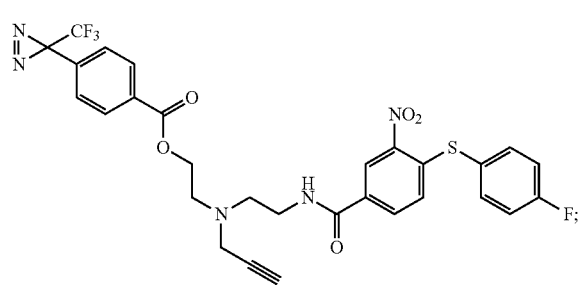

According to one embodiment, the compound is in form of a pharmaceutical composition comprising a therapeutic amount of the compound and a pharmaceutically acceptable carrier.

According to another aspect, the described invention provides a method of treating a cancer in a subject in need thereof, comprising administering to the subject the pharmaceutical composition of the described invention, wherein the therapeutic amount is effective to inhibit tumor growth, inhibit tumor proliferation, induce cell death, or a combination thereof.

According to one embodiment, the therapeutic amount is effective to inhibit a cholesterol biosynthesis pathway. According to another embodiment, the therapeutic amount is effective to down-regulate SHREBP2 and its target genes. According to another embodiment, the cancer is a solid brain tumor. According to another embodiment, the solid brain tumor is a glioma. According to another embodiment, the glioma is a glioblastoma. According to another embodiment, the solid brain tumor comprises cancer stem cells. According to another embodiment, the therapeutic amount of the composition is effective to selectively inhibit growth of cancer cells, proliferation of cancer cells, to induce cell death of cancer cells, or a combination thereof, without affecting normally dividing cells.

BRIEF DESCRIPTION OF THE DRAWINGS

FIG. 6(d) shows the overall screening strategy against glioblastoma tumor derived neuronal stem cells Mut6. FIG. 6(a) is a schematic showing that primary neuronal stem cells isolated from mouse GBM tumors (Mut6; glioblastoma) were used in a luminescence-based, cell viability high throughput primary screening assay against ~200,000 synthetic compounds, which yielded 4,480 positive hits with >50% inhibition of cell ATP consumption. The 4,480 compounds were further screened to identify 1,078 compounds that displayed greater than or equal to 70% inhibition of Mut6 ATP consumption. The 1,078 compounds were screened for toxicity against normally dividing wild-type mouse embryonic fibroblasts (MEFs), wild-type mouse astrocytes and wild-type mouse SVZ stem cells; and compounds toxic to all three cell-types were removed, which resulted in the identification of 713 compounds. FIG. 6(b) shows the results from the toxicity screen which identified 713 compounds. FIG. 6(c) shows counterscreeing of the 713 compounds against normal astrocytes and mouse embryonic fibroblasts (MEFs) which identified 61 compounds that only kill cancer stem cells. FIG. 6(d) is a schematic showing that the 61 compounds were analyzed by S9 fraction assay and hepatocyte assay which identified 17 candidate compounds.

FIG. 7C shows that compound 4C12 induces cell death in Mut6 tumor cells. Normal astrocytes, Mut6 cells and mouse embryonic fibroblasts were treated with increasing concentrations of compound 4C12. FIG. 7A is a plot of relative ATP activity (y axis, a measure of viability) versus concentration (nM), which shows that compound 4C12 has an ED50 of 50 nM against Mut6 cells. Normal astrocytes and mouse embryonic fibroblasts (MEFs) were unaffected by compound 4C12. FIG. 7B shows phase contrast microscopy of Mut6 cells and control MEFs after 14 hours, 23 hours and 38 hours treatment with compound 4C12 and a negative control containing vehicle only (Ctrl). FIG. 7C is a plot of live cells (%) versus time (hrs) which shows that all cells treated with vehicle (negative control (Ctrl)) remained viable, while only 50% of the Mut6 tumor cells treated with compound 4C12 were viable after 96 hours.

FIG. 8B shows the identification of molecular changes between 6 hr and 24 hr time points. FIG. 8A shows a schematic of a cell-based assay. Cells were plated 48 hours before treatment with test compounds Compound 1, Compound 2 and 4C12, and a negative control. Cultures then were treated with the test compound. The media was removed and cells washed twice. Fresh media was added without compound. Data points were 6 hr, 22 hr, 33 hr, 51 hr, 71 hr and continuous. Molecular changes were identified between the 6 hr and 24 hr time points. An ATP assay was performed at 96 hours. On day 2, Cells treated with 4C12 were round-shaped. On day 3, the cells were arrested in G2. On day 4, 10-20% of the cells were apoptotic. By day 5, 80-90% of the cells were apoptotic. FIG. 8B shows a plot of relative ATP activity (y axis) versus time (x axis) showing that cells treated with compounds Compound 1, Compound 2 and 4C12 reduced ATP activity as a function of time relative to the control (Ctrl).

FIG. 9A shows the chemical structure and 1050 curve of analog compound DS-1-033; FIG. 9B shows the chemical structure and 1050 curve of analog compound DS-1-023; FIG. 9C shows the chemical structure and 1050 curve of analog compound DS-1-031. FIG. 9D shows the chemical structure and 1050 curve of analog compound DS-1-043; FIG. 9E shows the chemical structure and 1050 curve of analog compound DS-1-053; FIG. 9F shows the chemical structure and 1050 curve of analog compound DS-1-055; FIG. 9G shows the chemical structure and 1050 curve of analog compound DS-1-061; FIG. 9H shows the chemical structure and 1050 curve of analog compound DS-1-063; FIG. 9I shows the chemical structure and 1050 curve of analog compound DS-1-065; FIG. 9J shows the chemical structure and 1050 curve of analog compound DS-1-067; FIG. 9K shows the chemical structure and 1050 curve of analog compound DS-1-069; FIG. 9L shows the chemical structure and 1050 curve of analog compound DS-1-071; FIG. 9M shows the chemical structure and 1050 curve of analog compound DS-1-075; FIG. 9N shows the chemical structure and 1050 curve of analog compound DS-1-077; FIG. 9O shows the chemical structure and 1050 curve of analog compound DS-1-079; FIG. 9P shows the chemical structure and 1050 curve of analog compound DS-1-085; FIG. 9Q shows the chemical structure and 1050 curve of analog compound DS-1-089; FIG. 9R shows the chemical structure and 1050 curve of analog compound DS-1-103; FIG. 9S shows the chemical structure and 1050 curve of analog compound DS-1-105; FIG. 9T shows the chemical structure and 1050 curve of analog compound DS-1-117; FIG. 9U shows the chemical structure and 1050 curve of analog compound DS-1-119; FIG. 9V shows the chemical structure and 1050 curve of analog compound DS-1-123; FIG. 9W shows the chemical structure and 1050 curve of analog compound DS-1-125; FIG. 9X shows the chemical structure and 1050 curve of analog compound DS-1-129; FIG. 9Y shows the chemical structure and 1050 curve of analog compound DS-1-131; FIG. 9Z shows the chemical structure and 1050 curve of analog compound DS-1-133; FIG. 9AA shows the chemical structure and 1050 curve of analog compound DS-1-135; FIG. 9BB shows the chemical structure and 1050 curve of analog compound DS-1-137; FIG. 9CC shows the chemical structure and 1050 curve of analog compound DS-1-139; FIG. 9DD shows the chemical structure and 1050 curve of analog compound DS-1-163; FIG. 9EE shows the chemical structure and 1050 curve of analog compound DS-1-177; FIG. 9FF shows the chemical structure and 1050 curve of analog compound DS-1-179; FIG. 9GG shows the chemical structure and 1050 curve of analog compound DS-1-181; FIG. 9HH shows the chemical structure and 1050 curve of analog compound DS-1-183; FIG. 9II shows the chemical structure and 1050 curve of analog compound DS-1-185; FIG. 9JJ shows the chemical structure and 1050 curve of analog compound DS-1-191; FIG. 9KK shows the chemical structure and 1050 curve of analog compound DS-1-195; FIG. 9LL shows the chemical structure and 1050 curve of analog compound DS-1-209; FIG. 9MM shows the chemical structure and 1050 curve of analog compound DS-1-205 (biotin); FIG. 9NN shows the chemical structure and 1050 curve of analog compound DS-1-213; FIG. 9OO shows the chemical structure and 1050 curve of analog compound DS-1-217; FIG. 9PP shows the chemical structure and 1050 curve of analog compound DS-1-225; FIG. 9QQ shows the chemical structure and 1050 curve of analog compound DS-1-227; FIG. 9RR shows the chemical structure and 1050 curve of analog compound DS-1-231; FIG. 9SS shows the chemical structure and 1050 curve of analog compound DS-1-239; FIG. 9TT shows the chemical structure and 1050 curve of analog compound DS-1-241; FIG. 9UU shows the chemical structure and 1050 curve of analog compound DS-1-261; FIG. 9VV shows the chemical structure and 1050 curve of analog compound DS-1-192; FIG. 9WW shows the chemical structure and 1050 curve of analog compound DS-1-265; FIG. 9XX shows the chemical structure and 1050 curve of analog compound DS-1-269; FIG. 9YY shows the chemical structure and 1050 curve of analog compound DS-1-271; FIG. 9ZZ shows the chemical structure and 1050 curve of analog compound DS-1-275; FIG. 9AAA shows the chemical structure and 1050 curve of analog compound DS-1-279; FIG. 9BBB shows the chemical structure and 1050 curve of analog compound DS-1-283; FIG. 9CCC shows the chemical structure and 1050 curve of analog compound DS-1-287; FIG. 9DDD shows the chemical structure and 1050 curve of analog compound DS-1-291; FIG. 9EEE shows the chemical structure and 1050 curve of analog compound DS-1-295; FIG. 9FFF shows the chemical structure and 1050 curve of analog compound DS-1-299; FIG. 9GGG shows the chemical structure and 1050 curve of analog compound DS-1-301; FIG. 9HHH shows the chemical structure and 1050 curve of analog compound DS-1-305; FIG. 9III shows the chemical structure and 1050 curve of analog compound DS-2-035; FIG. 9JJJ shows the chemical structure and 1050 curve of analog compound DS-2-045; FIG. 9KKK shows the 1050 curve of analog compound DS-2-045-072214; FIG. 9LLL shows the chemical structure and 1050 curve of analog compound DS-2-051; FIG. 9MMM shows the chemical structure and 1050 curve of analog compound DS-2-057; FIG. 9NNN shows the chemical structure and 1050 curve of analog compound JCH-109; FIG. 9OOO shows the chemical structure and 1050 curve of analog compound DS-2-053; FIG. 9PPP shows the chemical structure and 1050 curve of analog compound DS-2-055; FIG. 9QQQ shows the 1050 curve of analog compound DS-2-045-072214.

FIG. 10 shows a table depicting the results of microarray analysis to identify over-represented pathways associated with treatment with compound 4C12 for 48 hours.

FIG. 12 comprising FIG. 12A and FIG. 12B shows that cholesterol levels are decreased, TG levels are increased and cholesterol synthesis enzymes are down-regulated by 4C12. FIG. 12A shows a bar graphs showing cholesterol (pg/cell) (left graph), and triglyceride (pg/cell) (right graph) for Mut6 cells treated with a negative control (vehicle only (ctrl)), and with compound 4C12 for 24 hours and 48 hours. The figures show that in the presence of compound 4C12, cholesterol level decreases, and triglyceride level increases. FIG. 12B shows a bar graph of relative mRNA vs. enzymes of cholesterol synthesis showing that genes for cholesterol synthesis enzymes are down-regulated by compound 4C12. Mut6 cells were treated with compound 4C12 for 24 hours and then mRNA levels for Hydroxymethylglutaryl-CoA synthase(Hmgcs); 3-hydroxy-3-methylglutaryl-coenzyme A reductase (Hmgcr); acetoacetyl-CoA synthetase (AACS); Delta(24)-sterol reductase (Dhcr24); 7-dehydrocholesterol reductase (Dhcr7), Sterol C5-desaturase (Sc5d); Squalene synthase (SS); and farnesyl pyrophosphate (FPP) synthase (FPPS) were determined.

FIG. 13(f) shows that 4C12 inhibits Srebp2 activity. FIG. 13(a) is a bar graph showing cholesterol gene profile for Mut6 cells were treated with compound 4C12 for 2 hr compared to a DMSO control. FIG. 13(b) is a bar graph showing cholesterol gene profile for Mut6 cells were treated with compound 4C12 for 9 hr compared to a DMSO control. FIG. 13(c) is a bar graph showing cholesterol gene profile for Mut6 cells were treated with compound 4C12 for 16 hr compared to a DMSO control. FIG. 13(d) is a bar graph showing cholesterol gene profile for Mut6 cells were treated with compound 4C12 for 24 hr compared to a DMSO control. FIG. 13(e) is a bar graph showing cholesterol gene profile for Mut6 cells were treated with compound 4C12 for 48 hr compared to a DMSO control. The data shows that compound 4C12 inhibits Srebp2 target genes, and not Srebp1 target genes. FIG. 13(f) shows a Western blot. Mut6 cells were treated with vehicle only (−) or with compound 4C12 (+) for 7 hr (left panel), 13 hr (middle panel) and 23 hr (right panel). Cells were collected, lysed in SDS buffer, subjected to SDS PAGE, and cell proteins transferred to a membrane by a standard protocol. The membrane was washed, treated with antibodies to SREBP1, SREBP2 and a positive control (Cadherin), rewashed and bound antibodies then revealed. The blots showed that compound 4C12 was effective to decrease SREBP2 protein.

FIG. 14B shows that Compactin (statin) and 4C12 make a combination effect. FIG. 14A is a bar graph plotting ATP activity (a measure of viability) for Mut6 cells treated with compactin/mevastatin, compound 4C12, and the combination of compactin/mevastatin+compound 4C12, versus a negative control (vehicle only (Ctrl)). The results show that the combination of compactin/mevastatin and compound 4C12 exert an effect greater than each does alone. FIG. 14B illustrates a statin's inhibitory effect on the mevalonate arm of the cholesterol biosynthesis pathway.

FIG. 15 comprising FIG. 15(a), FIG. 15(b), FIG. 15(c) and FIG. 15(d) shows that Compactin (statin) and 4C12 make a combination effect; that addition of cholesterol inhibits 4C12-induced cell-death; and activation of SREBP2 by knock-down of Insig1/Insig2 makes cells less sensitive to 4C12. FIG. 15(a) is a bar graph plotting ATP activity (a measure of viability) for Mut6 cells treated with compactin/mevastatin, compound 4C12, and the combination of compactin/mevastatin+compound 4C12, versus a negative control (vehicle only (Ctrl)). FIG. 15 (b) is a bar graph showing ATP activity (a measure of viability) vs. concentration of cholesterol (µM)—Mut6 cells were treated with compound 4C12 versus a cells treated with DMSO (negative control).

Addition of cholesterol inhibits compound 4C12-induced cell-death. FIG. 15(c) shows a graph of relative ATP activity (y-axis, a measure of viability) vs. compound 4C12 concentration (nM (x axis)). Addition of SREBP2 by knock-down of Insig1/Insig2 makes Mut6 cells less sensitive to compound 4C12. FIG. 15(d) illustrates that Insig acts to suppress Srebp2 activity.

FIG. 16 comprising FIG. 16A and FIG. 16B shows that Srebp2 target genes were not decreased by 4C12 in MEFs and astrocytes. FIG. 16A is a bar graph of relative mRNA level for cholesterol biosynthesis pathway target genes Hmgcs, Hmgcr, FPPS, LDLR; and SREBP1c in mouse embryonic fibroblasts (MEFs) treated with compound 4C12 or dmso (negative control). FIG. 16B is a bar graph of relative mRNA level for cholesterol biosynthesis pathway target genes Hmgcs, Hmgcr, FPPS, LDLR; and SREBP1c in astrocytes treated with compound 4C12 or dmso (negative control). The figure shows that Srebp2 target genes were not decreased by compound 4C12 in MEFs and Astrocytes.

FIG. 17 comprising FIG. 17A and FIG. 17B compares cholesterol level (pg/cell) and triglyceride level (pg/cell) in Mut6 cells and in mouse embryonic fibroblast (MEF) cells treated with compound 4C12 for 24 hours and 48 hours to a negative control (vehicle). FIG. 17A shows cholesterol level (pg/cell) in Mut6 cells and in mouse embryonic fibroblast (MEF) cells treated with compound 4C12 for 24 hours and 48 hours to a negative control (vehicle). FIG. 17B shows triglyceride level (pg/cell) in Mut6 cells and in mouse embryonic fibroblast (MEF) cells treated with compound 4C12 for 24 hours and 48 hours to a negative control (vehicle). The results show that the observed decrease in cholesterol by compound 4C12 is specific to Mut6 tumor cells, and that Mut6 cells have a much lower basal level of cholesterol and triglycerides.

FIG. 18B shows the effect of inhibition of cholesterol biosynthesis pathway genes Hmgcs and the effect of inhibition of ABCa1. FIG. 18A is a bar graph showing the effect of inhibition of cholesterol biosynthesis pathway genes Hmgcs; Hmgcr, AACS, Dhcr24, Dhcr7, Sc5d, SS, FPPS, LDLR; and SREBP2 in Mut6 cells treated with DMSO or with compound 4C12 for 16 hours. FIG. 18B is a bar graph showing effect on level of ABCa1 of treating Mut6 cells with compound 4C12 for 16 hours versus a DMSO negative control.

FIG. 19 comprising FIG. 19A, FIG. 19B, FIG. 19C and FIG. 19D shows relative ATP level (y-axis, a measure of viability) vs. concentration of compound 4C12 (nM). FIG. 19A shows relative ATP level (y-axis, a measure of viability) vs. concentration of compound 4C12 (nM) for various primary patient derived glioblastoma cell lines. FIG. 19B shows relative ATP level (y-axis, a measure of viability) vs. concentration of compound 4C12 (nM) for various primary patient derived glioblastoma cell lines. FIG. 19C shows relative ATP level (y-axis, a measure of viability) vs. concentration of compound 4C12 (nM) for HeLa (cervical), HT-29 (colon), 435 (breast), 549 (lung), MCF7 (breast), HCC38 (breast), Daoy (medulloblastoma (brain) cancer cell lines, and mouse embryonic fibroblast (MEF) cells in the presence of serum. FIG. 19D shows relative ATP level (y-axis, a measure of viability) vs. concentration of compound 4C12 (nM) for HeLa (cervical), HT-29 (colon), 435 (breast), 549 (lung), MCF7 (breast), HCC38 (breast), Daoy (medulloblastoma (brain) cancer cell lines, and mouse embryonic fibroblast (MEF) cells in the absence of serum.

DETAILED DESCRIPTION OF THE INVENTION

Definitions

Figure 1:
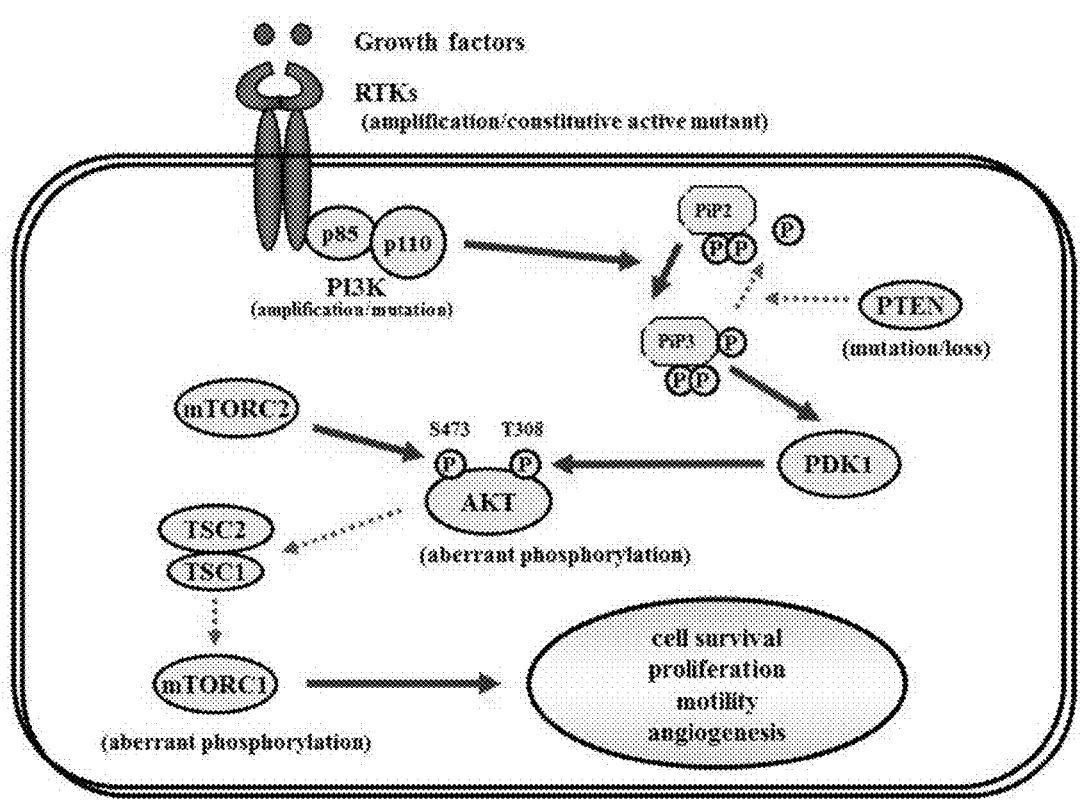
FIG. 1 depicts the Receptor Tyrosine Kinase (RTK/PI3K/Akt/mTOR) pathway.
Figure 2:
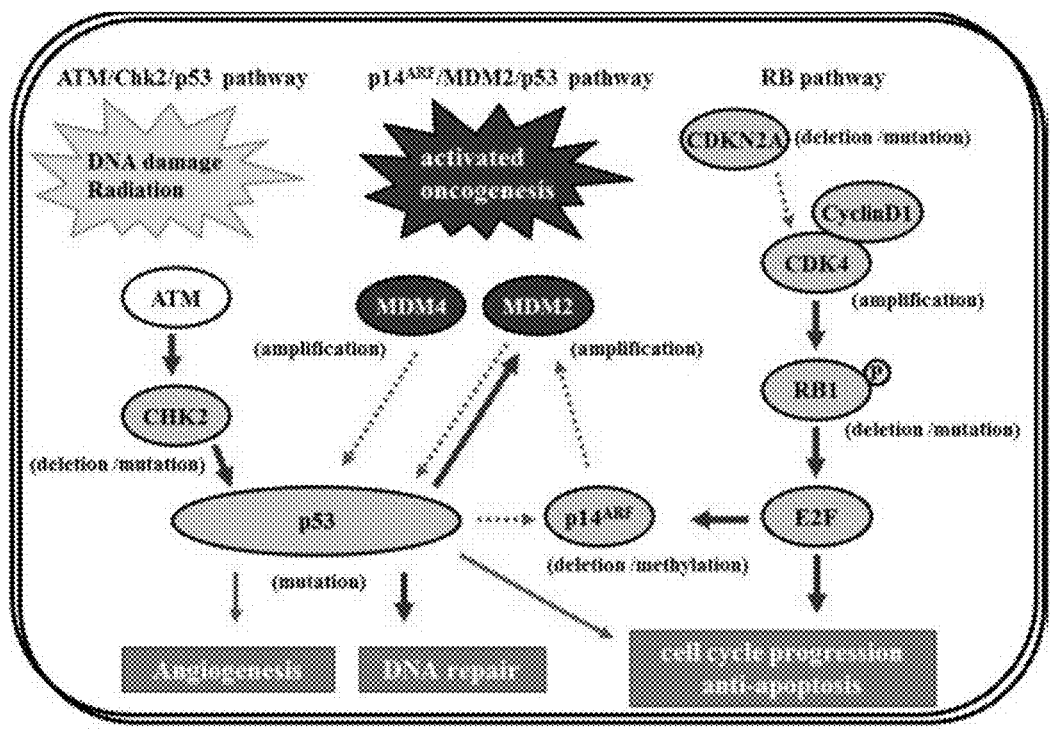
FIG. 2 depicts the p14ARF/MDM2/p53 pathway.
Figure 3:
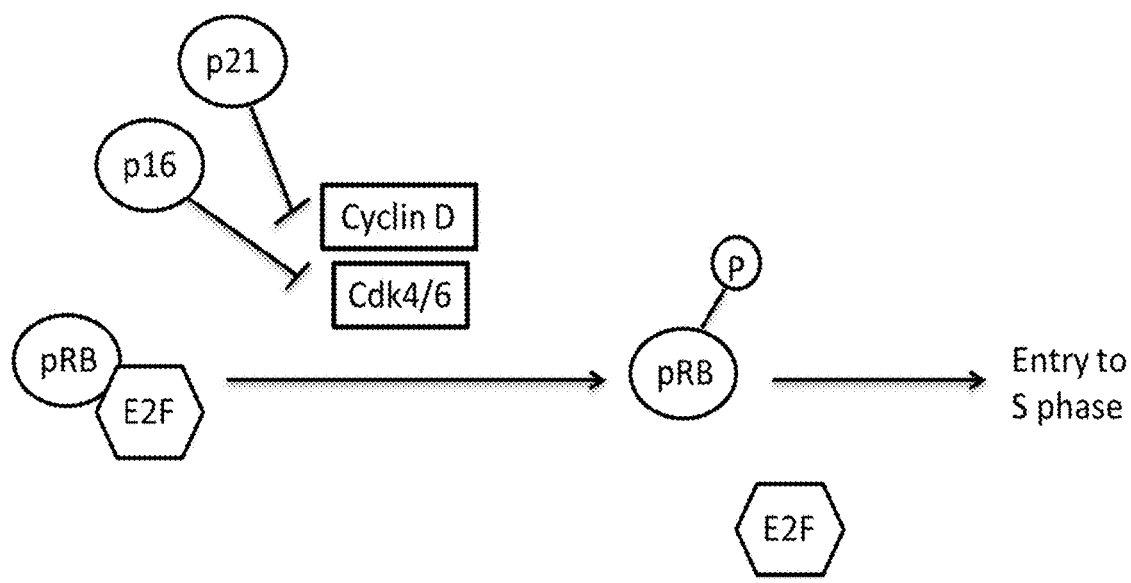
FIG. 3 depicts the retinoblastoma (RB) tumor suppressor protein pathway
Figure 4:
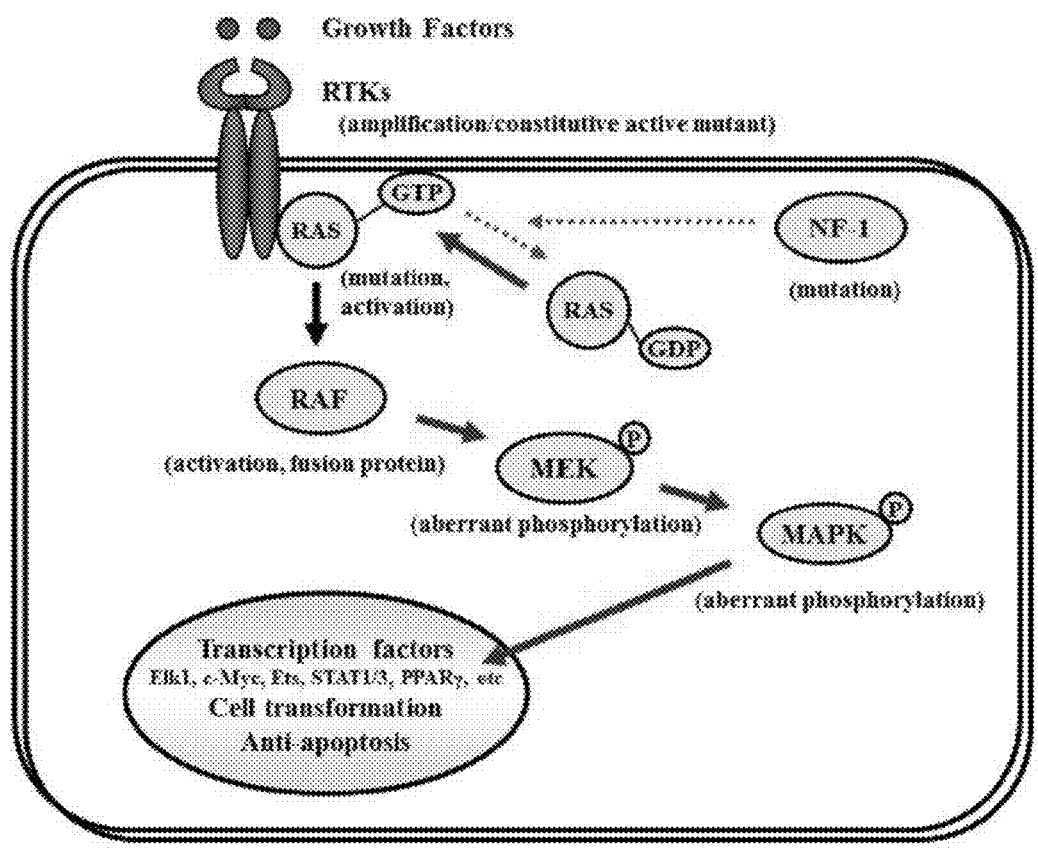
FIG. 4 depicts the Ras/MEK/MAPK pathway.
Figure 5:
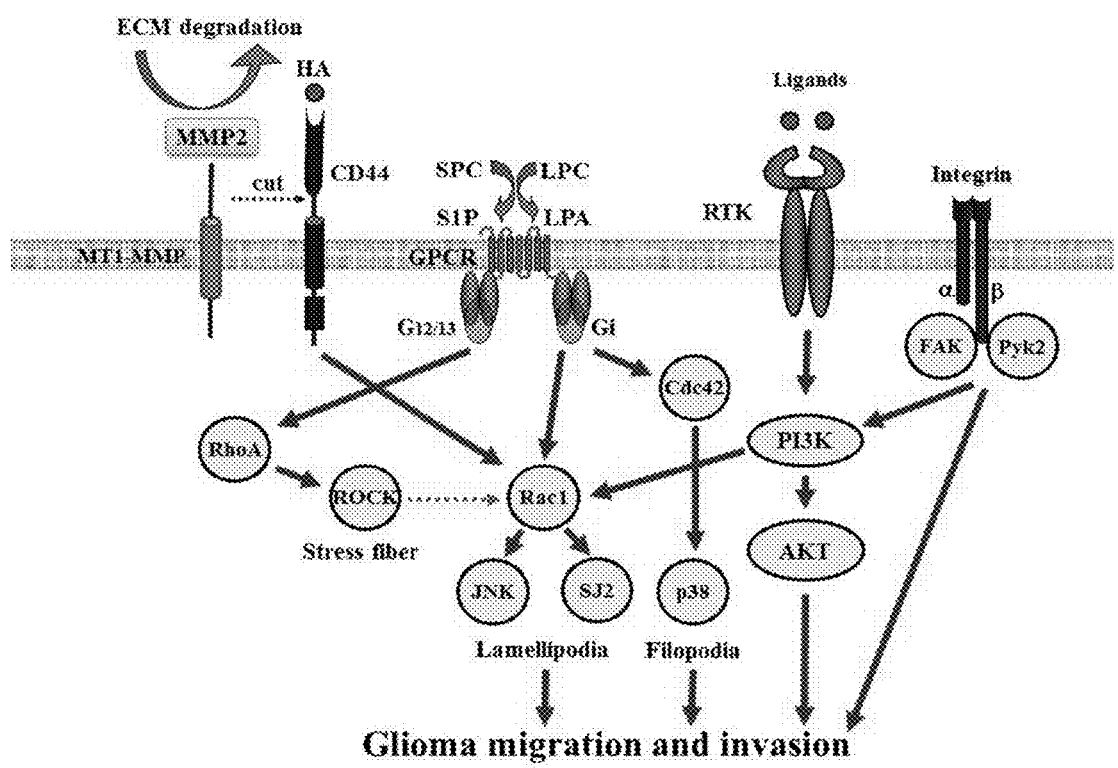
FIG. 5 depicts a global view of the Receptor Tyrosine Kinase (RTK/PI3K/Akt/mTOR) pathway; the p14ARF/MDM2/p53 pathway; the retinoblastoma (RB) tumor suppressor protein pathway and the Ras/MEK/MAPK pathway.

Various terms used throughout this specification shall have the definitions set out herein.

The term "adjuvant therapy" refers to a treatment added to a primary treatment to prevent recurrence of a disease, or the additional therapy given to enhance or extend the primary therapy's effect, as in chemotherapy's addition to a surgical regimen.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A super-agonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "antagonist" as used herein refers to a small molecule, peptide, protein, or antibody that can bind to an enzyme, a receptor or a co-receptor, competitively or non-competitively through a covalent bond, ionic bond, hydrogen bond, hydrophobic interaction, or a combination thereof and either directly or indirectly deactivate a related downstream signaling pathway.

The term "anti-cancer compounds" as used herein refers to small molecule compounds that selectively target cancer cells and reduce their growth, proliferation, or invasiveness, or tumor burden of a tumor containing such cancer cells The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be administered by means such as, but not limited to, injection, implantation, grafting, topical application, or parenterally.

The terms "analog" and "derivative" are used interchangeably to mean a compound produced from another compound of similar structure in one or more steps. A "derivative" or "analog" of a compound retains at least a degree of the desired function of the reference compound. Accordingly, an alternate term for "derivative" may be "functional derivative." Derivatives can include chemical modifications, such as akylation, acylation, carbamylation, iodination or any modification that derivatizes the compound. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives.

The term "allosteric modulation" as used herein refers to the process of modulating a receptor by the binding of allosteric modulators at a different site (i.e., regulatory site) other than of the endogenous ligand (orthosteric ligand) of the receptor and enhancing or inhibiting the effects of the endogenous ligand. It normally acts by causing a conformational change in a receptor molecule, which results in a change in the binding affinity of the ligand. Thus, an allosteric ligand "modulates" its activation by a primary "ligand" and can adjust the intensity of the receptor's activation. Many allosteric enzymes are regulated by their substrate, such a substrate is considered a "homotropic allosteric modulator." Non-substrate regulatory molecules are called "heterotropic allosteric modulators."

The term "allosteric regulation" is the regulation of an enzyme or other protein by binding an effector molecule at the proteins allosteric site (meaning a site other than the protein's active site). Effectors that enhance the protein's activity are referred to as "allosteric activators", whereas those that decrease the protein's activity are called "allosteric inhibitors." Thus, "allosteric activation" occurs when the binding of one ligand enhances the attraction between substrate molecules and other binding sites; "allosteric inhibition" occurs when the binding of one ligand decrease the affinity for substrate at other active sites. The term "antagonist" as used herein refers to a substance that counteracts the effects of another substance.

The terms "apoptosis" or "programmed cell death" refer to a highly regulated and active process that contributes to biologic homeostasis comprising a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin.

Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon aggregation and mitochondrial localization, induces cytochrome c release. Akt is a critical regulator of GSK-3, and phosphorylation and inactivation of GSK-3 may mediate some of the antiapoptotic effects of Akt.

The term "assay marker" or "reporter gene" (or "reporter") refers to a gene that can be detected, or easily identified and measured. The expression of the reporter gene may be measured at either the RNA level, or at the protein level. The gene product, which may be detected in an experimental assay protocol, includes, but is not limited to, marker enzymes, antigens, amino acid sequence markers, cellular phenotypic markers, nucleic acid sequence markers, and the like. Researchers may attach a reporter gene to another gene of interest in cell culture, bacteria, animals, or plants. For example, some reporters are selectable markers, or confer characteristics upon on organisms expressing them allowing the organism to be easily identified and assayed. To introduce a reporter gene into an organism, researchers may place the reporter gene and the gene of interest in the same DNA construct to be inserted into the cell or organism. For bacteria or eukaryotic cells in culture, this may be in the form of a plasmid. Commonly used reporter genes may include, but are not limited to, fluorescent proteins, luciferase, beta-galactosidase, and selectable markers, such as chloramphenicol and kanomycin.

As used herein, the term "bioavailability" refers to the rate and extent to which the active drug ingredient or therapeutic moiety is absorbed into the systemic circulation from an administered dosage form as compared to a standard or control.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The term "bound" or any of its grammatical forms as used herein refers to the capacity to hold onto, attract, interact with or combine with.

The terms "cancer" or "malignancy" as used herein refer to diseases in which abnormal cells divide without control and can invade nearby tissues. Cancer cells also can spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in cells of the immune system. Central nervous system cancers are cancers that begin in the tissues of the brain and spinal cord.

The term "carrier" as used herein describes a material that does not cause significant irritation to an organism and does not abrogate the biological activity and properties of the active compound of the composition of the described invention. Carriers must be of sufficiently high purity and of sufficiently low toxicity to render them suitable for administration to the mammal being treated. The carrier can be inert, or it can possess pharmaceutical benefits, cosmetic benefits or both. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "cell" is used herein to refer to the structural and functional unit of living organisms and is the smallest unit of an organism classified as living.

The term "cell line" as used herein refers to a population of immortalized cells, which have undergone transformation and can be passed indefinitely in culture.

The term "chemoresistance" as used herein refers to the development of a cell phenotype resistant to a variety of structurally and functionally distinct agents. Tumors can be intrinsically resistant prior to chemotherapy, or resistance may be acquired during treatment by tumors that are initially sensitive to chemotherapy. Drug resistance is a multifactorial phenomenon involving multiple interrelated or independent mechanisms. A heterogeneous expression of involved mechanisms may characterize tumors of the same type or cells of the same tumor and may at least in part reflect tumor progression. Exemplary mechanisms that can contribute to cellular resistance include: increased expression of defense factors involved in reducing intracellular drug concentration; alterations in drug-target interaction; changes in cellular response, in particular increased cell ability to repair DNA damage or tolerate stress conditions, and defects in apoptotic pathways.

The term "chemosensitive", "chemosensitivity" or "chemosensitive tumor" as used herein refers to a tumor that is responsive to a chemotherapy or a chemotherapeutic agent. Characteristics of a chemosensitive tumor include, but are not limit to, reduced proliferation of the population of tumor cells, reduced tumor size, reduced tumor burden, tumor cell death, and slowed/inhibited progression of the population of tumor cells.

The term "chemotherapeutic agent" as used herein refers to chemicals useful in the treatment or control of a disease, e.g., cancer The term "chemotherapy" as used herein refers to a course of treatment with one or more chemotherapeutic agents. In the context of cancer, the goal of chemotherapy is, e.g., to kill cancer cells, reduce proliferation of cancer cells, reduce growth of a tumor containing cancer cells, reduce invasiveness of cancer cells, increase apoptosis of cancer cells.

The term "chemotherapy regimen" ("combination chemotherapy") means chemotherapy with more than one drug in order to benefit from the dissimilar toxicities of the more than one drug. A principle of combination cancer therapy is that different drugs work through different cytotoxic mechanisms; since they have different dose-limiting adverse effects, they can be given together at full doses.

The term "compatible" as used herein means that the components of a composition are capable of being combined with each other in a manner such that there is no interaction that would substantially reduce the efficacy of the composition under ordinary use conditions.

The term "condition", as used herein, refers to a variety of health states and is meant to include disorders or diseases caused by any underlying mechanism or injury.

The term "contact" and its various grammatical forms as used herein refers to a state or condition of touching or of immediate or local proximity. Contacting a composition to a target destination, such as, but not limited to, an organ, a tissue, a cell, or a tumor, may occur by any means of administration known to the skilled artisan.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatives the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamate, and can include amino acids that are not linked by peptide bonds. Such peptide derivatives can be incorporated during synthesis of a peptide, or a peptide can be modified by wellknown chemical modification methods (see, e.g., Glazer et al., Chemical Modification of Proteins, Selected Methods and Analytical Procedures, Elsevier Biomedical Press, New York (1975)).

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like. When a nucleic acid is prepared or altered synthetically, advantage can be taken of known codon preferences of the intended host where the nucleic acid is to be expressed.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition.

The term "disease" or "disorder", as used herein, refers to an impairment of health or a condition of abnormal functioning.

The term "dose" as used herein refers to the quantity of medicine prescribed to be taken at one time.

The term "drug" as used herein refers to a therapeutic agent or any substance used in the prevention, diagnosis, alleviation, treatment, or cure of disease.

The terms "Emopamil Binding Protein" (EBP), "Human Sterol Isomerase" (HIS) and "delta8-delta7 sterol isomerase" are used interchangeably to refer to an integral membrane protein of the endoplasmic reticulum that catalyzes the conversion of delta(8)-sterols into delta(7)-sterols.

The term "effective amount" or "amount effective" refers to the amount necessary or sufficient to realize a desired biologic effect.

The term "effective dose" as used herein refers to the quantity of medicine prescribed to be taken at one time necessary or sufficient to realize a desired biologic effect.

As used herein, the term "enzymatic activity" refers to the amount of substrate consumed (or product formed) in a given time under given conditions. Enzymatic activity also may be referred to as "turnover number."

As used herein, the terms "formulation" and "composition" are used interchangeably to refer to a product of the described invention that comprises all active and inert ingredients.

The term "functional equivalent" or "functionally equivalent" are used interchangeably herein to refer to substances, molecules, polynucleotides, proteins, peptides, or polypeptides having similar or identical biological activity to a reference substance, molecule, polynucleotide, protein, peptide, or polypeptide. Any small molecule anti-cancer compound that retains the biological activity of compound 4C12, e.g. modulating a cancer cell sensitive to cholesterol biosynthesis inhibition, may be used as such a functional equivalent.

The term "growth" as used herein refers to a process of becoming larger, longer or more numerous, or an increase in size, number, or volume.

The term "half maximal inhibitory concentration" ("IC50") is a measure of the effectiveness of a compound in inhibiting a biological or biochemical function.

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a molecule that binds to an enzyme thereby decreasing enzyme activity. Enzyme inhibitors are molecules that bind to enzymes thereby decreasing enzyme activity. The binding of an inhibitor may stop substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury," as used herein, refers to damage or harm to a structure or function of the body caused by an outside agent or force, which may be physical or chemical.

The term "interfere" or "to interfere with" as used herein refers to the hampering, impeding, dampening, hindering, obstructing, blocking, reducing or preventing of an action or occurrence. By way of example, a receptor antagonist interferes with (e.g., blocks or dampens) an agonist-mediated response rather than provoking a biological response itself.

The term "invasion" or "invasiveness" as used herein refers to a process in malignant cells that includes penetration of and movement through surrounding tissues.

The term "Kaplan Meier plot" or "Kaplan Meier survival curve" as used herein refers to the plot of probability of clinical study subjects surviving in a given length of time while considering time in many small intervals. The Kaplan Meier plot assumes that: (i) at any time subjects who are censored (i.e., lost) have the same survival prospects as subjects who continue to be followed; (ii) the survival probabilities are the same for subjects recruited early and late in the study; and (iii) the event (e.g., death) happens at the time specified. Probabilities of occurrence of events are computed at a certain point of time with successive probabilities multiplied by any earlier computed probabilities to get a final estimate. The survival probability at any particular time is calculated as the number of subjects surviving divided by the number of subjects at risk. Subjects who have died, dropped out, or have been censored from the study are not counted as at risk.

The term "ligand" as used herein refers to a molecule that can bind selectively to a molecule, such that the binding interaction between the ligand and its binding partner is detectable over nonspecific interactions by a quantifiable assay. Derivatives, analogues and mimetic compounds are intended to be included within the definition of this term.

The terms "marker" and "cell surface marker" are used interchangeably herein to refer to a receptor, a combination of receptors, or an antigenic determinant or epitope found on the surface of a cell that allows a cell type to be distinguishable from other kinds of cells. Specialized protein receptors (markers) that have the capability of selectively binding or adhering to other signaling molecules coat the surface of every cell in the body. Cells use these receptors and the molecules that bind to them as a way of communicating with other cells and to carry out their proper function in the body. Cell sorting techniques are based on cellular biomarkers where a cell surface marker(s) may be used for either positive selection or negative selection, i.e., for inclusion or exclusion, from a cell population.

The term "maximum tolerated dose" (MTD) as used herein refers to the highest dose of a drug that does not produce unacceptable toxicity.

The term "median survival" as used herein refers to the time after which 50% of individuals with a particular condition are still living and 50% have died. For example, a median survival of 6 months indicates that after 6 months, 50% of individuals with, e.g., colon cancer would be alive, and 50% would have passed away. Median survival is often used to describe the prognosis (i.e., chance of survival) of a condition when the average survival rate is relatively short, such as for colon cancer. Median survival is also used in clinical studies when a drug or treatment is being evaluated to determine whether or not the drug or treatment will extend life.

The term "metastasis" as used herein refers to the transference of organisms or of malignant or cancerous cells, producing disease manifestations, from one part of the body to other parts.

The term "migration" as used herein refers to a movement of a population of cells from one place to another.

The term "mitotic index" as used herein refers to the ratio of the number of cells undergoing mitosis (cell division) to the number of cells not undergoing mitosis in a population of cells.

The term "modify" as used herein means to change, vary, adjust, temper, alter, affect or regulate to a certain measure or proportion in one or more particulars.

The term "modifying agent" as used herein refers to a substance, composition, therapeutic component, active constituent, therapeutic agent, drug, metabolite, active agent, protein, non-therapeutic component, non-active constituent, non-therapeutic agent, or non-active agent that reduces, lessens in degree or extent, or moderates the form, symptoms, signs, qualities, character or properties of a condition, state, disorder, disease, symptom or syndrome.

The term "modulate" as used herein means to regulate, alter, adapt, or adjust to a certain measure or proportion.

The term "neoplasm" as used herein refers to an abnormal proliferation of genetically altered cells. A malignant neoplasm (or malignant tumor) is synonymous with cancer. A benign neoplasm (or benign tumor) is a tumor (solid neoplasm) that stops growing by itself, does not invade other tissues and does not form metastases.

The term "neurosphere" as used herein refers to three-dimensional aggregates of cells in suspension when cultured in serum-free conditions supplemented with epidermal growth factor (EGF) and basic fibroblast growth factor (bFGF) that, can be dissociated to form numerous secondary spheres or, when grown in differentiating medium on an appropriate substrate, induced to differentiate, generating neurons, astrocytes and oligodendrocytes, the three major cell types of the CNS.

The term "normal healthy control subject" as used herein refers to a subject having no symptoms or other clinical evidence of a disease.

The term "outcome" as used herein refers to a specific result or effect that can be measured. Nonlimiting examples of outcomes include decreased pain, reduced tumor size, and survival (e.g., progression-free survival or overall survival).

The term "overall survival" (OS) as used herein refers to the length of time from either the date of diagnosis or the start of treatment for a disease, such as cancer, that patients diagnosed with the disease are still alive.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using exemplary dispersing or wetting agents and suspending agents.

The terms "pharmaceutical formulation" or "pharmaceutical composition" as used herein refer to a formulation or composition that is employed to prevent, reduce in intensity, cure or otherwise treat a target condition or disease.

The term "pharmaceutically acceptable carrier" as used herein refers to any substantially non-toxic carrier conventionally useable for administration of pharmaceuticals in which the small molecule anti-cancer compound of the described invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the described invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The terms "primary tumor" or "primary cancer" are used interchangeably to refer to the original, or first, tumor in the body. Cancer cells from a primary cancer may spread to other parts of the body and form new, or secondary tumors. This is called metastasis. The secondary tumors are the same type of cancer as the primary cancer.

The term "progression" as used herein refers to the course of a disease as it becomes worse or spreads in the body.

The term "progression-free survival" (PFS) as used herein refers to the length of time during and after the treatment of a disease that a patient lives with the disease but it does not get worse.

The term "proliferation" as used herein refers to expansion of a population of cells by the continuous division of single cells into identical daughter cells, leading to a multiplying or increasing in the number of cells.

The term "recurrence" as used herein refers to a disease (e.g., cancer) that has come back, usually after a period of time during which the disease could not be detected.

The term "reduce" or "reducing" as used herein refers to limit occurrence of a disorder in individuals at risk of developing the disorder.

The terms "refractory" or "resistant" are used interchangeably herein refers to a disease or condition that does not respond to treatment. The disease may be resistant at the beginning of treatment or it may become resistant during treatment.

The term "remission" as used herein refers to a decrease in or disappearance of signs and symptoms of a disease. In partial remission, some, but not all, signs and symptoms have disappeared. In complete remission, all signs and symptoms have disappeared although the disease may still be in the body.

The term Response Evaluation Criteria in Solid Tumors (or "RECIST") as used herein refers to a standard way to measure how well a cancer patient responds to treatment. It is based on whether tumors shrink, stay the same, or get bigger. To use RECIST, there must be at least one tumor that can be measured on x-rays, CT scans, or MRI scans. The types of response a patient can have are a complete response (CR), a partial response (PR), progressive disease (PD), and stable disease (SD).

The term "sign" as used herein refers to something found during a physical exam or from a laboratory test that shows that a person may have a condition or disease.

The terms "subject" or "individual" or "patient" are used interchangeably to refer to a member of an animal species of mammalian origin, including but not limited to, a mouse, a rat, a cat, a goat, sheep, horse, hamster, ferret, platypus, pig, a dog, a guinea pig, a rabbit and a primate, such as, for example, a monkey, ape, or human.

The term "subject in need of such treatment" as used herein refers to a patient who suffers from a disease, disorder, condition, or pathological process, e.g., a solid tumor, a brain cancer, or a glioma. According to some embodiments, the term "subject in need of such treatment" also is used to refer to a patient whose cancer comprises a population of cancer cells sensitive to cholesterol biosynthesis inhibition; (i) who will be administered a therapeutic amount of a small molecule anti-cancer compound of the described invention (ii) is receiving a therapeutic amount of a small molecule anti-cancer compound of the described invention; or (iii) has received a therapeutic amount of a small molecule anti-cancer compound of the described invention unless the context and usage of the phrase indicates otherwise.

The terms "substantial inhibition", "substantially inhibited" and the like as used herein refer to inhibition of at least 50%, inhibition of at least 55%, inhibition of at least 60%, inhibition of at least 65%, inhibition of at least 70%, inhibition of at least 75%, inhibition of at least 80%, inhibition of at least 85%, inhibition of at least 90%, inhibition of at least 95%, or inhibition of at least 99%.

The term "survival rate" as used herein refers to the percent of individuals who survive a disease (e.g., cancer) for a specified amount of time. For example, if the 5-year survival rate for a particular cancer is 34%, this means that 34 out of 100 individuals initially diagnosed with that cancer would be alive after 5 years.

The term "symptom" as used herein refers to a sign or a disease or condition. The terms "symptom management", "palliative care," and "supportive care" are used interchangeably herein to refer to care given to improve the quality of life (QOL) of patients who have a serious or life-threatening disease.

The term "therapeutic agent" as used herein refers to a drug, molecule, nucleic acid, protein, metabolite, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein.

The terms "therapeutically effective amount", an "amount effective", or "pharmaceutically effective amount" of one or more of the active agents and used interchangeably to refer to an amount that is sufficient to provide the intended benefit of treatment. Dosage levels are based on a variety of factors, including the type of injury, the age, weight, sex, medical condition of the patient, the severity of the condition, the route of administration, and the particular active agent employed. Thus, the dosage regimen may vary widely, but can be determined routinely by a physician using standard methods. Additionally, the terms "therapeutically effective amounts" and "pharmaceutically effective amounts" include prophylactic or preventative amounts.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "sterol" as used herein refers to a steroid alcohol, which contains a common steroid nucleus (a fused, reduced 17-carbon-atom ring system, cyclopentanoperhydrophenantrene) and a hydroxyl group.

As used herein the term "treating" includes abrogating, substantially inhibiting, slowing or reversing the progression of a condition, substantially ameliorating clinical symptoms of a condition, or substantially preventing the appearance of clinical symptoms of a condition. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder (s) in patients that have previously had the disorder(s); and (e) limiting recurrence of symptoms in patients that were previously asymptomatic for the disorder(s).

The term "tumor" as used herein refers to a diseases involving abnormal cell growth in numbers (proliferation) or in size with the potential to invade or spread to other parts of the body (metastasis).

The term "tumor burden" or "tumor load" are used interchangeably herein refers to the number of cancer cells, the size of a tumor, or the amount of cancer in the body.

Compounds

A small molecule anti-cancer compound of Formula I:

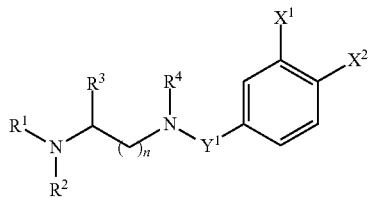

(Formula I)

Wherein:

$X^1$ is selected from the group consisting of H, F, Cl, CN, $NH_2$, $NO_2$, $N_3$, $SO_2Me$, and $L^1$-$R^5$;

$X^2$ is selected from the group consisting of H, F, Cl, CN, $NH_2$, $NO_2$, $N_3$, $SO_2Me$, and $L^2$-$R^6$;

$Y^1$ is selected from the group consisting of C=O, $CH_2$, and $SO_2$;

n=1, 2, or 3;

$L^1$ is selected from the group consisting of S, O, NH, CHOH, C=O, —$O(CH_2)$—, —$S(CH_2)$—, —$(CH_2)O$—, and —$(CH_2)S$—;

$L^2$ is selected from the group consisting of S, O, NH, CHOH, C=O, —$O(CH_2)$—, —$S(CH_2)$—, —$(CH_2)O$—, and —$(CH_2)S$—;

$R^1$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —$(CR^{10}R^{11})_m$—, where m=2, 3, 4, or 5;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^2$ and $R^4$ may optionally form a ring, such that $R^2$-$R^4$ consists of a one to four subunit chain comprising subunits independently selected from the group consisting of —$(CR^{12}R^{13})$—. Additionally, $R^2$ may simultaneously form a ring with $R^1$ as described above;

$R^3$ is selected from the group consisting of H, D, F, Me, and Et;

$R^4$ is selected from the group consisting of H, Me, $CD_3$, $CF_3$, Et, isopropyl, cyclopropyl, and $C_2$-$C_6$ alkynyl;

$R^5$ is selected from the group consisting of cycloalkyl, aryl, heteroaryl, heterocyclyl, benzyl, fused heteroarylaryl, fused arylheteroaryl, and fused arylaryl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to one embodiment, the described invention provides a small molecule anti-cancer compound of Formula I wherein:

$X^1$ is selected from the group consisting of H, F, Cl, CN, $NH_2$, $NO_2$, $N_3$, $SO_2Me$, and $L^1$-$R^5$;

$X^2$ is selected from the group consisting of H, F, Cl, CN, $NH_2$, $NO_2$, $N_3$, $SO_2Me$, and $L^2$-$R^6$;

$Y^1$ is selected from the group consisting of C=O, $CH_2$, and $SO_2$;

n=1 or 2;

$L^1$ is selected from the group consisting of S, O, NH, CHOH, C=O, —$O(CH_2)$—, —$S(CH_2)$—, —$(CH_2)O$—, and —$(CH_2)S$—;

$L^2$ is selected from the group consisting of S, O, NH, CHOH, C=O, —$O(CH_2)$—, —$S(CH_2)$—, —$(CH_2)O$—, and —$(CH_2)S$—;

$R^1$ and $R^2$ are independently selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —$(CR^{10}R^{11})_m$—, where m=2, 3, 4, or 5;

$R^2$ and $R^4$ may optionally form a ring, such that $R^2$-$R^4$ consists of a one to four subunit chain comprising subunits independently selected from the group consisting of —$(CR^{12}R^{13})$—. Additionally, $R^2$ may simultaneously form a ring with $R^1$ as described above;

$R^3$=H;

$R^4$ is selected from the group consisting of H, Me, and propargyl;

$R^5$ and $R^6$ are independently selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I wherein:

$X^1$ is selected from the group consisting of H, F, Cl, CN, $NH_2$, $NO_2$, $N_3$, $SO_2Me$, and $L^1$-$R^5$;

$X^2$ is selected from the group consisting of H, F, Cl, CN, $NH_2$, $NO_2$, $N_3$, $SO_2Me$, and $L^2$-$R^6$;

$Y^1$ is selected from the group consisting of C=O, $CH_2$, and $SO_2$;

n=1 or 2;

$L^1$ is selected from the group consisting of S, O, NH, CHOH, C=O, —$O(CH_2)$—, —$S(CH_2)$—, —$(CH_2)O$—, and —$(CH_2)S$—;

$L^2$ is selected from the group consisting of S, O, NH, CHOH, C=O, —$O(CH_2)$—, —$S(CH_2)$—, —$(CH_2)O$—, and —$(CH_2)S$—;

$R^1$ and $R^2$ are independently selected from the group consisting of H, $C_1$-$C_6$ alkyl, $C_2$-$C_6$ alkynyl, $C_1$-$C_6$ hydroxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, S;

$R^1$ and $R^3$ may optionally form a ring, such that $R^1$-$R^3$ comprises —$(CR^{10}R^{11})_m$—, where m=2, 3, 4, or 5;

$R^2$ and $R^4$ may optionally form a ring, such that $R^2$-$R^4$ consists of a one to four subunit chain comprising subunits independently selected from the group consisting of —$(CR^{12}R^{13})$—. Additionally, $R^2$ may simultaneously form a ring with $R^1$ as described above;

$R^3$=H;

$R^4$ is selected from the group consisting of H, Me, and propargyl;

$R^5$ and $R^6$ are independently selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I wherein:

$X^1$ is selected from the group consisting of H, F, Cl, CN, $NH_2$, $NO_2$, $N_3$, and $SO_2Me$;

$X^2$=$L^2$-$R^6$;

$Y^1$ is selected from the group consisting of C=O, $CH_2$, and $SO_2$;

n=1 or 2;

$L^2$ is selected from the group consisting of S, O, NH, CHOH, C=O, —$O(CH_2)$—, —$S(CH_2)$—, —$(CH_2)O$—, and —$(CH_2)S$—;

$R^1$ and $R^2$ are independently selected from the group consisting of H, $C_1$-$C_6$ alkyl, $C_2$-$C_6$ alkynyl, $C_1$-$C_6$ hydroxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —$(CR^{10}R^{11})_m$—, where m=2, 3, 4, or 5;

$R^2$ and $R^4$ may optionally form a ring, such that $R^2$-$R^4$ consists of a one to four subunit chain comprising subunits independently selected from the group consisting of —$(CR^{12}R^{13})$—. Additionally, $R^2$ may simultaneously form a ring with $R^1$ as described above;

$R^3$=H;

$R^4$ is selected from the group consisting of H, Me, and propargyl;

$R^5$ and $R^6$ are independently selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-a:

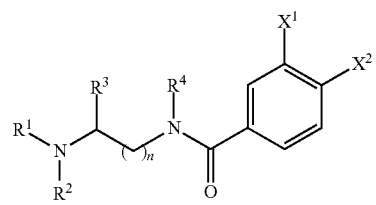

(Formula I-a)

Wherein:

$X^1$ is selected from the group consisting of H, F, Cl, CN, $NH_2$, $NO_2$, $N_3$, $SO_2Me$, and $L^1$-$R^5$;

$X^2$ is selected from the group consisting of H, F, Cl, CN, $NH_2$, $NO_2$, $N_3$, $SO_2Me$, and $L^2$-$R^6$;

n=1, 2, or 3;

$L^1$ is selected from the group consisting of S, O, NH, CHOH, C=O, —$O(CH_2)$—, —$S(CH_2)$—, —$(CH_2)O$—, and —$(CH_2)S$—;

$L^2$ is selected from the group consisting of S, O, NH, CHOH, C=O, —$O(CH_2)$—, —$S(CH_2)$—, —$(CH_2)O$—, and —$(CH_2)S$—;

$R^1$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —$(CR^{10}R^{11})_m$—, where m=2, 3, 4, or 5;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$ is selected from the group consisting of H, D, F, Me, and Et;

$R^4$ is selected from the group consisting of H, Me, $CD_3$, $CF_3$, Et, i-Pr, cyclopropyl, and $C_2$-$C_6$ alkynyl;

$R^5$ is selected from the group consisting of cycloalkyl, aryl, heteroaryl, heterocyclyl, benzyl, fused heteroarylaryl, fused arylheteroaryl, and fused arylaryl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-a wherein:

$X^1$ is selected from the group consisting of H, F, Cl, CN, $NH_2$, $NO_2$, $N_3$, $SO_2Me$, and $L^1$-$R^5$;

$X^2$ is selected from the group consisting of H, F, Cl, CN, $NH_2$, $NO_2$, $N_3$, $SO_2Me$, and $L^2$-$R^6$;

n=1 or 2;

$L^1$ is selected from the group consisting of S, O, NH, CHOH, C=O, —O($CH_2$)—, —S($CH_2$)—, —($CH_2$)O—, and —($CH_2$)S—;

$L^2$ is selected from the group consisting of S, O, NH, CHOH, C=O, —O($CH_2$)—, —S($CH_2$)—, —($CH_2$)O—, and —($CH_2$)S—;

$R^1$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —(CR where m=2, 3, 4, or 5;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$=H;

$R^4$ is selected from the group consisting of H, Me, and propargyl;

$R^5$ is selected from the group consisting of cycloalkyl, aryl, heteroaryl, heterocyclyl, benzyl, fused heteroarylaryl, fused arylheteroaryl, and fused arylaryl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-a wherein:

$X^1$ is selected from the group consisting of H, F, Cl, CN, $NH_2$, $NO_2$, $N_3$, $SO_2Me$, and $L^1$-$R^5$;

$X^2$ is selected from the group consisting of H, F, Cl, CN, $NH_2$, $NO_2$, $N_3$, $SO_2Me$, and $L^2$-$R^6$;

n=1 or 2;

$L^1$ is selected from the group consisting of S, O, NH, CHOH, C=O, —O($CH_2$)—, —S($CH_2$)—, —($CH_2$)O—, and —($CH_2$)S—;

$L^2$ is selected from the group consisting of S, O, NH, CHOH, C=O, —O($CH_2$)—, —S($CH_2$)—, —($CH_2$)O—, and —($CH_2$)S—;

$R^1$ and $R^2$ are independently selected from the group consisting of H, $C_1$-$C_6$ alkyl, $C_2$-$C_6$ alkynyl, $C_1$-$C_6$ hydroxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —(CR where m=2, 3, 4, or 5;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$=H;

$R^4$ is selected from the group consisting of H, Me, and propargyl;

$R^5$ is selected from the group consisting of cycloalkyl, aryl, heteroaryl, heterocyclyl, benzyl, fused heteroarylaryl, fused arylheteroaryl, and fused arylaryl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-a wherein:

$X^1$ is selected from the group consisting of H, F, Cl, CN, $NH_2$, $NO_2$, $N_3$, and $SO_2Me$;

$X^2=L^2-R^6$;

n=1 or 2;

$L^2$ is selected from the group consisting of S, O, NH, CHOH, C=O, —O(CH$_2$)—, —S(CH$_2$)—, —(CH$_2$)O—, and —(CH$_2$)S—;

$R^1$ and $R^2$ are independently selected from the group consisting of H, $C_1$-$C_6$ alkyl, $C_2$-$C_6$ alkynyl, $C_1$-$C_6$ hydroxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —($CR^{10}R^{11}$)$_m$—, where m=2, 3, 4, or 5;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$=H;

$R^4$ is selected from the group consisting of H, Me, propargyl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-b:

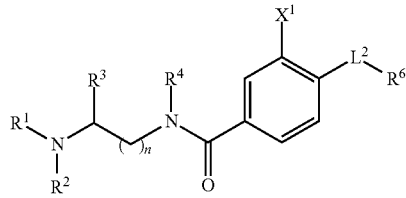

(Formula I-b)

Wherein:

$X^1$ is selected from the group consisting of H, F, Cl, CN, $NH_2$, $NO_2$, $N_3$, and $SO_2Me$;

n=1, 2, or 3;

$L^2$ is selected from the group consisting of S, O, NH, CHOH, C=O, —O(CH$_2$)—, —S(CH$_2$)—, —(CH$_2$)O—, and —(CH$_2$)S—;

$R^1$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —($CR^{10}R^{11}$)$_m$—, where m=2, 3, 4 or 5;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$ is selected from the group consisting of H, D, F, Me, and Et;

$R^4$ is selected from the group consisting of H, Me, $CD_3$, $CF_3$, Et, i-Pr, cyclopropyl, and $C_2$-$C_6$ alkynyl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-b wherein:

$X^1$ is selected from the group consisting of H, F, Cl, CN, $NH_2$, $NO_2$, $N_3$, and $SO_2Me$;

n=1 or 2;

$L^2$ is selected from the group consisting of S, O, NH, CHOH, C=O, —O(CH$_2$)—, —S(CH$_2$)—, —(CH$_2$)O—, and —(CH$_2$)S—;

$R^1$ and $R^2$ are independently selected from the group consisting of H, $C_1$-$C_6$ alkyl, $C_2$-$C_6$ alkynyl, $C_1$-$C_6$ hydroxyalkyl, and acyloxyalkyl;

$R^1$ and $R^2$ may optionally form a ring, such that $R^1$-$R^2$ consists of a three to six subunit chain comprising subunits independently selected from the group consisting of (CR$^7$R$^8$), NR$^9$, O, and S;

$R^1$ and $R^3$ may optionally form a ring, such that $R^1$-$R^3$ comprises —(CR$^{10}$R$^{11}$)$_m$—, where m=2, 3, 4 or 5;

$R^2$ and $R^4$ may optionally form a ring, such that $R^2$-$R^4$ consists of a one to four subunit chain comprising subunits independently selected from the group consisting of —(CR$^{12}$R$^{13}$)—. Additionally, $R^2$ may simultaneously form a ring with $R^1$ as described above;

$R^3$=H;

$R^4$ is selected from the group consisting of H, Me, and propargyl;

$R^6$ is selected from the group consisting of cycloalkyl, aryl, heteroaryl, heterocyclyl, benzyl, fused heteroarylaryl, fused arylheteroaryl, and fused arylaryl;

$R^7$ and $R^8$ are independently selected from the group consisting of H, D, F, Me, Et, OR, and NR$_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and NR$_2$. In the context of this paragraph, R is selected from the group consisting of H, Me, and Et;

$R^{12}$ and $R^{13}$ are independently selected from the group consisting of H, D, F, Me, and Et;

Such that all possible stereoisomers, including optically active isomers, are included whenever stereogenic centers are present;

or a pharmaceutically acceptable salt, prodrug, active metabolite, or solvate thereof.

According to another embodiment, the described invention provides small molecule anti-cancer compound of Formula I-c:

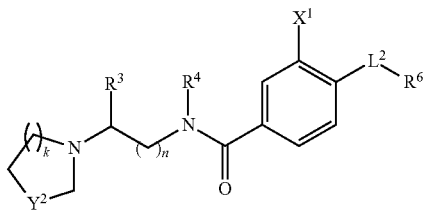

(Formula I-c)

Wherein:
$X^1$ is selected from the group consisting of H, F, Cl, CN, NH$_2$, NO$_2$, N$_3$, and SO$_2$Me;

$Y^2$ is selected from the group consisting of CR'R", NR, O, and S. In the context of this paragraph, R, R' and R" are independently selected from the group consisting of H, F, Me, Et, i-Pr, and cyclopropyl;

k=0, 1, 2, or 3;
n=1, 2, or 3;

$L^2$ is selected from the group consisting of S, O, NH, CHOH, C=O, —O(CH$_2$)—, —S(CH$_2$)—, —(CH$_2$)O—, and —(CH$_2$)S—;

$R^3$ is selected from the group consisting of H, D, F, Me, and Et;

$R^4$ is selected from the group consisting of H, Me, CD$_3$, CF$_3$, Et, i-Pr, cyclopropyl, and $C_2$-$C_6$ alkynyl;

$R^6$ is selected from the group consisting of cycloalkyl, aryl, heteroaryl, heterocyclyl, benzyl, fused heteroarylaryl, fused arylheteroaryl, and fused arylaryl;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-c wherein:

$X^1$ is selected from the group consisting of H, F, Cl, CN, NH$_2$, NO$_2$, N$_3$, and SO$_2$Me;

$Y^2$ is selected from the group consisting of CH$_2$, NR, O, and S. In the context of this paragraph, R is selected from the group consisting of H and Me;

k=1 or 2;
n=1 or 2;

$L^2$ is selected from the group consisting of NH, O, S, CHOH, C=O, and —S(CH$_2$)—;

$R^3$=H;

$R^4$ is selected from the group consisting of H, Me, and propargyl;

$R^6$ is selected from the group consisting of cycloalkyl, aryl, heteroaryl, heterocyclyl, benzyl, fused heteroarylaryl, fused arylheteroaryl, and fused arylaryl;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-c wherein:

$X^1$ is selected from the group consisting of H, F, Cl, CN, NH$_2$, NO$_2$, N$_3$, and SO$_2$Me;

$Y^2$ is selected from the group consisting of CH$_2$, NR, O, and S. In the context of this paragraph, R is selected from the group consisting of H and Me;

k=1 or 2;
n=1 or 2;

$L^2$ is selected from the group consisting of NH, O, and S;

$R^3$=H;

$R^4$ is selected from the group consisting of H, Me, and propargyl;

$R^6$ is selected from the group consisting of aryl, and heteroaryl;

Such that all possible stereoisomers, including optically active isomers, are included whenever stereogenic centers are present;

or a pharmaceutically acceptable salt, prodrug, active metabolite, or solvate thereof.

According to another embodiment, the described invention provides small molecule anti-cancer compound of Formula I-d:

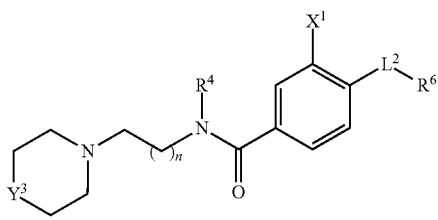

(Formula I-d)

Wherein:

$X^1$ is selected from the group consisting of H, F, Cl, CN, $NH_2$, $NO_2$, $N_3$, and $SO_2Me$;

$Y^3$ is selected from the group consisting of $CH_2$, NR, O, and S. In the context of this paragraph, R is selected from the group consisting of H, Me, $CD_3$, $CF_3$, Et, isopropyl, and cyclopropyl.

n=1 or 2;

$L^2$ is selected from the group consisting of S, O, NH;

$R^4$ is selected from the group consisting of H, Me, $CD_3$, $CF_3$, Et, and $C_2$-$C_6$ alkynyl;

$R^6$ is selected from the group consisting of aryl, heteroaryl, benzyl, fused heteroarylaryl, fused arylheteroaryl, and fused arylaryl;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-d wherein:

$X^1$ is selected from the group consisting of H, F, Cl, CN, $NH_2$, $NO_2$, $N_3$, and $SO_2Me$;

$Y^3$ is selected from the group consisting of $CH_2$, NH, NMe, and O;

n=1 or 2;

$L^2$ is selected from the group consisting of S, O, and NH;

$R^4$ is selected from the group consisting of H, Me, and propargyl;

$R^6$ is selected from the group consisting of aryl, and heteroaryl;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-e:

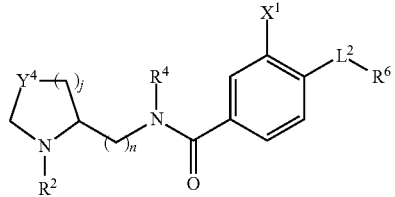

(Formula I-e)

Wherein:

$X^1$ is selected from the group consisting of H, F, Cl, CN, $NH_2$, $NO_2$, $N_3$, and $SO_2Me$;

$Y^4$ is selected from the group consisting of CR'R", NR, O, and S. In the context of this paragraph, R, R', and R" are independently selected from the group consisting of H, F, Me, Et, isopropyl and cyclopropyl;

j=0, 1, 2, or 3;

n=1, 2, or 3;

$L^2$ is selected from the group consisting of S, O, NH, CHOH, C=O, —O(CH$_2$)—, —S(CH$_2$)—, —(CH$_2$)O—, and —(CH$_2$)S—;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^4$ is selected from the group consisting of H, Me, $CD_3$, $CF_3$, Et, i-Pr, cyclopropyl, and $C_2$-$C_6$ alkynyl;

$R^6$ is selected from the group consisting of cycloalkyl, aryl, heteroaryl, heterocyclyl, benzyl, fused heteroarylaryl, fused arylheteroaryl, and fused arylaryl;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-e wherein:

$X^1$ is selected from the group consisting of H, F, Cl, CN, $NH_2$, $NO_2$, $N_3$, and $SO_2Me$;

$Y^4$=$CH_2$;

j=1;

n=1 or 2;

$L^2$ is selected from the group consisting of S, O, NH, CHOH, C=O, and —S(CH$_2$)—;

$R^2$ is selected from the group consisting of H, $C_1$-$C_3$ alkyl, propargyl, $C_1$-$C_3$ hydroxyalkyl, and acyloxyalkyl;

$R^4$ is selected from the group consisting of H, Me, and propargyl;

$R^6$ is selected from the group consisting of cycloalkyl, aryl, heteroaryl, heterocyclyl, benzyl, fused heteroarylaryl, fused arylheteroaryl, and fused arylaryl;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-f:

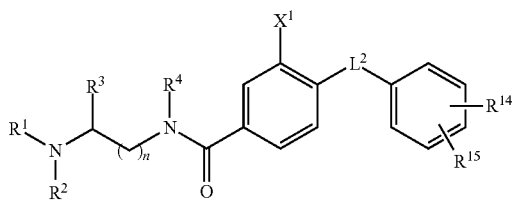

(Formula I-f)

Wherein:

$X^1$ is selected from the group consisting of H, F, Cl, CN, $NH_2$, $NO_2$, $N_3$, and $SO_2Me$;

n=1, 2, or 3;

$L^2$ is selected from the group consisting of S, O, NH, CHOH, C=O, —O(CH$_2$)—, —S(CH$_2$)—, —(CH$_2$)O—, and —(CH$_2$)S—;

$R^1$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^1$ and $R^2$ may optionally form a ring, such that $R^1$-$R^2$ consists of a three to six subunit chain comprising subunits independently selected from the group consisting of ($CR^7R^8$), $NR^9$, O, and S;

$R^1$ and $R^3$ may optionally form a ring, such that $R^1$-$R^3$ comprises —($CR^{10}R^{11}$)$_m$—, where m=2, 3, 4 or 5;

$R^2$ is selected from the group consisting of H, $C_1$-$C_6$ alkyl, $C_2$-$C_6$ alkenyl, $C_2$-$C_6$ alkynyl, cycloalkyl, $C_1$-$C_6$ hydroxyalkyl, $C_1$-$C_6$ alkoxyalkyl, and acyloxyalkyl;

$R^2$ and $R^4$ may optionally form a ring, such that $R^2$-$R^4$ consists of a one to four subunit chain comprising subunits independently selected from the group consisting of —($CR^{12}R^{13}$)—. Additionally, $R^2$ may simultaneously form a ring with $R^1$ as described above;

$R^3$ is selected from the group consisting of H, D, F, Me, and Et;

$R^4$ is selected from the group consisting of H, Me, $CD_3$, $CF_3$, Et, i-Pr, cyclopropyl, and $C_2$-$C_6$ alkynyl;

$R^7$ and $R^8$ are independently selected from the group consisting of H, D, F, Me, Et, OR, and $NR_2$. In the context of this paragraph, R is selected from the group consisting of H, Me, and Et;

$R^9$ is selected from the group consisting of H, Me, Et, isopropyl, and cyclopropyl;

$R^{10}$ and $R^{11}$ are independently selected from the group consisting of H, D, F, Me, Et, OR, and $NR_2$. In the context of this paragraph, R is selected from the group consisting of H, Me, and Et;

$R^{12}$ and $R^{13}$ are independently selected from the group consisting of H, D, F, Me, and Et;

$R^{14}$ and $R^{15}$ can be attached at any available position on the aromatic ring and are selected from the group consisting of H, D, F, Cl, Br, $CF_3$, $C_1$-$C_6$ alkyl, $C_2$-$C_6$ alkenyl, $C_2$-$C_6$ alkynyl, cycloalkyl, OR, $NR_2$, $NO_2$, $N_3$, CN, $CO_2R$, $CO_2NR_2$, SR, alkylacyl and arylacyl. In the context of this paragraph, R is independently selected from the group consisting of H, Me, Et, isopropyl, cyclopropyl, propargyl, and acyl;

Such that all possible stereoisomers, including optically active isomers, are included whenever stereogenic centers are present;

or a pharmaceutically acceptable salt, prodrug, active metabolite, or solvate thereof.

According to another embodiment, the described invention provides a small molecule anti-cancer compound of Formula I-f wherein:

$X^1$ is selected from the group consisting of H, F, Cl, CN, $NH_2$, $NO_2$, $N_3$, and $SO_2Me$;

n=1 or 2;

$L^2$ is selected from the group consisting of S, O, NH, CHOH, C=O, and —S($CH_2$)—;

$R^1$ and $R^2$ are independently selected from the group consisting of H, $C_1$-$C_3$ alkyl, propargyl, $C_1$-$C_3$ hydroxyalkyl, and acyloxyalkyl;

$R^1$ and $R^2$ may optionally form a ring, such that $R^1$-$R^2$ consists of a four or five subunit chain comprising subunits independently selected from the group consisting of $CH_2$, NH, NMe, and O;

$R^1$ and $R^3$ may optionally form a ring, such that $R^1$-$R^3$=—($CH_2$)$_3$—;

$R^2$ and $R^4$ may optionally form a ring, such that $R^2$-$R^4$ consists of a two subunit chain comprising subunits independently selected from the group consisting of $CH_2$ and CH-alkyl. Additionally, $R^2$ may simultaneously form a ring with $R^1$ as described above;

$R^3$=H;

$R^4$ is selected from the group consisting of H, Me, and propargyl;

$R^{14}$ and $R^{15}$ can be attached at any available position on the aromatic ring and are selected from the group consisting of H, F, Cl, Br, $CF_3$, $C_1$-$C_3$ alkyl, propargyl, OR, $NR_2$, $NO_2$, CN, $CO_2R$, $CO_2NR_2$, and SR. In the context of this paragraph, R is independently selected from the group consisting of H, Me, Et, and propargyl;

Such that all possible stereoisomers, including optically active isomers, are included whenever stereogenic centers are present;

or a pharmaceutically acceptable salt, prodrug, active metabolite, or solvate thereof.

Chemical Substituents

The term "Aliphatic" as used herein, denotes a straight- or branched-chain arrangement of constituent carbon atoms, including, but not limited to paraffins (alkanes), which are saturated, olefins (alkenes or alkadienes), which are unsaturated, and acetylenes (alkynes), which contain a triple bond. In complex structures, the chains may be branched or cross-linked.

The term "lower" as used herein refers to a group having between one and six carbons.

As used herein, the term "alkyl" refers to a straight or branched chain hydrocarbon having from 1 to 25 carbon atoms, or of the numbers of carbon atoms specified (e.g. $C_{1-6}$ alkyl) or any numbers within this range. It is implicitly implied within the context of this application that such alkyl groups can be optionally substituted with substituents such as, but not limited to, halogen, perfluoroalkyl, lower alkyl, lower alkenyl, lower alkynyl, lower cycloalkyl, lower alkoxy, lower cycloalkoxy, lower alkylsulfanyl, oxo, hydroxyl. Examples of "alkyl" as used herein include, but are not limited to, methyl, trifluoromethyl, ethyl, propyl, n-butyl, t-butyl, n-pentyl, isobutyl, and isopropyl, methoxymethy, methoxyethyl, isopropoxybutyl, propynyloxyethyl, and the like.

The term "Alkenyl," as used herein, denotes a monovalent, straight (unbranched) or branched hydrocarbon chain having one or more double bonds therein where the double bond can be unconjugated or conjugated to another unsaturated group (e.g., a polyunsaturated alkenyl) and can be unsubstituted or substituted, with multiple degrees of substitution being allowed. It may be optionally substituted with substituents such as, but not limited to, halogen, perfluoroalkyl, lower alkyl, lower alkenyl, lower alkynyl, lower cycloalkyl, lower alkoxy, lower cycloalkoxy, lower alkylsulfanyl, oxo, hydroxyl. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, 6-methoxyhexenyl, 2-trifluoromethyl-3-butenyl, and the like.

As used herein, the term "alkynyl" refers to a hydrocarbon radical having at least one carbon-carbon triple bond, optionally substituted with substituents such as, without limitation, halogen, perfluoroalkyl, lower alkyl, lower alkenyl, lower alkynyl, lower cycloalkyl, lower alkoxy, lower cycloalkoxy, lower alkylsulfanyl, oxo, hydroxyl.

The term "aryl" as used herein refers to a benzene ring or to an optionally substituted benzene ring system fused to one or more optionally substituted benzene rings, with multiple degrees of substitution being allowed. Substituents include, but are not limited to, cyano, halogen, perfluoroalkyl, aryl, heteroaryl, heterocyclyl, cycloalkyl, lower alkyl, lower alkoxy, lower alkylsulfanyl, oxo, hydroxy, amino optionally substituted by alkyl or aryl or heteroaryl or heterocyclyl or cycloalkyl, aminocarbonyl (—NRC(O)R) optionally substituted by alkyl or aryl or heteroaryl or heterocyclyl or cycloalkyl, carboxy, acyl, acyloxy, alkoxycarbonyl, aryloxy, heteroaryloxy, heterocyclyloxy, aroyloxy, heteroaroyloxy, heterocycloyloxy, carbamoyl optionally substituted by alkyl or cycloalkyl or aryl or heteroaryl or heterocyclyl, aminosulfonyl optionally substituted by alkyl or cycloalkyl or aryl or heteroaryl or heterocyclyl. Examples of aryl include, but are not limited to, phenyl, 2-napthyl, 1-naphthyl, 1-anthracenyl, and the like.

It should be understood that wherever the terms "alkyl" or "aryl" or either of their prefix roots appear in a name of a substituent, they are to be interpreted as including those limitations given above for alkyl and aryl. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, "cycloalkyl" (used interchangeably with "aliphatic cyclic" herein) refers to a non-aromatic monovalent, monocyclic or polycyclic ring structure having a total of from 3 to 10 carbon ring atoms (but no heteroatoms) optionally possessing one or more degrees of unsaturation, optionally substituted with substituents such as, without limitation, halogen, perfluoroalkyl, cycloalkyl, lower alkyl, lower alkoxy, lower alkylsulfanyl, oxo, hydroxyl. "Cycloalkyl" includes by way of example cyclopropyl, cyclobutyl, cyclopentyl, cyclopentenyl, cyclohexyl, cyclohehexenyl, adamantanyl, norbornyl, nobornenyl, cycloheptyl, or cyclooctyl, and the like.

The terms "heterocycle" and "heterocyclic" as used herein are used interchangeably to refer to a three to twelve-membered heterocyclic ring optionally possessing one or more degrees of unsaturation, containing one or more heteroatomic substitutions selected from —S—, —SO—, —SO₂—, —O—, or —N—, optionally substituted with substitutents, including, but not limited to, nitro, cyano, halogen, perfluoroalkyl, aryl, heteroaryl, heterocyclyl, cycloalkyl, lower alkyl, lower alkoxy, lower alkylsulfanyl, lower alkylsulfenyl, lower alkylsulfonyl, oxo, hydroxy, mercapto, amino optionally substituted by alkyl or aryl or heteroaryl or heterocyclyl or cycloalkyl, aminocarbonyl (—NRC(O)R) optionally substituted by alkyl or aryl or heteroaryl or heterocyclyl or cycloalkyl, carboxy, acyl, acyloxy, alkoxycarbonyl, aryloxy, heteroaryloxy, heterocyclyloxy, aroyloxy, heteroaroyloxy, heterocycloyloxy, carbamoyl optionally substituted by alkyl or cycloalkyl or aryl or heteroaryl or heterocyclyl, aminosulfonyl optionally substituted by alkyl or cycloalkyl or aryl or heteroaryl or heterocyclyl, silyloxy optionally substituted by alkyl or aryl, silyl optionally substituted by alkoxy or alkyl or aryl, multiple degrees of substitution being allowed. Such a ring optionally may be fused to one or more of another "heterocyclic" ring(s). Examples of "heterocyclic" include, but are not limited to, pyrrole, furan, thiophene, imidazole, oxazole, thiazole, pyrazole, 3-pyrroline, pyrrolidine, pyridine, pyrimidine, purine, quinoline, isoquinoline, carbazole, tetrahydrofuran, 1,4-dioxane, 1,3-dioxane, piperidine, pyrrolidine, morpholine, piperazine and the like.

Examples of heterocycles include, but are not limited to, pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, beta-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents including, but not limited to, nitro, cyano, halogen, perfluoroalkyl, aryl, heteroaryl, heterocyclyl, cycloalkyl, lower alkyl, lower alkoxy, lower alkylsulfanyl, lower alkylsulfenyl, lower alkylsulfonyl, oxo, hydroxy, mercapto, amino optionally substituted by alkyl or aryl or heteroaryl or heterocyclyl or cycloalkyl, aminocarbonyl (—NRC(O)R) optionally substituted by alkyl or aryl or heteroaryl or heterocyclyl or cycloalkyl, carboxy, acyl, acyloxy, alkoxycarbonyl, aryloxy, heteroaryloxy, heterocyclyloxy, aroyloxy, heteroaroyloxy, heterocycloyloxy, carbamoyl optionally substituted by alkyl or cycloalkyl or aryl or heteroaryl or heterocyclyl, aminosulfonyl optionally substituted by alkyl or cycloalkyl or aryl or heteroaryl or heterocyclyl, silyloxy optionally substituted by alkyl or aryl, silyl optionally substituted by alkoxy or alkyl or aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include, but are not limited to, 5-indanyl, 5,6,7,8-tetrahydro-2-naphthyl,

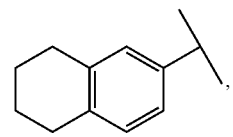

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include, but are not limited to, 1-indanyl, 2-indanyl, 1-(1,2,3,4-tetrahydronaphthyl),

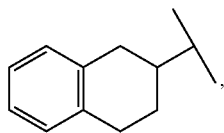

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include, but are not limited to, 3,4-methylenedioxy-1-phenyl,

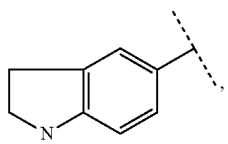

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include, but are not limited to, 2-(1,3-benzodioxolyl),

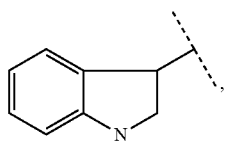

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include, but are not limited to, 5-aza-6-indanyl,

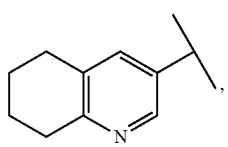

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include, but are not limited to, 5-aza-1-indanyl,

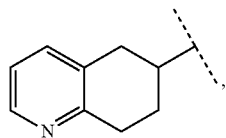

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include, but are not limited to, 1,2,3,4-tetrahydro-beta-carbolin-8-yl,

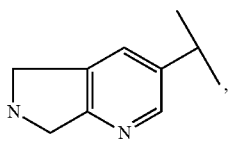

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include, but are not limited to, -5-aza-2,3-dihydrobenzofuran-2-yl,

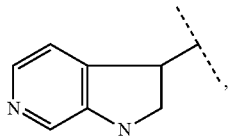

and the like.

As used herein, the term "direct bond", where part of a structural variable specification, refers to the direct joining of the substituents flanking (preceding and succeeding) the variable taken as a "direct bond".

As used herein, the term "O-linked moiety" means a moiety that is bonded through an oxygen atom. Thus, when an R group is an O-linked moiety, that R is bonded through oxygen and it thus can be an ether, an ester (e.g., —O—C(O)-optionally substituted alkyl), a carbonate or a carbamate (e.g., —O—C(O)—NH$_2$ or —O—C(O)—NH-optionally substituted alkyl). Similarly, the term "S-linked moiety" means a moiety that is bonded through a sulfur atom. Thus, when an R group is an S-linked moiety, that R is bonded through sulfur and it thus can be a thioether (e.g., —S-optionally substituted alkyl), a thioester (—S—C(O)-optionally substituted alkyl) or a disulfide (e.g., —S—S-optionally substituted alkyl). The term "N-linked moiety" means a moiety that is bonded through a nitrogen atom. Thus, when an R group is an N-linked moiety, the R group is bonded through nitrogen and one or more of these can thus be an N-linked amino acid such as —NH—CH$_2$—COOH, a carbamate such as —NH—C(O)—O-optionally substituted alkyl, an amine such as —NH-optionally substituted alkyl, an amide such as —NH—C(O)-optionally substituted alkyl or —N$_3$. The term "C-linked moiety" means a moiety that is bonded through a carbon atom. When one or more R group is bonded through carbon, one or more of these thus can be -optionally substituted alkyl such as —C(O)-optionally substituted alkyl hydroxyalkyl, mercaptoalkyl, aminoalkyl or =CH-optionally substituted alkyl.

The term "alkoxy" as used herein refers to the group $R_aO$—, where $R_a$ is alkyl.

The term "alkenyloxy" as used herein refers to the group $R_aO$—, where $R_a$ is alkenyl.

The term "alkynyloxy" as used herein refers to the group $R_aO$—, where $R_a$ is alkynyl.

The term "alkylsulfanyl" as used herein refers to the group $R_aS$—, where $R_a$ is alkyl.

The term "alkenylsulfanyl" as used herein refers to the group $R_aS$—, where $R_a$ is alkenyl.

The term "alkynylsulfanyl" as used herein refers to the group $R_aS$—, where $R_a$ is alkynyl.

The term "alkylsulfenyl" as used herein refers to the group $R_aS(O)$—, where $R_a$ is alkyl.

The term "alkenylsulfenyl" as used herein refers to the group $R_aS(O)$—, where $R_a$ is alkenyl.

The term "alkynylsulfenyl" as used herein refers to the group $R_aS(O)$—, where $R_a$ is alkynyl.

The term "alkylsulfonyl" as used herein refers to the group $R_aSO_2$—, where $R_a$ is alkyl.

The term "alkenylsulfonyl" as used herein refers to the group $R_aSO_2$—, where $R_a$ is alkenyl.

The term "alkynylsulfonyl" as used herein refers to the group $R_aSO_2$—, where $R_a$ is alkynyl.

The term "acyl" as used herein refers to the group $R_aC(O)$—, where $R_a$ is alkyl, alkenyl, alkynyl, cycloalkyl, cycloalkenyl, aryl, heteroaryl, or heterocyclyl.

The term "aroyl" as used herein refers to the group $R_aC(O)$—, where $R_a$ is aryl.

The term "heteroaroyl" as used herein refers to the group $R_aC(O)$—, where $R_a$ is heteroaryl.

The term "heterocycloyl" as used herein refers to the group $R_aC(O)$—, where $R_a$ is heterocyclyl.

The term "alkoxycarbonyl" as used herein refers to the group $R_aOC(O)$—, where $R_a$ is alkyl.

The term "acyloxy" as used herein refers to the group $R_aC(O)O$—, where $R_a$ is alkyl, alkenyl, alkynyl, cycloalkyl, cycloalkenyl, aryl, heteroaryl, or heterocyclyl.

The term "aroyloxy" as used herein refers to the group $R_aC(O)O$—, where $R_a$ is aryl.

The term "heteroaroyloxy" as used herein refers to the group $R_aC(O)O$—, where $R_a$ is heteroaryl.

The term "heterocycloyloxy" as used herein refers to the group $R_aC(O)O$—, where $R_a$ is heterocyclyl.

The term "substituted" as used herein refers to substitution with the named substituent or substituents, multiple degrees of substitution being allowed unless otherwise stated.

The terms "contain" or "containing" can as used herein refers to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$, —$CH_2$—NH—$CH_3$ and so forth.

The term "oxo" as used herein refers to the substituent =O.

The term "halogen" or "halo" as used herein includes iodine, bromine, chlorine and fluorine.

The term "mercapto" as used herein refers to the substituent —SH.

The term "carboxy" as used herein refers to the substituent —COOH.

The term "cyano" as used herein refers to the substituent —CN.

The term "aminosulfonyl" as used herein refers to the substituent —$SO_2NH_2$.

The term "carbamoyl" as used herein refers to the substituent —$C(O)NH_2$.

The term "sulfanyl" as used herein refers to the substituent —S—.

The term "sulfenyl" as used herein refers to the substituent —S(O)—.

The term "sulfonyl" as used herein refers to the substituent —$S(O)_2$—.

The term "ethoxy" as used herein refers to the substituent —O—$CH_2CH_3$.

The term "methoxy" as used herein refers to the substituent —O—$CH_3$.

As used herein, the term "optionally" means that the subsequently described event(s) may or may not occur, and includes both event(s) which occur and events that do not occur.

Compounds of structural formula I and formulas Ia-f may contain one or more asymmetric centers and can thus occur as racemates and racemic mixtures, single enantiomers, diastereomeric mixtures and individual diastereomers. The present invention is meant to comprehend all such isomeric forms of the compounds of structural formula I and formulas Ia-f.

Compounds of structural formula I and formulas Ia-f may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I and formulas Ia-f may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of generic Formula I and formulas Ia-f, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I and formulas Ia-g. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I and formulas Ia-f can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I and formulas Ia-f are meant to also include the pharmaceutically acceptable salts, and also salts that are not pharmaceutically acceptable when they are used as precursors to the free compounds or their pharmaceutically acceptable salts or in other synthetic manipulations.

Compositions

According to another aspect, the described invention provides pharmaceutical compositions comprising a therapeutic amount of at least one of the small molecule anticancer compounds and a pharmaceutically acceptable carrier.

The term "active" as used herein refers to having pharmacological or biological activity or affect. The term "active ingredient" ("AI", "active pharmaceutical ingredient", or "bulk active") is the substance in a drug that is pharmaceutically active.

The terms "formulation" and "composition" are used interchangeably herein to refer to a product of the described invention that comprises all active and inert ingredients. The terms "pharmaceutical formulation" or "pharmaceutical composition" as used herein refer to a formulation or composition that is employed to prevent, reduce in intensity, cure or otherwise treat a target condition or disease.

As used herein, the term "binder" refers to substances that bind or "glue" powders together and make them cohesive by forming granules, thus serving as the "adhesive" in the formulation. Binders add cohesive strength already available in the diluent or bulking agent. Exemplary binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

As used herein, the term "bioavailability" refers to the rate and extent to which the active drug ingredient or therapeutic moiety is absorbed into the systemic circulation from an administered dosage form as compared to a standard or control.

As used herein, the term "capsule" refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

As used herein, the term "coloring agents" refers to excipients that provide coloration to the composition or the dosage form. Such excipients can include food grade dyes and food grade dyes adsorbed onto a Exemplary adsorbent such as clay or aluminum oxide. The amount of the coloring agent can vary from about 0.1 to about 5% by weight of the composition, preferably from about 0.1 to about 1%.

As used herein, the term "diluent" refers to substances that usually make up the major portion of the composition or dosage form. Exemplary diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

As used herein, the term "disintegrant" refers to materials added to the composition to help it break apart (disintegrate) and release the medicaments. Exemplary disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

As used herein, the term "glident" refers to material that prevents caking and improves the flow characteristics of granulations, so that flow is smooth and uniform. Exemplary glidents include silicon dioxide and talc. The amount of glident in the composition can range from about 0.1% to about 5% by weight of the total composition, preferably from about 0.5 to about 2% by weight.

As used herein, the term "lubricant" refers to a substance added to the dosage form to enable the tablet, granules, etc. after it has been compressed, to release from the mold or die by reducing friction or wear. Exemplary lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

As used herein, the term "oral gel" refers to the active ingredients dispersed or solubilized in a hydrophillic semi-solid matrix.

As used herein, the term "tablet" refers to a compressed or molded solid dosage form containing the active ingredients with suitable diluents. The tablet can be prepared by compression of mixtures or granulations obtained by wet granulation, dry granulation or by compaction.

As used herein, the term "therapeutic amount" refers to the amount of a small molecule anti-cancer compound of the described invention that is effective to modulate a cancer cell sensitive to cholesterol biosynthesis pathway inhibition. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. The effective amount for any particular application may vary depending on such factors as the disease or condition being treated, the particular described compound, the size of the subject, or the severity of the disease or condition. One of ordinary skill in the art may determine empirically the therapeutically effective amount of a particular described compound and/or other therapeutic agent without necessitating undue experimentation. It is generally preferred that a maximum dose be used, that is, the highest safe dose according to some medical judgment. The terms "dose" and "dosage" are used interchangeably herein.

For any compound described herein the therapeutically effective amount can be initially determined from preliminary in vitro studies and/or animal models. A therapeutically effective dose can also be determined from human data. The applied dose can be adjusted based on the relative bioavailability and potency of the administered compound.

The formulations of inhibitors may be administered in pharmaceutically acceptable solutions, which may routinely contain pharmaceutically acceptable concentrations of salt, buffering agents, preservatives, compatible carriers, adjuvants, and optionally other therapeutic agents.

According to another embodiment, the compositions of the described invention can further include one or more additional compatible active ingredients. "Compatible" as used herein means that the components of such a composition are capable of being combined with each other in a manner such that there is no interaction that would substantially reduce the efficacy of the composition under ordinary use conditions. As used herein, the phrase "additional active ingredient" refers to an agent, other than a small molecule anticancer compound of the described composition, that exerts a pharmacological, or any other beneficial activity. Nonlimiting examples of such additional therapeutic agents include, without limitation, 5-fluorouracil, leucovorin, oxaliplatin capecitabine, leucovorin, irinotecan, capecitabine, oxaliplatin, bevacizumab, cetuximab, panitumumab, or a combination thereof.

Pharmaceutically Acceptable Carrier

The term "pharmaceutically-acceptable carrier" as used herein refers to one or more compatible solid or liquid filler, diluents or encapsulating substances which are Exemplary for administration to a human or other vertebrate animal. The term "carrier" as used herein refers to an organic or inorganic ingredient, natural or synthetic, with which the active ingredient is combined to facilitate the application. According to some embodiments, the carrier can be inert, or it can possess pharmaceutical benefits.

The components of the pharmaceutical compositions also are capable of being commingled in a manner such that there is no interaction which would substantially impair the desired pharmaceutical efficiency.

The carrier can be liquid or solid and is selected with the planned manner of administration in mind to provide for the desired bulk, consistency, etc., when combined with an active and the other components of a given composition.

Administration

For use in therapy, a therapeutic amount of a small molecule anticancer compound may be administered to a subject by any mode. Administering the pharmaceutical composition may be accomplished by any means known to the skilled artisan. Routes of administration include, but are not limited to, parenteral oral, buccal, topical, by inhalation or insufflation (i.e., through the mouth or through the nose), or rectal.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), intrasternal injection, or infusion techniques. A parenterally administered composition of the present invention is delivered using a needle, e.g., a surgical needle. The term "surgical needle" as used herein, refers to any needle adapted for delivery of fluid (i.e., capable of flow) compositions of the present invention into a selected anatomical structure. Injectable preparations, such as sterile injectable aqueous or oleaginous suspensions, may be formulated according to the known art using Exemplary dispersing or wetting agents and suspending agents.

The compositions of the present invention may be in the form of a sterile injectable aqueous solution or oleaginous suspension. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion in which a finely-divided species is combined with another species, with the former being so finely divided and mixed that it doesn't rapidly settle out. The term "dispersion", as used herein, refers to a two-phase system, in which one phase is distributed as particles or droplets in the second, or continuous phase. In these systems, the dispersed phase frequently is referred to as the discontinuous or internal phase, and the continuous phase is called the external phase or dispersion medium. For example, in coarse dispersions, the particle size is 0.5 mm. In colloidal dispersions, size of the dispersed particle is in the range of approximately 1 nm to 0.5 mm. Molecular dispersion is a dispersion, in which the dispersed phase consists of individual molecules; if the molecules are less than colloidal size, the result is a true solution.

The compositions of the described invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Exemplary emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate.

According to some embodiments, the composition may be formulated for parenteral administration by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Exemplary lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain Exemplary stabilizers or agents, which increase the solubility of the compounds to allow for the preparation of highly concentrated solutions. Alternatively, the active compounds may be in powder form for constitution with a Exemplary vehicle, e.g., sterile pyrogen-free water, before use.

The pharmaceutical compositions also may comprise Exemplary solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Exemplary liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are Exemplary for use in a variety of drug delivery systems. For a brief review of methods for drug delivery, see Langer 1990 Science 249, 1527-1533, which is incorporated herein by reference.

Depending upon the structure, a therapeutic amount of at least one small molecule anti-cancer compound effective to modulate a cancer cell sensitive to cholesterol biosynthesis inhibition of the described invention, and optionally at least one additional active agent, may be administered per se (neat) or, depending upon the structure of the inhibitor, in the form of a pharmaceutically acceptable salt. The inhibitors of the described invention may form pharmaceutically acceptable salts with organic or inorganic acids, or organic or inorganic bases. When used in medicine the salts should be pharmaceutically acceptable, but non-pharmaceutically acceptable salts conveniently may be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group.

By "pharmaceutically acceptable salt" is meant those salts which are, within the scope of sound medical judgment, Exemplary for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002).

The salts may be prepared in situ during the final isolation and purification of the compounds described within the described invention or separately by reacting a free base function with a Exemplary organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides, such as methyl, ethyl, propyl, and butyl chlorides, bromides and iodides; dialkyl sulfates like dimethyl, diethyl, dibutyl and diamyl sulfates; long chain halides, such as decyl, lauryl, myristyl and stearyl chlorides, bromides and iodides; arylalkyl halides, such as benzyl and phenethyl bromides, and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with an Exemplary base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts may be also obtained using standard procedures well known in the art, for example by reacting a sufficiently basic compound such as an amine with a Exemplary acid affording a physiologically acceptable anion. Alkali metal (for example, sodium, potassium or lithium) or alkaline earth metal (for example calcium or magnesium) salts of carboxylic acids may also be made.

The formulations may be presented conveniently in unit dosage form and may be prepared by any of the methods well known in the art of pharmacy. All methods include the step of bringing into association a composition, or a pharmaceutically acceptable salt or solvate thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of Exemplary aqueous and nonaqueous carriers, diluents, solvents or vehicles include water, ethanol, polyols (propylene glycol, polyethylene glycol, glycerol, and the like), Exemplary mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The therapeutic agent(s), including the composition(s) of the described invention may be provided in particles. The term "particles" as used herein refers to nano or microparticles (or in some instances larger) that may contain in whole or in part the composition or the other therapeutic agent(s) as described herein. The particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, non-erodible, biodegradable, or nonbiodegradable material or combinations thereof. The particles may be microcapsules that contain the composition in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. For example, bioadhesive polymers include bioerodible hydrogels as described by Sawhney et al in Macromolecules (1993) 26, 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that can result in substantially constant blood levels of a drug over an extended time period. Alternatively, delayed absorption of a parenterally administered drug form is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

According to some embodiments, use of a long-term sustained release implant may be desirable for treatment of chronic conditions. The term "long-term" release, as used herein, means that the implant is constructed and arranged to deliver therapeutic levels of the active ingredient for at least 7 days, and preferably about 30 to about 60 days. Long-term sustained release implants are well-known to those of ordinary skill in the art and include some of the release systems described above.

Injectable depot forms are made by forming microencapsulated matrices of a described inhibitor in biodegradable polymers such as polylactide-polyglycolide. Depending upon the ratio of inhibitor to polymer and the nature of the particular polymer employed, the rate of drug release may be controlled. Such long acting formulations may be formulated with appropriate polymeric or hydrophobic materials (for example as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations also are prepared by entrapping the inhibitor of the described invention in liposomes or microemulsions, which are compatible with body tissues.

The injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Exemplary buffering agents include: acetic acid and a salt (1-2% w/v); citric acid and a salt (1-3% w/v); boric acid and a salt (0.5-2.5% w/v); and phosphoric acid and a salt (0.8-2% w/v). Exemplary preservatives include benzalkonium chloride (0.003-0.03% w/v); chlorobutanol (0.3-0.9% w/v); parabens (0.01-0.25% w/v) and thimerosal (0.004-0.02% w/v).

For oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents also may be incorporated in the mixture. Powders and tablets may comprise from about 5 to about 95 percent of the described composition. Exemplary binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

For buccal administration, the compositions of the present invention may take the form of tablets or lozenges formulated in a conventional manner for this route.

Liquid form preparations include solutions, suspensions and emulsions.

Liquid form preparations also may include solutions for intranasal administration.

The compositions of the present invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the present invention is placed within a Exemplary dosage receptacle in an amount sufficient to provide a subject with a unit dosage treatment. The dosage receptacle is one that fits within a Exemplary inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027. Exemplary containers also include those used in conjunction with Glaxo's Ventolin® Rotohaler brand powder inhaler or Fison's Spinhaler® brand powder inhaler. Another Exemplary unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). Each of these references is incorporated herein by reference.

The compositions of the present invention may be in the form of suppositories for rectal administration of the composition. "Rectal" or "rectally" as used herein refers to introduction into the body through the rectum where absorption occurs through the walls of the rectum. These compositions can be prepared by mixing the drug with a Exemplary nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

The term "topical" refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably. For the purpose of this application, topical applications shall include mouthwashes and gargles.

Topical administration may also involve the use of transdermal administration such as transdermal patches or iontophoresis devices which are prepared according to techniques and procedures well known in the art. The terms "transdermal delivery system", transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for postmenopausal indications, and nicotine for smoking cessation.

Patches exemplary for use in the present invention include, but are not limited to, (1) the matrix patch; (2) the reservoir patch; (3) the multi-laminate drug-in-adhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

According to some embodiments, the solid tumor is a brain tumor. According to some embodiments the brain tumor is a glioma. According to some embodiments, the glioma is a glioblastoma multiforme. According to some embodiments, the solid brain tumor comprises cancer stem cells. According to some embodiments, the therapeutic amount of the small molecule anti-cancer compound is effective to inhibit tumor growth, inhibit tumor proliferation, induce cell death, or a combination thereof. According to some embodiments, the therapeutic amount of the small molecule anti-cancer compounds is effective to selectively inhibit growth of the cancer stem cells, proliferation of the cancer stem cells, to induce cell death of the cancer stem cells, or a combination thereof, without affecting normally dividing cells. According to some embodiments, the therapeutic amount is effective to inhibit a cholesterol biosynthesis pathway.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the described invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Compounds

A mouse colony with 100% incidence of GBM and with conditional knockout of p53, pTEN and NF1 genes (Mut6; glioblastoma) was used to isolate primary neuronal stem cells from GBM tumors cultured in 5% Oxygen and in serum free media with defined growth factors. Primary cells from multiple tumors were pooled for high throughput screening with controls against the University of Texas Southwestern (UTSW) compound file, which encompasses ~200,000 synthetic compounds that represent a large chemical space from several commercial vendors, including 1200 marketed drugs from the Prestwick Chemical Library®, and 600 compounds that went to pre-clinical tests from the NIH library.

A luminescence-based Celltiter-Glo® assay was performed to measure cell viability, using ATP levels as the readout. In brief, opaque-walled multiwell plates with Mut6 cells in culture medium (250 per well, 384-well plates) were prepared. Control wells containing medium without cells were prepared to obtain a value for background luminescence. Test compounds were added to experimental wells, and incubated according to culture protocol. The plate and its contents were incubated at 37° C., 5% Oxygen for 96 hours. An ATP standard curve was generated immediately prior to adding the CellTiter-Glo® Reagent. A volume of CellTiter-Glo® Reagent equal to the volume of cell culture medium present in each well (25 µl of reagent to 25 µl of medium containing cells for a 384-well plate) was added. The contents were mixed for 2 minutes on an orbital shaker to induce cell lysis. The plate was allowed to incubate at room temperature for 10 minutes to stabilize the luminescent signal and luminescence recorded. (e.g. GloMax®, Lumistar, SPECTROstar, PHERAstar FS).

Figure 6:
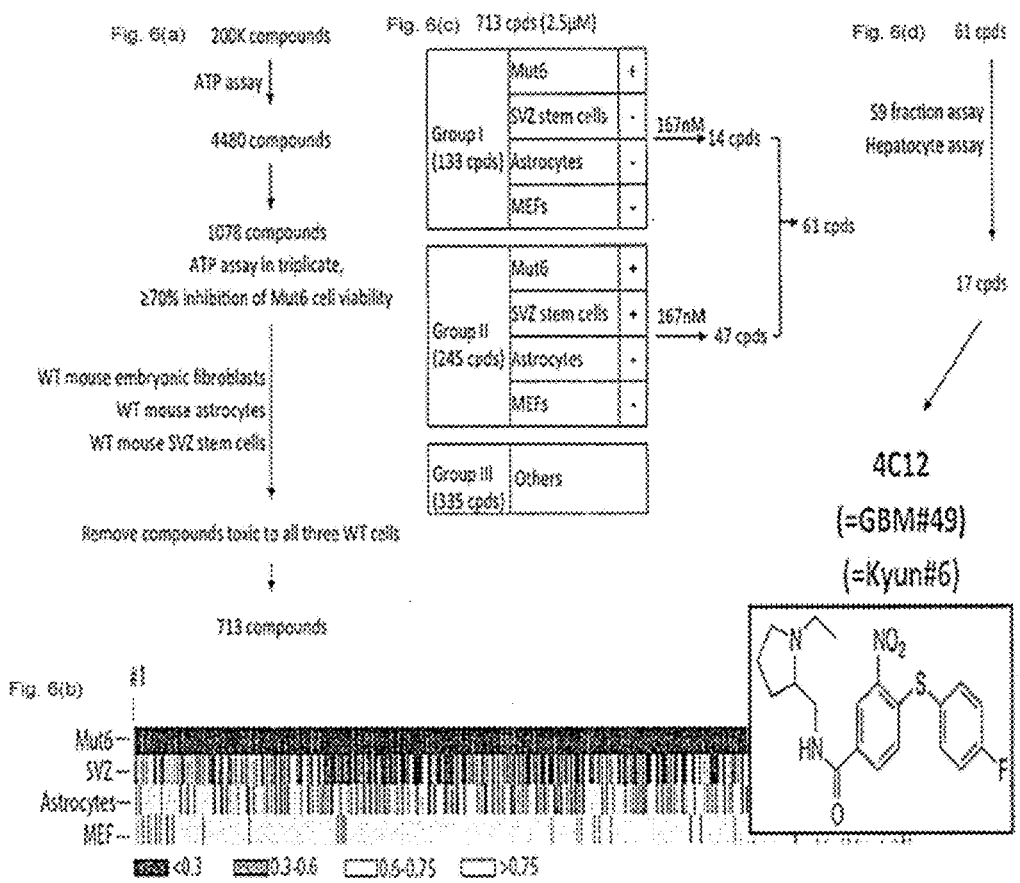
FIG. 6 comprising FIG. 6(a), FIG. 6(b), FIG. 6(c)

This primary screen yielded 4480 positive hits with ≥50% inhibition of cell consumption (based on a z-score of ≤−3, which means that the z-score of −3 was 3 standard deviations below the mean). The compounds were further screened to identify compounds that displayed ≥70% inhibition of Mut6 ATP consumption. This screen identified 1078 compounds. The compounds were tested against normally dividing cells, e.g., wild type mouse embryonic fibroblasts, wild type mouse astrocytes, and wild type mouse SVZ stem cells. Any compound toxic to all three wild type normally dividing cells was removed, resulting in 713 small molecules, of which, after counterscreening at lower molarity against normal astrocytes and mouse embryonic fibroblasts (MEFs), 61 compounds were determined to kill only the cancer stem cells. The 61 compounds were analyzed by S9 fraction assay and hepatocyte assay, leaving 17 candidate compounds. The overall screening strategy is shown in FIG. 6.

S9 Metabolism Assay

Female ICR/CD-1 mouse S9 fractions were purchased from Celsis/In Vitro Technologies (Baltimore, Md.). 25 µl (0.5 mg) of S9 protein was added to a 15 ml glass screw cap tube. 350 µl of a 50 mM Tris, pH 7.5 solution, containing the compound of interest was added on ice. The final concentration of compound after addition of all reagents was 2 µM. 125 µl of an NADPH-regenerating system (1.7 mg/ml NADP, 7.8 mg/ml glucose-6-phosphate, 6 U/ml glucose-6-phosphate dehydrogenase in 2% w/v $NaHCO_3$/10 mm $MgCl_2$) was added for analysis of Phase I metabolism. Uridine 5'-diphospho-α-D-glucuronic acid (UDPGA 1.9 mg/ml) and 3'-phosphoadenosine-5'-phosphosulphate (PAPS, 100 mg/ml) were additionally added for phase II reactions. The tube was then placed in a 37° C. shaking water bath. At varying time points after addition of phase I and phase II cofactors, the reaction was stopped by the addition of 0.5 ml of methanol containing 0.2% formic acid and 200 ng/ml internal standard (either n-benzylbenzamide or tolbutamide, Sigma, St. Louis, Mo.). The samples were incubated 10' at RT and then spun at 16,100×g for 5 min in a microcentrifuge. The supernatant was analyzed by LC-MS/MS. Metabolism of 7-ethoxycoumarin was used to monitor hepatocyte performance. Analytical methods were developed for each compound using an Applied Biosystems (Foster City, Calif.) 4000-QTrap, a combination triple quadrupole/ion trap instrument. The parent ion and the two most prominent daughter ions were followed to confirm compound identity, although only the most abundant daughter was used for quantitation. A Shimadzu (Columbia, Md.) Prominence LC with Agilent C18 XDB column (5 micron packing; 50×4.6 mm) was used for chromatography.

Hepatocyte Metabolism Assay

Male ICR/CD-1 mouse hepatocytes, InVitroGRO HI and HT Medium, and Celsis Torpedo Antibiotic Mix were purchased from Celsis/In Vitro Technologies (Baltimore, Md.). Cryopreserved hepatocytes were thawed in HT Media containing antibiotics, resuspended in HI media at 2×10$^6$/mL and plated in 96-well plates at 0.05 mL ($10^5$ cells)/well. Compounds to be tested were dissolved in DMSO at 2 mM, further diluted to 4 µM in HI media, and added to the cells in 50 µL so that the final compound concentration was 2 µM. Two additional wells containing compound and no cells were plated to serve as time 0 ($C_0$) and end-point solvent control (Cep). The cells were then placed in a 37° C., 5% $CO_2$ incubator. At the time points indicated, the well contents were harvested and a 2-fold volume of methanol containing 0.15% formic acid and 150 ng/ml internal standard (either n-benzylbenzamide or tolbutamide, Sigma, St. Louis, Mo.) added to lyse the cells and precipitate proteins. The samples were incubated 10 min at RT and then spun at 16,100 g for 5 min in a microcentrifuge. The supernatant was analyzed by LC-MS/MS. Metabolism of 7-ethoxycoumarin was used to monitor hepatocyte performance. Analytical methods were developed for each compound using an Applied Biosystems (Foster City, Calif.) 4000-QTrap, a combination triple quadrupole/ion trap instrument. The parent ion and the two most prominent daughter ions were followed to confirm compound identity, although only the most abundant daughter was used for quantitation. A Shimadzu (Columbia, Md.) Prominence LC with Agilent C18 XDB column (5 micron packing; 50×4.6 mm) was used for chromatography.

Figure 7:
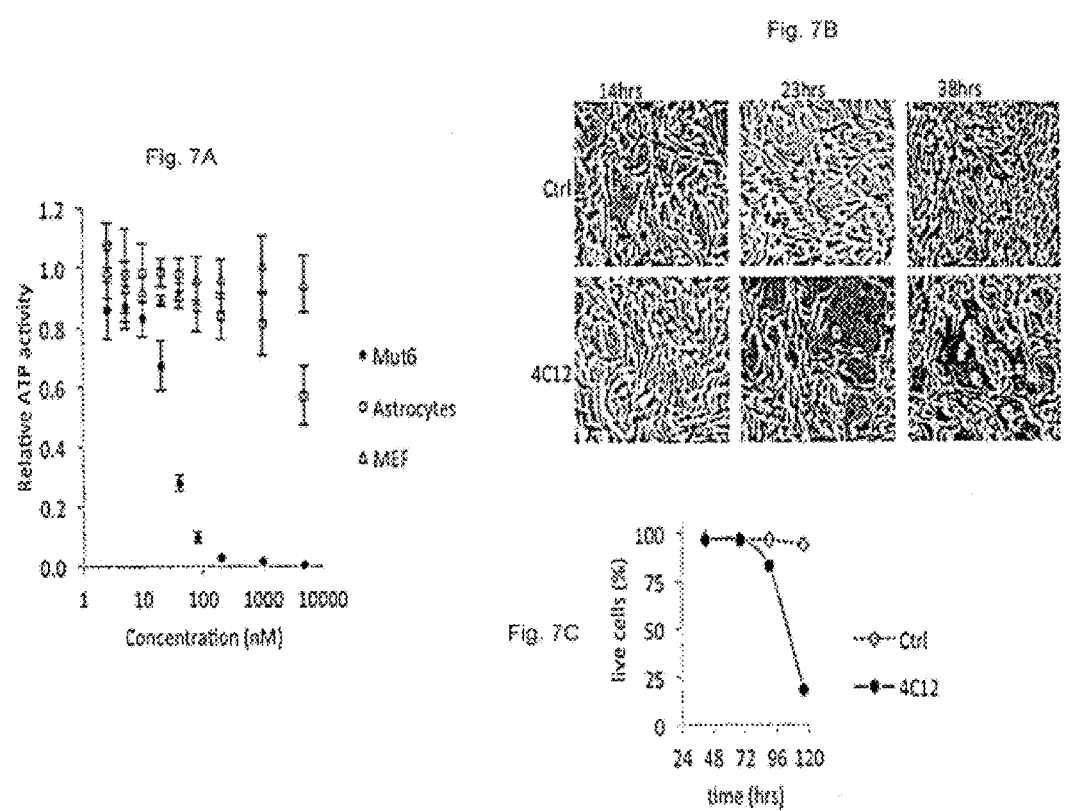
FIG. 7 comprising FIG. 7A, FIG. 7B
Figure 8:
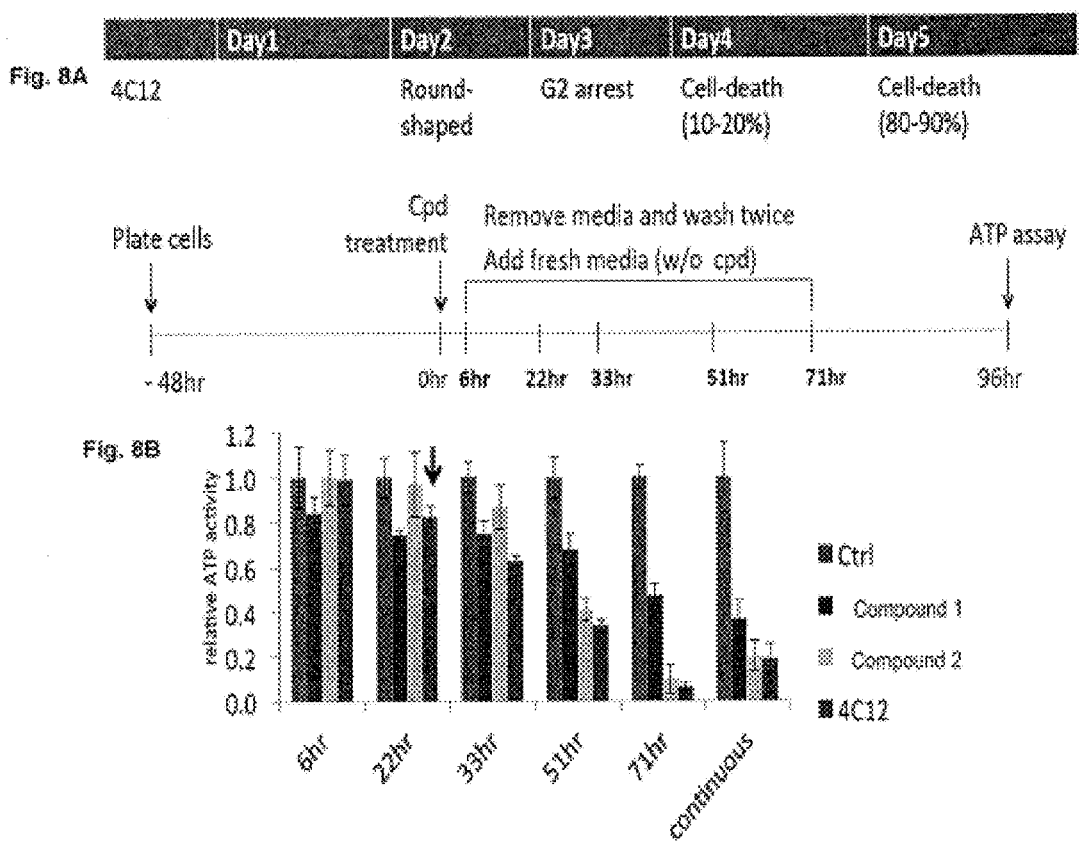
FIG. 8 comprising FIG. 8A

Example 2. Candidate Compound DS-1-033 (Hereinafter Compound 4C12) Showed Selective Toxicity Towards Mut6 Cells FIG. 7 shows that compound 4C12 induces cell death in Mut6 tumor cells. Normal astrocytes, Mut6 cells and mouse embryonic fibroblasts were treated with increasing concentrations of compound 4C12. FIG. 7A, which shows a plot of relative ATP activity (y axis, a measure of viability) versus concentration (nM), shows that compound 4C12 has an ED50 of 50 nM against Mut6 cells. Normal astrocytes and MEFs were unaffected by compound 4C12. FIG. 7B shows phase contrast microscopy of Mut6 cells and control MEFs after 14 hours, 23 hours and 38 hours treatment with compound 4C12 and a negative control containing vehicle only. The plot below shows that all cells treated with vehicle (negative control) remained viable, while only 50% of the Mut6 tumor cells treated with compound 4C12 were viable after 96 hours.

Figure 9:
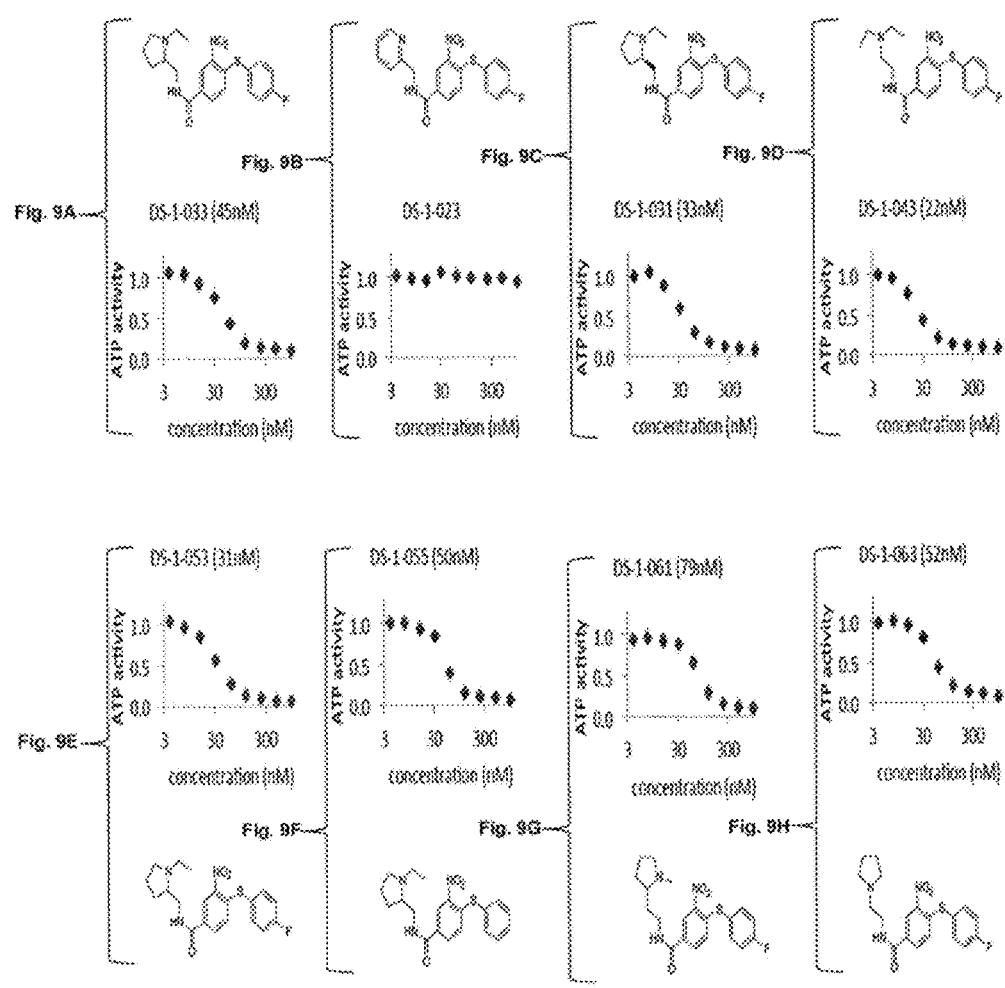
FIG. 9 comprising figures FIG. 9A to FIG. 9QQQ shows 1050 curves for each analog compound in Table A plotted as ATP activity (y axis, a measure of viability) vs. concentration (nM) (x-axis).
Figure 9:
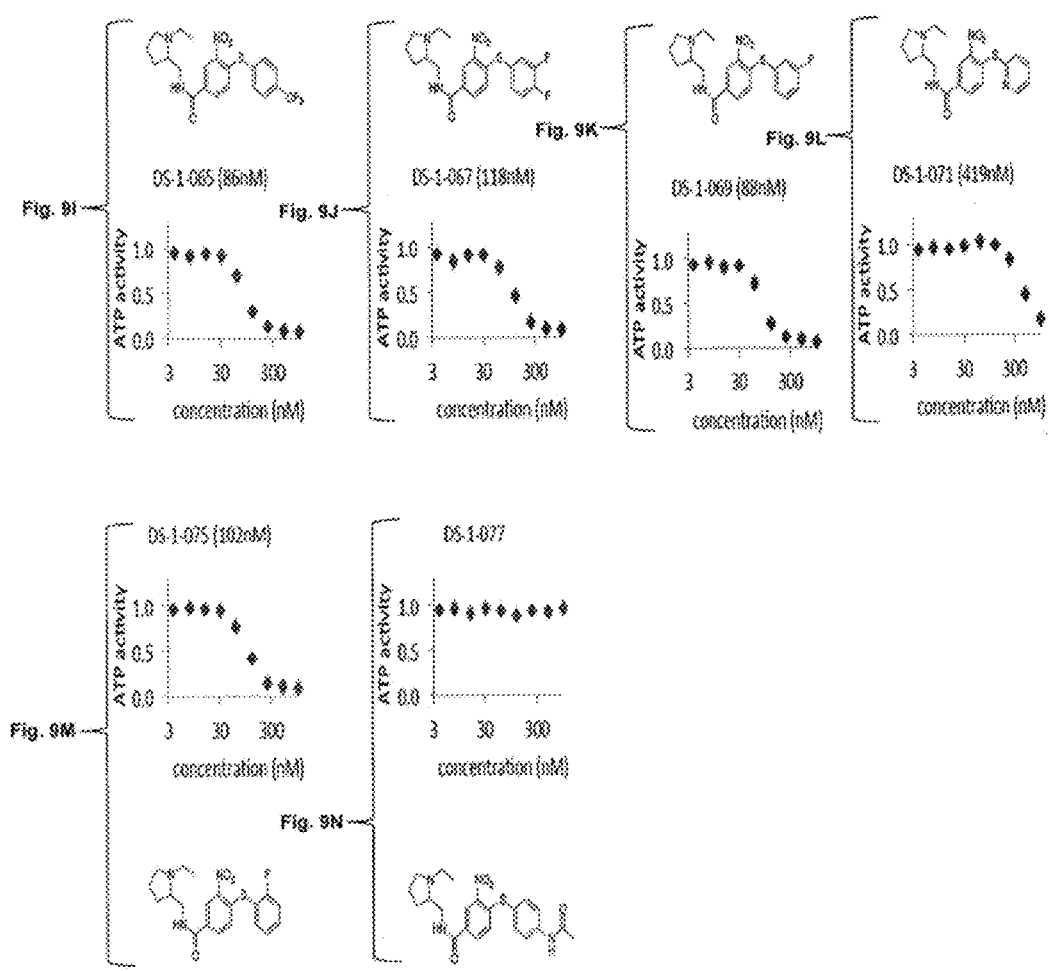
Figure 9:
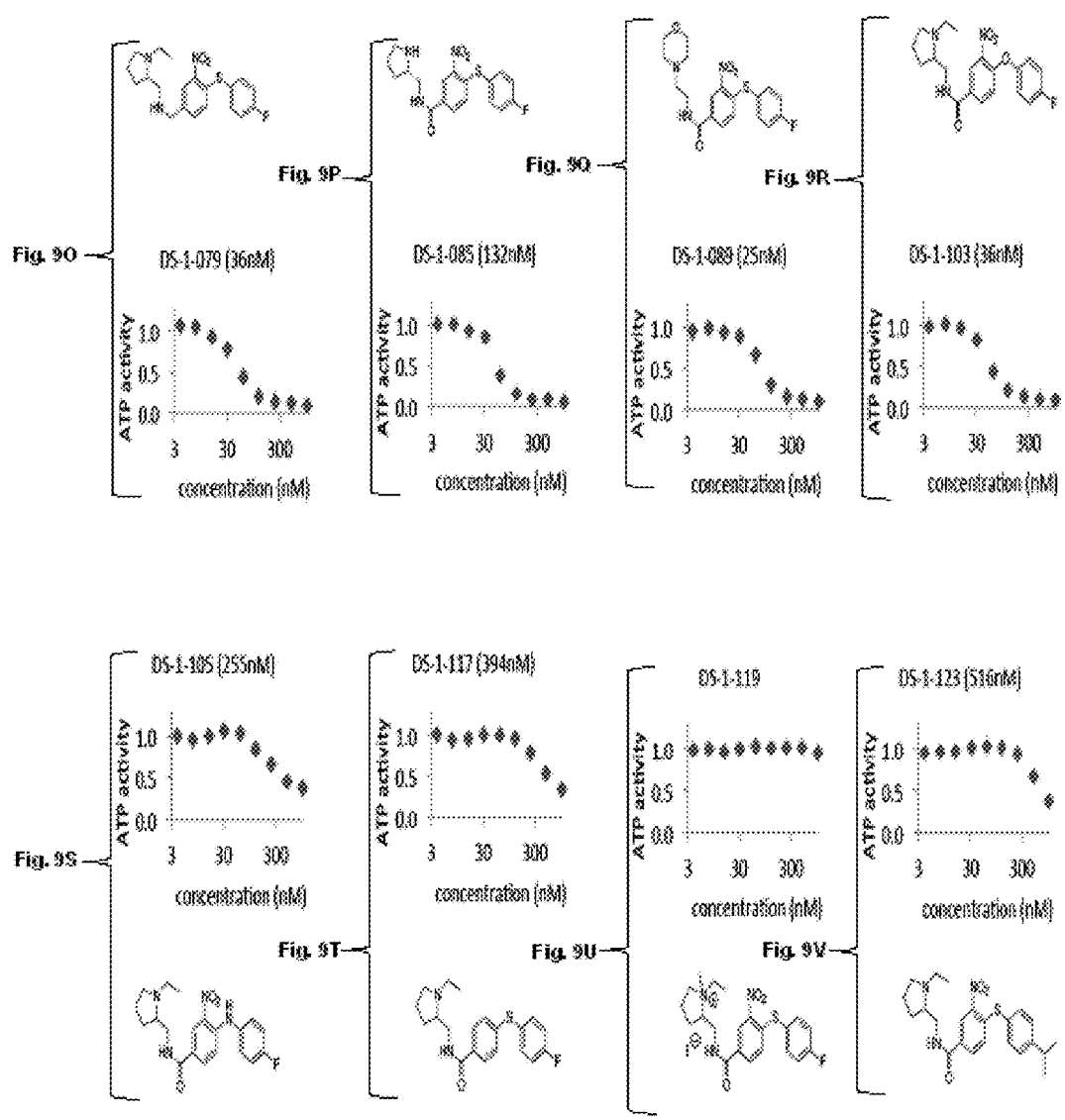
Figure 9:
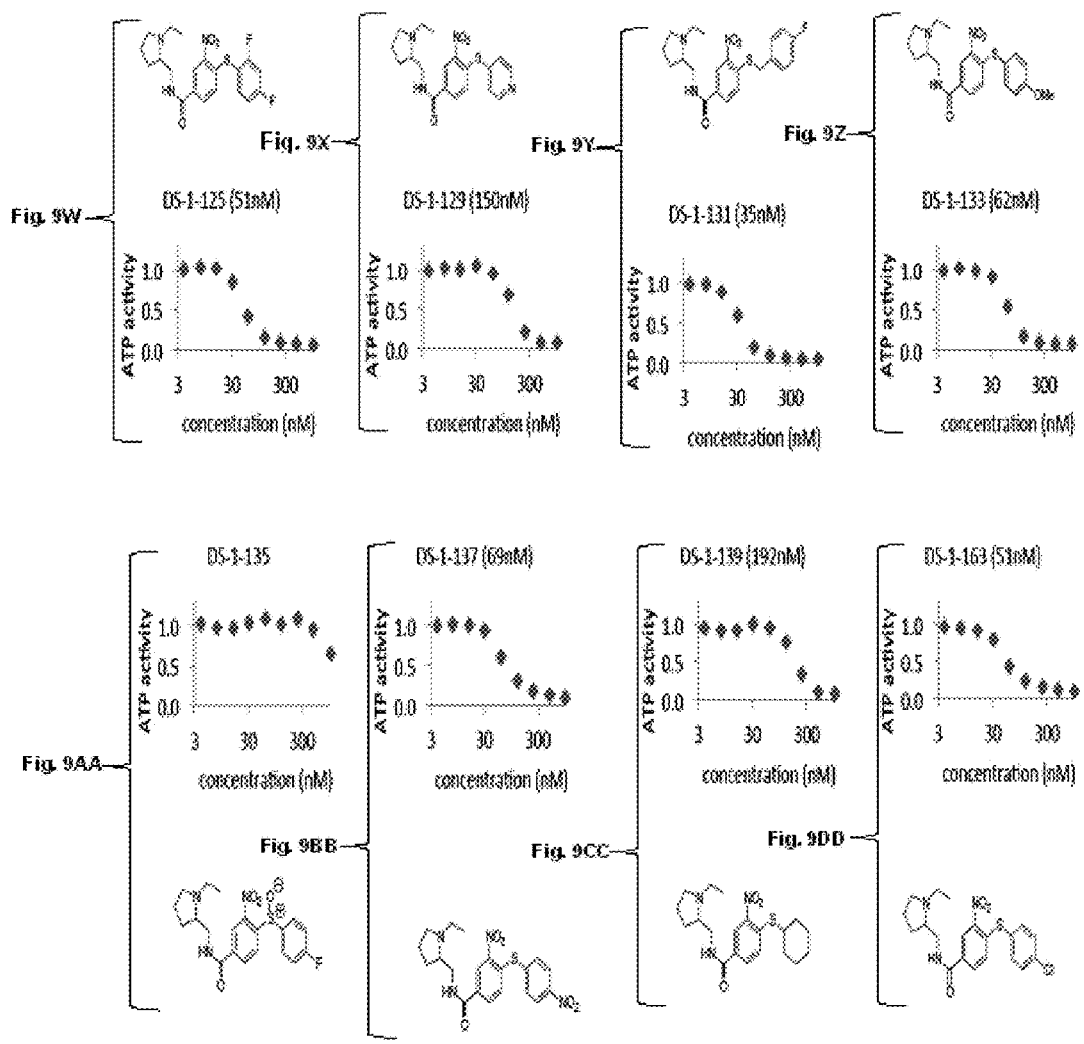
Figure 9:
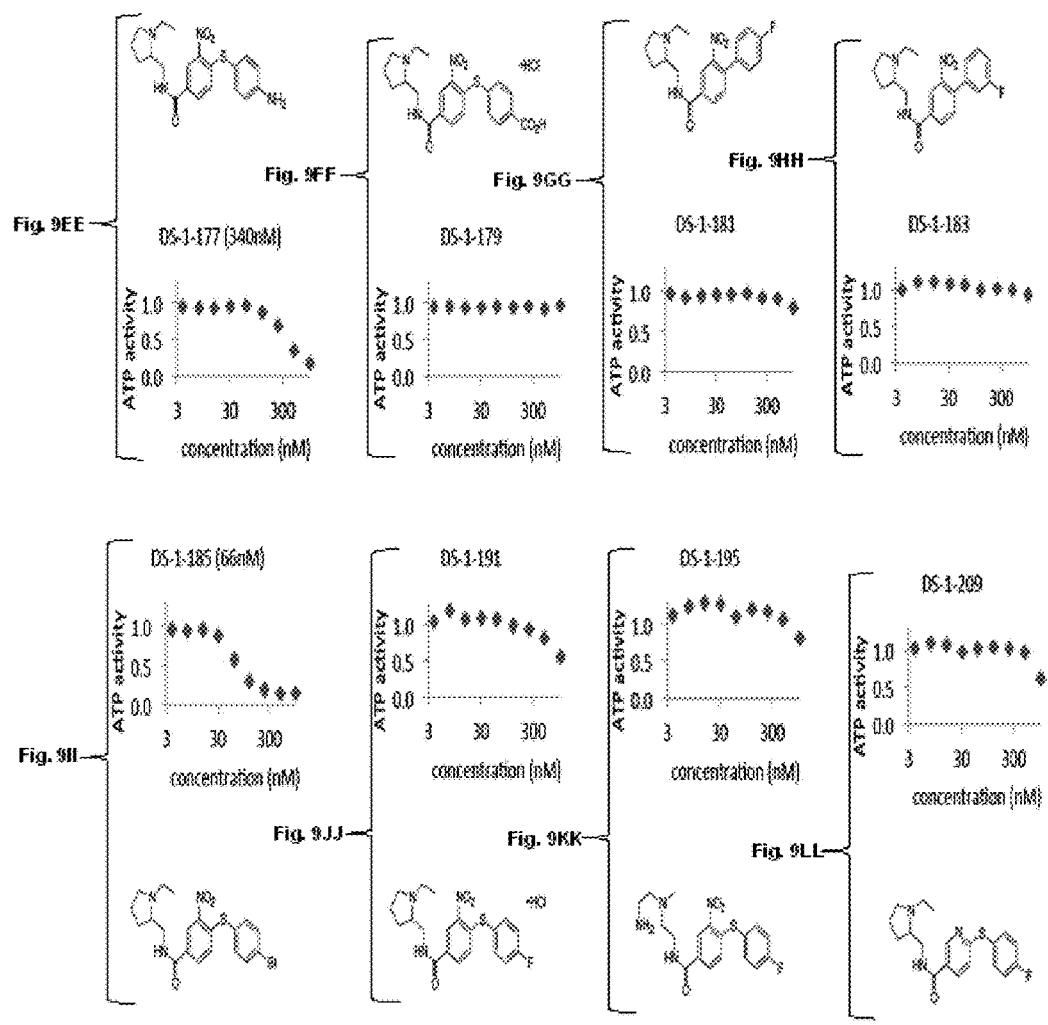
Figure 9:
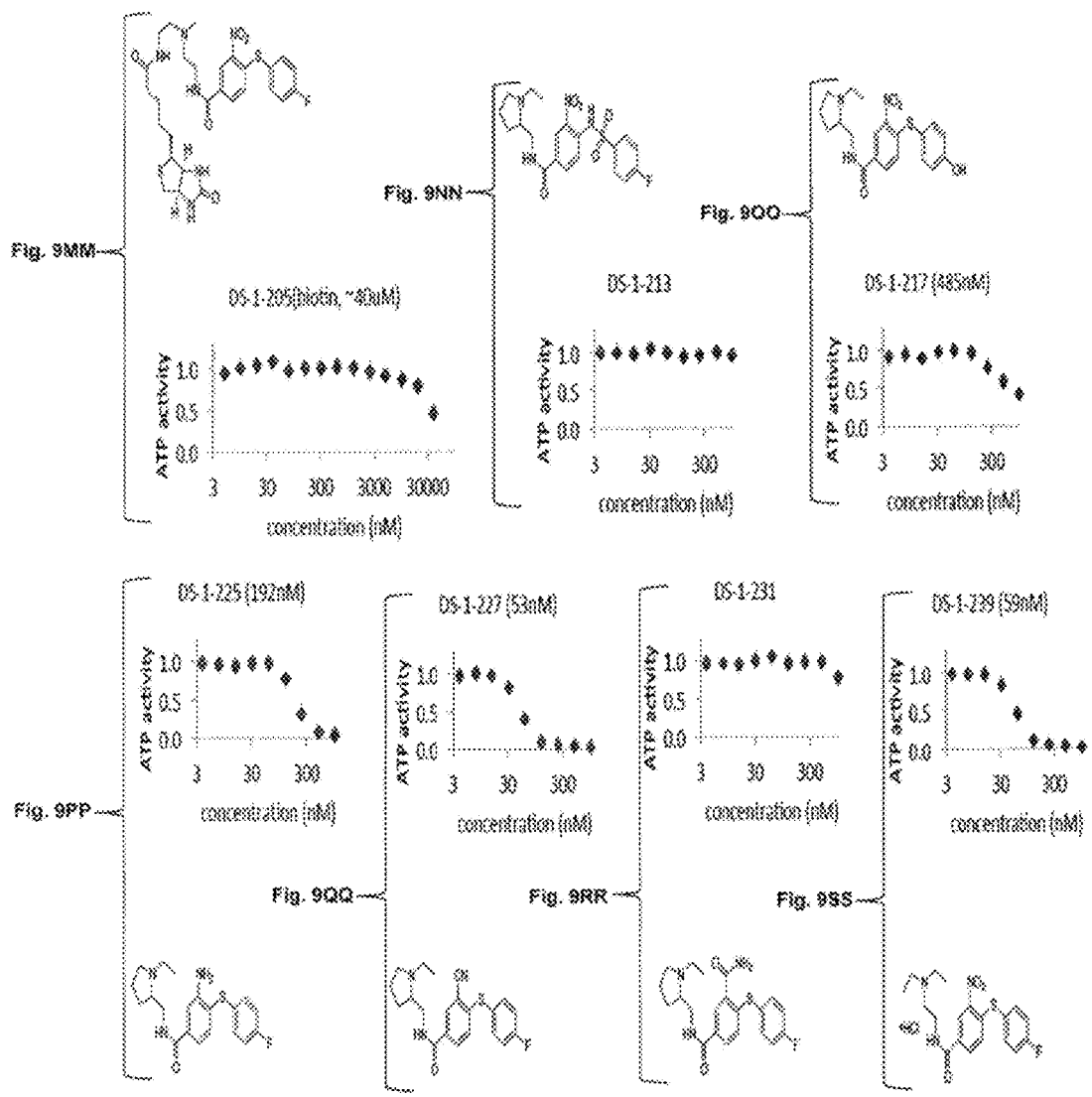
Figure 9:
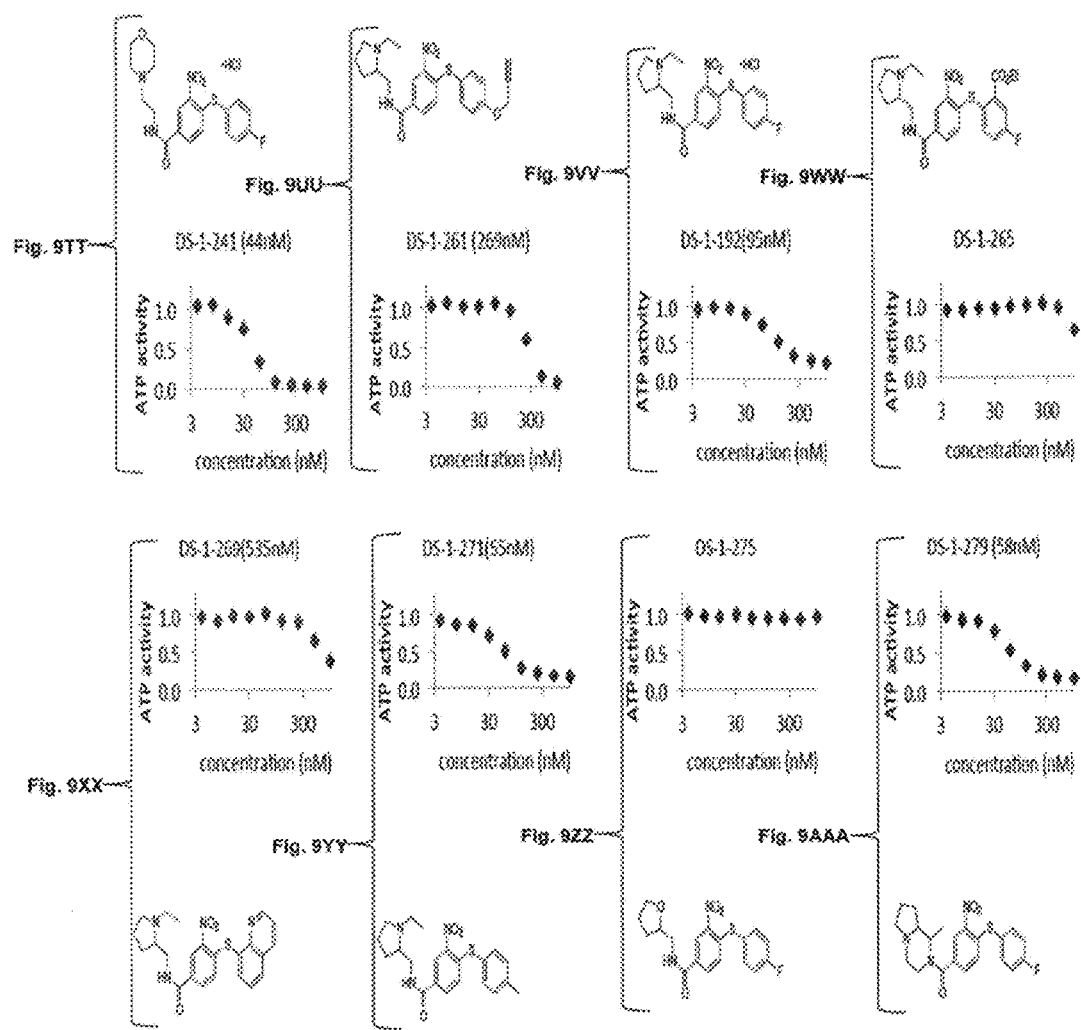
Figure 9:
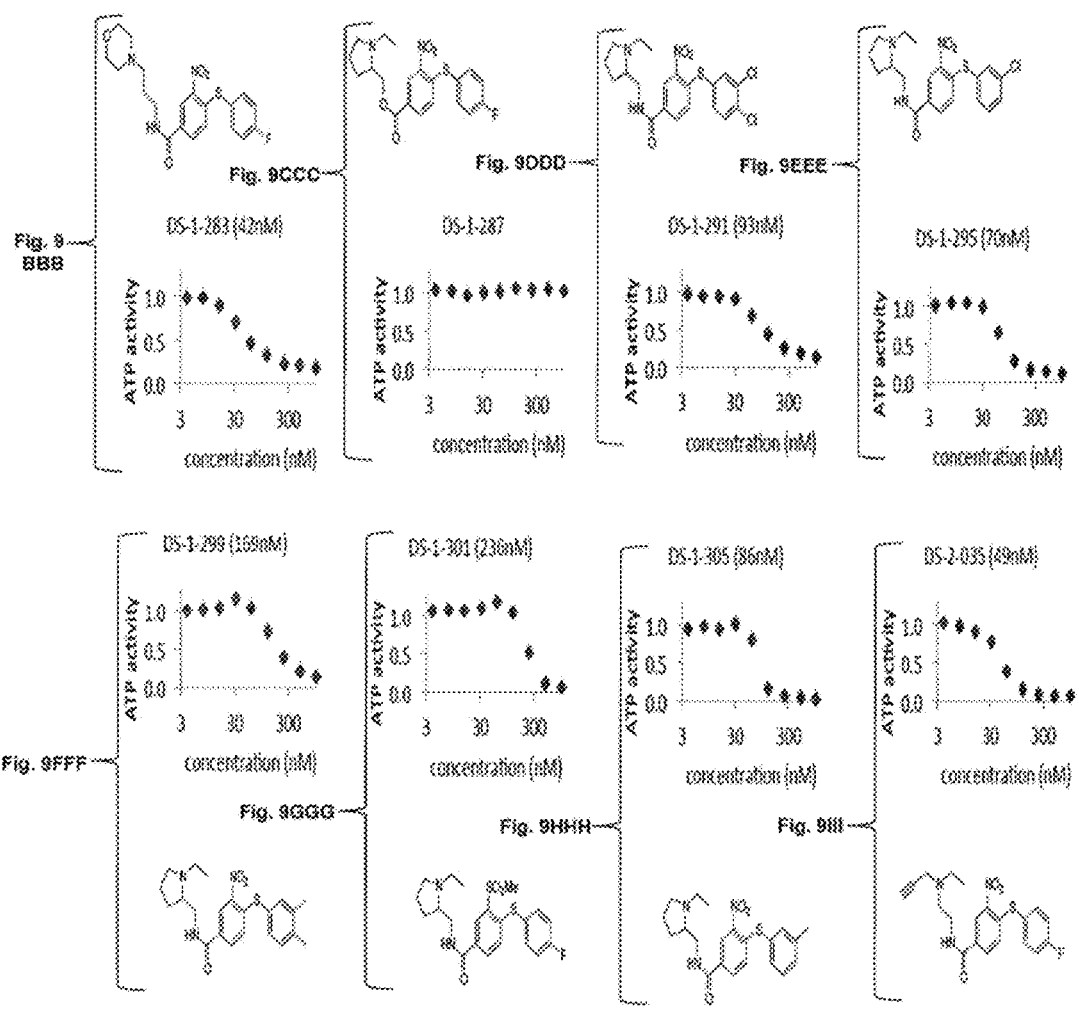
Figure 9:
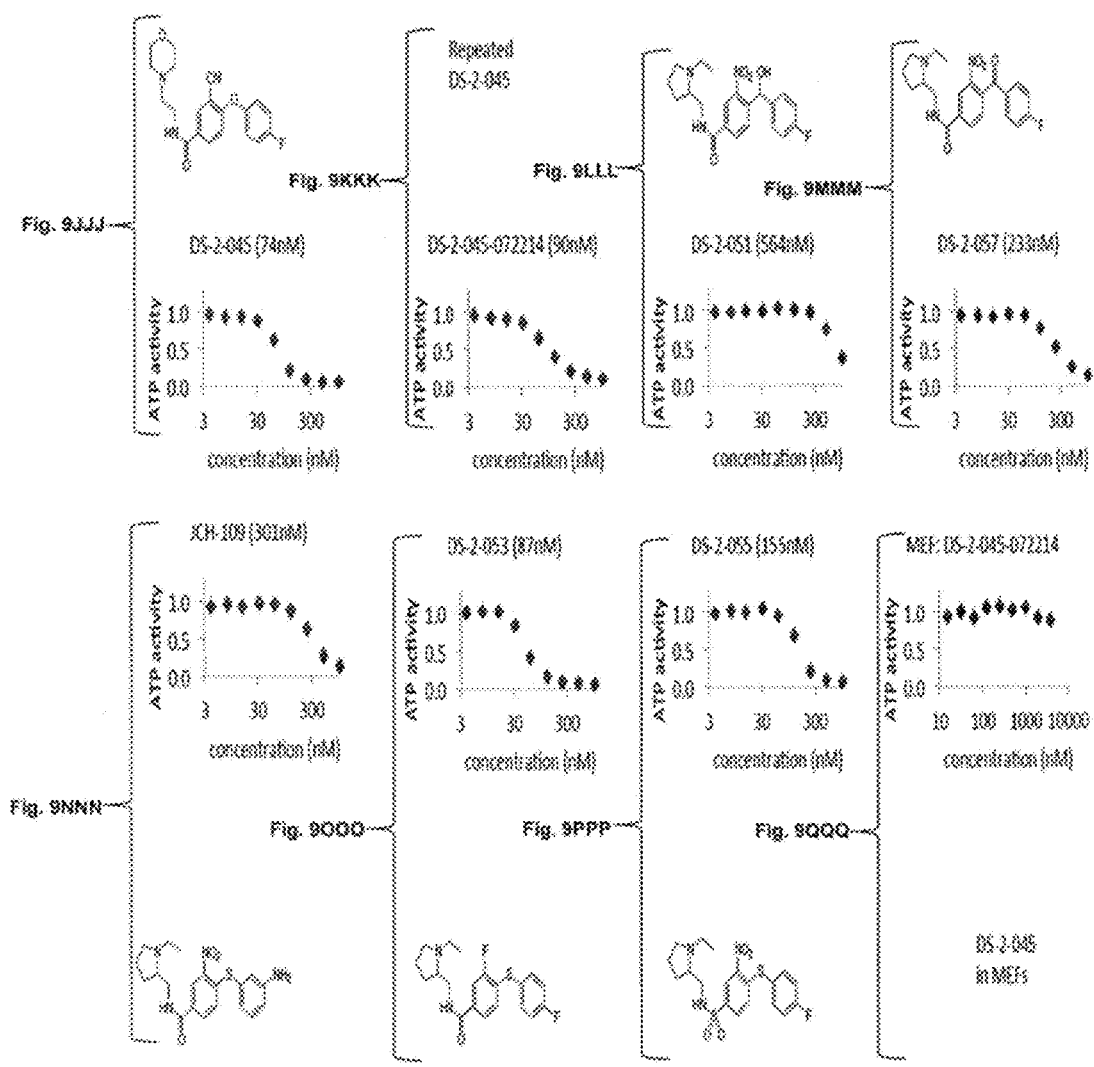

Compound 4C12 served as initial lead compound for analog development and for additional studies. Exemplary analog compounds and their properties are shown in Table A. A druglikeness central nervous system multiparameter optimization (CNS MPO) algorithm was built using a set of six physicochemical parameters, i.e., [(a) lipophilicity, calculated partition coefficient (ClogP); (b) calculated distribution coefficient at pH=7.4 (ClogD); (c) molecular weight (MW); (d) topological polar surface area (TPSA); (e) number of hydrogen bond donors (HBD); (f) most basic center (pK(a))). See Wager, T T et al, "Moving beyond rules: the development of a central nervous system multi-parameter-optimization (CNS MPO) approach to enable alignment of drug-like properties," ACS Chem. Neurosci. 1(6): 435-49 (2010). IC50 curves for the analog compounds plotted as ATP activity (y axis, a measure of viability) vs. concentration (nM) (x-axis) are shown in FIG. 9.

General Procedure A-1:

In a flask equipped with a reflux condenser, the carboxylic acid (10 mmol, 1 eq) and sodium acetate (1.1 eq) were suspended in water (20 mL). 4-Fluorothiophenol (1.1 eq) was introduced in one portion and the reaction mixture was stirred at 90° C. After 4-16 h, the resulting solid product was filtered at room temperature and washed with water (80 mL) and hexanes (30 mL), and dried under high vacuum.

General Procedure A-2:

A 15 mL pressure tube was charged with the aryl fluoride DS-1-095 (0.5 mmol, 1 eq), water (2 mL), the nucleophile (1.1 eq) and sodium bicarbonate (1.1 eq). The tube was sealed and the reaction mixture was stirred at 90° C. for 2 h. A precipitate appeared and the suspension was stirred overnight at room temperature. The solid product was filtered and washed with water (20 mL) and hexanes (10 mL), and dried under high vacuum.

General Procedure A-3:

A 15 mL pressure tube was charged with the aryl fluoride (1 mmol, 1 eq), water (5 mL), the nucleophile (1.1 eq) and sodium bicarbonate (2.1 eq). The tube was sealed and the reaction mixture was stirred at 90° C. for 2 h. A precipitate appeared and the suspension was stirred overnight at room temperature. The solid product was filtered and washed with water (20 mL) and hexanes (10 mL), and dried under high vacuum.

General Procedure A-4:

A 15 mL pressure tube was charged with the aryl fluoride (2.0 mmol, 1 eq), dry dimethylformamide (5 mL), the nucleophile (4.0 mmol, 2 eq) and potassium carbonate (829 mg, 6.0 mmol, 3 eq). The tube was sealed and the reaction mixture was stirred vigorously at 90° C. for 10 h. At room temperature, the reaction mixture was diluted with dichloromethane (30 mL) and sodium hydroxide 1 M (20 mL). The organic phase was washed with 15% aq. lithium chloride (5×20 mL), dried over anhydrous magnesium sulfate and concentrated under reduced pressure.

General Procedure B-1:

In a 10 mL oven-dried flask, the carboxylic acid DS-1-021 (1 mmol, 1 eq) was suspended in dry dichloromethane (5 mL). N-methyl morpholine (1 eq) was added dropwise and the resulting yellow homogeneous solution was cooled to 0° C. Isobutyl chloroformate (1 eq) was introduced dropwise. After 1 h, the amine (1.1 eq) was added dropwise and the reaction mixture was warmed to room temperature. After 4 h, dichloromethane (5 mL) and water (5 mL) were introduced and the organic phase was washed with water (10 mL), saturated sodium carbonate (3×10 mL). A precipitate appeared and was dissolved with water and the organic phase was washed with brine (10 mL). The organic phase was dried over magnesium sulfate, filtered and concentrated under reduced pressure. Purification by column chromatography on silica gel (0-10% MeOH in DCM, MeOH containing 1% Et₃N) afforded the pure product.

General Procedure B-2:

A 10 mL oven-dried flask was charged with the acyl chloride DS-1-059 (312 mg, 1.0 mmol, 1 eq), dry dichloromethane (1 mL) and 4-dimethylaminopyridine (2.5 mol %) and cooled to 0° C. A solution of the amine (1 eq) in dry dichloromethane (1 mL) was added dropwise over 10 min and the reaction mixture was slowly warmed to room temperature. After 16 h, the reaction mixture was diluted with dichloromethane (10 mL), washed with saturated sodium bicarbonate (2×5 mL), dried over magnesium sulfate and concentrated under reduced pressure. Purification by column chromatography on silica gel (0-20% MeOH in DCM, MeOH containing 1% NH₃) afforded the pure product.

General Procedure B-3:

A 50 mL oven-dried flask was charged with the carboxylic acid (30.0 mmol, 1 eq) and thionyl chloride (7.5 mL) and heated to reflux. After 4 h, the resulting homogeneous mixture was concentrated to dryness under reduced pressure. The residue obtained was then dissolved in dry toluene or dichloromethane (5 mL) and the solvent was evaporated. This process was repeated twice yielding the acyl chloride. Dry dichloromethane (20 mL) and 4-dimethylaminopyridine (0.1 mol %) were introduced and the flask was cooled to 0° C. A solution of the amine (1 eq) in dry dichloromethane (10 mL) was added dropwise over 15 min and the resulting solution was slowly warmed to room temperature. After 3 h, a suspension was obtained and the solid was filtered, washed with diethyl ether (3×20 mL) and dried under high vacuum to yield the pure product.

General Procedure C:

A 25 mL three-necked flask fitted with a reflux condenser was charged with DS-1-175 (492 mg, 1.3 mmol, 1 eq), the boronic acid (308 mg, 2.2 mmol, 1.76 eq), potassium carbonate (829 mg, 6.0 mmol, 4.8 eq), water (2 mL) and toluene (2.9 mL). The resulting suspension was degassed by 3 freeze-pump-thaw cycles and the tetrakis(triphenylphosphine)palladium(0) (46 mg, 0.04 mmol, 3.2 mol %) was introduced. The reaction mixture was heated to reflux under argon and the homogeneous yellow solution was vigorously stirred overnight. At room temperature, the reaction mixture was filtered through Celite, and was washed with diethyl ether (25 mL). The organic phase was extracted with 2 M HCl (2×10 mL), the aqueous layers were basified with solid potassium hydroxide to pH~12-13 and were extracted with dichloromethane (3×10 mL). The organic phases were dried over magnesium sulfate, filtered and concentrated under reduced pressure. Purification by column chromatography on silica gel (0-20% MeOH in DCM, MeOH containing 1% NH₃) afforded the pure product.

General Procedure D:

A 4 mL vial was charged with the amine and methanol (0.12 M). Hydrogen chloride was bubbled through the suspension until the solid entirely dissolved. The resulting homogeneous solution was concentrated under reduced pressure to afford the hydrochloride salt.

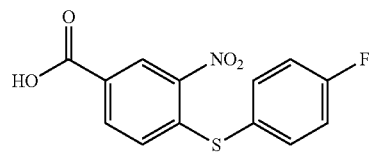 [SMILES: O=C(O)c1ccc(Sc2ccc(F)cc2)c([N+](=O)[O-])c1]

4-((4-fluorophenyl)thio)-3-nitrobenzoic acid (DS-1-021)

Following the general procedure A-1 using 4-fluoro-3-nitrobenzoic acid (10.0 mmol). Bright yellow microcrystalline powder (96%). $^1$H NMR (400 MHz, DMSO-d$_6$) δ 13.54 (bs, 1H), 8.61 (t, J=1.8 Hz, 1H), 8.00 (dt, J=8.5, 1.8 Hz, 1H), 7.73-7.67 (m, 2H), 7.42 (td, J=8.8, 1.5 Hz, 2H), 6.90 (dd, J=8.6, 1.6 Hz, 1H). $^{13}$C NMR (100 MHz, DMSO-d$_6$) δ 165.3, 163.6 (d, J$_{CF}$=249.3 Hz), 143.9, 143.4 (d, J$_{CF}$=1.0 Hz), 138.3 (d, J$_{CF}$=8.9 Hz), 134.1, 128.2, 128.1, 126.5, 125.1 (d, J$_{CF}$=3.3 Hz), 117.8 (d, J$_{CF}$=22.1 Hz). IR (thin film): 3100, 1691, 1606, 1524, 1490, 1412, 1337, 1239, 1159 cm$^{-1}$. MS (ES-API) m/z: 292.0 (100%, [M−H]$^-$, C$_{13}$H$_7$FNO$_4$S requires 292.0). mp: 214° C. (dec.).

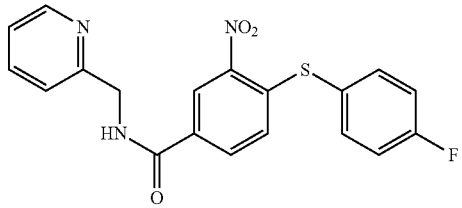 [SMILES: O=C(NCc1ccccn1)c1ccc(Sc2ccc(F)cc2)c([N+](=O)[O-])c1]

4-((4-fluorophenyl)thio)-3-nitro-N-(pyridin-2-ylmethyl)benzamide (DS-1-023)

Following the general procedure B-1 using 2-picolylamine. Yellow solid (85%). $^1$H NMR (400 MHz, DMSO-d$_6$) δ 9.42 (t, J=6.0 Hz, 1H), 8.83-8.78 (m, 1H), 8.53-8.48 (m, 1H), 8.05 (dt, J=8.5, 1.4 Hz, 1H), 7.78-7.70 (m, 3H), 7.44 (t, J=8.7 Hz, 2H), 7.32 (d, J=7.8 Hz, 1H), 7.27 (dd, J=7.5, 4.9 Hz, 1H), 6.93 (d, J=8.5 Hz, 1H), 4.57 (d, J=5.8 Hz, 2H). $^{13}$C NMR (100 MHz, DMSO-d$_6$) δ 163.8, 163.5 (d, J$_{CF}$=249.1 Hz), 158.3, 148.9, 144.1, 141.5 (d, J$_{CF}$=1.5 Hz), 138.2 (d, J$_{CF}$=8.9 Hz), 136.7, 132.7, 131.5, 128.0, 125.4 (d, J$_{CF}$=3.2 Hz), 124.7, 122.2, 121.1, 117.8 (d, J$_{CF}$=22.1 Hz), 44.8. IR (thin film): 3072, 1651, 1645, 1607, 1590, 1520, 1489, 1338, 1226, 1158 cm$^{-1}$. MS (ES-API) m/z: 384.1 (100%, [M+H]$^+$, C$_{19}$H$_{15}$FN$_3$O$_3$S requires 384.1). mp: 140-141° C.

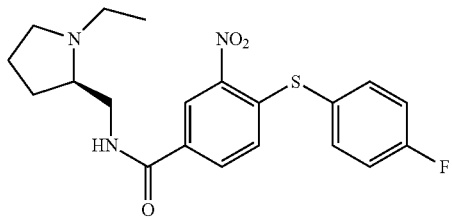 [SMILES: CCN1CCC[C@@H]1CNC(=O)c1ccc(Sc2ccc(F)cc2)c([N+](=O)[O-])c1]

(R)—N-((1-ethylpyrrolidin-2-yl)methyl)-4-((4-fluorophenyl)thio)-3-nitrobenzamide (DS-1-031)

Following the general procedure B-1 using (R)-(+)-2-aminomethyl-1-ethylpyrrolidine. Yellow solid (46%). $^1$H NMR (400 MHz, CDCl$_3$) δ 8.63 (t, J=2.4 Hz, 1H), 7.76 (dd, J=9.0, 2.6 Hz, 1H), 7.59 (ddd, J=8.0, 5.1, 2.7 Hz, 2H), 7.21 (t, J=8.6 Hz, 2H), 6.87 (d, J=8.5 Hz, 2H), 3.71-3.63 (m, 1H), 3.34-3.26 (m, 1H), 3.19 (t, J=8.2 Hz, 1H), 2.80 (td, J=7.9, 3.8 Hz, 1H), 2.68 (s, 1H), 2.31-2.15 (m, 2H), 1.97-1.86 (m, 1H), 1.78-1.55 (m, 3H), 1.11 (t, J=7.4 Hz, 3H). $^{13}$C NMR (100 MHz, CDCl$_3$) δ 164.9, 164.2 (d, J$_{CF}$=252.4 Hz), 144.4, 143.2, 138.3 (d, J$_{CF}$=8.6 Hz), 131.9, 131.6, 128.2, 125.6 (d, J$_{CF}$=3.6 Hz), 124.5 (d, J$_{CF}$=2.5 Hz), 117.8 (d, J$_{CF}$=21.9 Hz), 62.1, 53.6, 48.1, 40.9, 28.3, 23.1, 14.2. IR (thin film): 3097, 2971, 2877, 2807, 1652, 1645, 1607, 1590, 1520, 1490, 1338, 1294, 1235, 1157 cm$^{-1}$. [α]$_D$: +37.51° (0.885, MeOH). mp: 113° C.

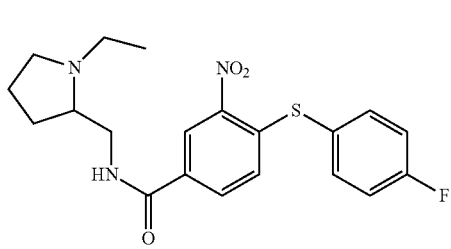

N-((1-ethylpyrrolidin-2-yl)methyl)-4-((4-fluorophenyl)thio)-3-nitrobenzamide (DS-1-033)

Following the general procedure B-1 using 2-aminomethyl-1-ethylpyrrolidine. Yellow solid (82%). $^1$H NMR (400 MHz, CDCl$_3$) δ 8.62 (d, J=2.0 Hz, 1H), 7.75 (dd, J=8.5, 2.0 Hz, 1H), 7.61-7.55 (m, 2H), 7.21 (t, J=8.5 Hz, 2H), 6.87 (d, J=8.5 Hz, 2H), 3.67 (ddd, J=13.8, 7.3, 2.6 Hz, 1H), 3.30 (ddd, J=13.7, 4.4, 2.5 Hz, 1H), 3.19 (td, J=8.3, 2.5 Hz, 1H), 2.80 (dq, J=12.0, 7.4 Hz, 1H), 2.72-2.64 (m, 1H), 2.30-2.15 (m, 2H), 1.96-1.86 (m, 1H), 1.78-1.54 (m, 3H), 1.11 (t, J=7.2 Hz, 3H). $^{13}$C NMR (100 MHz, CDCl$_3$) δ 164.9, 164.2 (d, J$_{CF}$=252.3 Hz), 144.4, 143.2 (d, J$_{CF}$=1.6 Hz), 138.3 (d, J$_{CF}$=8.6 Hz), 131.9, 131.6, 128.2, 125.6 (d, J$_{CF}$=3.6 Hz), 124.5 (d, J$_{CF}$=1.7 Hz), 117.8 (d, J$_{CF}$=22.0 Hz), 62.0, 53.6, 48.1, 40.9, 28.4, 23.1, 14.2.

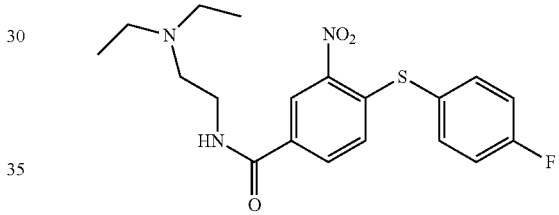

N-(2-(diethylamino)ethyl)-4-((4-fluorophenyl)thio)-3-nitrobenzamide (DS-1-043)

Following the general procedure B-2 using N,N-diethylethylenediamine. Yellow solid (32%). $^1$H NMR (400 MHz, CDCl$_3$) δ 8.60 (t, J=1.9 Hz, 1H), 7.74 (d, J=8.5 Hz, 1H), 7.61-7.52 (m, 2H), 7.23-7.15 (m, 2H), 7.07 (s, 1H), 6.84 (dd, J=8.6, 1.8 Hz, 1H), 3.45 (q, J=4.8 Hz, 2H), 2.63 (t, J=5.4 Hz, 2H), 2.54 (q, J=7.1 Hz, 4H), 1.01 (t, J=7.0 Hz, 6H). $^{13}$C NMR (100 MHz, CDCl$_3$) δ 164.4, 164.2 (d, J$_{CF}$=252.3 Hz), 144.4, 143.2 (d, J$_{CF}$=1.6 Hz), 138.3 (d, J$_{CF}$=8.6 Hz), 131.9, 131.6, 128.2 (d, J$_{CF}$=2.1 Hz), 125.6 (d, J$_{CF}$=3.6 Hz), 124.3 (d, J$_{CF}$=2.1 Hz), 117.8 (d, J$_{CF}$=22.0 Hz), 51.0, 46.8, 37.5, 12.1. IR (thin film): 3096, 2972, 2935, 2821, 1652, 1645, 1608, 1558, 1538, 1506, 1489, 1338, 1294, 1227, 1158 cm$^{-1}$. MS (ES-API) m/z: 392.1 (100%, [M+H]$^+$, C$_{19}$H$_{23}$FN$_3$O$_3$S requires 392.1). mp: 98° C.

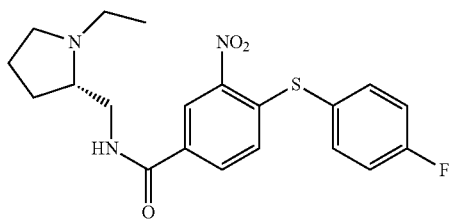 [SMILES: CCN1CCC[C@H]1CNC(=O)c1ccc(Sc2ccc(F)cc2)c([N+](=O)[O-])c1]

(S)—N-((1-ethylpyrrolidin-2-yl)methyl)-4-((4-fluorophenyl)thio)-3-nitrobenzamide (DS-1-053)

Following the general procedure B-2 using (S)-(−)-2-aminomethyl-1-ethylpyrrolidine. Yellow solid (82%). $^1$H NMR (400 MHz, CDCl$_3$) δ 8.61 (d, J=2.0 Hz, 1H), 7.74 (dd, J=8.6, 2.0 Hz, 1H), 7.60-7.53 (m, 2H), 7.22-7.16 (m, 2H), 7.03 (d, J=5.2 Hz, 1H), 6.84 (d, J=8.5 Hz, 1H), 3.65 (ddd, J=13.6, 7.3, 2.7 Hz, 1H), 3.27 (ddd, J=13.7, 4.7, 2.8 Hz, 1H), 3.16 (ddd, J=9.5, 7.1, 2.6 Hz, 1H), 2.79 (dq, J=12.0, 7.4 Hz, 1H), 2.66 (dddd, J=8.8, 6.9, 4.6, 2.7 Hz, 1H), 2.29-2.12 (m, 2H), 1.89 (dtd, J=12.3, 8.5, 7.0 Hz, 1H), 1.77-1.52 (m, 3H), 1.09 (t, J=7.2 Hz, 3H). $^{13}$C NMR (100 MHz, CDCl$_3$) δ 164.9, 164.2 (d, J$_{CF}$=252.4 Hz), 144.4, 143.2, 138.3 (d, J$_{CF}$=8.6 Hz), 131.9, 131.6, 128.2 (d, J$_{CF}$=1.5 Hz), 125.6, 124.5 (d, J$_{CF}$=2.0 Hz), 117.8 (d, J$_{CF}$=22.0 Hz), 62.0, 53.6, 48.1, 40.9, 28.4, 23.1, 14.2. [α]$_D$:—40.35° (1.13, MeOH).

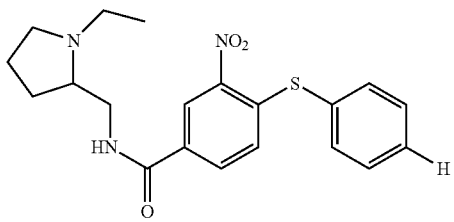 [SMILES: CCN1CCCC1CNC(=O)c1ccc(Sc2ccccc2)c([N+](=O)[O-])c1]

N-((1-ethylpyrrolidin-2-yl)methyl)-3-nitro-4-(phenylthio)benzamide (DS-1-055)

Following the general procedure A-2 using thiophenol. Light yellow solid (74%). $^1$H NMR (400 MHz, CDCl$_3$) δ 8.64 (s, 1H), 7.74 (d, J=8.6 Hz, 1H), 7.61-7.47 (m, 4H), 7.07-6.96 (m, 1H), 6.90 (d, J=8.5 Hz, 1H), 3.68 (dd, J=13.7, 7.6 Hz, 1H), 3.34-3.23 (m, 1H), 3.17 (t, J=8.0 Hz, 1H), 2.81 (dq, J=15.0, 7.4 Hz, 1H), 2.71-2.62 (m, 1H), 2.22 (m, 2H), 2.03 (bs, 1H), 1.89 (dt, J=16.9, 8.4 Hz, 1H), 1.79-1.53 (m, 3H), 1.11 (t, J=7.2 Hz, 3H). $^{13}$C NMR (100 MHz, CDCl$_3$) δ 165.1, 144.5, 143.4, 136.1, 131.7, 131.5, 130.6, 130.5, 130.4, 128.5, 124.4, 62.3, 53.6, 48.2, 40.8, 28.2, 23.1, 14.2. IR (thin film): 2969, 2807, 1639, 1608, 1546, 1521, 1460, 1338, 1294, 1241 cm$^{-1}$. MS (ES-API) m/z: 386.2 (100%, [M+H]$^+$, C$_{20}$H$_{24}$N$_3$O$_3$S requires 386.2). mp: 76° C.

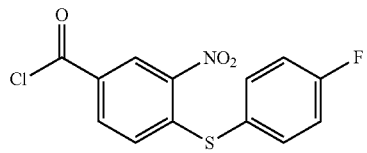 [SMILES: O=C(Cl)c1ccc(Sc2ccc(F)cc2)c([N+](=O)[O-])c1]

4-((4-fluorophenyl)thio)-3-nitrobenzoyl chloride (DS-1-059)

A 25 mL oven-dried flask equipped with a reflux condenser was charged with DS-1-021 (1.47 g, 5.0 mmol, 1 eq) and thionyl chloride (10 mL) and heated to reflux overnight. The resulting homogeneous mixture was then concentrated to dryness under reduced pressure. The yellow solid obtained was then dissolved in dry toluene (5 mL) and the solvent was evaporated. This process was repeated twice yielding the product (1.50 g, 4.8 mmol, 96%) as a bright yellow microcrystalline powder. $^1$H NMR (400 MHz, CDCl$_3$) δ 8.96 (t, J=1.6 Hz, 1H), 7.99 (d, J=8.7 Hz, 1H), 7.63-7.56 (m, 2H), 7.25 (t, J=8.0 Hz, 2H), 6.94 (dd, J=8.8, 1.3 Hz, 1H). $^{13}$C NMR (100 MHz, CDCl$_3$) δ 166.2, 164.5 (d, J$_{CF}$=253.3 Hz), 148.8 (d, J$_{CF}$=1.8 Hz), 144.4, 138.3 (d, J$_{CF}$=8.7 Hz), 134.2, 130.1, 129.0, 128.4, 124.7 (d, J$_{CF}$=3.6 Hz), 118.2 (d, J$_{CF}$=22.1 Hz). IR (thin film): 1739, 1597, 1525, 1490, 1394, 1298, 1196, 1159, 970, 836, 731 cm$^{-1}$. mp: 140° C.

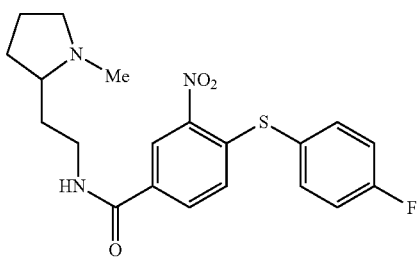 [SMILES: CN1CCCC1CCNC(=O)c1ccc(Sc2ccc(F)cc2)c([N+](=O)[O-])c1]

4-(4-fluorophenyl)thio)-N-(2-(1-methylpyrrolidin-2-yl)ethyl)-3-nitrobenzamide (DS-1-061)

Following the general procedure B-2 using 2-(2-aminoethyl)-1-methylpyrrolidine. Light yellow solid (84%). $^1$H NMR (400 MHz, CDCl$_3$) δ 9.51 (s, 1H), 8.54 (d, J=1.2 Hz, 1H), 7.87 (dd, J=8.6, 1.2 Hz, 1H), 7.57 (dd, J=8.2, 5.4 Hz, 2H), 7.20 (t, J=8.4 Hz, 2H), 6.84 (d, J=8.5 Hz, 1H), 3.74 (dq, J=15.1, 5.1 Hz, 1H), 3.49-3.38 (m, 1H), 3.25-3.17 (m, 1H), 2.63-2.54 (m, 1H), 2.43 (s, 3H), 2.29 (q, J=7.6 Hz, 1H), 2.04-1.85 (m, 2H), 1.82-1.67 (m, 4H). $^{13}$C NMR (100 MHz, CDCl$_3$) δ 164.18 (d, J$_{CF}$=252.2 Hz), 163.9, 144.2, 143.0 (d, J$_{CF}$=1.6 Hz), 138.3 (d, J$_{CF}$=8.7 Hz), 132.3, 131.9, 128.1, 125.6 (d, J$_{CF}$=3.6 Hz), 123.8, 117.8 (d, J$_{CF}$=22.0 Hz), 65.5, 57.0, 40.5, 37.3, 27.6, 27.4, 22.8. IR (thin film): 3072, 2945, 2877, 2789, 1652, 1645, 1608, 1591, 1549, 1538, 1520, 1490, 1463, 1338, 1312, 1227, 1158 cm$^{-1}$. MS (ES-API) m/z: 404.1 (100%, [M+H]$^+$, C$_{20}$H$_{23}$FN$_3$O$_3$S requires 404.1). mp: 152-153° C. (dec.).

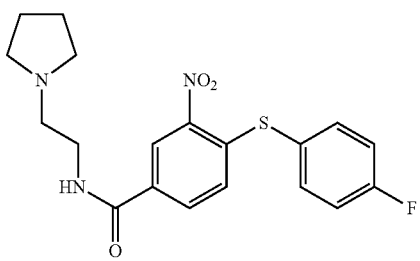 [SMILES: O=C(NCCN1CCCC1)c1ccc(Sc2ccc(F)cc2)c([N+](=O)[O-])c1]

4-(4-fluorophenyl)thio)-3-nitro-N-(2-(pyrrolidin-1-yl)ethyl)benzamide (DS-1-063)

Following the general procedure B-2 using 1-(2-aminoethyl)pyrrolidine. Yellow solid (73%). $^1$H NMR (400 MHz, CDCl$_3$) δ 8.63 (d, J=1.9 Hz, 1H), 7.79 (dd, J=8.5, 1.9 Hz, 1H), 7.56 (m, 2H), 7.30 (s, 1H), 7.19 (t, J=8.6 Hz, 2H), 6.83 (d, J=8.5 Hz, 1H), 3.56 (q, J=5.5 Hz, 2H), 2.77 (t, J=5.9 Hz, 2H), 2.66-2.61 (m, 4H), 1.85-1.76 (m, 4H). $^{13}$C NMR (100 MHz, CDCl$_3$) δ 164.8, 164.2 (d, J$_{CF}$=252.3 Hz), 144.3, 143.2 (d, J$_{CF}$=1.6 Hz), 138.3 (d, J$_{CF}$=8.6 Hz), 131.9, 131.7, 128.1, 125.6 (d, $J_{CF}$=3.6 Hz), 124.6, 117.8 (d, $J_{CF}$=22.0 Hz), 54.6, 54.0, 38.5, 23.6. IR (thin film): 2971, 2813, 1654, 1648, 1610, 1591, 1520, 1491, 1338, 1294, 1227, 1158 cm$^{-1}$. MS (ES-API) m/z: 390.1 (100%, [M+H]$^+$, $C_{19}H_{21}FN_3O_3S$ requires 390.1). mp: 173-175° C. (dec.).

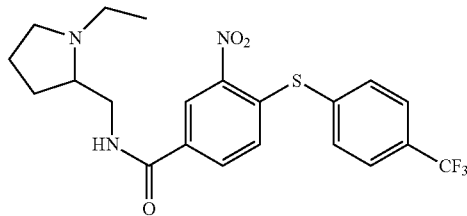 [SMILES: CCN1CCCC1CNC(=O)c1ccc(Sc2ccc(C(F)(F)F)cc2)c([N+](=O)[O-])c1]

N-((1-ethylpyrrolidin-2-yl)methyl)-3-nitro-4-((4-(trifluoromethyl)phenyl)thio)benzamide (DS-1-065)

Following the general procedure A-2 using 4-(trifluoromethyl)thiophenol. Light yellow solid (54%). $^1$H NMR (400 MHz, CDCl$_3$) δ 8.67 (s, 1H), 7.80 (d, J=8.5 Hz, 1H), 7.72 (q, J=8.4 Hz, 4H), 7.24 (s, 1H), 6.90 (d, J=8.5 Hz, 1H), 3.70 (ddd, J=13.7, 7.3, 2.3 Hz, 1H), 3.28 (dt, J=14.0, 3.4 Hz, 1H), 3.15 (t, J=7.8 Hz, 1H), 2.87 (s, 1H), 2.81 (dq, J=14.7, 7.6 Hz, 1H), 2.72-2.63 (m, 1H), 2.29-2.12 (m, 2H), 1.88 (dt, J=16.4, 8.1 Hz, 1H), 1.77-1.52 (m, 2H), 1.09 (t, J=7.2 Hz, 3H). $^{13}$C NMR (100 MHz, CDCl$_3$) δ 164.7, 144.9, 141.1, 135.8, 135.4 (d, $J_{CF}$=1.6 Hz), 132.3, 132.2 (q, $J_{CF}$=33.0 Hz), 131.6, 128.6, 127.0 (q, $J_{CF}$=3.7 Hz), 124.5, 123.6 (q, $J_{CF}$=272.6 Hz), 62.4, 53.5, 48.1, 40.8, 27.9, 22.9, 13.9. IR (thin film): 3091, 2972, 2877, 2803, 1634, 1607, 1557, 1520, 1465, 1398, 1326, 1293, 1170, 1127, 1104, 1063, 846 cm$^{-1}$. MS (ES-API) m/z: 454.1 (100%, [M+H]$^+$, $C_{21}H_{23}F_3N_3O_3S$ requires 454.1). mp: 153-154° C. (dec.).

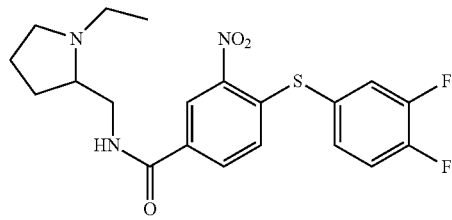 [SMILES: CCN1CCCC1CNC(=O)c1ccc(Sc2ccc(F)c(F)c2)c([N+](=O)[O-])c1]

4-((3,4-difluorophenyl)thio)-N-((1-ethylpyrrolidin-2-yl)methyl)-3-nitrobenzamide (DS-1-067)

Following the general procedure A-2 using 3,4-difluorothiophenol. Yellow solid (90%). $^1$H NMR (400 MHz, CDCl$_3$) δ 8.63 (s, 1H), 7.78 (d, J=8.4 Hz, 1H), 7.43 (t, J=8.3 Hz, 1H), 7.40-7.26 (m, 2H), 7.01 (s, 1H), 6.89 (d, J=8.5 Hz, 1H), 3.67 (ddd, J=13.7, 7.3, 2.6 Hz, 1H), 3.29 (d, J=13.7 Hz, 1H), 3.18 (t, J=7.2 Hz, 1H), 2.81 (dq, J=14.5, 7.2 Hz, 1H), 2.68 (s, 1H), 2.32-2.13 (m, 2H), 1.98-1.85 (m, 1H), 1.79-1.53 (m, 3H), 1.11 (t, J=7.1 Hz, 3H). $^{13}$C NMR (100 MHz, CDCl$_3$) δ 164.8, 152.1 (dd, $J_{CF}$=250.4, 8.1 Hz), 151.0 (dd, $J_{CF}$=253.2, 11.7 Hz), 144.5, 142.1, 132.9 (dd, $J_{CF}$=6.6, 3.7 Hz), 132.3, 131.7, 128.2, 126.7 (t, $J_{CF}$=4.9 Hz), 125.0 (d, $J_{CF}$=17.4 Hz), 124.5, 119.3 (d, $J_{CF}$=17.6 Hz), 62.0, 53.6, 48.1, 41.0, 28.4, 23.0, 14.2. IR (thin film): 3076, 2972, 2878, 2807, 1652, 1645, 1607, 1520, 1505, 1464, 1407, 1338, 1276, 1243, 1204, 1116, 1049 cm$^{-1}$. MS (ES-API) m/z: 422.1 (100%, [M+H]$^+$, $C_{20}H_{22}F_2N_3O_3S$ requires 422.1). mp: 122° C.

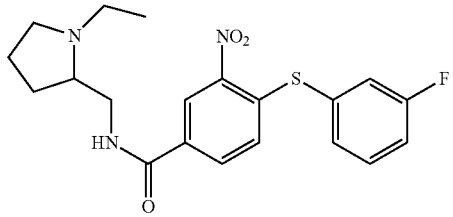 [SMILES: CCN1CCCC1CNC(=O)c1ccc(Sc2cccc(F)c2)c([N+](=O)[O-])c1]

N-((1-ethylpyrrolidin-2-yl)methyl)-4-((3-fluorophenyl)thio)-3-nitrobenzamide (DS-1-069)

Following the general procedure A-2 using 3-fluorothiophenol. Yellow solid (76%). $^1$H NMR (400 MHz, CDCl$_3$) δ 8.62 (d, J=2.0 Hz, 1H), 7.77 (dd, J=8.5, 2.0 Hz, 1H), 7.49 (td, J=8.1, 5.7 Hz, 1H), 7.39 (dt, J=7.7, 1.3 Hz, 1H), 7.32 (ddd, J=8.4, 2.5, 1.6 Hz, 1H), 7.23 (ddd, J=8.4, 2.6, 1.0 Hz, 1H), 6.94 (d, J=8.5 Hz, 1H), 6.89 (s, 1H), 3.67 (ddd, J=13.7, 7.3, 2.6 Hz, 1H), 3.30 (ddd, J=13.7, 4.5, 2.5 Hz, 1H), 3.19 (ddd, J=9.1, 7.1, 2.3 Hz, 1H), 2.81 (dq, J=12.0, 7.4 Hz, 1H), 2.72-2.65 (m, 1H), 2.30-2.15 (m, 2H), 1.92 (dq, J=12.4, 8.4 Hz, 1H), 1.80-1.53 (m, 3H), 1.11 (t, J=7.2 Hz, 3H). $^{13}$C NMR (100 MHz, CDCl$_3$) δ 164.9, 163.3 (d, $J_{CF}$=251.3 Hz), 144.7, 142.2, 132.5 (d, $J_{CF}$=7.3 Hz), 132.2, 131.8 (d, $J_{CF}$=8.2 Hz), 131.7 (d, $J_{CF}$=3.1 Hz), 131.6, 128.5, 124.5, 122.7 (d, $J_{CF}$=21.8 Hz), 117.8 (d, $J_{CF}$=20.9 Hz), 62.0, 53.6, 48.1, 40.9, 28.4, 23.1, 14.2. IR (thin film): 2971, 2810, 1645, 1609, 1521, 1472, 1338, 1296, 1219, 1106 cm$^{-1}$. MS (ES-API) m/z: 404.1 (100%, [M+H]$^+$, $C_{20}H_{23}FN_3O_3S$ requires 404.1). mp: 103° C.

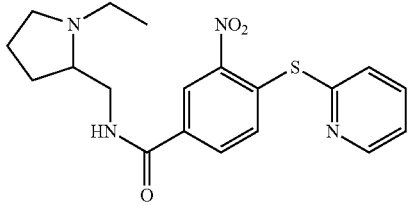 [SMILES: CCN1CCCC1CNC(=O)c1ccc(Sc2ccccn2)c([N+](=O)[O-])c1]

N-((1-ethylpyrrolidin-2-yl)methyl)-3-nitro-4-(pyridin-2-ylthio)benzamide (DS-1-071)

A 15 mL pressure tube was charged with the aryl fluoride DS-1-095 (164 mg, 0.50 mmol, 1 eq), water (5 mL), 2-mercaptopyridine (61 mg, 0.55 mmol, 1.1 eq) and sodium bicarbonate (47 mg, 0.55 mmol, 1.1 eq). The tube was sealed and the reaction mixture was stirred at 90° C. for 2 h and then at room temperature overnight. The reaction mixture was diluted with ethyl acetate (8 mL) and water (2 mL) before sodium bicarbonate (10 eq) was introduced. The organic phase was washed with water (2×4 mL) and brine (4 mL), dried over magnesium sulfate and concentrated under reduced pressure to afford a brown oil. Purification by column chromatography on silica gel (0-10% MeOH in DCM, MeOH containing 1% NH$_3$) afforded the product (87 mg, 0.22 mmol, 45%) as an orange oil. $^1$H NMR (400 MHz, CDCl$_3$) δ 8.65-8.62 (m, 1H), 8.59 (s, 1H), 7.90-7.82 (m, 1H), 7.80-7.70 (m, 1H), 7.58 (dd, J=7.9, 1.3 Hz, 1H), 7.37 (s, 1H), 7.34-7.30 (m, 1H), 7.28-7.24 (m, 1H), 3.69 (ddd, J=13.9, 7.1, 3.6 Hz, 1H), 3.37 (dt, J=13.9, 3.3 Hz, 1H), 3.26 (td, J=7.8, 3.0 Hz, 1H), 2.90-2.78 (m, 2H), 2.39-2.23 (m, 2H), 2.00-1.89 (m, 1H), 1.81-1.68 (m, 2H), 1.69-1.55 (m, 1H), 1.13 (t, J=7.2 Hz, 3H). $^{13}$C NMR (100 MHz, CDCl$_3$) δ 165.0, 154.6, 151.3, 146.7, 138.4, 138.1, 133.0, 131.4, 130.9, 128.9, 124.4, 123.7, 62.8, 53.7, 48.7, 41.0, 28.3, 23.1, 13.7. IR (thin film): 3051, 2969, 2876, 2804, 1661, 1652, 1645, 1608, 1574, 1557, 1538, 1520, 1470, 1455, 1421, 1338, 1311, 1246, 1150, 1108, 1049 cm$^{-1}$. MS (ES-API) m/z: 387.1 (100%, [M+H]$^+$, C$_{19}$H$_{23}$N$_4$O$_3$S requires 387.1).

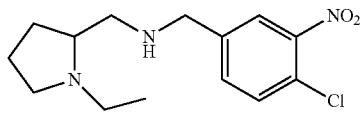 [SMILES: CCN1CCCC1CNCc1ccc(Cl)c([N+](=O)[O-])c1]

N-(4-chloro-3-nitrobenzyl)-1-(1-ethylpyrrolidin-2-yl)methanamine (DS-1-073)

A 10 mL oven-dried flask was charged with 4-chloro-3-nitrobenzaldehyde (371 mg, 2.0 mmol, 1 eq), 2-(aminomethyl)-1-ethylpyrrolidine (0.29 mL, 2.0 mmol, 1 eq), dry dichloromethane (4 mL) and acetic acid (0.23 mL, 4.0 mmol, 2 eq). After stirring for 1 h at room temperature, sodium triacetoxyborohydride (636 mg, 3.0 mmol, 1.5 eq) was introduced in one portion at 0° C. The reaction mixture was slowly warmed to room temperature and stirred overnight, upon which time it clogged. Saturated sodium bicarbonate (5 mL) was carefully added followed by dichloromethane (6 mL). The organic phase was washed with saturated sodium bicarbonate (5 mL), water (5 mL), dried over magnesium sulfate and concentrated under reduced pressure to afford a brown oil. Purification by column chromatography on silica gel (0-20% MeOH in DCM, MeOH containing 1% NH$_3$) yielded the product (170 mg, 0.58 mmol, 29%) as a light brown oil that was used in the next step without further purification. $^1$H NMR (400 MHz, CDCl$_3$) δ 7.87 (s, 1H), 7.48 (dd, J=13.3, 8.5 Hz, 2H), 3.84 (dd, J=18.6, 14.6 Hz, 2H), 3.18-3.09 (m, 1H), 2.78 (dq, J=14.8, 7.4 Hz, 2H), 2.66-2.53 (m, 1H), 2.54-2.43 (m, 1H), 2.20 (dq, J=11.3, 5.8 Hz, 1H), 2.13 (q, J=7.3 Hz, 1H), 1.93-1.83 (m, 1H), 1.80-1.64 (m, 3H), 1.08 (t, J=7.2 Hz, 3H). $^{13}$C NMR (100 MHz, CDCl$_3$) δ 147.0, 140.9, 131.7, 130.7, 124.1, 123.9, 63.0, 53.0, 51.9, 51.4, 48.1, 28.2, 22.1, 13.1. IR (thin film): 2969, 2874, 2799, 1569, 1538, 1479, 1455, 1354, 1289, 1198, 1132, 1049 cm$^{-1}$.

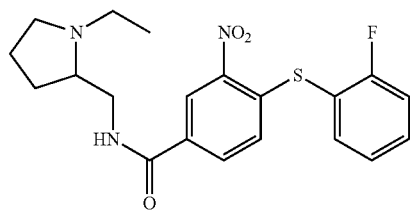 [SMILES: CCN1CCCC1CNC(=O)c1ccc(Sc2ccccc2F)c([N+](=O)[O-])c1]

N-((1-ethylpyrrolidin-2-yl)methyl)-4-((2-fluorophenyl)thio)-3-nitrobenzamide (DS-1-075)

Following the general procedure A-2 using 2-fluorothiophenol. Yellow solid (88%). $^1$H NMR (400 MHz, CDCl$_3$) δ 8.65 (d, J=2.0 Hz, 1H), 7.78 (dd, J=8.5, 2.0 Hz, 1H), 7.64 (td, J=7.3, 1.8 Hz, 1H), 7.57 (dddd, J=8.2, 7.1, 5.1, 1.8 Hz, 1H), 7.30 (td, J=7.6, 1.3 Hz, 1H), 7.26 (td, J=8.4, 1.1 Hz, 1H), 6.90 (dd, J=8.5, 1.3 Hz, 2H), 3.67 (ddd, J=13.7, 7.3, 2.6 Hz, 1H), 3.30 (ddd, J=13.8, 4.5, 2.6 Hz, 1H), 3.19 (ddd, J=9.5, 7.1, 2.5 Hz, 1H), 2.81 (dq, J=12.0, 7.4 Hz, 1H), 2.68 (s, 1H), 2.30-2.15 (m, 2H), 1.91 (dq, J=12.3, 8.3 Hz, 1H), 1.80-1.63 (m, 2H), 1.63-1.54 (m, 1H), 1.11 (t, J=7.2 Hz, 3H). $^{13}$C NMR (100 MHz, CDCl$_3$) δ 165.0, 163.2 (d, J$_{CF}$=251.0 Hz), 144.7, 141.3, 137.9, 133.4 (d, J$_{CF}$=8.1 Hz), 132.2, 131.8, 128.0, 125.9 (d, J$_{CF}$=4.0 Hz), 124.6, 117.6 (d, J$_{CF}$=18.8 Hz), 117.1 (d, J$_{CF}$=22.5 Hz), 62.0, 53.6, 48.1, 40.9, 28.3, 23.1, 14.2. IR (thin film): 3076, 2970, 2876, 2805, 1652, 1645, 1608, 1549, 1520, 1474, 1338, 1295, 1262, 1048 cm$^{-1}$. MS (ES-API) m/z: 404.1 (100%, [M+H]$^+$, C$_{20}$H$_{23}$FN$_3$O$_3$S requires 404.1). mp: 136° C.

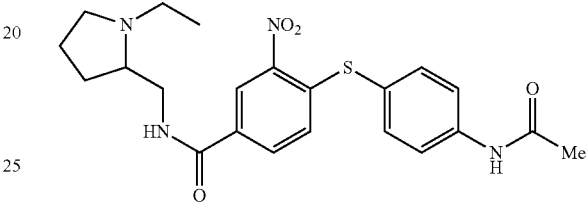

4-(4-acetamidophenyl)thio)-N-((1-ethylpyrrolidin-2-yl)methyl)-3-nitrobenzamide (DS-1-077)

Following the general procedure A-2 using 4-acetamidothiophenol (1.73 mmol, 1.1 eq). Yellow-orange solid (93%). $^1$H NMR (400 MHz, CDCl$_3$) δ 8.62 (d, J=2.0 Hz, 1H), 7.72 (dd, J=8.5, 2.0 Hz, 1H), 7.67 (d, J=8.5 Hz, 2H), 7.55-7.51 (m, 2H), 7.45-7.39 (m, 1H), 6.93 (s, 1H), 6.90 (d, J=8.5 Hz, 1H), 3.67 (ddd, J=13.7, 7.3, 2.6 Hz, 1H), 3.30 (ddd, J=13.7, 4.5, 2.6 Hz, 1H), 3.20 (ddd, J=9.2, 6.8, 2.4 Hz, 1H), 2.81 (dq, J=12.0, 7.4 Hz, 1H), 2.72-2.65 (m, 1H), 2.24 (s, 3H), 2.30-2.16 (m, 1H), 1.91 (dq, J=12.4, 8.4 Hz, 1H), 1.79-1.53 (m, 4H), 1.11 (t, J=7.2 Hz, 3H). $^{13}$C NMR (100 MHz, CDCl$_3$) δ 168.9, 165.3, 144.5, 144.2, 140.4, 137.1, 131.3, 130.9, 128.4, 125.2, 124.4, 121.2, 64.6, 53.9, 49.8, 40.7, 28.1, 24.9, 23.4, 12.7. IR (thin film): 3101, 2969, 2808, 1646, 1607, 1591, 1520, 1464, 1397, 1371, 1338, 1312, 1292, 1257, 1179 cm$^{-1}$. MS (ES-API) m/z: 443.2 (100%, [M+H]$^+$, C$_{22}$H$_{27}$N$_4$O$_4$S requires 443.2). mp: 138-140° C. (dec.).

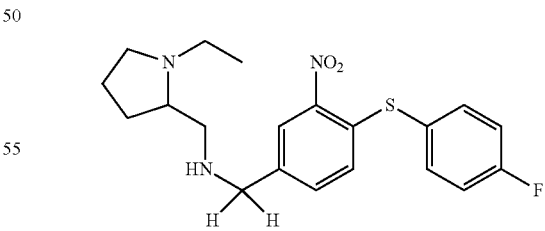

1-(1-ethylpyrrolidin-2-yl)-N-(4-((4-fluorophenyl)thio)-3-nitrobenzyl)methanamine (DS-1-079)

A 15 mL pressure tube was charged with the aryl chloride DS-1-073 (170 mg, 0.58 mmol, 1 eq), water (6 mL), 4-fluorothiophenol (0.07 mL, 0.64 mmol, 1.1 eq) and sodium bicarbonate (54 mg, 0.64 mmol, 1.1 eq). The tube was sealed and the reaction mixture was stirred at 90° C. for 2 h and then overnight at room temperature. The reaction mixture was diluted with saturated sodium bicarbonate (4 mL) and the aqueous phase was extracted with hexane (3×5 mL) and dichloromethane (3×5 mL). The combined organic phase was washed with water (2×15 mL), dried over magnesium sulfate and concentrated under reduced pressure to afford a brown oil. Purification by column chromatography on silica gel (0-10% MeOH in DCM, MeOH containing 1% NH$_3$) afforded the product (206 mg, 0.53 mmol, 91%) as an orange-red oil. $^1$H NMR (400 MHz, CDCl$_3$) δ 8.20 (d, J=1.9 Hz, 1H), 7.56 (ddd, J=8.7, 5.3, 0.9 Hz, 2H), 7.35 (dd, J=8.4, 0.8 Hz 1H), 7.17 (t, J=8.4 Hz, 2H), 6.75 (d, J=8.4 Hz, 1H), 3.81 (s, 2H), 3.17-3.10 (m, 1H), 2.83-2.72 (m, 1H), 2.63 (dd, J=11.2, 3.7 Hz, 1H), 2.59-2.49 (m, 1H), 2.50-2.42 (m, 1H), 2.23-2.07 (m, 2H), 1.93-1.83 (m, 1H), 1.78-1.62 (m, 3H), 1.57 (s, 1H), 1.07 (t, J=7.1 Hz, 3H). $^{13}$C NMR (100 MHz, CDCl$_3$) □ 163.8 (d, J$_{CF}$=251.3 Hz), 144.9, 139.1, 138.1 (d, J$_{CF}$=8.5 Hz), 137.2 (d, J$_{CF}$=1.5 Hz), 133.4, 128.1, 126.6 (d, J$_{CF}$=3.6 Hz), 125.0, 117.4 (d, J$_{CF}$=21.9 Hz), 64.0, 53.9, 52.8, 52.4, 49.0, 29.1, 23.0, 14.0. IR (thin film): 2967, 2798, 1590, 1556, 1519, 1490, 1336, 1291, 1226, 1156, 1108, 1048, 834 cm$^{-1}$. MS (ES-API) m/z: 390.2 (100%, [M+H]$^+$, C$_{20}$H$_{25}$FN$_3$O$_2$S requires 390.2).

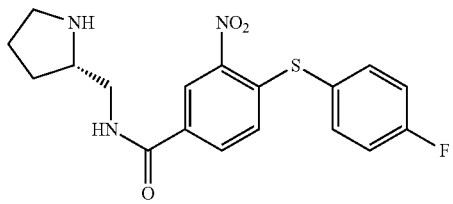 [SMILES: O=C(NC[C@@H]1CCCN1)c1ccc(Sc2ccc(F)cc2)c([N+](=O)[O-])c1]

(S)-4-((4-fluorophenyl)thio)-3-nitro-N-(pyrrolidin-2-ylmethyl)benzamide (DS-1-085)

A 10 mL oven-dried flask was charged with (S)-(+)-2-(aminomethyl)pyrrolidine (0.16 mL, 1.50 mmol, 1.5 eq) and dry dichloromethane (2.5 mL) and immersed in an ice bath. A solution of the acyl chloride DS-1-059 (312 mg, 1.00 mmol, 1 eq) in dry dichloromethane (2.5 mL) was then added dropwise. After 14 h, saturated sodium bicarbonate (5 mL) was introduced and the organic phase was washed with saturated sodium bicarbonate (2×5 mL) and water (5 mL), dried over magnesium sulfate, filtered and concentrated to obtain a brown oil. Purification by column chromatography on silica gel (0-20% MeOH in DCM, MeOH containing 1% NH$_3$) afforded the product (27 mg, 0.07 mmol, 7%) as a yellow oil. $^1$H NMR (400 MHz, CDCl$_3$) δ 8.40 (d, J=1.9 Hz, 1H), 7.61-7.50 (m, 3H), 7.19 (t, J=8.5 Hz, 2H), 6.82 (d, J=8.4 Hz, 1H), 4.31-4.20 (m, 1H), 3.55-3.40 (m, 2H), 3.07-3.01 (m, 1H), 2.86 (dd, J=12.5, 6.6 Hz, 1H), 2.12 (dt, J=10.7, 6.4 Hz, 1H), 1.98-1.73 (m, 3H), 1.40 (s, 2H). $^{13}$C NMR (100 MHz, CDCl$_3$) δ 167.5, 164.2 (d, J$_{CF}$=252.3 Hz), 144.1, 141.9, 138.3 (d, J$_{CF}$=8.8 Hz), 134.1, 132.5, 128.1, 125.7, 125.0, 117.8 (d, J$_{CF}$=22.0 Hz), 60.4, 50.8, 44.7, 28.5, 25.2. IR (thin film): 3069, 2969, 2875, 1622, 1608, 1590, 1548, 1520, 1491, 1418, 1337, 1292, 1225, 1157, 1049 cm$^{-1}$. MS (ES-API) m/z: 376.1 (100%, [M+H]$^+$, C$_{18}$H$_{19}$FN$_3$O$_3$S requires 376.1). [α]$_D$: −89.02 (c 1.35, CHCl$_3$).

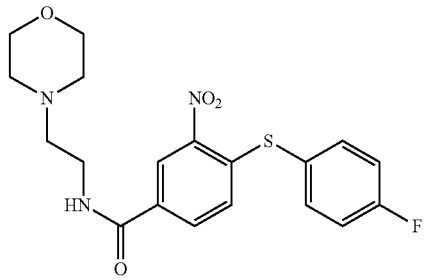

4-((4-fluorophenyl)thio)-N-(2-morpholinoethyl)-3-nitrobenzamide (DS-1-089)

Following the general procedure B-2 using 4-(2-aminoethyl)morpholine. Yellow solid (66%). $^1$H NMR (400 MHz, CDCl$_3$) δ 8.61 (d, J=2.0 Hz, 1H), 7.78 (dd, J=8.5, 2.0 Hz, 1H), 7.61-7.55 (m, 2H), 7.25-7.18 (m, 2H), 6.88 (d, J=8.5 Hz, 1H), 6.78 (s, 1H), 3.75-3.70 (m, 4H), 3.55 (q, J=5.6 Hz, 2H), 2.60 (t, J=6.0 Hz, 2H), 2.53-2.47 (m, 4H). $^{13}$C NMR (100 MHz, CDCl$_3$) δ 164.7, 164.2 (d, J$_{CF}$=252.4 Hz), 144.3, 143.5 (d, J$_{CF}$=1.6 Hz), 138.3 (d, J$_{CF}$=8.7 Hz), 131.8, 131.6, 128.3, 125.5 (d, J$_{CF}$=3.6 Hz), 124.3, 117.8 (d, J$_{CF}$=22.0 Hz), 67.1, 56.8, 53.4, 36.3. IR (thin film): 3095, 2955, 2856, 2814, 1643, 1608, 1590, 1548, 1520, 1491, 1338, 1296, 1227, 1158, 1117, 837 cm$^{-1}$. MS (ES-API) m/z: 406.1 (100%, [M+H]$^+$, C$_{19}$H$_{21}$FN$_3$O$_4$S requires 406.1). mp: 159-161° C. (dec.).

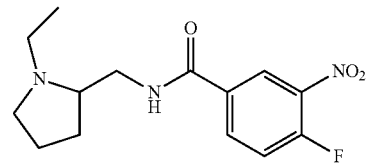 [SMILES: CCN1CCCC1CNC(=O)c1ccc(F)c([N+](=O)[O-])c1]

N-((1-ethylpyrrolidin-2-yl)methyl)-4-fluoro-3-nitrobenzamide (DS-1-095)

A 50 mL oven-dried flask equipped with a reflux condenser, fitted with a drying tube, was charged with 4-fluoro-3-nitrobenzoic acid (5.56 g, 30.0 mmol, 1 eq) and thionyl chloride (7.5 mL) and heated to reflux. After 4 h, the resulting homogeneous mixture was concentrated to dryness under reduced pressure. The colorless liquid obtained was then dissolved in dry toluene (5 mL) and the solvent was evaporated. This process was repeated twice yielding 4-fluoro-3-nitrobenzoyl chloride (4.06 g, 19.9 mmol, quantitative) as a colorless liquid.

Dry dichloromethane (30 mL) was introduced and the flask was immersed in a water bath. To this solution was added dropwise 2-(aminomethyl)-1-ethylpyrrolidine (3.7 mL, 27.0 mmol, 0.9 eq). After 14 h, the resulting beige suspension was diluted with dichloromethane (20 mL) and saturated sodium bicarbonate (50 mL) and the aqueous layer was basified to pH~9 with a concentrated potassium hydroxide solution. The organic phase was washed with saturated sodium bicarbonate (2×50 mL) and water (50 mL), dried over magnesium sulfate, filtered and concentrated to obtain a brown oil. Purification by column chromatography on silica gel (0-20% MeOH in DCM, MeOH containing 1%

NH$_3$) afforded the crude product that was dissolved in dichloromethane (20 mL) and extracted with HCl 2 M (3×10 mL). The aqueous phases were washed with dichloromethane (20 mL), basified to pH~13 with a concentrated potassium hydroxide solution and extracted with dichloromethane (3×10 mL). The organic layers were washed with sodium bicarbonate (20 mL), water (20 mL), dried over magnesium sulfate, filtered and concentrated to yield the pure product (6.00 g, 20.3 mmol, 75%) as a light brown oil which darkens over days. $^1$H NMR (400 MHz, CDCl$_3$) δ 8.45 (dd, J=7.0, 2.3 Hz, 1H), 8.05 (ddd, J=8.6, 4.2, 2.3 Hz, 1H), 7.39-7.28 (m, 1H), 7.20 (bs, 1H), 3.63 (ddd, J=13.6, 7.1, 2.7 Hz, 1H), 3.31-3.22 (m, 1H), 3.19-3.11 (m, 1H), 2.79 (dq, J=14.7, 7.3 Hz, 1H), 2.71-2.61 (m, 1H), 2.27-2.13 (m, 2H), 1.88 (ddd, J=16.4, 12.0, 8.3 Hz, 1H), 1.76-1.49 (m, 3H), 1.07 (t, J=7.2 Hz, 3H). $^{13}$C NMR (100 MHz, CDCl$_3$) δ 164.3, 157.0 (d, J$_{CF}$=269.5 Hz), 137.1 (d, J$_{CF}$=7.7 Hz), 134.2 (d, J$_{CF}$=9.4 Hz), 131.8, 125.1 (d, J$_{CF}$=2.1 Hz), 118.8 (d, J$_{CF}$=21.3 Hz), 62.1, 53.5, 48.1, 41.3, 28.3, 22.9, 14.0. IR (thin film): 3090, 2970, 2877, 2802, 1646, 1620, 1538, 1494, 1351, 1316, 1268 cm$^{-1}$. MS (ES-API) m/z: 296.2 (100%, [M+H]$^+$, C$_{14}$H$_{19}$FN$_3$O$_3$ requires 296.1).

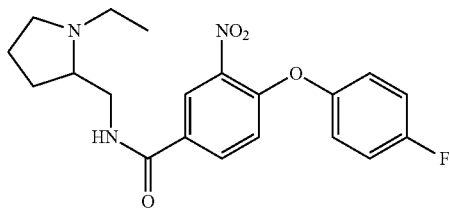

N-((1-ethylpyrrolidin-2-yl)methyl)-4-(4-fluorophenoxy)-3-nitrobenzamide (DS-1-103)

Following the general procedure A-2 using 4-fluorophenol. Purification by column chromatography on silica gel (0-20% MeOH in DCM, MeOH containing 1% NH$_3$). Beige solid (48%). $^1$H NMR (400 MHz, CDCl$_3$) δ 8.36 (d, J=2.2 Hz, 1H), 7.93 (dd, J=8.7, 2.2 Hz, 1H), 7.16 (bs, 1H), 7.14-7.03 (m, 4H), 6.95 (d, J=8.7 Hz, 1H), 3.68 (ddd, J=13.7, 7.2, 3.0 Hz, 1H), 3.33 (dt, J=13.7, 3.5 Hz, 1H), 3.26-3.19 (m, 1H), 2.89-2.79 (m, 1H), 2.78-2.72 (m, 1H), 2.37-2.19 (m, 2H), 2.01-1.86 (m, 1H), 1.82-1.55 (m, 3H), 1.13 (t, J=7.2 Hz, 3H). $^{13}$C NMR (100 MHz, CDCl$_3$) δ 164.9, 160.1 (d, J$_{CF}$=244.8 Hz), 153.5, 150.5 (d, J$_{CF}$=2.7 Hz), 140.3, 132.7, 129.4, 124.9, 121.8 (d, J$_{CF}$=8.5 Hz), 118.8, 117.1 (d, J$_{CF}$=23.6 Hz), 62.6, 53.7, 48.4, 40.9, 28.3, 23.1, 13.9. IR (thin film): 3078, 2971, 2877, 2804, 1652, 1645, 1623, 1538, 1532, 1504, 1487, 1354, 1266, 1226, 1188, 1148, 1090 cm$^{-1}$. MS (ES-API) m/z: 388.2 (100%, [M+H]$^+$, C$_{20}$H$_{23}$FN$_3$O$_4$ requires 388.2). mp: 91-94° C. (dec.).

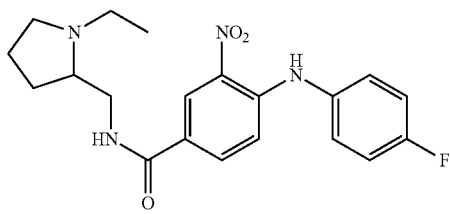 [SMILES: CCN1CCCC1CNC(=O)c1ccc(Nc2ccc(F)cc2)c([N+](=O)[O-])c1]

N-((1-ethylpyrrolidin-2-yl)methyl)-4-((4-fluorophenyl)amino)-3-nitrobenzamide (DS-1-105)

Following the general procedure A-2 using 4-fluoroaniline. Purification by column chromatography on silica gel (0-10% MeOH in DCM, MeOH containing 1% NH$_3$). Orange solid (71%). $^1$H NMR (400 MHz, CDCl$_3$) δ 9.60 (s, 1H), 8.68 (s, 1H), 7.87 (d, J=8.6 Hz, 1H), 7.32-7.22 (m, 2H), 7.19-7.12 (m, 2H), 7.06 (d, J=9.0 Hz, 1H), 3.69 (ddd, J=13.6, 7.1, 3.4 Hz, 1H), 3.42-3.25 (m, 2H), 2.93-2.77 (m, 2H), 2.43-2.24 (m, 2H), 1.95 (dt, J=17.0, 8.5 Hz, 1H), 1.84-1.61 (m, 3H), 1.17 (t, J=7.1 Hz, 3H). $^{13}$C NMR (100 MHz, CDCl$_3$) δ 165.5, 161.2 (d, J$_{CF}$=247.2 Hz), 145.5, 134.4, 133.9 (d, J$_{CF}$=3.2 Hz), 132.1, 127.5 (d, J$_{CF}$=8.4 Hz), 125.9, 123.8, 117.0 (d, J$_{CF}$=22.8 Hz), 115.8, 62.7, 53.7, 48.5, 40.9, 28.3, 23.2, 14.0. IR (thin film): 3077, 2970, 2877, 2802, 1651, 1622, 1558, 1506, 1411, 1353, 1268, 1212, 1153, 1072 cm$^{-1}$. MS (ES-API) m/z: 387.2 (100%, [M+H]$^+$, C$_{20}$H$_{24}$FN$_4$O$_3$ requires 387.2). mp: 120° C.

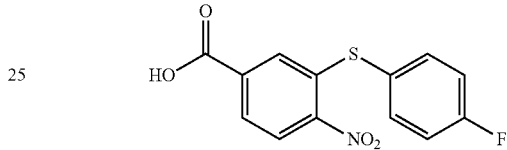

3-((4-fluorophenyl)thio)-4-nitrobenzoic acid (DS-1-113)

Following the general procedure A-1 using 3-fluoro-4-nitrobenzoic acid (10.0 mmol). Yellow needles (100%). $^1$H NMR (400 MHz, DMSO-d$_6$) δ 13.64 (s, 1H), 8.34 (d, J=8.5 Hz, 1H), 7.85 (d, J=8.5 Hz, 1H), 7.74 (dd, J=8.3, 5.5 Hz, 2H), 7.45 (t, J=8.7 Hz, 2H), 7.39 (s, 1H). IR (thin film): 1698, 1574, 1510, 1423, 1334, 1288, 1088, 822 cm$^{-1}$. MS (ES-API) m/z: 291.9 (100%, [M–H]$^-$, C$_{13}$H$_7$FNO$_4$S requires 292.0), 585.0 (12%, [2M–H]$^-$), 607.0 (17%, [2M+Na–2H]$^-$).

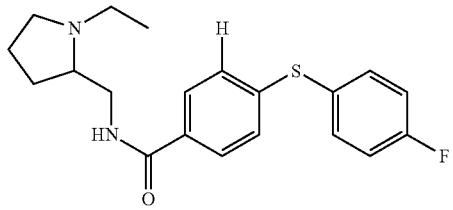 [SMILES: CCN1CCCC1CNC(=O)c1ccc(Sc2ccc(F)cc2)cc1]

N-((1-ethylpyrrolidin-2-yl)methyl)-4-((4-fluorophenyl)thio)benzamide (DS-1-117)

A 20 mL oven-dried Schlenk tube was charged with potassium tert-butoxide (269 mg, 2.40 mmol, 2.4 eq) and heated to 110° C. under high vacuum. After 30 min, 4-bromobenzoic acid was introduced at room temperature (201 mg, 1.00 mmol, 1 eq) and the solid blend was heated to 110° C. under high vacuum. After 30 min, dry toluene (6 mL) was added under argon at room temperature. A 4 mL oven-dried vial was charged with palladium acetate (6.7 mg, 0.03 mmol, 3 mol %) and Josiphos CyPF-tBu (16.6 mg, 0.03 mmol, 3 mol %). The vial was then evacuated and back-filled with argon three times before introducing dry toluene (3 mL). After 1 min, the resulting orange solution was added in one portion to the white suspension in the Schlenk tube, immediately followed by 4-fluorothiophenol (0.13 mL, 1.20 mmol, 1.2 eq) in one portion. The Schlenk tube was sealed with a screw cap and heated to 110° C. After 16 h, the resulting brown suspension was cooled to room temperature, silica gel was introduced (500 mg) and the solvent was evaporated under reduced pressure. Purification by column chromatography on silica gel (0-20% EtOAc in hexanes, EtOAc containing 4% AcOH) afforded the product (203 mg) in a 3:1 mixture with 4-bromobenzoic acid as a white solid.

A 10 mL oven-dried flask equipped with a reflux condenser was charged with the mixture of carboxylic acids (203 mg) obtained from the previous step and thionyl chloride (3 mL) and heated to reflux overnight. The resulting homogeneous mixture was then concentrated to dryness under reduced pressure. The colorless liquid obtained was then dissolved in dry toluene (2.5 mL) and the solvent was evaporated. This process was repeated twice yielding the mixture of acyl chlorides as a colorless oil.

Dry dichloromethane (4 mL) was introduced and 2-(aminomethyl)-1-ethylpyrrolidine (0.10 mL, 0.72 mmol, 0.72 eq) was added dropwise. After 8 h, the solution was diluted with dichloromethane (6 mL) and saturated sodium bicarbonate (10 mL). The organic phase was washed with saturated sodium bicarbonate (2×10 mL) and water (10 mL), dried over magnesium sulfate, filtered and concentrated to obtain a brown oil. Purification by column chromatography on silica gel (0-10% MeOH in DCM, MeOH containing 1% $NH_3$) afforded the desired amide (20 mg, 0.056 mmol, 8% over 3 steps) as a light brown oil. $^1H$ NMR (400 MHz, $CDCl_3$) δ 7.70 (d, J=8.5 Hz, 2H), 7.49-7.43 (m, 2H), 7.22-7.13 (m, 2H), 7.11-7.04 (m, 2H), 3.69 (ddd, J=13.8, 7.3, 3.6 Hz, 1H), 3.35 (dt, J=13.8, 3.5 Hz, 1H), 3.27 (dt, J=9.5, 4.7 Hz, 1H), 2.93-2.78 (m, 2H), 2.41-2.22 (m, 2H), 1.93 (dq, J=12.2, 8.0 Hz, 1H), 1.81-1.58 (m, 3H), 1.14 (t, J=7.2 Hz, 3H). $^{13}C$ NMR (100 MHz, $CDCl_3$) δ 167.1, 163.1 (d, $J_{CF}$=249.4 Hz), 142.3, 136.0 (d, $J_{CF}$=8.4 Hz), 132.1, 131.9, 128.8, 127.8 (d, $J_{CF}$=4.3 Hz), 116.9 (d, $J_{CF}$=22.1 Hz), 63.1, 53.7, 48.7, 40.7, 28.2, 23.2, 13.7. IR (thin film): 3063, 2969, 2875, 2801, 1652, 1644, 1634, 1595, 1538, 1488, 1397, 1296, 1225, 1156, 1085, 1014, 834, 758 cm$^{-1}$. MS (ES-API) m/z: 359.2 (100%, [M+H]$^+$, $C_{20}H_{24}FN_2OS$ requires 359.2).

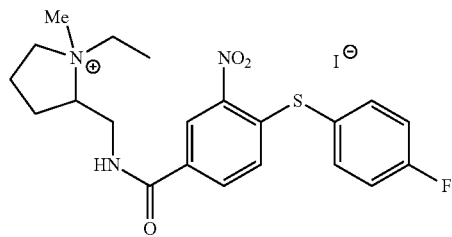 [SMILES: CC[N+]1(C)CCCC1CNC(=O)c1ccc(Sc2ccc(F)cc2)c([N+](=O)[O-])c1 ; [I-]]

1-ethyl-2-((4-((4-fluorophenyl)thio)-3-nitrobenzamido)methyl)-1-methylpyrrolidin-1-ium iodide (DS-1-119)

A 5 mL flask was charged with DS-1-033 (171 mg, 0.42 mmol, 1 eq), ethanol (1 mL) and iodomethane (80 μL, 0.85 mmol, 2 eq). The yellow solution was stirred for 3 h and the resulting suspension was filtered, washed with ethanol (1 mL) and diethyl ether (2 mL) to afford a yellow solid. Purification by column chromatography on silica gel (0-50% MeOH in DCM) yielded the desired ammonium salt (39 mg, 0.07 mmol, 17%) as a mixture of two diastereoisomers as a yellow solid. $^1H$ NMR (400 MHz, $CDCl_3$) δ 8.97-8.86 (m, 1H), 8.85 (d, J=1.9 Hz, 1H), 8.17 (dt, J=8.6, 2.5 Hz, 1H), 7.57-7.49 (m, 2H), 7.22-7.15 (m, 2H), 6.82 (d, J=8.6 Hz, 1H), 4.54-4.45* (m), 4.43-4.33 (m, 1H), 4.12-3.75 (m, 3H), 3.73-3.49 (m, 3H), 3.39-3.32* (m), 3.28* (s), 3.27 (s, 3H), 3.23-3.16* (m), 2.57-2.48 (m, 1H), 2.25-2.08 (m, 3H), 1.45* (t, J=7.2 Hz), 1.41 (t, J=7.3 Hz, 3H). $^{13}C$ NMR (100 MHz, $CDCl_3$) δ 165.4, 164.2 (d, $J_{CF}$=266.8 Hz), 144.2, 143.9 (d, $J_{CF}$=1.5 Hz), 138.2 (d, $J_{CF}$=8.6 Hz), 132.3, 129.7, 128.1, 125.9, 125.1 (d, $J_{CF}$=3.5 Hz), 117.9 (d, $J_{CF}$=22.0 Hz), 75.8*, 73.6, 64.5, 62.4*, 59.8, 51.3*, 49.0*, 46.5*, 43.5, 37.9, 37.6*, 26.2, 19.2*, 18.9, 9.8, 8.7*. * minor diastereoisomer. IR (thin film): 3260, 2940, 1652, 1607, 1590, 1520, 1489, 1465, 1397, 1338, 1308, 1225, 1157, 749 cm$^{-1}$. MS (ES-API) m/z: 418.2 (100%, [M+H]$^+$, $C_{21}H_{25}FN_3O_3S$ requires 418.2). mp: 95-97° C. (dec.).

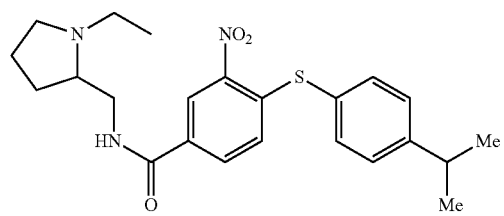 [SMILES: CCN1CCCC1CNC(=O)c1ccc(Sc2ccc(C(C)C)cc2)c([N+](=O)[O-])c1]

N-((1-ethylpyrrolidin-2-yl)methyl)-4-((4-isopropylphenyl)thio)-3-nitrobenzamide (DS-1-123)

Following the general procedure A-2 using 4-isopropylthiophenol. Purification by column chromatography on silica gel (0-20% MeOH in DCM, MeOH containing 1% $NH_3$). Yellow solid (28%). $^1H$ NMR (400 MHz, $CDCl_3$) δ 8.66 (d, J=1.8 Hz, 1H), 7.78 (dd, J=8.6, 1.8 Hz, 1H), 7.47 (d, J=8.1 Hz, 2H), 7.40 (bs, 1H), 7.34 (d, J=8.1 Hz, 2H), 6.91 (d, J=8.5 Hz, 1H), 3.67 (ddd, J=13.8, 7.1, 3.7 Hz, 1H), 3.36 (dt, J=13.9, 3.4 Hz, 1H), 3.31-3.21 (m, 1H), 2.97 (hept, J=7.0 Hz, 1H), 2.93-2.79 (m, 2H), 2.42-2.23 (m, 2H), 1.94 (dq, J=12.5, 8.4 Hz, 1H), 1.81-1.58 (m, 3H), 1.29 (d, J=6.9 Hz, 6H), 1.13 (t, J=7.2 Hz, 3H). $^{13}C$ NMR (100 MHz, $CDCl_3$) δ 165.1, 151.7, 144.4, 144.0, 136.0, 131.29, 131.26, 128.6, 128.4, 126.8, 124.7, 63.0, 53.6, 48.7, 40.9, 34.1, 28.3, 23.9, 23.1, 13.6. IR (thin film): 2963, 1654, 1605, 1559, 1520, 1490, 1458, 1386, 1339, 1241, 1100, 1049 cm$^{-1}$. MS (ES-API) m/z: 428.2 (100%, [M+H]$^+$, $C_{23}H_{29}N_3O_3S$ requires 428.2). mp: 93-94° C.

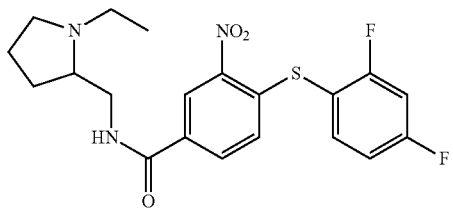 [SMILES: CCN1CCCC1CNC(=O)c1ccc(Sc2ccc(F)cc2F)c([N+](=O)[O-])c1]

4-((2,4-difluorophenyl)thio)-N-((1-ethylpyrrolidin-2-yl)methyl)-3-nitrobenzamide (DS-1-125)

Following the general procedure A-2 using 2,4-difluorothiophenol. Yellow solid (77%). $^1H$ NMR (400 MHz, CDCl$_3$) δ 8.69 (s, 1H), 7.85 (d, J=8.5 Hz, 1H), 7.63 (td, J=8.4, 6.3 Hz, 1H), 7.09-6.99 (m, 2H), 6.87 (dd, J=8.5, 1.0 Hz, 1H), 3.70 (ddd, J=14.0, 7.4, 3.0 Hz, 1H), 3.41-3.32 (m, 1H), 3.31-3.21 (m, 1H), 2.91-2.73 (m, 2H), 2.38-2.24 (m, 2H), 2.01-1.90 (m, 1H), 1.82-1.59 (m, 3H), 1.15 (t, J=7.1 Hz, 3H). $^{13}$C NMR (100 MHz, CDCl$_3$) δ 165.2 (dd, J$_{CF}$=255.1, 11.3 Hz), 164.9, 163.8 (dd, J$_{CF}$=253.4, 12.5 Hz), 144.7, 141.0, 139.0 (dd, J$_{CF}$=9.9, 1.7 Hz), 132.2, 132.0, 127.6, 124.8, 113.5 (dd, J$_{CF}$=21.6, 3.9 Hz), 113.3 (dd, J$_{CF}$=19.1, 4.1 Hz), 105.8 (dd, J$_{CF}$=26.1, 26.1 Hz), 62.5, 53.6, 48.4, 40.8, 28.1, 23.1, 14.0. IR (thin film): 2969, 1648, 1608, 1546, 1522, 1485, 1466, 1420, 1339, 1294, 1267, 1241, 1144, 967 cm$^{-1}$. MS (ES-API) m/z: 422.1 (100%, [M+H]$^+$, C$_{20}$H$_{21}$F$_2$N$_3$O$_3$S requires 422.1). mp: 63-65° C.

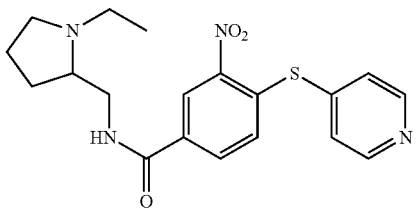 [SMILES: CCN1CCCC1CNC(=O)c1ccc(Sc2ccncc2)c([N+](=O)[O-])c1]

N-((1-ethylpyrrolidin-2-yl)methyl)-3-nitro-4-(pyridin-4-ylthio)benzamide (DS-1-129)

A 15 mL pressure tube was charged with DS-1-095 (295 mg, 1.00 mmol, 1 eq), water (5 mL), 4-mercaptopyridine (145 mg, 1.30 mmol, 1.3 eq) and sodium bicarbonate (109 mg, 1.30 mmol, 1.3 eq). The tube was sealed and the reaction mixture was stirred at 90° C. for 2 h and at room temperature overnight. The reaction mixture was diluted with dichloromethane (20 mL) and the organic layer was washed with saturated sodium bicarbonate (2×20 mL) and then extracted with 2M HCl (3×10 mL). The acidic aqueous phases were basified to pH~12 with a concentrated potassium hydroxide solution and extracted with dichloromethane (3×10 mL). The organic layers were dried over magnesium sulfate, filtered and silica gel (1 g) was introduced before the solvent was evaporated under reduced pressure. Purification by column chromatography on silica gel (0-20% MeOH in DCM, MeOH containing 1% NH$_3$) afforded the product (191 mg, 0.49 mmol, 49%) as a brown solid. $^1$H NMR (400 MHz, CDCl$_3$) δ 8.69-8.65 (m, 2H), 8.60 (d, J=1.9 Hz, 1H), 7.83 (dd, J=8.5, 2.0 Hz, 1H), 7.44-7.39 (m, 2H), 7.13 (d, J=8.4 Hz, 1H), 7.13 (bs, 1H), 3.68 (ddd, J=13.8, 7.3, 2.8 Hz, 1H), 3.35-3.28 (m, 1H), 3.24-3.17 (m, 1H), 2.82 (dq, J=12.1, 7.4 Hz, 1H), 2.76-2.70 (m, 1H), 2.32-2.19 (m, 2H), 1.92 (dq, J=12.4, 8.3 Hz, 1H), 1.80-1.54 (m, 3H), 1.11 (t, J=7.2 Hz, 3H). $^{13}$C NMR (100 MHz, CDCl$_3$) δ 164.6, 151.2, 146.3, 142.4, 138.4, 133.4, 131.7, 130.0, 128.2, 124.5, 62.3, 53.6, 48.3, 40.9, 28.3, 23.1, 14.0. IR (thin film): 2968, 2801, 1660, 1652, 1608, 1573, 1538, 1520, 1470, 1404, 1339, 1294, 1213, 1048, 749 cm$^{-1}$. MS (ES-API) m/z: 387.1 (36%, [M+H]$^+$, C$_{19}$H$_{23}$N$_4$O$_3$S requires 387.1). mp: 155-157° C. (dec.).

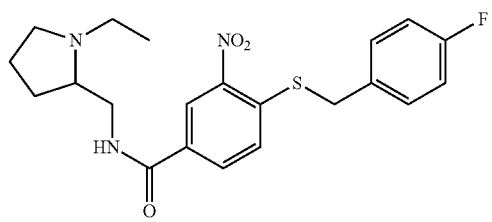 [SMILES: CCN1CCCC1CNC(=O)c1ccc(SCc2ccc(F)cc2)c([N+](=O)[O-])c1]

N-((1-ethylpyrrolidin-2-yl)methyl)-4-((4-fluorobenzyl)thio)-3-nitrobenzamide (DS-1-131)

Following the general procedure A-2 using 4-fluorobenzyl mercaptan. Yellow solid (70%). $^1$H NMR (400 MHz, CDCl$_3$) δ 8.59 (d, J=1.9 Hz, 1H), 7.96 (dd, J=8.4, 2.0 Hz, 1H), 7.49 (d, J=8.5 Hz, 1H), 7.42-7.35 (m, 2H), 7.07-7.00 (m, 2H), 7.01 (bs, 1H), 4.20 (s, 2H), 3.68 (ddd, J=13.7, 7.2, 2.7 Hz, 1H), 3.32 (ddd, J=13.7, 4.4, 2.9 Hz, 1H), 3.25-3.17 (m, 1H), 2.83 (dq, J=12.1, 7.4 Hz, 1H), 2.74-2.67 (m, 1H), 2.33-2.17 (m, 2H), 1.93 (dq, J=12.4, 8.3 Hz, 1H), 1.81-1.56 (m, 3H), 1.13 (t, J=7.2 Hz, 3H). $^{13}$C NMR (100 MHz, CDCl$_3$) δ 165.0, 162.5 (d, J$_{CF}$=247.2 Hz), 145.2, 141.5, 132.0, 131.5, 130.8 (d, J$_{CF}$=8.2 Hz), 130.2 (d, J$_{CF}$=3.3 Hz), 126.9, 124.5, 116.0 (d, J$_{CF}$=21.7 Hz), 62.2, 53.7, 48.2, 41.0, 36.9, 28.4, 23.1, 14.2. IR (thin film): 3075, 2969, 2876, 2801, 1652, 1607, 1548, 1510, 1465, 1338, 1292, 1230, 1158, 1107, 1052 cm$^{-1}$. MS (ES-API) m/z: 418.2 (100%, [M+H]$^+$, C$_{21}$H$_{25}$FN$_3$O$_3$S requires 418.2). mp: 142-143° C.

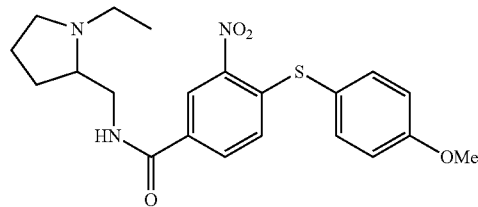 [SMILES: CCN1CCCC1CNC(=O)c1ccc(Sc2ccc(OC)cc2)c([N+](=O)[O-])c1]

N-((1-ethylpyrrolidin-2-yl)methyl)-4-((4-methoxyphenyl)thio)-3-nitrobenzamide (DS-1-133)

Following the general procedure A-2 using 4-methoxythiophenol. Yellow solid (53%). $^1$H NMR (400 MHz, CDCl$_3$) δ 8.65 (d, J=1.9 Hz, 1H), 7.76 (dd, J=8.6, 2.0 Hz, 1H), 7.52-7.46 (m, 2H), 7.08 (bs, 1H), 7.05-6.99 (m, 2H), 6.89 (d, J=8.6 Hz, 1H), 3.88 (s, 3H), 3.69 (ddd, J=13.8, 7.3, 3.0 Hz, 1H), 3.32 (dt, J=13.8, 3.5 Hz, 1H), 3.24-3.18 (m, 1H), 2.83 (dq, J=12.1, 7.4 Hz, 1H), 2.78-2.68 (m, 1H), 2.32-2.19 (m, 2H), 1.92 (dq, J=12.3, 8.3 Hz, 1H), 1.81-1.55 (m, 3H), 1.12 (t, J=7.2 Hz, 3H). $^{13}$C NMR (100 MHz, CDCl$_3$) δ 165.1, 161.6, 144.6, 144.3, 137.8, 131.5, 131.4, 128.3, 124.5, 120.6, 116.0, 62.5, 55.6, 53.7, 48.4, 40.8, 28.2, 23.1, 14.0. IR (thin film): 2969, 2837, 1648, 1607, 1592, 1546, 1520, 1494, 1461, 1338, 1290, 1251, 1173, 1106, 1048, 1028 cm$^{-1}$. MS (ES-API) m/z: 416.2 (100%, [M+H]$^+$, C$_{21}$H$_{26}$N$_3$O$_4$S requires 416.2). mp: 69-71° C.

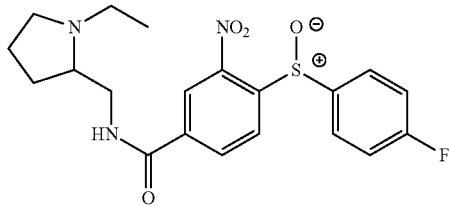 [SMILES: CCN1CCCC1CNC(=O)c1ccc([S+]([O-])c2ccc(F)cc2)c([N+](=O)[O-])c1]

N-((1-ethylpyrrolidin-2-yl)methyl)-4-((4-fluorophenyl)sulfinyl)-3-nitrobenzamide (DS-1-135)

A 15 mL pressure tube was charged with DS-1-033 (101 mg, 0.25 mmol, 1 eq), acetic acid (1.25 mL), and 35% aqueous hydrogen peroxide (31 mg, 0.33 mmol, 1.3 eq). The tube was sealed and the homogeneous solution was stirred at 60° C. After 16 h, the solution is cooled to room temperature, poured into ice-water (20 mL) and basified to pH~11 with 30% aqueous ammonium hydroxide. The resulting precipitate was filtered and washed with water (10 mL) to afford the product (57 mg, 0.14 mmol, 54%) as a 1:1 mixture of diastereoisomers as a light brown solid. $^1$H NMR (400 MHz, CDCl$_3$) δ 8.65 (dd, J=2.9, 1.7 Hz, 1H), 8.61 (d, J=8.2 Hz, 1H), 8.38 (ddd, J=8.2, 2.7, 1.8 Hz, 1H), 7.73-7.67 (m, 2H), 7.34 (bs, 1H), 7.13-7.03 (m, 2H), 3.70 (ddd, J=13.6, 7.1, 2.8 Hz, 1H), 3.34 (dt, J=13.8, 3.5 Hz, 1H), 3.26-3.17 (m, 1H), 2.88-2.79 (m, 1H), 2.79-2.72 (m, 1H), 2.35-2.20 (m, 2H), 2.00-1.89 (m, 1H), 1.81-1.56 (m, 3H), 1.13 (t, J=7.2 Hz, 1.5H), 1.12* (t, J=7.2 Hz, 1.5H). $^{13}$C NMR (100 MHz, CDCl$_3$) δ 164.5 (d, J$_{CF}$=253.7 Hz), 164.3, 146.6, 144.7, 140.4 (d, J$_{CF}$=3.3 Hz), 138.6, 133.5 (d, J$_{CF}$=8.5 Hz), 129.4 (d, J$_{CF}$=9.0 Hz), 126.7, 124.4 (d, J$_{CF}$=8.0 Hz), 116.7 (d, J$_{CF}$=22.6 Hz), 62.3, 53.6, 48.3, 41.1, 28.4, 23.08, 23.06*, 13.98, 13.96*. * second diastereoisomer. IR (thin film): 3073, 2970, 2876, 2799, 1667, 1652, 1608, 1588, 1532, 1493, 1346, 1294, 1235, 1157, 1078, 1059 cm$^{-1}$. MS (ES-API) m/z: 420.1 (100%, [M+H]$^+$, C$_{20}$H$_{23}$FN$_3$O$_4$S requires 420.1), 442.2 (12%, [M+Na]$^+$). mp: 88-90° C. (dec.).

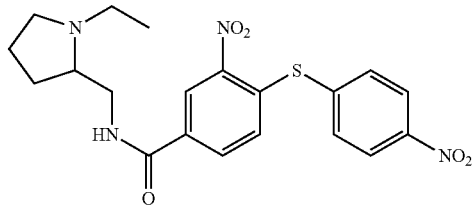 [SMILES: CCN1CCCC1CNC(=O)c1ccc(Sc2ccc([N+](=O)[O-])cc2)c([N+](=O)[O-])c1]

N-((1-ethylpyrrolidin-2-yl)methyl)-3-nitro-4-((4-nitrophenyl)thio)benzamide (DS-1-137)

Following the general procedure A-2 using 4-nitrothiophenol. Purification by chromatography on silica gel (0-15% MeOH in DCM, MeOH containing 1% NH$_3$). Yellow solid (45%). $^1$H NMR (400 MHz, CDCl$_3$) δ 8.66 (d, J=1.6 Hz, 1H), 8.35-8.28 (m, 2H), 7.86 (d, J=8.5 Hz, 1H), 7.77-7.71 (m, 2H), 7.21 (bs, 1H), 7.02 (d, J=8.5 Hz, 1H), 3.71 (ddd, J=13.8, 7.3, 3.0 Hz, 1H), 3.41-3.32 (m, 1H), 3.30-3.23 (m, 1H), 2.92-2.76 (m, 2H), 2.40-2.23 (m, 2H), 1.96 (dq, J=12.6, 8.2 Hz, 1H), 1.84-1.58 (m, 3H), 1.15 (t, J=7.2 Hz, 3H). $^{13}$C NMR (100 MHz, CDCl$_3$) δ 164.6, 148.7, 145.8, 139.9, 139.6, 135.6, 133.2, 131.8, 129.4, 125.1, 124.6, 62.3, 53.6, 48.3, 40.9, 28.3, 23.1, 14.1. IR (thin film): 3098, 2970, 2876, 2804, 1659, 1652, 1607, 1578, 1548, 1520, 1464, 1344, 1294, 1244, 1178, 1109, 1047, 1014 cm$^{-1}$. MS (ES-API) m/z: 431.2 (100%, [M+H]$^+$, C$_{20}$H$_{23}$N$_4$O$_5$S requires 431.1). mp: 128-129° C.

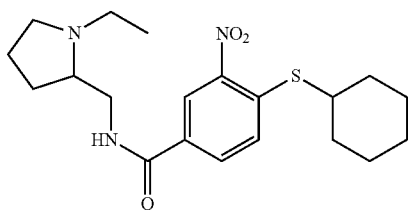 [SMILES: CCN1CCCC1CNC(=O)c1ccc(SC2CCCCC2)c([N+](=O)[O-])c1]

4-(cyclohexylthio)-N-((1-ethylpyrrolidin-2-yl)methyl)-3-nitrobenzamide (DS-1-139)

Following the general procedure A-2 using cyclohexanethiol. Yellow solid (74%). $^1$H NMR (400 MHz, CDCl$_3$) δ 8.50 (d, J=1.9 Hz, 1H), 7.95 (dd, J=8.5, 1.9 Hz, 1H), 7.51 (d, J=8.5 Hz, 1H), 6.99 (bs, 1H), 3.69 (ddd, J=13.6, 7.2, 2.7 Hz, 1H), 3.37-3.29 (m, 2H), 3.25-3.17 (m, 1H), 2.83 (dq, J=12.2, 7.4 Hz, 1H), 2.74-2.67 (m, 1H), 2.32-2.17 (m, 2H), 2.12-2.03 (m, 2H), 1.92 (dq, J=12.3, 8.3 Hz, 1H), 1.87-1.80 (m, 2H), 1.78-1.56 (m, 4H), 1.53-1.23 (m, 5H), 1.13 (t, J=7.2 Hz, 3H). $^{13}$C NMR (100 MHz, CDCl$_3$) δ 165.1, 146.4, 140.7, 131.4, 131.1, 127.7, 124.5, 62.2, 53.7, 48.2, 44.2, 41.0, 32.5, 28.4, 26.1, 25.7, 23.1, 14.2. IR (thin film): 2969, 2933, 2855, 2800, 1639, 1609, 1539, 1520, 1450, 1328, 1288, 1179, 1101, 1052 cm$^{-1}$. MS (ES-API) m/z: 392.2 (100%, [M+H]$^+$, C$_{20}$H$_{30}$N$_3$O$_3$S requires 392.2). mp: 145-146° C.

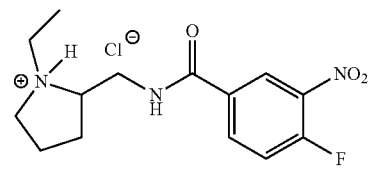 [SMILES: CC[NH+]1CCCC1CNC(=O)c1ccc(F)c([N+](=O)[O-])c1 ; [Cl-]]

N-((1-ethylpyrrolidin-2-yl)methyl)-4-fluoro-3-nitrobenzamide hydrochloride (DS-1-153)

Following the general procedure B-3 using 4-fluoro-3-nitrobenzoic acid and 2-(aminomethyl)-1-ethylpyrrolidine. White solid (89%). $^1$H NMR (400 MHz, DMSO-d$_6$) δ 10.71 (bs, 1H), 9.50 (t, J=5.6 Hz, 1H), 8.69 (dd, J=7.3, 2.2 Hz, 1H), 8.43 (ddd, J=8.7, 4.1, 2.3 Hz, 1H), 7.74 (dd, J=11.1, 8.8 Hz, 1H), 3.89-3.78 (m, 1H), 3.71-3.60 (m, 2H), 3.55 (dq, J=12.1, 5.6 Hz, 1H), 3.50-3.36 (m, 1H), 3.13-3.02 (m, 2H), 2.17-2.06 (m, 1H), 2.03-1.74 (m, 3H), 1.30 (t, J=7.2 Hz, 3H). $^{13}$C NMR (100 MHz, DMSO-d$_6$) δ 163.8, 156.4 (d, J$_{CF}$=266.4 Hz), 136.7 (d, J$_{CF}$=7.8 Hz), 135.1 (d, J$_{CF}$=10.1 Hz), 130.5 (d, J$_{CF}$=3.6 Hz), 125.6 (d, J$_{CF}$=2.0 Hz), 118.9 (d, J$_{CF}$=21.4 Hz), 65.9, 52.6, 48.5, 38.9, 27.1, 21.7, 10.2. IR (thin film): 3249, 3058, 2946, 2655, 2508, 1655, 1618, 1534, 1492, 1352, 1316, 1269 cm$^{-1}$. mp: 161° C.

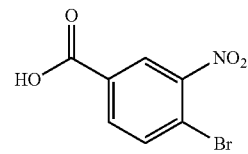 [SMILES: O=C(O)c1ccc(Br)c([N+](=O)[O-])c1]

4-bromo-3-nitrobenzoic acid (DS-1-159)

A 200 mL flask was charged with 4-bromobenzoic acid (9.84 g, 49.0 mmol), nitric acid (70%, 90 mL) and fuming nitric acid (90%, 70 mL), fitted with a reflux condenser and the resulting suspension was stirred under reflux overnight. The homogeneous yellow solution obtained was cooled to 0° C., filtered and the solid washed with cold water (100 mL) to yield a white powder. Recrystallization from methanol/water afforded the product (10.82 g, 44.0 mmol, 90%) as a microcrystalline white powder. $^1$H NMR (400 MHz, DMSO-$d_6$) δ 13.74 (bs, 1H), 8.39 (s, 1H), 8.09-7.94 (m, 2H). $^{13}$C NMR (100 MHz, DMSO-$d_6$) δ 165.0, 149.6, 135.4, 133.8, 131.7, 126.0, 118.2.

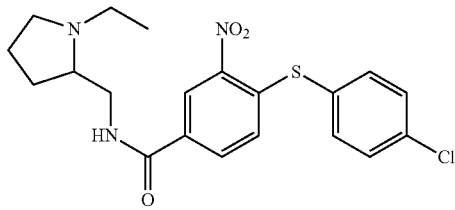 [SMILES: CCN1CCCC1CNC(=O)c1ccc(Sc2ccc(Cl)cc2)c([N+](=O)[O-])c1]

4-((4-chlorophenyl)thio)-N-((1-ethylpyrrolidin-2-yl)methyl)-3-nitrobenzamide (DS-1-163)

Following the general procedure A-3 using DS-1-153 and 4-chlorothiophenol. Purification by chromatography on silica gel (0-20% MeOH in DCM, MeOH containing 1% NH$_3$). Yellow solid (64%). $^1$H NMR (400 MHz, CDCl$_3$) δ 8.64 (d, J=1.9 Hz, 1H), 7.77 (dd, J=8.5, 1.9 Hz, 1H), 7.55-7.45 (m, 4H), 7.02 (s, 1H), 6.89 (d, J=8.5 Hz, 1H), 3.68 (ddd, J=13.7, 7.3, 2.7 Hz, 1H), 3.31 (dt, J=13.7, 3.4 Hz, 1H), 3.23-3.17 (m, 1H), 2.81 (dq, J=12.2, 7.4 Hz, 1H), 2.70 (bs, 1H), 2.33-2.15 (m, 2H), 1.92 (dq, J=12.3, 8.3 Hz, 1H), 1.80-1.54 (m, 3H), 1.11 (t, J=7.2 Hz, 3H). $^{13}$C NMR (100 MHz, CDCl$_3$) δ 164.9, 144.6, 142.7, 137.3, 137.2, 132.1, 131.6, 130.8, 128.9, 128.4, 124.5, 62.2, 53.6, 48.2, 40.9, 28.3, 23.1, 14.1. IR (thin film): 2971, 2877, 2810, 1645, 1609, 1548, 1520, 1475, 1389, 1338, 1294, 1242, 1093, 1048, 1013 cm$^{-1}$. MS (ES-API) m/z: 420.1 (100%, [M+H]$^+$, C$_{20}$H$_{23}$ClN$_3$O$_3$S requires 420.1). mp: 126° C.

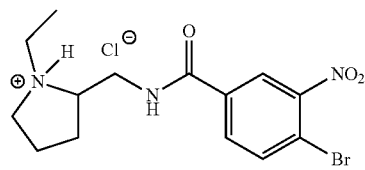 [SMILES: CC[NH+]1CCCC1CNC(=O)c1ccc(Br)c([N+](=O)[O-])c1 ; [Cl-]]

4-bromo-N-((1-ethylpyrrolidin-2-yl)methyl)-3-nitrobenzamide hydrochloride (DS-1-175)

Following the general procedure B-3 using DS-1-159 (8.13 mmol) and 2-(aminomethyl)-1-ethylpyrrolidine. White solid (85%). $^1$H NMR (400 MHz, DMSO-$d_6$) δ 10.76 (bs, 1H), 9.52 (t, J=5.6 Hz, 1H), 8.55 (d, J=1.4 Hz 1H), 8.17 (dd, J=8.3, 1.6 Hz, 1H), 8.05 (d, J=8.3 Hz, 1H), 3.87-3.78 (m, 1H), 3.71-3.60 (m, 2H), 3.54 (dt, J=11.8, 6.0 Hz, 1H), 3.49-3.38 (m, 1H), 3.16-3.01 (m, 2H), 2.20-2.06 (m, 1H), 2.03-1.75 (m, 3H), 1.29 (t, J=7.1 Hz, 3H). $^{13}$C NMR (100 MHz, DMSO-$d_6$) δ 163.9, 149.5, 135.1, 134.2, 132.2, 124.4, 116.6, 65.8, 52.5, 48.5, 38.9, 27.1, 21.6, 10.3. IR (thin film): 2684, 1648, 1538, 1470, 1397, 1354, 1311, 1247, 1032 cm$^{-1}$. MS (ES-API) m/z: 356.1 (100%, [M−Cl]$^+$, C$_{14}$H$_{19}$BrN$_3$O$_3$ requires 356.1). mp: 165° C. (dec.).

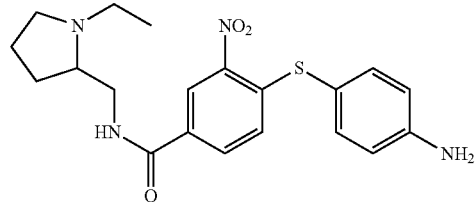

4-(4-aminophenyl)thio)-N-((1-ethylpyrrolidin-2-yl)methyl)-3-nitrobenzamide (DS-1-177)

Following the general procedure A-3 using DS-1-153 (1 eq), 4-aminothiophenol (2 eq) and sodium bicarbonate (3 eq). After overnight reaction, the reaction mixture was diluted with dichloromethane (20 mL) and the aqueous layer was basified to pH~12 by adding solid potassium hydroxide. The organic phase was washed with saturated sodium bicarbonate (2×20 mL) and then extracted with 2M HCl (3×10 mL). The acidic aqueous phases were basified to pH~10 with a concentrated potassium hydroxide solution and extracted with dichloromethane (3×10 mL). The organic layers were dried over magnesium sulfate, filtered and evaporated under reduced pressure to afford a red-orange oil. Purification by column chromatography on silica gel (0-25% MeOH in DCM, MeOH containing 1% NH$_3$). Orange solid (53%). $^1$H NMR (400 MHz, CDCl$_3$) δ 8.65 (d, J=1.6 Hz, 1H), 7.77 (dd, J=8.4, 1.5 Hz, 1H), 7.35-7.30 (m, 2H), 7.13 (bs, 1H), 6.95 (d, J=8.6 Hz, 1H), 6.79-6.74 (m, 2H), 4.00 (s, 2H), 3.69 (ddd, J=14.0, 7.3, 3.4 Hz, 1H), 3.40-3.31 (m, 1H), 3.30-3.23 (m, 1H), 2.90-2.74 (m, 2H), 2.37-2.23 (m, 2H), 1.94 (dq, J=11.8, 7.9 Hz, 1H), 1.80-1.59 (m, 3H), 1.15 (t, J=7.2 Hz, 3H). $^{13}$C NMR (100 MHz, CDCl$_3$) δ 165.2, 149.0, 145.4, 144.0, 137.5, 131.2, 131.0, 128.1, 124.5, 116.3, 116.3, 62.4, 53.6, 48.3, 41.0, 28.2, 23.0, 13.9. IR (thin film): 2970, 2876, 2806, 1652, 1644, 1598, 1548, 1520, 1498, 1463, 1338, 1293, 1240, 1178, 1106, 1049, 910, 829, 733 cm$^{-1}$. MS (ES-API) m/z: 401.1 (55%, [M+H]$^+$, C$_{20}$H$_{25}$N$_4$O$_3$S requires 401.2). mp: 166-168° C. (dec.).

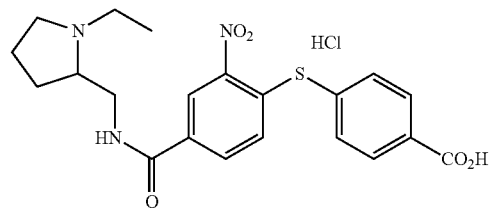 [SMILES: CCN1CCCC1CNC(=O)c1ccc(Sc2ccc(C(=O)O)cc2)c([N+](=O)[O-])c1 ; Cl]

4-((4-(((1-ethylpyrrolidin-2-yl)methyl)carbamoyl)-2-nitrophenyl)thio)benzoic acid hydrochloride (DS-1-179)

A 15 mL pressure tube was charged with the aryl fluoride DS-1-153 (332 mg, 1.00 mmol, 1 eq), water (5 mL) and 4-mercaptobenzoic acid (170 mg, 1.10 mmol, 1.1 eq). The tube was sealed and the reaction mixture was stirred at 90° C. for 2 h. A yellow precipitate appeared and the suspension was stirred overnight at room temperature. The solid was dissolved by adding 2M sodium hydroxide (50 mL) and the aqueous phase was washed with dichloromethane (3×50 mL), acidified to pH~2-3 with concentrated HCl, washed with dichloromethane (3×50 mL) and concentrated under reduced pressure to afford a yellow slurry. Toluene (20 mL) was introduced and the solvent was evaporated. This process was repeated twice to yield a yellow solid that was triturated with 2M HCl (60 mL), filtered, washed with water (20 mL) and diethyl ether (50 mL) and dried under high vacuum. Trituration with a minimum amount of acetone afforded the product (180 mg, 0.39 mmol, 39%) as a yellow solid. $^1$H NMR (400 MHz, DMSO-d$_6$) δ 13.15 (s, 1H), 10.54 (s, 1H), 9.39 (s, 1H), 8.77 (d, J=1.9 Hz, 1H), 8.13 (dd, J=8.6, 1.8 Hz, 1H), 8.07 (d, J=8.3 Hz, 2H), 7.75 (d, J=8.3 Hz, 2H), 7.04 (d, J=8.5 Hz, 1H), 3.83-3.74 (m, 1H), 3.67-3.58 (m, 2H), 3.56-3.49 (m, 1H), 3.45-3.27 (m, 1H), 3.10-3.01 (m, 2H), 2.09 (dt, J=13.2, 6.7 Hz, 1H), 2.02-1.72 (m, 3H), 1.27 (t, J=7.2 Hz, 3H). $^{13}$C NMR (100 MHz, DMSO-d$_6$) δ 166.6, 164.2, 145.0, 139.9, 135.5, 135.0, 132.6, 132.3, 131.5, 131.0, 129.0, 124.8, 65.9, 52.6, 48.5, 39.9, 27.1, 21.6, 10.3. IR (thin film): 2977, 1714, 1694, 1652, 1645, 1634, 1607, 1538, 1520, 1506, 1464, 1456, 1394, 1336, 1103, 1047, 1014 cm$^{-1}$. MS (ES-API) m/z: 430.1 (100%, [M−Cl]$^+$, C$_{21}$H$_{24}$N$_3$O$_5$S requires 430.1). mp: 135-137° C. (dec.).

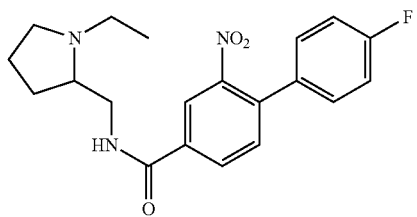 [SMILES: CCN1CCCC1CNC(=O)c1ccc(-c2ccc(F)cc2)c([N+](=O)[O-])c1]

N-((1-ethylpyrrolidin-2-yl)methyl)-4'-fluoro-2-nitro-[1,1'-biphenyl]-4-carboxamide (DS-1-181)

Following general procedure C using 4-fluorophenylboronic acid. Light yellow solid (53%). $^1$H NMR (400 MHz, CDCl$_3$) δ 8.27 (d, J=1.7 Hz, 1H), 8.03 (dd, J=8.0, 1.7 Hz, 1H), 7.50-7.46 (m, 1H), 7.31-7.25 (m, 2H), 7.14-7.08 (m, 2H), 3.73 (ddd, J=13.8, 7.2, 3.0 Hz, 1H), 3.36 (dt, J=13.8, 3.5 Hz, 1H), 3.29-3.20 (m, 1H), 2.91-2.81 (m, 1H), 2.81-2.75 (m, 1H), 2.30 (ddt, J=22.6, 17.0, 8.2 Hz, 2H), 1.95 (dq, J=12.4, 7.9 Hz, 1H), 1.82-1.59 (m, 3H), 1.14 (t, J=7.2 Hz, 3H). $^{13}$C NMR (100 MHz, CDCl$_3$) δ 165.1, 163.1 (d, J$_{CF}$=248.9 Hz), 149.2, 137.8, 135.1, 132.6 (d, J$_{CF}$=3.6 Hz), 132.4, 130.6, 129.7 (d, J$_{CF}$=8.4 Hz), 123.1, 116.0 (d, J$_{CF}$=21.9 Hz), 62.6, 53.6, 48.4, 401.0, 28.3, 23.1, 13.9. IR (thin film): 3075, 2972, 2878, 2812, 1659, 1652, 1645, 1557, 1538, 1532, 1520, 1487, 1456, 1356, 1314, 1296, 1229, 1162, 1098, 1008, 911, 837, 734 cm$^{-1}$. MS (ES-API) m/z: 372.2 (100%, [M+H]$^+$, C$_{20}$H$_{23}$FN$_3$O$_3$ requires 372.2). mp: 101° C. (dec.).

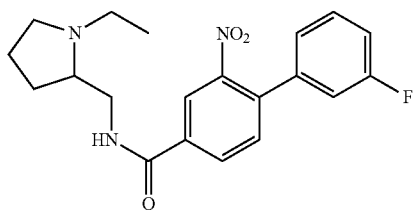 [SMILES: CCN1CCCC1CNC(=O)c1ccc(-c2cccc(F)c2)c([N+](=O)[O-])c1]

N-((1-ethylpyrrolidin-2-yl)methyl)-3'-fluoro-2-nitro-[1,1'-biphenyl]-4-carboxamide (DS-1-183)

Following general procedure C using 3-fluorophenylboronic acid. Light brown wax (90%). $^1$H NMR (400 MHz, CDCl$_3$) δ 8.30 (d, J=1.5 Hz, 1H), 8.05 (dd, J=8.0, 1.6 Hz, 1H), 7.47 (d, J=8.0 Hz, 1H), 7.40 (td, J=8.0, 5.9 Hz, 1H), 7.12 (td, J=8.5, 2.5 Hz, 1H), 7.06 (d, J=7.7 Hz, 1H), 7.02 (dt, J=9.4, 2.0 Hz, 1H), 3.71 (ddd, J=13.9, 7.1, 3.5 Hz, 1H), 3.39 (dt, J=13.8, 3.3 Hz, 1H), 3.31-3.24 (m, 1H), 2.94-2.80 (m, 2H), 2.41-2.28 (m, 2H), 1.96 (dq, J=12.3, 7.8 Hz, 1H), 1.85-1.60 (m, 3H), 1.16 (t, J=7.2 Hz, 3H). $^{13}$C NMR (100 MHz, CDCl$_3$) δ 165.2, 162.7 (d, J$_{CF}$=247.4 Hz), 149.0, 138.6 (d, J$_{CF}$=8.0 Hz), 137.6 (d, J$_{CF}$=2.3 Hz), 135.2, 132.2, 130.6, 130.5 (d, J=8.5 Hz), 123.6 (d, J=3.1 Hz), 123.2, 115.7 (d, J=21.1 Hz), 115.0 (d, J$_{CF}$=22.8 Hz), 62.9, 53.6, 48.6, 41.1, 28.2, 23.0, 13.6. IR (thin film): 3073, 2973, 2879, 2814, 1660, 1652, 1645, 1614, 1588, 1557, 1538, 1532, 1476, 1436, 1357, 1300, 1270, 1188, 1159 cm$^{-1}$. MS (ES-API) m/z: 372.2 (100%, [M+H]$^+$, C$_{20}$H$_{23}$FN$_3$O$_3$ requires 372.2).

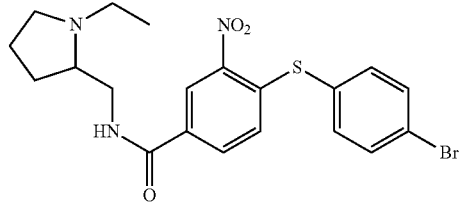 [SMILES: CCN1CCCC1CNC(=O)c1ccc(Sc2ccc(Br)cc2)c([N+](=O)[O-])c1]

4-((4-bromophenyl)thio)-N-((1-ethylpyrrolidin-2-yl)methyl)-3-nitrobenzamide (DS-1-185)

Following the general procedure A-3 using DS-1-153 and 4-bromothiophenol. Purification by trituration with pentane/diethyl ether 2:1 (3×3 mL). Yellow solid (87%). $^1$H NMR (400 MHz, CDCl$_3$) δ 8.67 (d, J=1.8 Hz, 1H), 7.80 (dd, J=8.5, 1.9 Hz, 1H), 7.66-7.62 (m, 2H), 7.47-7.43 (m, 2H), 7.20 (bs, 1H), 6.90 (d, J=8.5 Hz, 1H), 3.70 (ddd, J=13.8, 7.4, 3.1 Hz, 1H), 3.38-3.31 (m, 1H), 3.24 (t, J=6.8 Hz, 1H), 2.89-2.79 (m, 1H), 2.77 (bs, 1H), 2.36-2.21 (m, 2H), 1.94 (dq, J=12.7, 8.3 Hz, 1H), 1.81-1.57 (m, 3H), 1.14 (t, J=7.2 Hz, 3H). $^{13}$C NMR (100 MHz, CDCl$_3$) δ 165.0, 144.6, 142.4, 137.5, 133.7, 131.9, 131.7, 129.5, 128.4, 125.4, 124.7, 62.6, 53.6, 48.4, 40.8, 28.1, 23.1, 13.9. IR (thin film): 2968, 1660, 1652, 1644, 1607, 1564, 1548, 1538, 1520, 1470, 1338, 1293, 1068, 1049, 1010 cm$^{-1}$. MS (ES-API) m/z: 464.1 (100%, [M+H]$^+$, C$_{20}$H$_{23}$BrN$_3$O$_3$S requires 464.1). mp: 131-132° C.

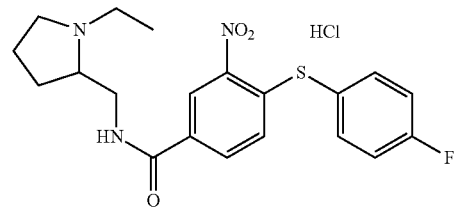 [SMILES: CCN1CCCC1CNC(=O)c1ccc(Sc2ccc(F)cc2)c([N+](=O)[O-])c1 ; Cl]

N-((1-ethylpyrrolidin-2-yl)methyl)-4-((4-fluorophenyl)thio)-3-nitrobenzamide hydrochloride (DS-1-191)

In a 5 mL flask, DS-1-033 (110 mg, 0.27 mmol, 1 eq) was suspended in methanol (2 mL) and a solution of hydrochloric acid in methanol (0.55 M, 1 mL, 0.55 mmol, 2 eq) was added dropwise. The resulting yellow homogeneous solution was concentrated under reduced pressure to afford the hydrochloride salt (117 mg, 0.27 mmol, 97%) as a yellow powder. 1H NMR (400 MHz, CDCl$_3$) δ 11.61 (bs, 1H), 9.26 (bs, 1H), 8.95 (s, 1H), 8.16 (d, J=8.7 Hz, 1H), 7.57 (dd, J=8.3, 5.3 Hz, 2H), 7.22 (t, J=8.5 Hz, 2H), 6.91 (d, J=8.4 Hz, 1H), 3.97-3.80 (m, 3H), 3.78-3.66 (m, 1H), 3.34-3.18 (m, 1H), 3.15-2.97 (m, 1H), 3.00-2.88 (m, 1H), 2.32-2.16 (m, 1H), 2.14-2.05 (m, 2H), 2.02-1.91 (m, 1H), 1.45 (bs, 3H). $^{13}$C NMR (100 MHz, CDCl$_3$) δ 165.1, 164.2 (d, J$_{CF}$=252.4 Hz), 144.7, 143.7, 138.3 (d, J$_{CF}$=8.7 Hz), 131.3, 130.2, 128.4, 126.3, 125.3 (d, J$_{CF}$=3.5 Hz), 117.9 (d, J$_{CF}$=22.1 Hz), 67.8, 54.1, 51.8, 40.1, 27.7, 23.9, 10.8. IR (thin film): 3252, 3061, 2943, 2649, 2505, 2214, 1660, 1652, 1608, 1590, 1538, 1520, 1489, 1464, 1398, 1338, 1309, 1227, 1158, 1107, 1092, 1049 cm$^{-1}$. MS (ES-API) m/z: 404.1 (100%, [M−Cl]$^+$, C$_{20}$H$_{23}$FN$_3$O$_3$S requires 404.1). mp: 186-187° C. (dec.).

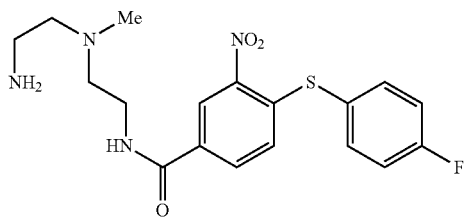 [SMILES: CN(CCN)CCNC(=O)c1ccc(Sc2ccc(F)cc2)c([N+](=O)[O-])c1]

N-(2-((2-aminoethyl)(methyl)amino)ethyl)-4-((4-fluorophenyl)thio)-3-nitrobenzamide (DS-1-195)

A 50 mL oven-dried flask was charged with 2,2'-diamino-N-methyldiethylamine (3.2 mL, 25.00 mmol, 5 eq) and dichloromethane (13 mL) and cooled to −15° C. A solution of the acyl chloride DS-1-059 in dichloromethane (15 mL) was added dropwise over 30 min and the reaction mixture was slowly warmed to room temperature. After 10 h, the resulting yellow suspension was diluted with dichloromethane (20 mL) and quenched carefully with saturated sodium bicarbonate (50 mL). The organic layer was washed with saturated sodium bicarbonate (2×25 mL) and water (25 mL), dried over magnesium sulfate and concentrated under reduced pressure. Purification by column chromatography on silica gel (0-50% MeOH in DCM, MeOH containing 1% NH$_3$) afforded the product (408 mg, 1.04 mmol, 21%) as a yellow solid. $^1$H NMR (400 MHz, CDCl$_3$) δ 8.80 (dd, J=4.6, 1.7 Hz, 1H), 8.16-8.10 (m, 1H), 7.90 (ddd, J=8.5, 3.5, 1.9 Hz, 1H), 7.57 (ddd, J=8.0, 5.1, 2.5 Hz, 2H), 7.21 (td, J=8.6, 2.5 Hz, 2H), 6.83 (dd, J=8.5, 3.7 Hz, 1H), 3.55-3.48 (m, 2H), 2.89-2.83 (m, 2H), 2.62 (t, J=5.4 Hz, 2H), 2.53 (q, J=5.9 Hz, 2H), 2.30 (s, 3H), 2.14 (s, 2H). $^{13}$C NMR (100 MHz, CDCl$_3$) δ 164.6, 164.1 (d, J$_{CF}$=252.1 Hz), 144.1, 142.9, 138.2 (d, J$_{CF}$=8.6 Hz), 132.4, 131.8, 127.9, 125.6 (d, J$_{CF}$=3.3 Hz), 124.5, 117.7 (d, J$_{CF}$=22.0 Hz), 58.5, 54.8, 42.6, 39.2, 38.2. IR (thin film): 3290, 3095, 2950, 2852, 2804, 1652, 1645, 1634, 1608, 1590, 1549, 1520, 1490, 1464, 1398, 1338, 1227, 1158, 1107, 1092, 1050, 1014 cm$^{-1}$. MS (ES-API) m/z: 393.1 (100%, [M+H]$^+$, C$_{18}$H$_{22}$FN$_4$O$_3$S requires 393.1). mp: 95-97° C. (dec.).

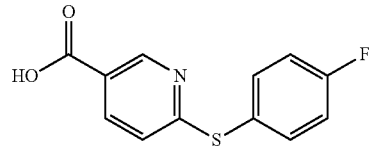 [SMILES: O=C(O)c1ccc(Sc2ccc(F)cc2)nc1]

6-((4-fluorophenyl)thio)nicotinic acid (DS-1-203)

Following the general procedure A-1 using 6-chloronicotinic acid (5.00 mmol). White powder (97%). $^1$H NMR (400 MHz, DMSO-d$_6$) δ 13.30 (s, 1H), 8.84 (dd, J=2.3, 0.8 Hz, 1H), 8.07 (dd, J=8.4, 2.3 Hz, 1H), 7.73-7.66 (m, 2H), 7.42-7.34 (m, 2H), 6.99 (dd, J=8.4, 0.8 Hz, 1H). $^{13}$C NMR (100 MHz, DMSO-d$_6$) δ 166.0, 165.5 (d, J$_{CF}$=1.4 Hz), 163.2 (d, J$_{CF}$=248.2 Hz), 150.3, 137.93 (d, J$_{CF}$=9.1 Hz), 137.88, 124.4 (d, J$_{CF}$=3.4 Hz), 123.0, 119.8, 117.3 (d, J$_{CF}$=22.1 Hz). IR (thin film): 2363, 1678, 1587, 1489, 1421, 1369, 1301, 1281, 1226, 1148, 1104, 1090, 1015 cm$^{-1}$. MS (ES-API) m/z: 248.0 (100%, [M−H]$^-$, C$_{12}$H$_7$FNO$_2$S requires 248.0), 519.1 (12%, [2M−2H+Na]$^-$). mp: 194° C.

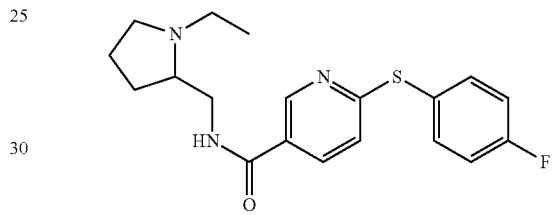

N-((1-ethylpyrrolidin-2-yl)methyl)-6-((4-fluorophenyl)thio)nicotinamide (DS-1-209)

Following the general procedure B-3 using DS-1-203 and 2-(aminomethyl)-1-ethylpyrrolidine. Purification by column chromatography on silica gel (0-50% MeOH in DCM, MeOH containing 1% NH$_3$). Colorless oil (69%). $^1$H NMR (400 MHz, CDCl$_3$) δ 8.81 (d, J=2.0 Hz, 1H), 7.97 (dd, J=8.4, 2.3 Hz, 1H), 7.60-7.55 (m, 2H), 7.48 (bs, 1H), 7.18-7.10 (m, 2H), 6.89 (d, J=8.4 Hz, 1H), 3.70 (ddd, J=13.9, 7.2, 4.0 Hz, 1H), 3.40 (dt, J=14.0, 3.4 Hz, 1H), 3.34-3.29 (m, 1H), 2.95-2.84 (m, 2H), 2.46-2.32 (m, 2H), 1.96 (dq, J=12.4, 7.9 Hz, 1H), 1.85-1.62 (m, 3H), 1.16 (t, J=7.2 Hz, 3H). $^{13}$C NMR (100 MHz, CDCl$_3$) δ 165.6, 165.3 (d, J$_{CF}$=1.4 Hz), 163.8 (d, J$_{CF}$=250.8 Hz), 148.3, 137.8 (d, J$_{CF}$=8.5 Hz), 135.7, 126.1, 125.0 (d, J$_{CF}$=3.5 Hz), 120.1, 117.2 (d, J$_{CF}$=22.0 Hz), 63.5, 53.7, 49.0, 40.4, 28.2, 23.2, 13.3. IR (thin film): 3289, 3061, 2970, 2876, 2803, 1659, 1652, 1645, 1588, 1549, 1538, 1491, 1455, 1360, 1316, 1272, 1225, 1157, 1111, 1092, 1014 cm$^{-1}$. MS (ES-API) m/z: 360.1 (100%, [M+H]$^+$, C$_{19}$H$_{23}$FN$_3$OS requires 360.2).

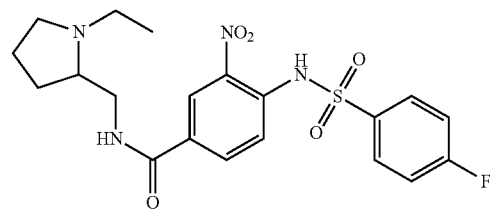 [SMILES: CCN1CCCC1CNC(=O)c1ccc(NS(=O)(=O)c2ccc(F)cc2)c([N+](=O)[O-])c1]

N-((1-ethylpyrrolidin-2-yl)methyl)-4-(4-fluorophenylsulfonamido)-3-nitrobenzamide (DS-1-213)

A 10 mL oven-dried flask was charged with 4-fluorobenzenesulfonamide (193 mg, 1.10 mmol, 1.1 eq) and dry dimethylformamide (2.8 mL), and potassium tert-butoxide (129 mg, 1.15 mmol, 1.15 eq) was added at 0° C. The resulting suspension was added to a 15 mL oven-dried pressure tube containing the aryl fluoride DS-1-153 (332 mg, 1.00 mmol, 1 eq) and potassium tert-butoxide (112 mg, 1.00 mmol, 1 eq) in dry dimethylformamide (2.5 mL) cooled to 0° C. The pressure tube was sealed and heated to 90° C. After 16 h, the reaction mixture was concentrated under reduced pressure and the residue taken in dichloromethane (20 mL). The organic phase was washed with 10% lithium chloride (3×10 mL), dried over magnesium sulfate and concentrated under reduced pressure to afford an orange solid. Purification by column chromatography on silica gel (0-50% MeOH in DCM, MeOH containing 1% $NH_3$) yielded the product (67 mg, 0.15 mmol, 15%) as a yellow solid. $^1$H NMR (400 MHz, $CDCl_3$) δ 8.53 (s, 1H), 8.44 (bs, 1H), 8.04 (dd, J=8.7, 1.4 Hz, 1H), 7.94-7.88 (m, 2H), 7.70 (d, J=8.7 Hz, 1H), 7.18-7.11 (m, 2H), 3.85-3.71 (m, 1H), 3.70-3.60 (m, 2H), 3.51-3.43 (m, 1H), 3.18-3.06 (m, 1H), 2.86-2.68 (m, 2H), 2.19-2.08 (m, 1H), 2.04-1.91 (m, 2H), 1.91-1.78 (m, 1H), 1.30 (t, J=7.2 Hz, 3H). $^{13}$C NMR (100 MHz, $CDCl_3$) δ 165.8, 165.4 (d, $J_{CF}$=255.8 Hz), 139.0, 138.4, 136.0 (d, $J_{CF}$=3.2 Hz), 133.3, 130.1 (d, $J_{CF}$=9.5 Hz), 127.3, 125.7, 120.5, 116.8 (d, $J_{CF}$=22.7 Hz), 66.1, 54.0, 50.8, 40.8, 28.0, 23.5, 11.8. IR (thin film): 3282, 2983, 2661, 1710, 1652, 1608, 1520, 1493, 1354, 1304, 1226, 1127, 1088, 970 cm$^{-1}$. MS (ES-API) m/z: 451.1 (100%, [M+H]$^+$, $C_{20}H_{24}FN_4O_5S$ requires 451.1). mp: 94-95° C. (dec.).

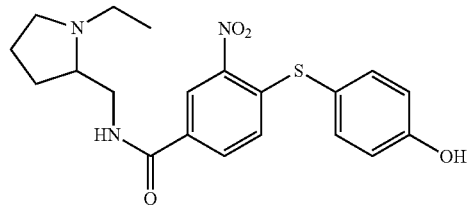 [SMILES: CCN1CCCC1CNC(=O)c1ccc(Sc2ccc(O)cc2)c([N+](=O)[O-])c1]

N-((1-ethylpyrrolidin-2-yl)methyl)-4-((4-hydroxyphenyl)thio)-3-nitrobenzamide (DS-1-217)

A 250 mL pressure flask was charged with the aryl fluoride DS-1-153 (3.32 g, 10.0 mmol, 1 eq), water (50 mL), 4-mercaptophenol (1.33 g, 10.5 mmol, 1.05 eq) and sodium bicarbonate (1.76 g, 21.0 mmol, 2.1 eq). The flask was sealed and the reaction mixture was stirred at 90° C. for 4 h. A reddish oil separated and the reaction mixture was stirred overnight at room temperature. The reaction mixture was diluted with saturated sodium bicarbonate (50 mL), dichloromethane (25 mL) and methanol (25 mL). The aqueous layer was extracted with dichloromethane (2×20 mL). The organic phase was washed with water (50 mL) and brine (50 mL), dried over magnesium sulfate and evaporated under reduced pressure to afford the product (3.97 g, 9.9 mmol, 99%) as an orange solid. $^1$H NMR (400 MHz, $CDCl_3$) δ 8.75 (d, J=1.8 Hz, 1H), 7.84 (bs, 1H), 7.82 (dd, J=8.6, 1.7 Hz, 1H), 7.40-7.37 (m, 2H), 6.91-6.88 (m, 3H), 5.43 (bs, 1H), 3.87-3.77 (m, 1H), 3.55-3.45 (m, 1H), 3.41-3.32 (m, 1H), 3.03-2.91 (m, 2H), 2.54-2.39 (m, 1H), 2.07-1.96 (m, 1H), 1.90-1.69 (m, 3H), 1.20 (t, J=7.2 Hz, 3H). $^{13}$C NMR (100 MHz, $CDCl_3$) δ 165.8, 160.0, 145.4, 144.2, 138.0, 131.1, 130.7, 128.2, 125.1, 118.4, 118.4, 64.0, 53.7, 49.1, 40.6, 27.7, 23.0, 13.1. IR (thin film): 3289, 3094, 2972, 1652, 1607, 1520, 1496, 1455, 1338, 1279, 1167, 1106, 1049 cm$^{-1}$. MS (ES-API) m/z: 402.1 (100%, [M+H]$^+$, $C_{20}H_{24}N_3O_4S$ requires 402.1). mp: 93-94° C. (dec.).

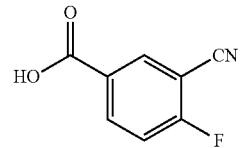 [SMILES: N#Cc1cc(C(=O)O)ccc1F]

3-cyano-4-fluorobenzoic acid (DS-1-219)

A 1 L flask was charged with 5-fluoro-2-formylbenzonitrile (10.0 g, 67.0 mmol, 1 eq), water (100 mL) and tert-butanol (450 mL). After 10 min, sodium phosphate monobasic hydrate (21.8 g, 158.0 mmol, 2.36 eq) and sodium chlorite (28.0 g, 248.0 mmol, 3.7 eq) were introduced successively in one portion under vigorous stirring. The colorless suspension rapidly turned orange and an orange gas formed. After 18 h, the reaction mixture has turned yellow and concentrated hydrochloric acid was added at 0° C. until the white solid was entirely dissolved. The tert-butanol was evaporated under reduced pressure in a well-ventilated fume-hood (caution: a yellow gas escaped) and the resulting suspension was diluted to 500 mL with water, filtered and washed with water (1 L). The white solid obtained was dissolved in ethyl acetate (80 mL), washed with brine (2×30 mL), dried over magnesium sulfate, filtered and concentrated under reduced pressure to yield the product (7.14 g, 43.2 mmol, 65%) as a white powder. $^1$H NMR (400 MHz, DMSO-$d_6$) δ 13.57 (s, 1H), 8.35 (dd, J=6.3, 2.2 Hz, 1H), 8.26 (ddd, J=8.8, 5.3, 2.2 Hz, 1H), 7.61 (t, J=9.0 Hz, 1H). $^{13}$C NMR (100 MHz, DMSO-$d_6$) δ 164.9, 164.9 (d, $J_{CF}$=261.5 Hz), 137.0 (d, $J_{CF}$=10.2 Hz), 135.2 (d, $J_{CF}$=1.2 Hz), 128.5 (d, $J_{CF}$=3.3 Hz), 117.1 (d, $J_{CF}$=20.3 Hz), 113.3, 101.0 (d, $J_{CF}$=16.1 Hz).

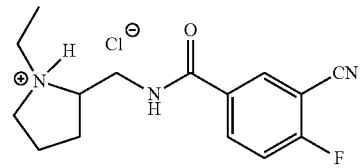 [SMILES: CC[NH+]1CCCC1CNC(=O)c1ccc(F)c(C#N)c1 ; [Cl-]]

3-cyano-N-((1-ethylpyrrolidin-2-yl)methyl)-4-fluorobenzamide hydrochloride (DS-1-223)

Following the general procedure B-3 using 3-cyano-4-fluorobenzoic acid (DS-1-219) and 2-(aminomethyl)-1-ethylpyrrolidine. Beige solid (93%). $^1$H NMR (400 MHz, DMSO-$d_6$) δ 10.63 (bs, 1H), 9.39 (t, J=5.6 Hz, 1H), 8.51 (dd, J=6.2, 2.3 Hz, 1H), 8.35 (ddd, J=8.8, 5.2, 2.3 Hz, 1H), 7.68 (t, J=9.0 Hz, 1H), 3.86-3.77 (m, 1H), 3.70-3.49 (m, 3H), 3.50-3.34 (m, 1H), 3.13-3.01 (m, 2H), 2.18-2.05 (m, 1H), 2.01-1.75 (m, 3H), 1.29 (t, J=7.2 Hz, 3H). $^{13}$C NMR (100 MHz, DMSO-$d_6$) δ 164.0, 164.0 (d, $J_{CF}$=260.3 Hz), 135.4 (d, $J_{CF}$=9.8 Hz), 133.3, 131.0 (d, $J_{CF}$=3.3 Hz), 116.9 (d, $J_{CF}$=20.1 Hz), 113.5, 100.4 (d, $J_{CF}$=15.9 Hz), 65.9, 52.6, 48.5, 38.7, 27.0, 21.6, 10.3. IR (thin film): 3249, 2947, 2652, 1661, 1611, 1588, 1549, 1496, 1318, 1271, 1106 cm$^{-1}$. MS (ES-API) m/z: 276.1 (100%, [M+H]$^+$, $C_{15}H_{19}FN_3O$ requires 276.1). mp: 164-166° C. (dec.).

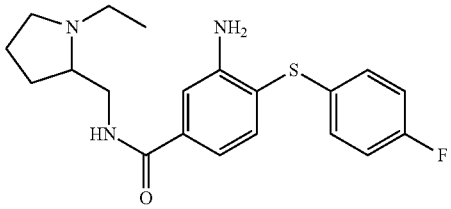 [SMILES: CCN1CCCC1CNC(=O)c1ccc(Sc2ccc(F)cc2)c(N)c1]

3-amino-N-((1-ethylpyrrolidin-2-yl)methyl)-4-((4-fluorophenyl)thio)benzamide (DS-1-225)

A 50 mL flask equipped with a reflux condenser was charged with DS-1-033 (403 mg, 1.00 mmol, 1 eq), iron powder (343 mg, 6.15 mmol, 6.15 eq), ammonium chloride (350 mg, 6.55 mmol, 6.55 eq), water (6.6 mL) and ethanol (13.3 mL). The reaction mixture was heated to 90° C. and stirred vigorously. After 1 h, the reaction mixture was cooled to room temperature and diluted with ethyl acetate (50 mL). The organic phase was washed with water (2×25 mL) and brine (25 mL), dried over magnesium sulfate and concentrated under reduced pressure to afford the product (360 mg, 0.96 mmol, 96%) as a colorless oil. $^1$H NMR (400 MHz, CDCl$_3$) δ 7.38 (d, J=8.0 Hz, 1H), 7.27 (d, J=1.8 Hz, 1H), 7.15-7.05 (m, 2H), 7.02 (dd, J=8.0, 1.8 Hz, 2H), 6.96-6.89 (m, 2H), 4.46 (s, 2H), 3.68 (ddd, J=13.7, 7.4, 3.2 Hz, 1H), 3.33-3.26 (m, 1H), 3.22 (ddd, J=9.5, 6.3, 3.5 Hz, 1H), 2.84 (dq, J=12.2, 7.4 Hz, 1H), 2.78-2.68 (m, 1H), 2.34-2.17 (m, 2H), 1.90 (dq, J=12.2, 8.2 Hz, 1H), 1.78-1.57 (m, 3H), 1.12 (t, J=7.2 Hz, 3H). $^{13}$C NMR (100 MHz, CDCl$_3$) δ 167.2, 161.1 (d, $J_{CF}$=245.8 Hz), 148.3, 136.4, 135.8, 130.3 (d, $J_{CF}$=3.1 Hz), 129.4 (d, $J_{CF}$=7.9 Hz), 118.3, 115.8 (d, $J_{CF}$=22.1 Hz), 115.7, 114.0, 62.5, 53.2, 48.1, 40.9, 27.9, 22.6, 13.4. IR (thin film): 2970, 2877, 2809, 1711, 1652, 1634, 1615, 1591, 1558, 1538, 1489, 1424, 1226, 1157 cm$^{-1}$. MS (ES-API) m/z: 374.2 (100%, [M+H]$^+$, $C_{20}H_{25}FN_3OS$ requires 374.2).

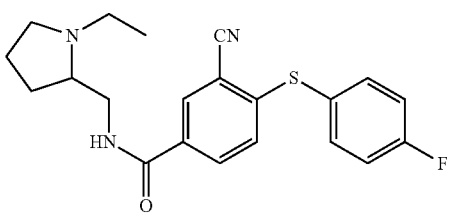 [SMILES: CCN1CCCC1CNC(=O)c1ccc(Sc2ccc(F)cc2)c(C#N)c1]

3-cyano-N-((1-ethylpyrrolidin-2-yl)methyl)-4-((4-fluorophenyl)thio)benzamide (DS-1-227)

Following the general procedure A-3 using DS-1-223 and 4-fluorothiophenol. White solid (88%). $^1$H NMR (400 MHz, CDCl$_3$) δ 8.07 (d, J=1.6 Hz, 1H), 8.22 (dd, J=8.5, 1.5 Hz, 1H), 7.60-7.50 (m, 2H), 7.20-7.13 (m, 2H), 6.95 (d, J=8.5 Hz, 1H), 3.70 (ddd, J=13.9, 7.3, 3.3 Hz, 1H), 3.39-3.32 (m, 1H), 3.30-3.25 (m, 1H), 2.92-2.76 (m, 2H), 2.40-2.23 (m, 2H), 2.04 (bs, 1H), 1.95 (dq, J=12.4, 8.1 Hz, 1H), 1.84-1.58 (m, 3H), 1.15 (t, J=7.2 Hz, 3H). $^{13}$C NMR (100 MHz, DMSO-d$_6$) δ 163.9, 163.0 (d, $J_{CF}$=248.2 Hz), 144.9, 136.7 (d, $J_{CF}$=8.8 Hz), 132.8, 132.7, 132.4, 128.2, 125.1 (d, $J_{CF}$=3.4 Hz), 117.5 (d, $J_{CF}$=22.2 Hz), 116.3, 110.1, 62.6, 53.2, 48.2, 43.4, 28.7, 22.4, 13.8. IR (thin film): 2970, 2876, 2803, 2226, 1645, 1592, 1538, 1490, 1463, 1312, 1227, 1157, 1054, 836 cm$^{-1}$. MS (ES-API) m/z: 384.2 (100%, [M+H]$^+$, $C_{21}H_{23}FN_3OS$ requires 384.2). mp: 79° C. (dec.).

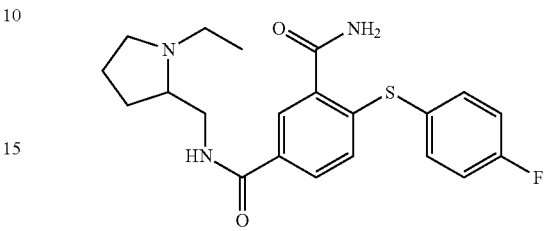

N$^1$-((1-ethylpyrrolidin-2-yl)methyl)-4-((4-fluorophenyl)thio)isophthalamide (DS-1-231-M)

In a 25 mL flask, DS-1-227 (100 mg, 0.261 mmol, 1 eq) was dissolved in ethanol (5 mL). Aqueous 2M sodium hydroxide (5 mL) was introduced and the resulting white suspension was heated to reflux. After 1 h, the reaction mixture was extracted with dichloromethane (3×10 mL) at room temperature. The organic layers were dried over anhydrous magnesium sulfate and concentrated under reduced pressure to afford the crude product as a yellow oil. Purification by column chromatography on silica gel (0-50% MeOH in DCM, MeOH containing 1% NH$_3$) afforded the product (50 mg, 0.12 mmol, 48%) as an off-white solid. $^1$H NMR (400 MHz, CDCl$_3$) δ 8.17 (d, J=1.6 Hz, 1H), 7.60 (dd, J=8.4, 1.7 Hz, 1H), 7.48 (dd, J=8.6, 5.3 Hz, 2H), 7.37 (bs, 1H), 7.10 (t, J=8.6 Hz, 2H), 7.00 (bs, 1H), 6.83 (d, J=8.4 Hz, 1H), 3.59 (ddd, J=13.5, 6.9, 3.5 Hz, 1H), 3.45 (bs, 1H), 3.30 (dt, J=13.6, 3.7 Hz, 1H), 3.16-3.09 (m, 1H), 2.81 (dq, J=14.7, 7.3 Hz, 1H), 2.69 (dt, J=9.9, 4.2 Hz, 1H), 2.30-2.13 (m, 2H), 1.88 (dq, J=12.1, 8.1 Hz, 1H), 1.76-1.50 (m, 3H), 1.08 (t, J=7.2 Hz, 3H). $^{13}$C NMR (100 MHz, CDCl$_3$) δ 169.8, 166.5, 163.4 (d, $J_{CF}$=250.4 Hz), 143.8, 137.3 (d, $J_{CF}$=8.4 Hz), 131.8, 131.0, 129.0, 127.7, 127.33, 127.29 (d, $J_{CF}$=3.7 Hz), 117.1 (d, $J_{CF}$=21.9 Hz), 62.5, 53.5, 48.5, 41.4, 28.2, 22.9, 13.8. IR (thin film): 2970, 2876, 2808, 1668, 1652, 1644, 1591, 1538, 1490, 1469, 1408, 1378, 1310, 1225, 1156, 1046, 834 cm$^{-1}$. MS (ES-API) m/z: 402.2 (100%, [M+H]$^+$, $C_{21}H_{25}FN_3O_2S$ requires 402.2). mp: 75-76° C.

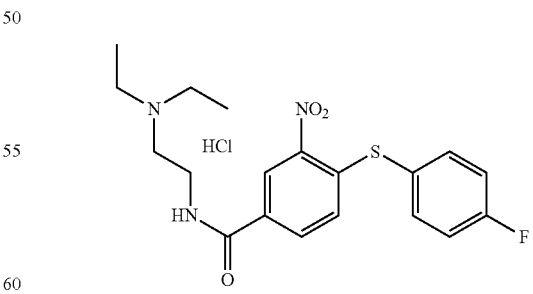

N-(2-(diethylamino)ethyl)-4-((4-fluorophenyl)thio)-3-nitrobenzamide hydrochloride (DS-1-239)

Following the general procedure D using DS-1-043 (0.13 mmol). Yellow solid (100%). $^1$H NMR (400 MHz, DMSO-d$_6$) δ 10.47 (bs, 1H), 9.31 (t, J=5.4 Hz, 1H), 8.76 (d, J=1.8 Hz, 1H), 8.12 (dd, J=8.6, 1.9 Hz, 1H), 7.72 (dd, J=8.7, 5.4 Hz, 2H), 7.44 (t, J=8.8 Hz, 2H), 6.89 (d, J=8.6 Hz, 1H), 3.66 (q, J=6.0 Hz, 2H), 3.22 (t, J=5.9 Hz, 2H), 3.16 (q, J=6.9 Hz, 4H), 1.22 (t, J=7.2 Hz, 6H). $^{13}$C NMR (100 MHz, DMSO-d$_6$) δ 164.0, 163.5 (d, J$_{CF}$=249.1 Hz), 144.1, 141.6 (d, J$_{CF}$=1.2 Hz), 138.3 (d, J$_{CF}$=8.9 Hz), 132.6, 131.1, 127.9, 125.3 (d, J$_{CF}$=3.3 Hz), 124.8, 117.8 (d, J$_{CF}$=22.1 Hz), 49.6, 46.5, 34.3, 8.3. IR (thin film): 3246, 2980, 2644, 1652, 1608, 1590, 1540, 1520, 1489, 1472, 1398, 1338, 1312, 1224, 1158, 1048, 838 cm$^{-1}$. MS (ES-API) m/z: 392.1 (100%, [M−Cl]$^+$, C$_{19}$H$_{23}$FN$_3$O$_3$S requires 392.1). mp: 170-171° C.

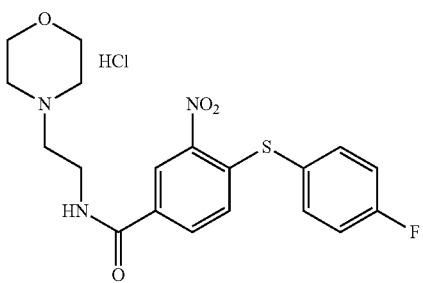 [SMILES: O=C(NCCN1CCOCC1)c1ccc(Sc2ccc(F)cc2)c([N+](=O)[O-])c1 ; Cl]

4-((4-fluorophenyl)thio)-N-(2-morpholinoethyl)-3-nitrobenzamide hydrochloride (DS-1-241)

Following the general procedure D using DS-1-089 (0.12 mmol). Yellow solid (100%). $^1$H NMR (400 MHz, DMSO-d$_6$) δ 11.12 (bs, 1H), 9.27 (t, J=5.2 Hz, 1H), 8.77 (d, J=1.5 Hz, 1H), 8.12 (dd, J=8.5, 1.5 Hz, 1H), 7.72 (dd, J=8.3, 5.4 Hz, 2H), 7.44 (t, J=8.7 Hz, 2H), 6.89 (d, J=8.5 Hz, 1H), 3.95 (d, J=11.3 Hz, 2H), 3.87-3.78 (m, 2H), 3.70 (d, J=5.4 Hz, 2H), 3.52 (d, J=12.0 Hz, 2H), 3.30 (d, J=5.1 Hz, 2H), 3.15-3.04 (m, 2H). $^{13}$C NMR (100 MHz, DMSO-d$_6$) δ 164.0, 163.5 (d, J$_{CF}$=249.2 Hz), 144.1, 141.5, 138.3 (d, J$_{CF}$=8.9 Hz), 132.7, 131.2, 127.8, 125.3 (d, J$_{CF}$=3.2 Hz), 124.8, 117.8 (d, J$_{CF}$=22.1 Hz), 63.1, 55.2, 51.1, 33.8. IR (thin film): 1652, 1608, 1590, 1548, 1520, 1489, 1456, 1338, 1226, 1158, 1104, 1048, 836 cm$^{-1}$. MS (ES-API) m/z: 406.1 (52%, [M−Cl]$^+$, C$_{19}$H$_{21}$FN$_3$O$_4$S requires 406.1), 169.1 (100%). mp: 184-185° C. (dec.).

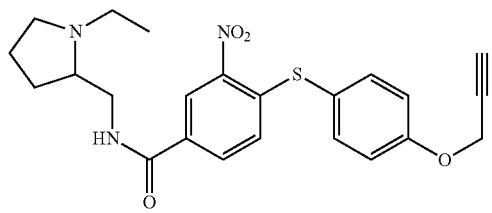 [SMILES: C#CCOc1ccc(Sc2ccc(C(=O)NCC3CCCN3CC)cc2[N+](=O)[O-])cc1]

N-((1-ethylpyrrolidin-2-yl)methyl)-3-nitro-4-((4-(prop-2-yn-1-yloxy)phenyl)thio)benzamide (DS-1-261)

A 5 mL flask was charged with DS-1-217 (201 mg, 0.50 mmol, 1 eq), dimethylformamide (2.5 mL), potassium carbonate (138 mg, 1.00 mmol, 2 eq) and propargyl bromide (80% wt. in toluene, 50 μL, 0.45 mmol, 0.9 eq). The resulting suspension was stirred overnight and concentrated under reduced pressure to afford a black residue that was partitioned between dichloromethane (10 mL) and saturated sodium bicarbonate (10 mL). The aqueous phase was extracted with dichloromethane (2×10 mL) and the organic layers were washed with water (30 mL) and brine (30 mL), dried over anhydrous magnesium sulfate and concentrated under reduced pressure to furnish a brown oil. Purification by column chromatography on silica gel (0-50% MeOH in DCM, MeOH containing 1% NH$_3$) yielded the product (38 mg, 0.09 mmol, 19%) as a brown oil. $^1$H NMR (400 MHz, CDCl$_3$) δ 8.68 (d, J=1.9 Hz, 1H), 7.80 (dd, J=8.6, 1.9 Hz, 1H), 7.54-7.49 (m, 2H), 7.34 (bs, 1H), 7.13-7.08 (m, 2H), 6.90 (d, J=8.5 Hz, 1H) 4.78 (d, J=2.4 Hz, 2H), 3.71 (ddd, J=13.8, 7.2, 3.4 Hz, 1H), 3.37 (dt, J=13.9, 3.6 Hz, 1H), 3.29-3.25 (m, 1H), 2.94-2.78 (m, 2H), 2.60 (t, J=2.4 Hz, 1H), 2.43-2.24 (m, 2H), 1.95 (dq, J=12.4, 8.1 Hz, 1H), 1.83-1.60 (m, 3H), 1.16 (t, J=7.2 Hz, 3H). $^{13}$C NMR (100 MHz, CDCl$_3$) δ 165.0, 159.3, 144.2, 144.1, 137.6, 131.3, 131.2, 128.2, 124.6, 121.5, 116.7, 77.8, 76.3, 62.8, 55.9, 53.6, 48.5, 40.7, 28.1, 23.0, 13.6. IR (thin film): 2972, 1652, 1645, 1608, 1548, 1519, 1493, 1338, 1290, 1242, 1176, 1108, 1049, 1022 cm$^{-1}$. MS (ES-API) m/z: 440.2 (100%, [M+H]$^+$, C$_{23}$H$_{26}$N$_3$O$_4$S requires 440.2).

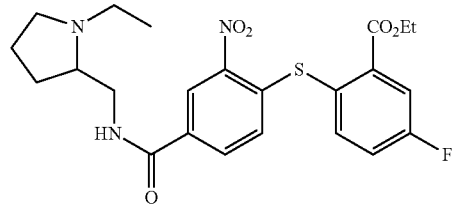 [SMILES: CCOC(=O)c1cc(F)ccc1Sc1ccc(C(=O)NCC2CCCN2CC)cc1[N+](=O)[O-]]

Ethyl 2-((4-(((1-ethylpyrrolidin-2-yl)methyl)carbamoyl)-2-nitrophenyl)thio)-5-fluorobenzoate (DS-1-265)

Following the general procedure A-3 using DS-1-153 (5.18 mmol) and ethyl 5-fluoro-2-mercaptobenzoate (5.44 mmol). Purification by washing the crude solid with 1M sodium hydroxide (50 mL), water (50 mL) and hexanes (50 mL), and dried under vacuum. Yellow solid (94%). $^1$H NMR (400 MHz, CDCl$_3$) δ 8.65 (d, J=1.6 Hz, 1H), 7.78 (dd, J=8.5, 1.7 Hz, 1H), 7.67-7.61 (m, 2H), 7.29 (td, J=8.3, 2.9 Hz, 1H), 7.08 (bs, 1H), 6.89 (d, J=8.5 Hz, 1H), 4.25 (q, J=7.1 Hz, 2H), 3.69 (ddd, J=13.7, 7.3, 2.7 Hz, 1H), 3.31 (dt, J=13.8, 3.1 Hz, 1H), 3.24-3.18 (m, 1H), 2.82 (dq, J=14.7, 7.4 Hz, 1H), 2.72 (bs, 1H), 2.34-2.16 (m, 2H), 1.92 (dq, J=12.3, 8.2 Hz, 1H), 1.81-1.53 (m, 3H), 1.19 (t, J=7.1 Hz, 3H), 1.12 (t, J=7.2 Hz, 3H). $^{13}$C NMR (100 MHz, CDCl$_3$) δ 165.2 (d, J$_{CF}$=2.4 Hz), 165.0, 163.5 (d, J$_{CF}$ 253.8 Hz), 144.8, 142.3 (d, J$_{CF}$=0.9 Hz), 140.0 (d, J$_{CF}$=8.1 Hz), 139.0 (d, J$_{CF}$=7.8 Hz), 132.1, 131.4, 129.3, 126.0 (d, J$_{CF}$=3.8 Hz), 124.4, 120.0 (d, J$_{CF}$=21.4 Hz), 118.7 (d, J$_{CF}$=24.0 Hz), 62.3, 62.2, 53.6, 48.2, 40.9, 28.2, 23.0, 14.04, 14.02. IR (thin film): 3073, 2971, 2876, 2803, 1732, 1646, 1607, 1578, 1520, 1465, 1339, 1293, 1271, 1248, 1200, 1103, 1044 cm$^{-1}$. MS (ES-API) m/z: 476.2 (100%, [M+H]$^+$, C$_{23}$H$_{27}$FN$_3$O$_5$S requires 476.2). mp: 56° C.

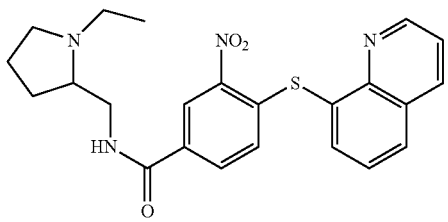 [SMILES: CCN1CCCC1CNC(=O)c1ccc(Sc2cccc3cccnc23)c([N+](=O)[O-])c1]

N-((1-ethylpyrrolidin-2-yl)methyl)-3-nitro-4-(quinolin-8-ylthio)benzamide (DS-1-269)

Following the general procedure A-3 using DS-1-153, 8-quinolinethiol hydrochloride and sodium bicarbonate (3 eq). Yellow solid (96%). $^1$H NMR (400 MHz, CDCl$_3$) δ 8.95 (d, J=2.6 Hz, 1H), 8.66 (s, 1H), 8.29 (d, J=8.1 Hz, 1H), 8.14 (d, J=6.9 Hz, 1H), 8.05 (d, J=8.1 Hz, 1H), 7.66 (t, J=7.6 Hz, 1H), 7.59 (d, J=8.1 Hz, 1H), 7.52 (dd, J=8.0, 3.9 Hz, 1H), 6.99 (bs, 1H), 6.68 (d, J=8.5 Hz, 1H), 3.65 (ddd, J=13.1, 6.9, 2.3 Hz, 1H), 3.28 (d, J=13.3 Hz, 1H), 3.21-3.15 (m, 1H), 2.80 (dq, J=14.4, 7.4 Hz, 1H), 2.69 (bs, 1H), 2.31-2.15 (m, 2H), 1.95-1.84 (m, 1H), 1.78-1.53 (m, 3H), 1.10 (t, J=7.0 Hz, 3H). $^{13}$C NMR (100 MHz, CDCl$_3$) δ 165.2, 151.8, 148.0, 144.8, 142.7, 138.4, 137.1, 131.6, 131.5, 131.2, 130.4, 129.5, 129.3, 127.2, 124.3, 122.3, 62.3, 53.6, 48.2, 41.0, 28.3, 23.1, 14.1. IR (thin film): 2970, 2803, 1654, 1606, 1548, 1519, 1491, 1457, 1337, 1293, 1050, 828, 790 cm$^{-1}$. MS (ES-API) m/z: 437.2 (35%, [M+H]$^+$, C$_{23}$H$_{25}$N$_4$O$_3$S requires 437.2), 219.1 (100%). mp: 203° C. (dec.).

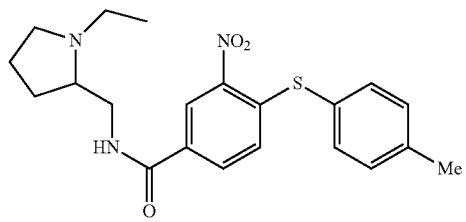 [SMILES: CCN1CCCC1CNC(=O)c1ccc(Sc2ccc(C)cc2)c([N+](=O)[O-])c1]

N-((1-ethylpyrrolidin-2-yl)methyl)-3-nitro-4-(p-tolylthio)benzamide (DS-1-271)

Following the general procedure A-3 using DS-1-153 and p-thiocresol. Pale yellow solid (95%). $^1$H NMR (400 MHz, CDCl$_3$) δ 8.67 (s, 1H), 7.78 (dd, J=8.5, 1.2 Hz, 1H), 7.46 (d, J=7.8 Hz, 2H), 7.31 (d, J=7.8 Hz, 2H), 7.19 (bs, 1H), 6.90 (d, J=8.5 Hz, 1H). 3.71 (ddd, J=13.4, 7.2, 2.4 Hz, 1H), 3.31 (d, J=13.8 Hz, 1H), 3.20 (t, J=7.0 Hz, 1H), 2.84 (dq, J=14.6, 7.3 Hz, 1H), 2.71 (bs, 1H), 2.44 (s, 3H), 2.34-2.15 (m, 2H), 1.98-1.84 (m, 1H), 1.79-1.56 (m, 2H), 1.12 (t, J=7.2 Hz, 3H). $^{13}$C NMR (100 MHz, CDCl$_3$) δ 165.0, 144.3, 143.9, 140.9, 135.9, 131.4, 131.3, 131.1, 128.3, 126.5, 124.4, 62.4, 53.5, 48.2, 40.7, 28.0, 22.9, 21.4, 13.9. IR (thin film): 2968, 2875, 2802, 1639, 1608, 1546, 1521, 1461, 1337, 1293, 1049, 812 cm$^{-1}$. MS (ES-API) m/z: 400.2 (100%, [M+H]$^+$, C$_{21}$H$_{26}$N$_3$O$_3$S requires 400.2). mp: 83-85° C.

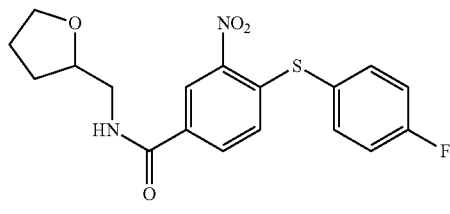 [SMILES: O=C(NCC1CCCO1)c1ccc(Sc2ccc(F)cc2)c([N+](=O)[O-])c1]

4-((4-fluorophenyl)thio)-3-nitro-N-((tetrahydrofuran-2-yl)methyl)benzamide (DS-1-275)

In a 4 mL oven-dried vial, was suspended the acyl chloride DS-1-059 (312 mg, 1.00 mmol, 1 eq) in dry dichloromethane (1 mL). Pyridine (0.16 mL, 2.0 mmol, 2 eq) and tetrahydrofurfurylamine (0.12 mL, 1.2 mmol, 1.2 eq) were added sequentially dropwise. After 48 h, the yellow suspension was filtered and the solid washed with diethyl ether (10 mL) and dissolved in dichloromethane (20 mL). The organic phase was washed with 10% hydrochloric acid (6×15 mL), saturated sodium bicarbonate (20 mL), water (20 mL) and brine (20 mL), dried over anhydrous magnesium sulfate and concentrated under reduced pressure to afford the product (257 mg, 0.68 mmol, 68%) as a yellow solid. $^1$H NMR (400 MHz, CDCl$_3$) δ 8.62 (d, J=1.9 Hz, 1H), 7.79 (dd, J=8.5, 2.0 Hz, 1H), 7.63-7.53 (m, 2H), 7.25-7.18 (m, 2H), 6.86 (d, J=8.5 Hz, 1H), 6.54 (bs, 1H), 4.05 (qd, J=7.2, 3.2 Hz, 1H), 3.88 (dt, J=8.3, 6.7 Hz, 1H), 3.84-3.74 (m, 2H), 3.30 (ddd, J=13.7, 7.9, 4.5 Hz, 1H), 2.09-1.99 (m, 1H), 1.93 (p, J=6.8 Hz, 2H), 1.64-1.53 (m, 1H). $^{13}$C NMR (100 MHz, CDCl$_3$) δ 164.7, 164.2 (d, J$_{CF}$=252.3 Hz), 144.3, 143.4 (d, J$_{CF}$=1.6 Hz), 138.3 (d, J$_{CF}$=8.6 Hz), 131.9, 131.5, 128.2, 125.6 (d, J$_{CF}$=3.6 Hz), 124.3, 117.8 (d, J$_{CF}$=22.0 Hz), 77.6, 68.2, 44.1, 28.9, 26.0. IR (thin film): 2870, 1639, 1607, 1590, 1547, 1520, 1491, 1338, 1293, 1226, 1158, 1078, 1049, 836 cm$^{-1}$. MS (ES-API) m/z: 377.1 (100%, [M+H]$^+$, C$_{18}$H$_{18}$FN$_2$O$_4$S requires 377.1), 775.2 (37%, [2M+Na]$^+$). mp: 172° C.

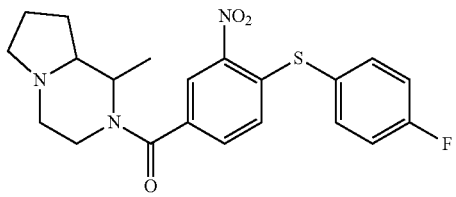 [SMILES: CC1C2CCCN2CCN1C(=O)c1ccc(Sc2ccc(F)cc2)c([N+](=O)[O-])c1]

(4-((4-fluorophenyl)thio)-3-nitrophenyl)(1-methylhexahydropyrrolo[1,2-a]pyrazin-2(1H)-yl)methanone (DS-1-279)

In a 4 mL oven-dried vial, was suspended the acyl chloride (312 mg, 1.00 mmol, 1 eq) in dry dichloromethane (1 mL). Dimethylaminopyridine (2 mg, 0.02 mmol, 2 mol %) and 1-methyloctahydropyrrolo[1,2-a]pyrazine (168 mg, 1.20 mmol, 1.2 eq) were added sequentially. After 48 h, the yellow suspension was filtered and the solid washed with diethyl ether (10 mL) and dissolved in dichloromethane (20 mL). The organic phase was washed with 1M sodium hydroxide (3×20 mL), water (20 mL) and brine (20 mL), dried over anhydrous magnesium sulfate and concentrated under reduced pressure to afford a yellow solid. Purification by column chromatography on silica gel (0-50% MeOH in DCM, MeOH containing 1% NH$_3$) yielded the product (169 mg, 0.41 mmol, 41%) as a yellow solid. $^1$H NMR (400 MHz, CDCl$_3$) δ 8.29 (d, J=1.8 Hz, 1H), 7.60-7.54 (m, 2H), 7.40 (dd, J=8.4, 1.9 Hz, 1H), 7.23-7.16 (m, 2H), 6.83 (d, J=8.4 Hz, 1H), 4.20-4.13 (m, 1H), 3.81 (d, J=13.8 Hz, 1H), 3.35 (ddd, J=13.8, 11.1, 4.1 Hz, 1H), 2.90 (ddd, J=10.4, 8.2, 1.8 Hz, 1H), 2.74-2.58 (m, 3H), 2.50 (dt, J=11.0, 3.5 Hz, 1H), 1.98-1.86 (m, 1H), 1.85-1.64 (m, 2H), 1.66-1.51 (m, 1H), 1.42 (d, J=6.8 Hz, 3H). $^{13}$C NMR (100 MHz, CDCl$_3$) δ 168.4, 164.2 (d, J$_{CF}$=252.2 Hz), 144.3, 141.6 (d, J$_{CF}$=1.6 Hz), 138.3 (d, J$_{CF}$=8.7 Hz), 133.4, 132.1, 128.3, 125.6 (d, J$_{CF}$=3.5 Hz), 124.6, 117.8 (d, J$_{CF}$=22.0 Hz), 64.4, 54.6, 52.0, 48.1, 40.6, 26.3, 21.5, 18.2. IR (thin film): 2968, 2878, 2809, 1633, 1608, 1590, 1547, 1520, 1491, 1428, 1337, 1291, 1227, 1157, 1050, 836 cm$^{-1}$. MS (ES-API) m/z: 416.1 (100%, [M+H]$^+$, C$_{21}$H$_{23}$FN$_3$O$_3$S requires 416.1). mp: 67-68° C.

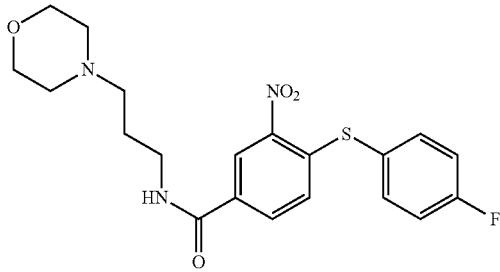 [SMILES: O=C(NCCCN1CCOCC1)c1ccc(Sc2ccc(F)cc2)c([N+](=O)[O-])c1]

4-(4-fluorophenyl)thio)-N-(3-morpholinopropyl)-3-nitrobenzamide (DS-1-283)

In a 4 mL oven-dried vial, was suspended the acyl chloride DS-1-059 (312 mg, 1.00 mmol, 1 eq) in dry dichloromethane (1 mL). Dimethylaminopyridine (1 mg, 0.01 mmol, 1 mol %) and 3-morpholinopropylamine (0.17 mL, 1.20 mmol, 1.2 eq) were added sequentially. After 48 h, the yellow suspension was filtered and the solid washed with diethyl ether (20 mL) and dissolved in dichloromethane (40 mL). The organic phase was washed with 1M sodium hydroxide (3×15 mL), brine (20 mL), dried over anhydrous magnesium sulfate and concentrated under reduced pressure to afford the product (363 mg, 0.87 mmol, 87%) as a yellow solid. $^1$H NMR (400 MHz, CDCl$_3$) δ 8.62 (s, 1H), 8.35 (bs, 1H), 7.90 (dd, J=8.6, 1.9 Hz, 1H), 7.63-7.53 (m, 2H), 7.25-7.18 (m, 2H), 6.89 (d, J=8.6 Hz, 1H) 3.75 (s, 4H), 3.59 (q, J=5.8 Hz, 2H), 2.66-2.50 (m, 6H), 1.84 (s, 2H). $^{13}$C NMR (100 MHz, CDCl$_3$) δ 164.5, 164.2 (d, J$_{CF}$=252.3 Hz), 144.0, 143.4, 138.2 (d, J$_{CF}$=8.7 Hz), 132.3, 131.9, 128.2, 125.5 (d, J$_{CF}$=3.5 Hz), 123.7, 117.8 (d, J$_{CF}$=22.0 Hz), 66.9, 58.9, 54.0, 41.1, 23.9. IR (thin film): 3286, 3076, 2956, 2855, 2814, 1640, 1608, 1590, 1547, 1520, 1491, 1462, 1337, 1292, 1223, 1158, 1117, 1048, 836 cm$^{-1}$. MS (ES-API) m/z: 420.1 (100%, [M+H]$^+$, C$_{20}$H$_{23}$FN$_3$O$_4$S requires 420.1). mp: 144° C.

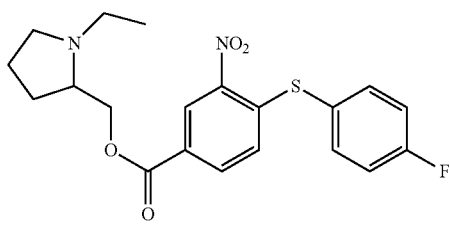 [SMILES: CCN1CCCC1COC(=O)c1ccc(Sc2ccc(F)cc2)c([N+](=O)[O-])c1]

(1-ethylpyrrolidin-2-yl)methyl 4-((4-fluorophenyl)thio)-3-nitrobenzoate (DS-1-287)

In a 10 mL oven-dried flask, were suspended the acyl chloride DS-1-059 (623 mg, 2.00 mmol, 2 eq) and dimethylaminopyridine (12 mg, 0.10 mmol, 0.1 eq) in dry dichloromethane (5 mL). 1-Ethyl-2-hydroxymethylpyrrolidine (0.135 mL, 1.00 mmol, 1 eq) was added dropwise at 0° C. After 24 h, the reaction mixture was diluted with dichloromethane (20 mL) and 1M sodium hydroxide (40 mL). The aqueous phase was extracted with dichloromethane (3×10 mL). The combined organic layers were washed with 1M sodium hydroxide (5×10 mL), water (30 mL) and brine (30 mL), dried over anhydrous magnesium sulfate and concentrated under reduced pressure to afford the product (212 mg, 0.52 mmol, 52%) as a brown oil. $^1$H NMR (400 MHz, CDCl$_3$) δ 8.84 (d, J=1.8 Hz, 1H), 7.94 (dd, J=8.6, 1.8 Hz, 1H), 7.62-7.52 (m, 2H), 7.24-7.17 (m, 2H), 6.86 (d, J=8.6 Hz, 1H), 4.31 (dd, J=11.0, 5.3 Hz, 1H), 4.21 (dd, J=11.0, 6.4 Hz, 1H), 3.15 (ddd, J=9.2, 6.5, 2.8 Hz, 1H), 2.91 (dq, J=12.0, 7.4 Hz, 1H), 2.81 (dq, J=8.5, 5.6 Hz, 1H), 2.41 (dq, J=12.1, 6.6 Hz, 1H), 2.25 (td, J=9.2, 7.5 Hz, 1H), 1.96 (dq, J=12.2, 8.4 Hz, 1H), 1.84-1.72 (m, 2H), 1.74-1.62 (m, 1H), 1.11 (d, J=14.4 Hz, 3H). $^{13}$C NMR (100 MHz, CDCl$_3$) δ 164.4, 164.3 (d, J$_{CF}$=252.5 Hz), 145.2, 144.4, 138.3 (d, J$_{CF}$=8.7 Hz), 133.6, 128.0, 127.6, 127.2, 125.4, 117.9 (d, J$_{CF}$=22.0 Hz), 68.6, 62.1, 54.0, 49.5, 28.7, 23.2, 14.0. IR (thin film): 3100, 2970, 2877, 2798, 1723, 1608, 1591, 1556, 1526, 1491, 1385, 1339, 1306, 1287, 1234, 1158, 1132, 1105, 1051, 837, 750 cm$^{-1}$. MS (ES-API) m/z: 405.1 (100%, [M+H]$^+$, C$_{20}$H$_{22}$FN$_2$O$_4$S requires 405.1), 391.1 (6%, [M−CH$_3$+H]$^+$).

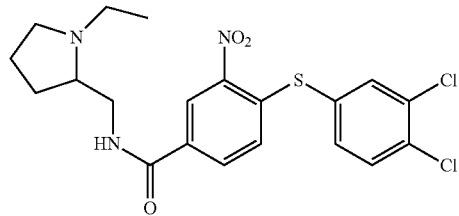 [SMILES: CCN1CCCC1CNC(=O)c1ccc(Sc2ccc(Cl)c(Cl)c2)c([N+](=O)[O-])c1]

4-((3,4-dichlorophenyl)thio)-N-((1-ethylpyrrolidin-2-yl)methyl)-3-nitrobenzamide (DS-1-291)

Following the general procedure A-3 using DS-1-153 and 3,4-dichlorothiophenol. Yellow solid (56%). $^1$H NMR (400 MHz, CDCl$_3$) δ 8.71 (s, 1H), 7.87 (d, J=8.0 Hz, 1H), 7.70 (d, J=1.8 Hz, 1H), 7.59 (d, J=8.3 Hz, 1H), 7.42 (dd, J=8.3, 1.8 Hz, 1H), 6.94 (d, J=8.5 Hz, 1H), 3.72 (ddd, J=13.1, 6.7, 3.0 Hz, 1H), 3.43-3.35 (m, 1H), 3.32-3.25 (m, 1H), 2.94-2.81 (m, 2H), 2.43-2.27 (m, 2H), 1.96 (dq, J=16.7, 7.6 Hz, 1H), 1.83-1.61 (m, 4H), 1.17 (t, J=6.9 Hz, 3H). $^{13}$C NMR (100 MHz, DMSO-d$_6$) δ 163.6, 144.5, 139.6, 136.6, 135.4, 133.6, 132.8, 132.7, 132.4, 132.3, 131.0, 128.8, 124.4, 62.5, 53.2, 48.3, 43.5, 28.7, 22.4, 13.9. IR (thin film): 2969, 2799, 1659, 1652, 1634, 1607, 1548, 1520, 1454, 1338, 1293, 1247, 1141, 1048, 1033 cm$^{-1}$. MS (ES-API) m/z: 454.1 (100%, [M+H]$^+$, C$_{20}$H$_{22}$Cl$_2$N$_3$O$_3$S requires 454.1). mp: 146-148° C. (dec.).

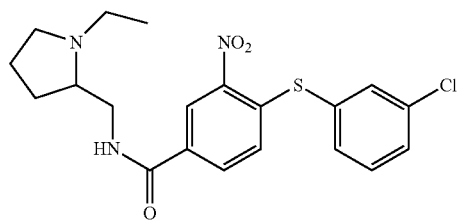 [SMILES: CCN1CCCC1CNC(=O)c1ccc(Sc2cccc(Cl)c2)c([N+](=O)[O-])c1]

4-((3-chlorophenyl)thio)-N-((1-ethylpyrrolidin-2-yl)methyl)-3-nitrobenzamide (DS-1-295)

Following the general procedure A-3 using DS-1-153 and 3-chlorothiophenol. Yellow solid (80%). $^1$H NMR (400 MHz, CDCl$_3$) δ 8.68 (d, J=1.3 Hz, 1H), (dd, J=8.4, 1.1 Hz, 1H), 7.60 (s, 1H), 7.53-7.42 (m, 3H), 7.19 (bs, 1H), 6.93 (d, J=8.5 Hz, 1H), 3.71 (ddd, J=13.8, 7.3, 3.1 Hz, 1H), 3.39-3.32 (m, 1H), 3.29-3.22 (m, 1H), 2.90-2.75 (m, 2H), 2.39-2.21 (m, 2H), 1.94 (dq, J=12.3, 8.2 Hz, 1H), 1.84-1.56 (m, 3H), 1.15 (t, J=7.2 Hz, 3H). $^{13}$C NMR (100 MHz, CDCl$_3$) δ 164.9, 144.7, 142.2, 135.9, 135.6, 134.1, 132.4, 132.1, 131.8, 131.5, 130.8, 128.5, 124.6, 62.6, 53.6, 48.3, 40.8, 28.0, 23.0, 14.0. IR (thin film): 3072, 2969, 2875, 2799, 1644, 1607, 1564, 1548, 1520, 1463, 1338, 1293, 1242, 1116, 1048, 782 cm$^{-1}$. MS (ES-API) m/z: 420.1 (100%, [M+H]$^+$, C$_{20}$H$_{23}$ClN$_3$O$_3$S requires 420.1). mp: 73-74° C.

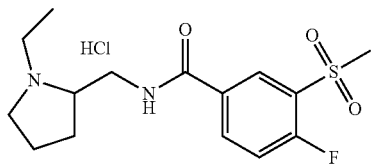 [SMILES: CCN1CCCC1CNC(=O)c1ccc(F)c(S(C)(=O)=O)c1 ; Cl]

N-((1-ethylpyrrolidin-2-yl)methyl)-4-fluoro-3-(methylsulfonyl)benzamide hydrochloride (DS-1-297)

Following the general procedure B-3 using 4-fluoro-3-(methylsulfonyl)benzoic acid and 2-(aminomethyl)-1-ethylpyrrolidine. Brown solid (100%). $^1$H NMR (400 MHz, DMSO-d$_6$/H$_2$O) δ 10.21 (bs, 1H), 9.32 (t, J=5.1 Hz, 1H), 8.38 (dd, J=6.8, 2.0 Hz, 2H), 7.70 (t, J=9.6 Hz, 1H), 3.80-3.72 (m, 1H), 3.70-3.65 (m, 1H), 3.66-3.53 (m, 2H), 3.51-3.39 (m, 1H), 3.38 (s, 3H), 3.07 (bs, 2H), 2.12 (dt, J=12.8, 6.4 Hz, 1H), 1.96 (dt, J=12.7, 5.7 Hz, 1H), 1.93-1.74 (m, 2H), 1.28 (t, J=7.2 Hz, 3H). $^{13}$C NMR (100 MHz, DMSO-d$_6$/H$_2$O) δ 164.4, 160.5 (d, J$_{CF}$=258.3 Hz), 135.3 (d, J$_{CF}$=9.7 Hz), 130.6 (d, J$_{CF}$=3.4 Hz), 129.0, 128.5 (d, J$_{CF}$=15.8 Hz), 117.8 (d, J$_{CF}$=22.1 Hz), 65.9, 52.6, 48.5, 43.6, 39.0, 27.2, 21.7, 10.3. IR (thin film): 3243, 2933, 2638, 1652, 1602, 1557, 1486, 1455, 1393, 1315, 1261, 1146, 1066, 963, 844, 776 cm$^{-1}$. MS (ES-API) m/z: 329.1 (100%, [M−Cl]$^+$, C$_{15}$H$_{22}$FN$_2$O$_3$S requires 329.1).

4-((3,4-dimethylphenyl)thio)-N-((1-ethylpyrrolidin-2-yl)methyl)-3-nitrobenzamide (DS-1-299)

Following the general procedure A-3 using DS-1-153 and 3,4-dimethylthiophenol. Yellow solid (93%). $^1$H NMR (400 MHz, CDCl$_3$) δ 8.67 (s, 1H), 7.79 (d, J=8.4 Hz, 1H), 7.36-7.23 (m, 3H), 6.92 (d, J=8.6 Hz, 1H), 3.71 (ddd, J=13.5, 6.9, 3.1 Hz, 1H), 3.37 (d, J=13.8 Hz, 1H), 3.27 (bs, 1H), 3.32-3.21 (m, 1H), 2.92-2.77 (m, 1H), 2.39-2.19 (m, 8H), 1.94 (dt, J=17.0, 8.3 Hz, 1H), 1.83-1.59 (m, 4H), 1.15 (t, J=7.0 Hz, 3H). $^{13}$C NMR (100 MHz, DMSO-d$_6$) δ 164.1, 144.1, 142.1, 139.1, 139.2, 136.4, 133.2, 132.5, 131.7, 128.1, 126.2, 124.6, 62.9, 53.4, 48.5, 43.3, 28.7, 22.5, 19.5, 19.4, 13.8. IR (thin film): 2968, 2805, 1634, 1608, 1557, 1538, 1520, 1470, 1348, 1294, 1250, 1115, 1050 cm$^{-1}$. MS (ES-API) m/z: 414.2 (100%, [M+H]$^+$, C$_{22}$H$_{28}$N$_3$O$_3$S requires 414.2). mp: 91-92° C.

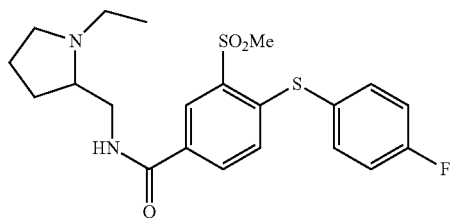 [SMILES: CCN1CCCC1CNC(=O)c1ccc(Sc2ccc(F)cc2)c(S(C)(=O)=O)c1]

N-((1-ethylpyrrolidin-2-yl)methyl)-4-((4-fluorophenyl)thio)-3-(methylsulfonyl)benzamide (DS-1-301)

A 15 mL pressure tube was charged with the aryl fluoride DS-1-297 (332 mg, 1.00 mmol, 1 eq), water (5 mL), 4-fluorothiophenol (0.12 mL, 1.10 mmol, 1.1 eq) and sodium bicarbonate (176 mg, 2.10 mmol, 2.1 eq). The tube was sealed and the reaction mixture was stirred at 90° C. for 2 h and then overnight at room temperature. The reaction mixture was diluted with water (20 mL) and dichloromethane (20 mL). The aqueous phase was extracted with dichloromethane (3×10 mL) and the combined organic layers were washed with water (20 mL) and brine (20 mL), dried over anhydrous magnesium sulfate and concentrated under reduced pressure to afford the crude product as a brown oil. Purification by column chromatography on silica gel (0-50% MeOH in DCM, MeOH containing 1% NH$_3$) yielded the product (241 mg, 0.55 mmol, 55%) as a white solid. $^1$H NMR (400 MHz, CDCl$_3$) δ 8.44 (s, 1H), 7.86 (d, J=8.3 Hz, 1H), 7.61-7.51 (m, 2H), 7.22-7.15 (m, 2H), 6.95 (d, J=8.4 Hz, 1H), 3.70 (ddd, J=13.8, 7.2, 3.5 Hz, 1H), 3.35 (s, 3H), 3.40-3.24 (m, 2H), 2.93-2.77 (m, 2H), 2.41-2.24 (m, 2H), 1.95 (dq, J=16.7, 8.0 Hz, 1H), 1.83-1.59 (m, 4H), 1.16 (t, J=7.1 Hz, 3H). $^{13}$C NMR (100 MHz, CDCl$_3$) δ 165.5, 164.0 (d, J$_{CF}$=252.0 Hz), 144.1 (d, J$_{CF}$=1.3 Hz), 137.8 (d, J$_{CF}$=8.6 Hz), 136.6, 132.4, 132.3, 128.8, 128.4, 125.5 (d, J$_{CF}$=3.6

Hz), 117.7 (d, $J_{CF}$=22.1 Hz), 62.5, 53.6, 48.4, 41.9, 41.0, 28.3, 23.1, 14.0. IR (thin film): 3063, 2970, 2877, 2803, 1652, 1634, 1592, 1532, 1490, 1455, 1312, 1227, 1142, 1038, 959, 837, 737 cm$^{-1}$. MS (ES-API) m/z: 437.1 (100%, [M+H]$^+$, $C_{21}H_{26}FN_2O_3S_2$ requires 437.1). mp: 82-83° C.

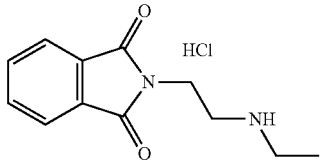 [SMILES: CCNCCN1C(=O)c2ccccc2C1=O ; Cl]

2-(2-(ethylamino)ethyl)isoindoline-1,3-dione hydrochloride (DS-1-303)

In a 200 mL flask, N-ethyl ethylenediamine (5.3 mL, 50.0 mmol, 1 eq) was heated to 100° C. and phthalimide (7.36 g, 50.0 mmol, 1 eq) was added over 15 min under vigorous stirring. Gaseous ammonia instantaneously evolved from the reaction mixture. After 3 h, the resulting yellow oil was heated to 130° C. After 2 h, the heating bath was removed and ethanol (100 mL) was added in one portion to the hot reaction mixture, immediately followed by 5-6N HCl in isopropanol (12 mL) dropwise. The reaction mixture clogged upon cooling and was cooled in an ice bath. The solid was filtered, washed with cold ethanol (100 mL) until the filtrate was colorless, and dried under high vacuum to afford the product (8.07 g, 31.7 mmol, 63%) as a white solid. $^1$H NMR (400 MHz, DMSO-d$_6$) δ 8.86 (bs, 2H), 7.93-7.84 (m, 4H), 3.89 (t, J=5.9 Hz, 2H), 3.22-3.15 (m, 2H), 3.02-2.92 (m, 2H), 1.17 (t, J=7.2 Hz, 3H). $^{13}$C NMR (100 MHz, DMSO-d$_6$) δ 167.9, 134.3, 132.0, 123.0, 44.1, 41.7, 33.9, 10.8.

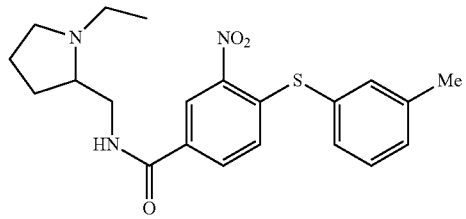 [SMILES: CCN1CCCC1CNC(=O)c1ccc(Sc2cccc(C)c2)c([N+](=O)[O-])c1]

N-((1-ethylpyrrolidin-2-yl)methyl)-3-nitro-4-(m-tolylthio)benzamide (DS-1-305)

Following the general procedure A-3 using DS-1-153 and 3-methylthiophenol. Yellow solid (92%). $^1$H NMR (400 MHz, CDCl$_3$) δ 8.67 (s, 1H), 7.79 (d, J=8.2 Hz, 1H), 7.42-7.37 (m, 3H), 7.38-7.28 (m, 1H), 6.93 (d, J=8.5 Hz, 1H), 3.71 (ddd, J=13.8, 7.2, 3.3 Hz, 1H), 3.37 (bd, J=13.0 Hz, 1H), 3.27 (bs, 1H), 2.86 (dq, J=14.7, 7.2 Hz, 2H), 2.41 (s, 3H), 2.38-2.22 (m, 2H), 1.95 (dq, J=16.9, 8.2 Hz, 1H), 1.83-1.59 (m, 4H), 1.15 (t, J=7.2 Hz, 3H). $^{13}$C NMR (100 MHz, CDCl$_3$) δ 165.1, 144.4, 143.7, 140.5, 136.5, 133.0, 131.5, 131.4, 130.2, 129.9, 128.5, 124.5, 62.5, 53.6, 48.3, 40.8, 28.1, 23.0, 21.4, 14.0. IR (thin film): 3060, 2969, 2875, 2799, 1644, 1607, 1548, 1520, 1464, 1337, 1293, 1242, 1107, 1049 cm$^{-1}$. MS (ES-API) m/z: 400.2 (100%, [M+H]$^+$, $C_{21}H_{26}N_3O_3S$ requires 400.2).

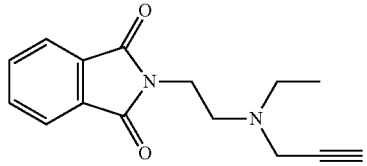 [SMILES: C#CCN(CC)CCN1C(=O)c2ccccc2C1=O]

2-(2-(ethyl(prop-2-yn-1-yl)amino)ethyl)isoindoline-1,3-dione (DS-1-307)

A 100 mL oven-dried flask was charged with DS-1-303 (2.55 g, 10.00 mmol, 1 eq), dry acetonitrile (40 mL) and potassium carbonate (1.38 g, 10.00 mmol, 1 eq). Propargyl bromide (80% wt in toluene, 1.1 mL, 10.00 mmol, 1 eq) was added dropwise and the reaction mixture was stirred vigorously for 40 h. The solid was filtered and the filtrate concentrated under reduced pressure to afford the crude product as a yellow solid. Purification by column chromatography on silica gel (0-5% MeOH in DCM, MeOH containing 1% NH$_3$) yielded the product (1.71 g, 6.68 mmol, 67%) as a white powder. $^1$H NMR (400 MHz, CDCl$_3$) δ 7.84-7.79 (m, 2H), 7.74-7.64 (m, 2H), 3.77 (t, J=6.5 Hz, 2H), 3.47 (d, J=2.4 Hz, 2H), 2.79 (t, J=6.5 Hz, 2H), 2.56 (q, J=7.1 Hz, 2H), 2.15 (t, J=2.4 Hz, 1H), 0.96 (t, J=7.1 Hz, 3H). $^{13}$C NMR (100 MHz, CDCl$_3$) δ 168.5, 133.9, 132.3, 123.3, 78.6, 73.0, 50.7, 47.5, 41.5, 36.0, 12.9. IR (thin film): 3273, 2971, 2941, 2828, 1772, 1713, 1468, 1433, 1398, 1358, 1326, 1190, 1172, 1156, 1098, 1087, 1030, 720 cm$^{-1}$. MS (ES-API) m/z: 257.1 (100%, [M+H]$^+$, $C_{15}H_{17}N_2O_2$ requires 257.1).

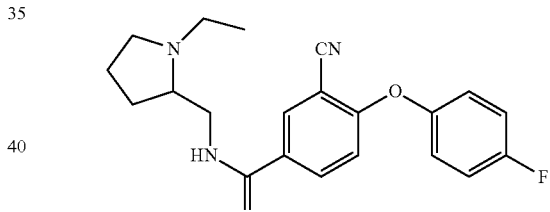

3-cyano-N-((1-ethylpyrrolidin-2-yl)methyl)-4-(4-fluorophenoxy)benzamide (DS-1-311)

A 15 mL pressure tube was charged with the aryl fluoride DS-1-223 (182 mg, 0.58 mmol, 1 eq), water (3 mL), 4-fluorophenol (72 mg, 0.64 mmol, 1.1 eq) and sodium bicarbonate (103 mg, 1.23 mmol, 2.1 eq). The tube was sealed and the reaction mixture was stirred at 90° C. for 2 h and then overnight at room temperature. The reaction mixture was diluted with water (10 mL) and dichloromethane (10 mL). The aqueous phase was extracted with dichloromethane (2×10 mL) and the combined organic layers were washed with brine (20 mL), dried over anhydrous magnesium sulfate and concentrated under reduced pressure to afford the crude product as a brown oil. Purification by column chromatography on silica gel (0-5% MeOH in DCM, MeOH containing 1% NH$_3$) yielded the product (101 mg, 0.28 mmol, 47%) as a white solid. $^1$H NMR (400 MHz, CDCl$_3$) δ 8.11 (d, J=2.2 Hz, 1H), 7.93 (dd, J=8.9, 2.3 Hz, 1H), 7.17-7.08 (m, 4H), 6.82 (d, J=8.8 Hz, 1H), 3.70 (ddd, J=13.8, 7.4, 3.0 Hz, 1H), 3.33 (ddd, J=13.8, 4.0, 2.7 Hz, 1H), 3.24 (td, J=6.9, 2.4 Hz, 1H), 2.85 (dq, J=12.1, 7.3 Hz, 1H), 2.75 (ddd, J=10.7, 6.7, 3.7 Hz, 1H), 2.44 (bs, 1H), 2.35-2.20 (m, 2H), 1.99-1.89 (m, 1H), 1.83-1.57 (m, 3H), 1.13 (t, J=7.2 Hz, 3H). $^{13}$C NMR (100 MHz, CDCl$_3$) δ 165.1, 162.2 (d, $J_{CF}$=0.8 Hz), 160.3 (d, $J_{CF}$=245.1 Hz), 150.1 (d, $J_{CF}$=2.8 Hz), 133.3, 133.1, 129.5, 122.3 (d, $J_{CF}$=8.5 Hz), 117.2 (d, $J_{CF}$=23.6 Hz), 115.7, 115.4, 103.3, 62.5, 53.7, 48.3, 40.7, 28.2, 23.1, 14.0. IR (thin film): 3075, 2970, 2936, 2876, 2802, 2234, 1660, 1652, 1645, 1608, 1548, 1538, 1505, 1486, 1268, 1228, 1191, 1147, 1091, 852 cm$^{-1}$. MS (ES-API) m/z: 368.2 (100%, [M+H]$^+$, C$_{21}$H$_{23}$FN$_3$O$_2$ requires 368.2).

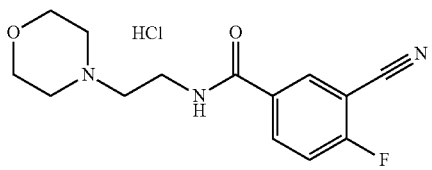 [SMILES: N#Cc1cc(C(=O)NCCN2CCOCC2)ccc1F ; Cl]

3-cyano-4-fluoro-N-(2-morpholinoethyl)benzamide hydrochloride (DS-2-025)

Following the general procedure B-3 using 3-cyano-4-fluorobenzoic acid and 4-(2-aminoethyl)morpholine. White solid (92%). $^1$H NMR (400 MHz, DMSO-d$_6$) δ 11.01 (bs, 1H), 9.21 (bs, 1H), 8.50 (dd, J=6.2, 2.2 Hz, 1H), 8.38-8.28 (m, 1H), 7.67 (t, J=9.0 Hz, 1H), 4.01-3.92 (m, 2H), 3.89-3.78 (m, 2H), 3.70 (q, J=5.7 Hz, 2H), 3.53 (d, J=12.1 Hz, 2H), 3.37-3.28 (m, 2H), 3.17-3.06 (m, 2H). $^{13}$C NMR (100 MHz, DMSO-d$_6$) δ 163.9 (d, $J_{CF}$=260.1 Hz), 163.8, 135.5 (d, $J_{CF}$=9.7 Hz), 133.4, 131.3 (d, $J_{CF}$=3.3 Hz), 116.8 (d, $J_{CF}$=20.0 Hz), 113.6, 100.3 (d, $J_{CF}$=15.8 Hz), 63.1, 55.3, 51.1, 33.8. IR (thin film): 1652, 1538, 1495, 1102 cm$^{-1}$. MS (ES-API) m/z: 278.1 (100%, [M−Cl]$^+$, C$_{14}$H$_{17}$FN$_3$O$_2$ requires 278.1).

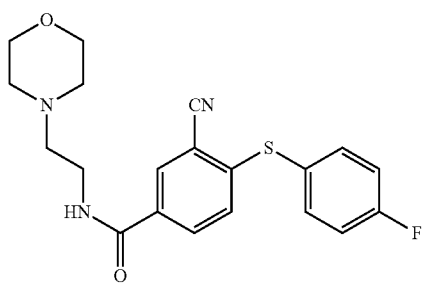 [SMILES: N#Cc1cc(C(=O)NCCN2CCOCC2)ccc1Sc1ccc(F)cc1]

3-cyano-4-((4-fluorophenyl)thio)-N-(2-morpholinoethyl)benzamide (DS-2-027)

Following the general procedure A-3 using DS-2-025 and 4-fluorothiophenol. White solid (90%). $^1$H NMR (400 MHz, CDCl$_3$) δ 8.06 (d, J=1.6 Hz, 1H), 7.82 (d, J=8.5 Hz, 1H), 7.59-7.52 (m, 2H), 7.21-7.13 (m, 2H), 6.95 (d, J=8.5 Hz, 1H), 3.78 (bs, 4H), 3.58 (q, J=5.3 Hz, 2H), 2.72-2.55 (m, 6H), 1.83 (bs, 1H). $^{13}$C NMR (100 MHz, CDCl$_3$) δ 164.7, 163.8 (d, $J_{CF}$=251.8 Hz), 147.5 (d, $J_{CF}$=1.3 Hz), 137.3 (d, $J_{CF}$=8.7 Hz), 132.1 (2C), 131.3, 127.5, 124.7 (d, $J_{CF}$=3.5 Hz), 117.5 (d, $J_{CF}$=22.2 Hz), 116.1, 110.7, 66.8, 56.7, 53.3, 36.1. IR (thin film): 3065, 2955, 2893, 2856, 2814, 2226, 1641, 1596, 1542, 1490, 1461, 1309, 1227, 1157, 1144, 1117, 1054, 836 cm$^{-1}$. MS (ES-API) m/z: 386.1 (100%, [M+H]$^+$, C$_{20}$H$_{21}$FN$_3$O$_2$S requires 386.1).

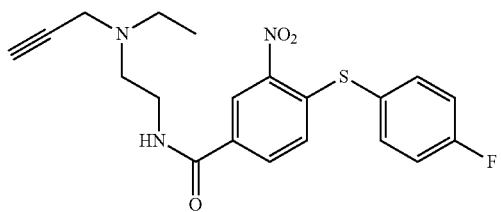 [SMILES: C#CCN(CC)CCNC(=O)c1ccc(Sc2ccc(F)cc2)c([N+](=O)[O-])c1]

N-(2-(ethyl(prop-2-yn-1-yl)amino)ethyl)-4-((4-fluorophenyl)thio)-3-nitrobenzamide (DS-2-035)

A 50 mL flask was charged with DS-1-307 (768 mg, 3.00 mmol, 1 eq) and ethanol (20 mL). Anhydrous hydrazine (0.28 mL, 9.00 mmol, 3 eq) was added dropwise and the homogeneous solution was stirred 60 h. The resulting white precipitate was filtered and washed with ethanol (3×10 mL). The colorless filtrate was concentrated under reduced pressure to afford the crude diamine as a yellow oil.

A 10 mL oven-dried flask was charged with the acyl chloride DS-1-059 (826 mg, 2.65 mmol, 1 eq), dry dichloromethane (1.8 mL) and 4-dimethylaminopyridine (3 mg, 0.03 mmol, 1 mol %) and cooled to 0° C. A solution of the crude diamine in dry dichloromethane (2 mL) was added dropwise over 10 min and the reaction mixture was slowly warmed to room temperature. After 16 h, the reaction mixture was diluted with 1M sodium hydroxide (30 mL) and dichloromethane (50 mL). The organic phase was washed with 1M sodium hydroxide (30 mL), water (30 mL) and brine (30 mL), dried over anhydrous magnesium sulfate and concentrated under reduced pressure to afford the crude product as a yellow solid. Purification by column chromatography on silica gel (0-20% MeOH in DCM, MeOH containing 1% NH$_3$) yielded the product (679 mg, 1.69 mmol, 64%) as a yellow solid. $^1$H NMR (400 MHz, CDCl$_3$) δ 8.69 (s, 1H), 7.86 (d, J=9.4 Hz, 1H), 7.60-7.55 (m, 2H), 7.21 (t, J=8.6 Hz, 2H), 6.87 (d, J=8.5 Hz, 1H), 3.62-3.49 (m, 4H), 2.89 (bs, 2H), 2.73 (bs, 2H), 2.32 (s, 1H), 1.67 (bs, 1H), 1.16 (t, J=6.9 Hz, 3H). $^{13}$C NMR (100 MHz, CDCl$_3$) δ 164.6, 164.2 (d, $J_{CF}$=252.3 Hz), 144.3, 143.3 (d, $J_{CF}$=1.6 Hz), 138.3 (d, $J_{CF}$=8.7 Hz), 131.8, 131.7, 128.2, 125.6 (d, $J_{CF}$=3.6 Hz), 124.3, 117.8 (d, $J_{CF}$=22.0 Hz), 78.4, 73.4, 51.6, 47.5, 41.5, 37.4, 12.8. IR (thin film): 3094, 2973, 2840, 1652, 1644, 1634, 1608, 1590, 1549, 1520, 1491, 1464, 1338, 1294, 1226, 1184, 1157, 1109, 1089, 1049, 839 cm$^{-1}$. MS (ES-API) m/z: 402.1 (100%, [M+H]$^+$, C$_{20}$H$_{21}$FN$_3$O$_3$S requires 402.1).

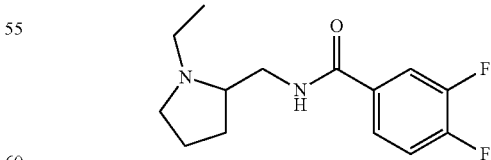

N-((1-ethylpyrrolidin-2-yl)methyl)-3,4-difluorobenzamide (DS-2-039)

Following the general procedure B-3 using 3,4-difluorobenzoic acid and 2-(aminomethyl)-1-ethylpyrrolidine.

Off-white solid (80%). $^1$H NMR (400 MHz, CDCl$_3$) δ 11.79 (s, 1H), 9.09 (t, J=5.9 Hz, 1H), 7.98-7.90 (m, 2H), 7.28-7.21 (m, 1H), 3.93-3.80 (m, 3H), 3.77-3.65 (m, 1H), 3.29-3.14 (m, 1H), 3.11-2.96 (m, 1H), 2.97-2.87 (m, 1H), 2.27-1.95 (m, 4H), 1.45 (t, J=7.3 Hz, 3H). $^{13}$C NMR (100 MHz, DMSO-d$_6$) δ 164.5, 151.6 (dd, $J_{CF}$=241.8, 12.7 Hz), 149.1 (dd, $J_{CF}$=237.4, 12.7 Hz), 131.1 (dd, $J_{CF}$=4.8, 3.6 Hz), 124.9 (dd, $J_{CF}$=7.4, 3.4 Hz), 117.7 (d, $J_{CF}$=17.6 Hz), 116.8 (d, $J_{CF}$=18.5 Hz), 66.0, 52.6, 48.6, 38.8, 27.0, 21.8, 10.3. IR (thin film): 3260, 3042, 2947, 2651, 2507, 1660, 1652, 1606, 1557, 1513, 1506, 1428, 1300, 1283, 1203, 1108, 776 cm$^{-1}$. MS (ES-API) m/z: 269.1 (100%, [M+H]$^+$, C$_{14}$H$_{19}$F$_2$N$_2$O requires 269.1).

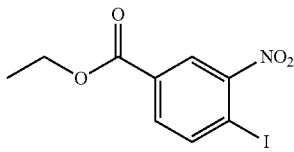

Ethyl 4-iodo-3-nitrobenzoate (DS-2-041)

A 25 mL flask was charged with ethyl 4-iodobenzoate (5.52 g, 20.0 mmol, 1 eq) and sulfuric acid (5 mL) and cooled to 0° C. An ice-cooled mixture of fuming nitric acid (1.9 mL) and sulfuric acid (2.7 mL) was added dropwise over 30 min under vigorous stirring with a Pasteur pipette. The resulting black homogeneous mixture was warmed to room temperature and stirred 5 h to afford a yellow suspension that was poured onto ice (100 g). The yellow precipitate was filtered, dissolved in ethyl acetate (100 mL), washed with saturated sodium carbonate (2×100 mL) and brine (100 mL), dried over anhydrous magnesium sulfate and concentrated under reduced pressure to yield the crude product as a yellow powder. Purification by recrystallization from ethanol at reflux afforded the product (4.09 g, 12.7 mmol, 65%). $^1$H NMR (400 MHz, CDCl$_3$) δ 8.45 (d, J=1.9 Hz, 1H), 8.14 (d, J=8.2 Hz, 1H), 7.89 (dd, J=8.2, 2.0 Hz, 1H), 4.42 (q, J=7.1 Hz, 2H), 1.42 (t, J=7.1 Hz, 3H). $^{13}$C NMR (100 MHz, CDCl$_3$) δ 164.2, 153.3, 142.4, 133.6, 132.0, 126.1, 92.1, 62.2, 14.4.

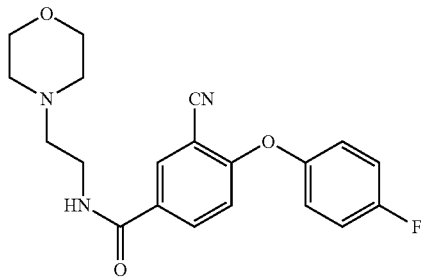 [SMILES: N#Cc1cc(C(=O)NCCN2CCOCC2)ccc1Oc1ccc(F)cc1]

3-cyano-4-(4-fluorophenoxy)-N-(2-morpholinoethyl) benzamide (DS-2-045)

Following the general procedure A-4 using the aryl fluoride DS-2-025 and 4-fluorophenol. Purification by column chromatography on silica gel (0-20% MeOH in DCM, MeOH containing 1% NH$_3$). White solid (74%). $^1$H NMR (400 MHz, CDCl$_3$) δ 8.10 (d, J=1.2 Hz, 1H), 7.93 (d, J=8.8 Hz, 1H), 7.19-7.07 (m, 4H), 6.87 (bs, 1H), 6.83 (d, J=8.8 Hz, 1H), 3.77 (bs, 4H), 3.58 (q, J=4.9 Hz, 2H), 2.71-2.50 (m, 6H). $^{13}$C NMR (100 MHz, CDCl$_3$) δ 164.8, 162.3, 160.3 (d, $J_{CF}$=245.3 Hz), 150.0 (d, $J_{CF}$=2.8 Hz), 133.4, 133.0, 129.3, 122.3 (d, $J_{CF}$=8.5 Hz), 117.2 (d, $J_{CF}$=23.6 Hz), 115.7, 115.4, 103.2, 66.9, 57.0, 53.4, 36.2. IR (thin film): 3076, 2942, 2857, 2817, 2233, 1659, 1652, 1644, 1609, 1548, 1505, 1486, 1311, 1269, 1226, 1191, 1146, 1118, 1011, 852 cm$^{-1}$. MS (ES-API) m/z: 370.2 (100%, [M+H]$^+$, C$_{20}$H$_{21}$FN$_3$O$_3$ requires 370.2).

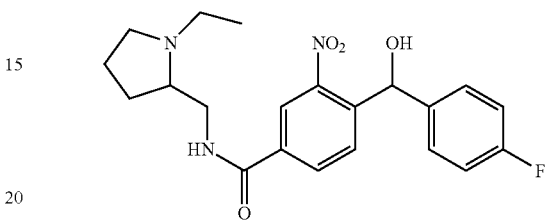

N-((1-ethylpyrrolidin-2-yl)methyl)-4-((4-fluorophenyl)(hydroxy)methyl)-3-nitrobenzamide (DS-2-051)

An oven-dried 25 mL flask was charged with ethyl 4-iodo-3-nitrobenzoate (642 mg, 2.00 mmol, 1 eq) and evacuated and backfilled with argon three times. Dry tetrahydrofuran (5 mL) was introduced and the flask was cooled to −40° C. Phenylmagnesium chloride (2M in tetrahydrofuran, 1.1 mL, 2.20 mmol, 1.1 eq) was added dropwise over 10 min and the homogeneous solution progressively turned from yellow to dark grey. After 5 min, 4-fluorobenzaldehyde (0.26 mL, 2.40 mmol, 1.2 eq) was introduced dropwise over 5 min and the reaction mixture gradually turned dark red. After 30 min, the cooling bath was removed and the solution was stirred at room temperature for 1 h. Saturated ammonium chloride (2 mL) was added and the reaction mixture was then poured into water (25 mL). The aqueous phase was extracted with ethyl acetate (3×20 mL) and the combined organic layers were washed with brine (50 mL), dried over anhydrous magnesium sulfate and concentrated under reduced pressure to afford the crude product as a brown oil. Purification by column chromatography on silica gel (0-100% ethyl acetate in hexanes) yielded the product as a yellow oil that was used in the next step without further purification.

A 10 mL flask was charged with the ethyl ester previously prepared and 2-(aminomethyl)-1-ethylpyrrolidine (2.8 mL, 20.00 mmol, 10 eq). The yellow solution immediately turned red and potassium cyanide was introduced (7 mg, 0.20 mmol, 0.1 eq). After 5 days, the reaction mixture was loaded onto silica gel and purified by column chromatography (0-20% MeOH in DCM, MeOH containing 1% NH$_3$) to yield the product (140 mg, 0.35 mmol, 17% in two steps) as an orange solid in a 1:1 mixture of two diastereoisomers. $^1$H NMR (400 MHz, CDCl$_3$) δ 8.28 (dd, J=3.5, 1.6 Hz, 1H), 7.91 (ddd, J=8.0, 2.9, 1.7 Hz, 1H), 7.69 (dd, J=14.7, 8.2 Hz, 1H), 7.54-7.47 (m, 1H), 7.31-7.24 (m, 2H), 6.98 (t, J=8.6 Hz, 2H), 6.44 (d, J=5.6 Hz, 1H), 6.08 (bs, 1H), 3.78 (dtd, J=11.4, 8.1, 3.3 Hz, 1H), 3.33 (dq, J=11.1, 3.2 Hz, 1H), 2.93 (dt, J=21.7, 7.6 Hz, 1H), 2.88-2.73 (m, 1H), 2.69 (bs, 1H), 2.27-2.08 (m, 2H), 1.88 (dt, J=13.8, 7.4 Hz, 1H), 1.76-1.54 (m, 3H), 1.04 (dt, J=13.0, 7.2 Hz, 3H). $^{13}$C NMR (100 MHz, CDCl$_3$) δ 165.8, 165.7, 162.49 (d, $J_{CF}$=247.1 Hz), 162.48 (d, $J_{CF}$=247.2 Hz), 148.02, 147.99, 141.4 (2C), 137.91 (d, $J_{CF}$=3.3 Hz), 137.87 (d, $J_{CF}$=3.3 Hz), 135.33, 135.28, 131.2, 131.1, 129.07 (2C), 129.02 (d, $J_{CF}$=8.8 Hz, 2C), 128.96 (d, $J_{CF}$=8.8 Hz, 2C), 123.9 (2C), 115.7 (d, $J_{CF}$=21.5 Hz, 4C), 70.1, 70.0, 63.3 (2C), 53.5, 53.4, 48.5 (2C), 40.3, 40.2, 27.33, 27.28, 22.8, 22.6, 13.4, 13.3. IR (thin film): 3077, 2973, 2879, 2815, 1660, 1652, 1645, 1604, 1564, 1538, 1506, 1354, 1300, 1224, 1181, 1158, 1099, 1045, 842, 814, 738 cm$^{-1}$. MS (ES-API) m/z: 402.2 (100%, [M+H]$^+$, $C_{21}H_{25}FN_3O_4$ requires 402.2).

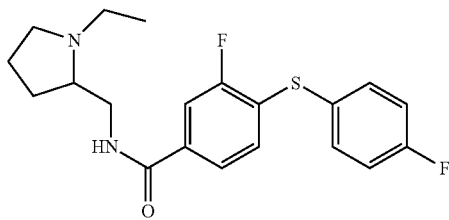 [SMILES: CCN1CCCC1CNC(=O)c1ccc(Sc2ccc(F)cc2)c(F)c1]

N-((1-ethylpyrrolidin-2-yl)methyl)-3-fluoro-4-((4-fluorophenyl)thio)benzamide (DS-2-053)

A 15 mL pressure tube was charged with the aryl fluoride DS-2-039 (305 mg, 1.00 mmol, 1 eq), water (5 mL), 4-fluorothiophenol (0.12 mL, 1.10 mmol, 1.1 eq) and sodium bicarbonate (176 mg, 2.10 mmol, 2.1 eq). The tube was sealed and the reaction mixture was stirred at 90° C. for 2 h and then overnight at room temperature. The reaction mixture was diluted with 1M sodium hydroxide (10 mL) and dichloromethane (10 mL). The aqueous phase was extracted with dichloromethane (3×5 mL) and the combined organic layers were washed with brine (20 mL), dried over anhydrous magnesium sulfate and concentrated under reduced pressure to afford the crude product as a yellow oil. Purification by column chromatography on silica gel (0-20% MeOH in DCM, MeOH containing 1% NH$_3$) yielded the product (50 mg, 0.13 mmol, 13%) as a yellow oil. $^1$H NMR (400 MHz, CDCl$_3$) δ 7.52 (dd, J=10.2, 1.7 Hz, 1H), 7.50-7.45 (m, 2H), 7.41 (dd, J=8.2, 1.7 Hz, 1H), 7.13-7.07 (m, 2H), 7.00-6.95 (m, 1H), 6.94 (bs, 1H), 3.68 (ddd, J=13.8, 7.4, 2.8 Hz, 1H), 3.29 (ddd, J=13.7, 4.1, 2.8 Hz, 1H), 3.24-3.17 (m, 1H), 2.82 (dq, J=12.2, 7.3 Hz, 1H), 2.74-2.67 (m, 1H), 2.32-2.17 (m, 2H), 1.91 (dq, J=12.2, 8.2 Hz, 1H), 1.80-1.56 (m, 3H), 1.11 (t, J=7.2 Hz, 3H). $^{13}$C NMR (100 MHz, CDCl$_3$) δ 165.8 (d, $J_{CF}$=2.1 Hz), 163.2 (d, $J_{CF}$=249.9 Hz), 159.3 (d, $J_{CF}$=246.9 Hz), 136.0 (d, $J_{CF}$=8.4 Hz), 134.57 (d, $J_{CF}$=6.4 Hz), 129.8 (d, $J_{CF}$=1.8 Hz), 129.2 (d, $J_{CF}$=16.6 Hz), 126.3 (d, $J_{CF}$=3.3 Hz), 122.7 (d, $J_{CF}$=3.4 Hz), 116.9 (d, $J_{CF}$=22.1 Hz), 114.5 (d, $J_{CF}$=23.2 Hz), 62.3, 53.5, 48.1, 40.6, 28.1, 23.0, 14.0. IR (thin film): 3068, 2970, 2876, 2800, 1644, 1607, 1590, 1557, 1520, 1490, 1292, 1225, 1157, 1090, 1059, 1014, 834 cm$^{-1}$. MS (ES-API) m/z: 377.1 (100%, [M+H]$^+$, $C_{20}H_{23}F_2N_2OS$ requires 377.1).

N-((1-ethylpyrrolidin-2-yl)methyl)-4-((4-fluorophenyl)thio)-3-nitrobenzenesulfonamide (DS-2-055)

A 25 mL flask equipped with a reflux condenser was charged with chlorosulfonic acid (5.2 mL, 78.0 mmol, 2.2 eq) and heated to 65° C. 1-Fluoro-2-nitrobenzene (3.7 mL, 35.0 mmol, 1 eq) was added dropwise. The resulting brown mixture was then heated to 100° C. After 14 h, the cooled reaction mixture was poured onto ice (50 g) and the aqueous phase was extracted with dichloromethane (2×50 mL). The combined organic layers were washed with saturated sodium bicarbonate (2×50 mL) and brine (50 mL), dried over anhydrous magnesium sulfate and concentrated under reduced pressure to yield the sulfonyl chloride (5.06 g, 21.1 mmol, 60%) as a brown liquid that was used in the next step without further purification.

In a 100 mL flask, the sulfonyl chloride was dissolved in dichloromethane (21 mL) and cooled to 0° C. 2-(Aminomethyl)-1-ethylpyrrolidine (2.9 mL, 21.0 mmol, 1 eq) was added dropwise over 5 min and the reaction mixture was allowed to warm to room temperature overnight. After 18 h, the resulting yellow precipitate was filtered and washed with diethyl ether (100 mL) to afford the crude sulfonamide as a hygroscopic yellow powder that was used in the next step without further purification.

A 15 mL pressure tube was charged with the crude sulfonamide (368 mg, 1.00 mmol, 1 eq), water (5 mL), 4-fluorothiophenol (0.12 mL, 1.10 mmol, 1.1 eq) and sodium bicarbonate (176 mg, 2.10 mmol, 2.1 eq). The tube was sealed and the reaction mixture was stirred at 90° C. for 2 h and then overnight at room temperature. The reaction mixture was diluted with saturated sodium bicarbonate (10 mL) and dichloromethane (10 mL). The aqueous phase was extracted with dichloromethane (2×10 mL) and the combined organic layers were washed with sodium bicarbonate (2×10 mL) and brine (20 mL), dried over anhydrous magnesium sulfate and concentrated under reduced pressure to afford the crude product as an orange oil. Purification by column chromatography on silica gel (0-20% MeOH in DCM, MeOH containing 1% NH$_3$) yielded the product (223 mg, 0.51 mmol, 25% in three steps) as a yellow oil. $^1$H NMR (400 MHz, CDCl$_3$) δ 8.67 (d, J=2.0 Hz, 1H), 7.75 (dd, J=8.6, 2.0 Hz, 1H), 7.60-7.55 (m, 2H), 7.25-7.19 (m, 2H), 6.92 (d, J=8.6 Hz, 1H), 4.20 (bs, 1H), 3.11-3.05 (m, 1H), 2.97 (dd, J=11.8, 2.6 Hz, 1H), 2.89 (dd, J=11.8, 4.3 Hz, 1H), 2.60-2.53 (m, 1H), 2.53-2.44 (m, 1H), 2.18-2.07 (m, 2H), 1.89-1.78 (m, 1H), 1.73-1.54 (m, 3H), 0.96 (t, J=7.2 Hz, 3H). $^{13}$C NMR (100 MHz, CDCl$_3$) δ 164.3 (d, $J_{CF}$=253.0 Hz), 145.1 (d, $J_{CF}$=1.5 Hz), 144.1, 138.3 (d, $J_{CF}$=8.7 Hz), 137.3, 131.0, 128.7, 124.9 (d, $J_{CF}$=3.6 Hz), 124.8, 118.0 (d, $J_{CF}$=22.1 Hz), 61.8, 53.4, 47.9, 44.1, 28.2, 23.1, 13.9. IR (thin film): 3098, 2971, 2877, 2804, 1593, 1554, 1520, 1491, 1455, 1393, 1338, 1291, 1227, 1171, 1157, 1102, 1048, 1014, 942, 890, 837 cm$^{-1}$. MS (ES-API) m/z: 440.1 (100%, [M+H]$^+$, $C_{19}H_{23}FN_3O_4S_2$ requires 440.1).

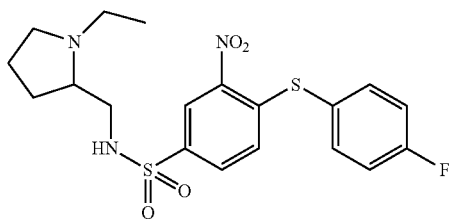 [SMILES: CCN1CCCC1CNS(=O)(=O)c1ccc(Sc2ccc(F)cc2)c([N+](=O)[O-])c1]

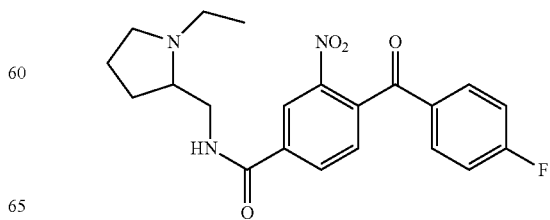

N-((1-ethylpyrrolidin-2-yl)methyl)-4-(4-fluorobenzoyl)-3-nitrobenzamide (DS-2-057)

A 5 mL flask was charged with the alcohol DS-2-051 (50 mg, 0.13 mmol, 1 eq), manganese dioxide (109 mg, 1.25 mmol, 9.6 eq) and dry dichloromethane (2.5 mL). The resulting black suspension was stirred at room temperature. After 6 h, TLC analysis indicated incomplete conversion of the starting material and more manganese dioxide (109 mg, 1.25 mmol, 9.6 eq) was added. After 14 h, the alcohol was fully consumed and the reaction mixture was filtered through Celite, washing with dichloromethane until the filtrate was colorless. The filtrate was concentrated under reduced pressure to afford the crude product as a yellow oil. Purification by column chromatography on silica gel (0-20% MeOH in DCM, MeOH containing 1% $NH_3$) yielded the product (47 mg, 0.12 mmol, 94%) as a yellow oil. 1H NMR (400 MHz, $CDCl_3$) δ 8.67 (d, J=1.5 Hz, 1H), 8.23 (dd, J=7.8, 1.6 Hz, 1H), 7.78-7.72 (m, 2H), 7.53 (bs, 1H), 7.53 (d, J=7.8 Hz, 1H), 7.15-7.08 (m, 2H), 3.76 (ddd, J=13.9, 7.2, 3.3 Hz, 1H), 3.43-3.36 (m, 1H), 3.25 (ddd, J=9.6, 7.0, 2.8 Hz, 1H), 2.94-2.85 (m, 1H), 2.86-2.76 (m, 1H), 2.39-2.23 (m, 2H), 2.03-1.89 (m, 1H), 1.85-1.60 (m, 3H), 1.15 (t, J=7.2 Hz, 3H). $^{13}C$ NMR (100 MHz, $CDCl_3$) δ 191.4, 166.3 (d, $J_{CF}$=257.0 Hz), 164.6, 146.7, 138.1, 137.4, 132.7, 132.1 (d, $J_{CF}$=2.9 Hz), 132.0 (d, $J_{CF}$=9.6 Hz), 129.3, 123.5, 116.3 (d, $J_{CF}$=22.2 Hz), 62.8, 53.6, 48.5, 41.0, 28.1, 23.1, 13.8. IR (thin film): 3075, 2971, 2877, 2803, 1668, 1598, 1538, 1506, 1412, 1349, 1299, 1281, 1241, 1152, 938, 852 $cm^{-1}$. MS (ES-API) m/z: 400.2 (100%, $[M+H]^+$, $C_{21}H_{23}FN_3O_4$ requires 400.2).

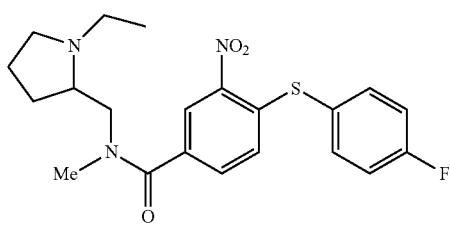 [SMILES: CCN1CCCC1CN(C)C(=O)c1ccc(Sc2ccc(F)cc2)c([N+](=O)[O-])c1]

N-((1-ethylpyrrolidin-2-yl)methyl)-4-((4-fluorophenyl)thio)-N-methyl-3-nitrobenzamide (DS-2-061)

A 10 mL flask was charged with sodium hydride (95% purity, 48 mg, 2.00 mmol, 2 eq) and dry tetrahydrofuran (3 mL) and cooled to 0° C. A solution of the secondary amide DS-1-033 (403 mg, 1.00 mmol, 1 eq) in dry tetrahydrofuran (2 mL) was added dropwise and the yellow mixture was stirred 1 h at 0° C. and 0.5 h at room temperature. A solution of iodomethane (0.11 mL, 1.20 mmol, 1.2 eq) in dry tetrahydrofuran (1.2 mL) was introduced dropwise to the yellow suspension. After 2 h, the conversion was complete by TLC analysis and the homogeneous reaction mixture was diluted with water (10 mL). The aqueous phase was extracted with ethyl acetate (3×10 mL) and the combined organic layers were dried over anhydrous magnesium sulfate and concentrated under reduced pressure to afford the crude product as an orange oil. Purification by column chromatography on silica gel (0-20% MeOH in DCM, MeOH containing 1% $NH_3$) yielded the product (183 mg, 0.44 mmol, 44%) as an orange oil in a 1:1.4 mixture of two rotamers. $^1H$ NMR (400 MHz, $CDCl_3$) δ 8.64* (s, 0.52H), 8.28† (s, 0.38H), 7.59-7.54 (m, 2H), 7.48-7.39 (m, 1H), 7.22-7.16 (m, 2H), 6.81 (d, J=7.6 Hz, 1H), 3.75-3.67† (m, 0.38H), 3.46-3.35 (m, 1H), 3.25-3.14* (m, 0.48H), 3.07 (s, 4H, 0.33H†), 2.93-2.62 (m, 2H), 2.41-2.13 (m, 2H, 0.57H*), 1.98-1.63 (m, 3H), 1.15-1.00 (m, 3H). $^{13}C$ NMR (100 MHz, $CDCl_3$) δ 169.5*, 168.7†, 144.1 (2C), 141.3†, 141.0*, 164.1 (d, $J_{CF}$=252.1 Hz, 2C), 138.3 (d, $J_{CF}$=8.6 Hz, 2C), 133.7 (2C), 132.9*, 132.1†, 128.1 (2C), 125.8*, 125.5†, 124.7 (2C), 117.7 (d, $J_{CF}$=22.0 Hz, 2C), 62.7, 61.5, 56.4, 53.8, 53.7, 52.1, 49.9, 49.3, 39.7, 33.8, 29.8, 29.3, 29.1, 23.2, 23.0, 14.0. * and † label the rotamers. IR (thin film): 2970, 2875, 2797, 1644, 1634, 1608, 1591, 1548, 1520, 1489, 1455, 1403, 1338, 1290, 1226, 1157, 1108, 1092, 1050, 1014, 836 $cm^{-1}$. MS (ES-API) m/z: 418.2 (100%, $[M+H]^+$, $C_{21}H_{25}FN_3O_3S$ requires 418.2).

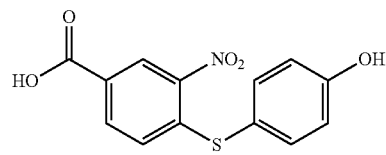 [SMILES: O=C(O)c1ccc(Sc2ccc(O)cc2)c([N+](=O)[O-])c1]

4-((4-hydroxyphenyl)thio)-3-nitrobenzoic acid (DS-2-073)

In a 250 mL flask equipped with a reflux condenser, 4-fluoro-3-nitrobenzoic acid (9.26 g, 50.0 mmol, 1 eq) and sodium bicarbonate (4.41 g, 52.5 mmol, 1.05 eq) were suspended in water (100 mL). After gas evolution ended, 4-mercaptophenol (6.62 g, 52.5 mmol, 1.05 eq) was introduced over 5 min and the orange reaction mixture was stirred at 90° C. After 4 h, the resulting yellow solid was filtered at room temperature and washed with water (200 mL) and dried under high vacuum to afford the product (11.97 g, 41.09 mmol, 82%) as a yellow powder. $^1H$ NMR (400 MHz, DMSO-$d_6$) δ 13.51 (s, 1H), 10.21 (s, 1H), 8.64 (d, J=1.7 Hz, 1H), 8.02 (dd, J=8.6, 1.8 Hz, 1H), 7.44 (d, J=8.5 Hz, 2H), 7.01-6.88 (m, 3H). $^{13}C$ NMR (100 MHz, DMSO-$d_6$) δ 165.4, 159.9, 145.1, 143.7, 137.7, 133.9, 127.9, 127.8, 126.5, 117.6, 117.1.

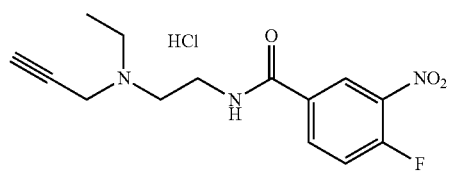 [SMILES: C#CCN(CC)CCNC(=O)c1ccc(F)c([N+](=O)[O-])c1 ; Cl]

N-(2-(ethyl(prop-2-yn-1-yl)amino)ethyl)-4-fluoro-3-nitrobenzamide hydrochloride (DS-2-077)

Following the general procedure B-3 using 4-fluoro-3-nitrobenzoic acid and N-ethyl-N-(prop-2-yn-1-yl)ethane-1,2-diamine (see DS-2-035). Beige solid (84%). $^1H$ NMR (400 MHz, DMSO-$d_6$) δ 11.39 (s, 1H), 9.40 (t, J=5.4 Hz, 1H), 8.68 (dd, J=7.3, 2.2 Hz, 1H), 8.40 (ddd, J=8.7, 4.2, 2.3 Hz, 1H), 7.73 (dd, J=11.1, 8.8 Hz, 1H), 4.30-4.18 (m, 2H), 3.82 (s, 1H), 3.72 (q, J=5.8 Hz, 2H), 3.41-3.15 (m, 4H), 1.28 (t, J=7.2 Hz, 3H). $^{13}C$ NMR (100 MHz, DMSO-$d_6$) δ 163.7, 156.3 (d, $J_{CF}$=266.1 Hz), 136.6 (d, $J_{CF}$=7.7 Hz), 135.3 (d, $J_{CF}$=10.0 Hz), 130.8 (d, $J_{CF}$=3.7 Hz), 125.5 (d, $J_{CF}$=1.9 Hz), 118.8 (d, $J_{CF}$=21.3 Hz), 81.4, 72.7, 50.7, 47.9, 40.9, 34.5, 8.8. IR (thin film): 3204, 2948, 2480, 2125, 1661, 1652, 1621, 1538, 1495, 1470, 1456, 1352, 1316, 1270 cm$^{-1}$. MS (ES-API) m/z: 294.1 (100%, [M–Cl]$^+$, $C_{14}H_{17}FN_3O_3$ requires 294.1).

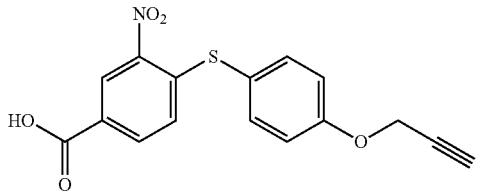 [SMILES: C#CCOc1ccc(Sc2ccc(C(=O)O)cc2[N+](=O)[O-])cc1]

3-nitro-4-((4-(prop-2-yn-1-yloxy)phenyl)thio)benzoic acid (DS-2-079)

A 100 mL flask was charged with the phenol DS-2-073 (2.91 g, 10.0 mmol, 1 eq) and a solution of sodium hydroxide (1.20 g, 30.0 mmol, 3 eq) in ethanol (50 mL). To the resulting deep purple solution was added propargyl bromide (80% wt. in toluene, 3.35 mL, 30.0 mmol, 3 eq) in one portion and the reaction mixture was heated under reflux. After 3.5 h, the yellow precipitate was filtered at room temperature and washed with ethanol (3×50 mL) and dried under high vacuum to afford the product (1.33 g, 4.05 mmol, 41%) as a yellow powder. $^1$H NMR (400 MHz, DMSO-d$_6$) δ 8.59 (d, J=1.6 Hz, 1H), 7.92 (dd, J=8.3, 1.7 Hz, 1H), 7.60-7.54 (m, 2H), 7.18-7.13 (m, 2H), 6.73 (d, J=8.3 Hz, 1H), 4.90 (d, J=2.4 Hz, 2H), 3.65 (t, J=2.3 Hz, 1H). $^{13}$C NMR (100 MHz, DMSO-d$_6$) δ 167.3, 158.9, 143.8, 139.2, 138.0, 137.4, 134.4, 126.8, 125.9, 121.3, 116.8, 78.9, 78.8, 55.8. IR (thin film): 1586, 1538, 1404, 1327, 1179 cm$^{-1}$. MS (ES-API) m/z: 328.0 (100%, [M–H]$^-$, $C_{16}H_{10}NO_5S$ requires 328.0).

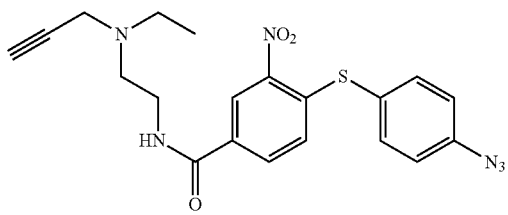 [SMILES: C#CCN(CC)CCNC(=O)c1ccc(Sc2ccc(N=[N+]=[N-])cc2)c([N+](=O)[O-])c1]

4-(4-azidophenyl)thio)-N-(2-(ethyl(prop-2-yn-1-yl)amino)ethyl)-3-nitrobenzamide (DS-2-091)

A 15 mL pressure tube was charged with the aryl fluoride DS-2-077 (330 mg, 1.00 mmol, 1 eq), water (5 mL), 4-aminothiophenol (138 mg, 1.10 mmol, 1.1 eq) and potassium carbonate (290 mg, 2.10 mmol, 2.1 eq). The tube was sealed and the reaction mixture was stirred at 90° C. for 2 h and then overnight at room temperature. The reaction mixture was diluted with 1M sodium hydroxide (15 mL) and dichloromethane (20 mL). The organic phase was washed with 1M sodium hydroxide (2×20 mL), water (20 mL), dried over anhydrous magnesium sulfate and concentrated under reduced pressure to afford the crude product as an orange thick oil. Purification by column chromatography on silica gel (0-10% MeOH in DCM, MeOH containing 1% NH$_3$) yielded the aniline (300 mg, 0.75 mmol, 75%) as an orange oil.

A 10 mL flask was charged with the aniline (300 mg, 0.75 mmol, 1 eq) and 2M hydrochloric acid (3 mL) and cooled to 0° C. A solution of sodium nitrite (62 mg, 0.90 mmol, 1.2 eq) in water (0.3 mL) was added dropwise. After 1 h, a solution of sodium azide (73 mg, 1.10 mmol, 1.5 eq) in water (0.6 mL) was introduced dropwise resulting in rapid gas evolution. The reaction mixture was slowly warmed to room temperature overnight and diluted with water (15 mL) and dichloromethane (20 mL) and slowly basified by adding 1M sodium hydroxide (9 mL). The aqueous phase was extracted with dichloromethane (3×10 mL). The combined organic layers were washed with water (20 mL) and brine (20 mL), dried over anhydrous magnesium sulfate and concentrated under reduced pressure to afford the crude product as yellow solid. Purification by column chromatography on silica gel (0-2.5% MeOH in DCM, MeOH containing 1% NH$_3$) yielded the product (210 mg, 0.50 mmol, 66%) as yellow solid. $^1$H NMR (400 MHz, CDCl$_3$) δ 8.61 (d, J=1.6 Hz, 1H), 7.78 (dd, J=8.5, 1.7 Hz, 1H), 7.57 (d, J=8.5 Hz, 2H), 7.16 (d, J=8.5 Hz, 2H), 6.91 (s, 1H), 6.88 (d, J=8.6 Hz, 1H), 3.52 (q, J=5.3 Hz, 2H), 3.43 (d, J=2.1 Hz, 2H), 2.78 (t, J=5.8 Hz, 2H), 2.62 (q, J=7.1 Hz, 2H), 2.24 (t, J=2.1 Hz, 1H), 1.08 (t, J=7.1 Hz, 3H). $^{13}$C NMR (100 MHz, CDCl$_3$) δ 164.5, 144.2, 143.3, 142.7, 137.5, 131.7, 131.6, 128.2, 125.9, 124.2, 120.9, 78.3, 73.3, 51.4, 47.4, 41.4, 37.2, 12.7. IR (thin film): 2971, 2130, 2096, 1637, 1608, 1589, 1548, 1520, 1488, 1464, 1338, 1293, 1180, 1106, 1049, 832 cm$^{-1}$. MS (ES-API) m/z: 425.1 (100%, [M+H]$^+$, $C_{20}H_{21}N_6O_3S$ requires 425.1).

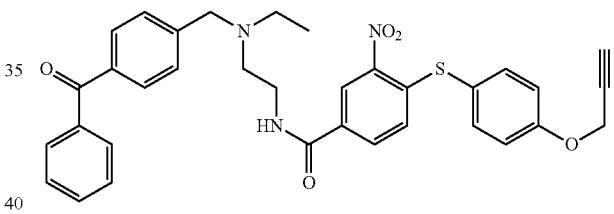

N-(2-((4-benzoylbenzyl)(ethyl)amino)ethyl)-3-nitro-4-((4-(prop-2-yn-1-yloxy)phenyl)thio)benzamide (DS-2-093)

A 10 mL flask was charged with the amine DS-2-111 (297 mg, 0.74 mmol, 1 eq), acetonitrile (4 mL), potassium carbonate (103 mg, 0.74 mmol, 1 eq) and 4-(bromomethyl)benzophenone (205 mg, 0.74 mmol, 1 eq). The resulting suspension was stirred vigorously for 16 h. The solid was filtered and the filtrate concentrated under reduced pressure to afford the crude product as a yellow solid. Purification by column chromatography on silica gel (0-1% MeOH in DCM, MeOH containing 1% NH$_3$) yielded the product (249 mg, 0.42 mmol, 56%) as a yellow solid. $^1$H NMR (400 MHz, CDCl$_3$) δ 8.58 (d, J=1.9 Hz, 1H), 7.76-7.69 (m, 5H), 7.59 (tt, J=7.0, 7.0, 1.3 Hz, 1H), 7.52-7.41 (m, 6H), 7.12-7.07 (m, 2H), 6.88 (d, J=8.6 Hz, 1H), 6.84 (bs, 1H), 4.77 (d, J=2.4 Hz, 2H), 3.70 (s, 2H), 3.49 (q, J=5.4 Hz, 2H), 2.72 (t, J=5.7 Hz, 2H), 2.66 (q, J=7.0 Hz, 2H), 2.59 (t, J=2.4 Hz, 1H), 1.13 (t, J=7.0 Hz, 3H). $^{13}$C NMR (100 MHz, CDCl$_3$) δ 196.2, 164.4, 159.3, 144.4, 144.0, 137.6, 137.5, 136.6, 132.4, 131.4, 131.0, 130.3, 129.9, 128.6, 128.3, 128.2, 123.9, 121.5, 116.8, 77.8, 76.2, 57.8, 55.9, 51.6, 47.7, 37.3, 11.8. IR (thin film): 3063, 2970, 2934, 2818, 2122, 1660, 1652, 1645, 1607, 1548, 1520, 1494, 1463, 1338, 1282, 1242, 1176, 1109, 1049, 1023, 925, 831 cm$^{-1}$. MS (ES-API) m/z: 594.2 (100%, [M+H]$^+$, C$_{34}$H$_{32}$N$_3$O$_5$S requires 594.2).

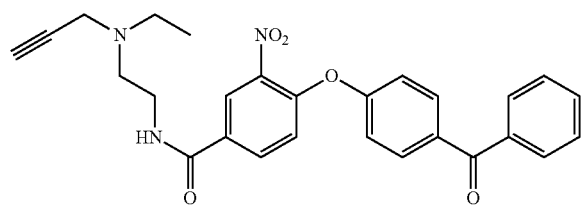 [SMILES: C#CCN(CC)CCNC(=O)c1ccc(Oc2ccc(C(=O)c3ccccc3)cc2)c([N+](=O)[O-])c1]

4-(4-benzoylphenoxy)-N-(2-(ethyl(prop-2-yn-1-yl) amino)ethyl)-3-nitrobenzamide (DS-2-097)

Following the general procedure A-4 using the aryl fluoride DS-2-077 and 4-hydroxybenzophenone. Purification by column chromatography on silica gel (0-5% MeOH in DCM, MeOH containing 1% NH$_3$). Yellow oil (88%). $^1$H NMR (400 MHz, CDCl$_3$) δ 8.43 (d, J=2.1 Hz, 1H), 8.05 (dd, J=8.6, 2.2 Hz, 1H), 7.91-7.86 (m, 2H), 7.82-7.77 (m, 2H), 7.63-7.58 (m, 1H), 7.50 (t, J=7.6 Hz, 2H), 7.18 (d, J=8.6 Hz, 1H), 7.15-7.11 (m, 2H), 7.00 (bs, 1H), 3.56 (q, J=5.1 Hz, 2H), 3.48 (d, J=2.3 Hz, 2H), 2.86-2.80 (m, 2H), 2.67 (q, J=7.1 Hz, 2H), 2.27 (t, J=2.3 Hz, 1H), 1.12 (t, J=7.2 Hz, 3H). $^{13}$C NMR (100 MHz, CDCl$_3$) δ 195.4, 164.4, 159.0, 151.7, 141.3, 137.6, 134.2, 133.2, 132.8, 132.7, 130.9, 130.0, 128.5, 125.0, 121.5, 118.5, 78.1, 73.8, 51.7, 47.7, 41.5, 37.3, 12.7. IR (thin film): 3066, 2972, 2831, 1660, 1652, 1622, 1596, 1537, 1487, 1352, 1307, 1259, 1204, 1167, 1150, 1082, 925 cm$^{-1}$. MS (ES-API) m/z: 472.2 (100%, [M+H]$^+$, C$_{27}$H$_{26}$N$_3$O$_5$ requires 472.2).

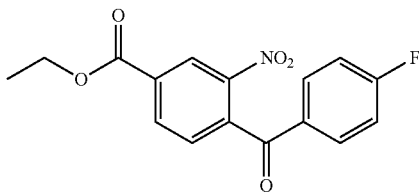 [SMILES: CCOC(=O)c1ccc(C(=O)c2ccc(F)cc2)c([N+](=O)[O-])c1]

Ethyl 4-(4-fluorobenzoyl)-3-nitrobenzoate (DS-2-099)

An oven-dried 25 mL flask was charged with ethyl 4-iodo-3-nitrobenzoate (3.21 g, 10.0 mmol, 1 eq) and evacuated and backfilled with argon three times. Dry tetrahydrofuran (25 mL) was introduced and the flask was cooled to −40° C. Phenylmagnesium chloride (2M in tetrahydrofuran, 5.5 mL, 11 mmol, 1.1 eq) was added dropwise over 1 h and the homogeneous solution progressively turned from yellow to dark grey. After 10 min, 4-fluorobenzaldehyde (1.3 mL, 12.0 mmol, 1.2 eq) was introduced dropwise over 30 min and the reaction mixture gradually turned dark red. After 30 min, the cooling bath was removed and the solution was stirred at room temperature for 6 h. Saturated ammonium chloride (10 mL) was added and the reaction mixture was then poured into water (100 mL). The aqueous phase was extracted with ethyl acetate (3×30 mL) and the combined organic layers were washed with brine (100 mL), dried over anhydrous magnesium sulfate and concentrated under reduced pressure to afford the crude product as a brown oil. Purification by column chromatography on silica gel (0-25% ethyl acetate in hexanes) yielded the product as an orange oil (3.02 g) that was used in the next step without further purification.

A 100 mL flask was charged with the alcohol (1.51 g), manganese dioxide (8.69 g, 100 mmol, 20 eq) and dry dichloromethane (50 mL). The resulting black suspension was stirred at room temperature. After 40 h, further manganese dioxide (4.35 g, 50 mmol, 10 eq) was added and the reaction mixture was heated under reflux. After 4 h, the reaction mixture was filtered at room temperature through Celite, washing with dichloromethane until the filtrate was colorless. The filtrate was concentrated under reduced pressure to afford the crude product as a yellow solid. Purification by column chromatography on silica gel (0-10% EtOAc in Hexanes) yielded the product (869 mg, 2.74 mmol, 55% in two steps) as a white powder. $^1$H NMR (400 MHz, CDCl$_3$) δ 8.87 (d, J=1.3 Hz, 1H), 8.44 (dd, J=7.9, 1.4 Hz, 1H), 7.80-7.44 (m, 2H), 7.57 (d, J=7.8 Hz, 1H), 7.18-7.11 (m, 2H), 4.49 (q, J=7.1 Hz, 2H), 1.46 (t, J=7.1 Hz, 3H). $^{13}$C NMR (100 MHz, CDCl$_3$) δ 191.1, 166.3 (d, J$_{CF}$=257.1 Hz), 163.8, 146.6, 139.4, 134.9, 133.2, 132.0, 131.9, 129.0, 125.7, 116.2 (d, J$_{CF}$=22.2 Hz), 62.3, 14.3. IR (thin film): 1726, 1678, 1598, 1537, 1349, 1284, 1240, 1151, 1112, 1016, 940, 852 cm$^{-1}$. MS (ES-API) m/z: 318.1 (100%, [M+H]$^+$, C$_{16}$H$_{13}$FNO$_5$ requires 318.1).

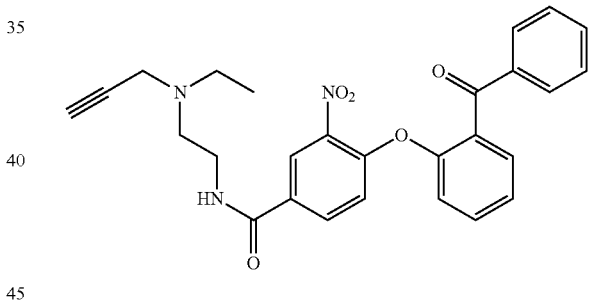

4-(2-benzoylphenoxy)-N-(2-(ethyl(prop-2-yn-1-yl) amino)ethyl)-3-nitrobenzamide (DS-2-101)

Following the general procedure A-4 using the aryl fluoride DS-2-077 and 2-hydroxybenzophenone. Purification by column chromatography on silica gel (0-2% MeOH in DCM, MeOH containing 1% NH$_3$). Yellow oil (34%). $^1$H NMR (400 MHz, CDCl$_3$) δ 8.25 (d, J=2.1 Hz, 1H), 7.88 (dd, J=8.7, 2.2 Hz, 1H), 7.75-7.70 (m, 2H), 7.63-7.54 (m, 3H), 7.41 (t, J=7.5 Hz, 3H), 7.16-7.13 (m, 1H), 6.93 (d, J=8.7 Hz, 1H), 6.86 (bs, 1H), 3.51 (q, J=5.2 Hz, 2H), 3.43 (d, J=2.3 Hz, 2H), 2.79-2.75 (m, 2H), 2.62 (q, J=7.2 Hz, 2H), 2.23 (t, J=2.3 Hz, 1H), 1.08 (t, J=7.2 Hz, 3H). $^{13}$C NMR (100 MHz, CDCl$_3$) δ 194.5, 164.4, 153.1, 152.0, 139.5, 136.7, 133.6, 132.73, 132.69, 132.0, 130.9, 129.8, 129.3, 128.4, 125.8, 124.6, 121.0, 119.0, 78.3, 73.3, 51.4, 47.4, 41.4, 37.2, 12.7. IR (thin film): 3063, 2972, 2937, 2829, 1660, 1652, 1644, 1620, 1602, 1532, 1479, 1449, 1352, 1317, 1294, 1264, 1200, 1183, 1149, 1104, 1079, 930 cm$^{-1}$. MS (ES-API) m/z: 472.2 (100%, [M+H]$^+$, C$_{27}$H$_{25}$N$_3$O$_5$ requires 472.2).

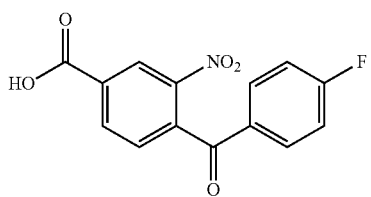 [SMILES: O=C(O)c1ccc(C(=O)c2ccc(F)cc2)c([N+](=O)[O-])c1]

4-(4-fluorobenzoyl)-3-nitrobenzoic acid (DS-2-103)

A 50 mL flask was charged with the ethyl ester (635 mg, 2.00 mmol, 1 eq), lithium hydroxide monohydrate (168 mg, 4 mmol, 2 eq) and water (10 mL). The resulting suspension was heated under reflux for 2 h. To the resulting homogeneous orange solution was added dropwise 1M hydrochloric acid (4 mL), precipitating a white solid. The reaction mixture was cooled to room temperature and filtered, washing with water (50 mL) to afford the crude product as a white power. Purification by column chromatography on silica gel (0-60% EtOAc in Hex, 1% AcOH) yielded the product (372 mg, 1.29 mmol, 64%) as a white solid. $^1$H NMR (400 MHz, DMSO-d$_6$) δ 13.94 (s, 1H), 8.66 (s, 1H), 8.41 (dd, J=7.8, 1.2 Hz, 1H), 7.87-7.83 (m, 2H), 7.81 (d, J=7.9 Hz, 1H), 7.42-7.36 (m, 2H). $^{13}$C NMR (100 MHz, DMSO-d$_6$) δ 191.3, 165.6 (d, $J_{CF}$=253.9 Hz), 165.0, 146.2, 138.3, 135.2, 133.6, 132.3 (d, $J_{CF}$=9.8 Hz), 132.0, 129.6, 125.4, 116.3 (d, $J_{CF}$=22.3 Hz). IR (thin film): 1704, 1681, 1596, 1532, 1505, 1417, 1351, 1281, 1243, 1150, 857 cm$^{-1}$. MS (ES-API) m/z: 288.0 (100%, [M–H]$^-$, C$_{14}$H$_7$FNO$_5$ requires 288.0), 577.0 (20%, [2M–H]$^-$).

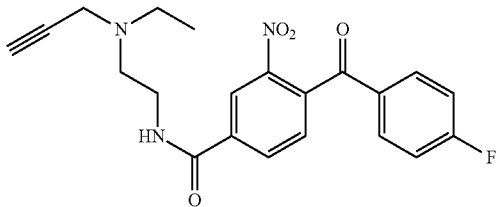 [SMILES: C#CCN(CC)CCNC(=O)c1ccc(C(=O)c2ccc(F)cc2)c([N+](=O)[O-])c1]

N-(2-(ethyl(prop-2-yn-1-yl)amino)ethyl)-4-(4-fluorobenzoyl)-3-nitrobenzamide (DS-2-107)

A 10 mL oven-dried flask equipped with a reflux condenser was charged with the carboxylic acid (145 mg, 0.50 mmol, 1 eq) and thionyl chloride (1.5 mL) and heated under reflux 4 h. The resulting homogeneous mixture was then concentrated to dryness under reduced pressure. The white solid obtained was then dissolved in dry dichloromethane (2 mL) and the solvent was evaporated. This process was repeated twice yielding the acyl chloride as a white solid.

A 10 mL oven-dried flask was charged with the acyl chloride, dry dichloromethane (1.5 mL) and 4-dimethylaminopyridine (1 mg, 0.008 mmol, 1 mol %) and cooled to 0° C. A solution of N-ethyl-N-(prop-2-yn-1-yl)ethane-1,2-diamine (see DS-2-035) (95 mg, 0.75 mmol, 1.5 eq) in dry dichloromethane (1.5 mL) was added dropwise over 10 min and the reaction mixture was slowly warmed to room temperature. After 16 h, the reaction mixture was diluted with dichloromethane (20 mL) and water (20 mL) and basified with 1M sodium hydroxide to reach pH~12. The aqueous phase was extracted with dichloromethane (3×10 mL). The combined organic layers were washed with water (30 mL), brine (30 mL), dried over anhydrous magnesium sulfate and concentrated under reduced pressure to afford the crude product as a yellow oil. Purification by column chromatography on silica gel (0-5% MeOH in DCM, MeOH containing 1% NH$_3$) yielded the product (169 mg, 0.43 mmol, 85%) as a light yellow oil. $^1$H NMR (400 MHz, CDCl$_3$) δ 8.62 (d, J=1.4 Hz, 1H), 8.21 (dd, J=7.8, 1.5 Hz, 1H), 7.82-7.72 (m, 2H), 7.55 (d, J=7.8 Hz, 1H), 7.17-7.11 (m, 2H), 7.08 (bs, 1H), 3.59 (q, J=5.2 Hz, 2H), 3.47 (d, J=2.3 Hz, 2H), 2.86-2.81 (m, 2H), 2.65 (q, J=7.1 Hz, 2H), 2.27 (t, J=2.3 Hz, 1H), 1.11 (t, J=7.1 Hz, 3H). $^{13}$C NMR (100 MHz, CDCl$_3$) δ 191.2, 166.3 (d, $J_{CF}$=257.1 Hz), 164.1, 146.6, 138.0, 137.3, 132.7, 132.0 (d, $J_{CF}$=3.1 Hz), 131.9 (d, $J_{CF}$=9.6 Hz), 129.2, 123.1, 116.2 (d, $J_{CF}$=22.2 Hz), 78.3, 73.4, 51.4, 47.5, 41.4, 37.4, 12.7. IR (thin film): 3078, 2973, 2939, 2831, 2361, 1674, 1652, 1645, 1598, 1538, 1506, 1349, 1307, 1281, 1241, 1184, 1152, 940, 852 cm$^{-1}$. MS (ES-API) m/z: 398.2 (100%, [M+H]$^+$, C$_{21}$H$_{21}$FN$_3$O$_4$ requires 398.1).

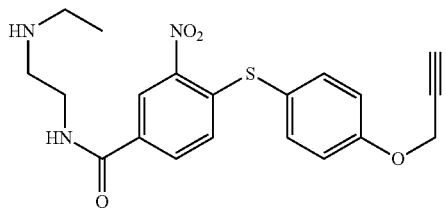 [SMILES: C#CCOc1ccc(Sc2ccc(C(=O)NCCNCC)cc2[N+](=O)[O-])cc1]

N-(2-(ethylamino)ethyl)-3-nitro-4-((4-(prop-2-yn-1-yloxy)phenyl)thio)benzamide (DS-2-111)

A 10 mL oven-dried flask equipped with a reflux condenser, fitted with a drying tube, was charged with the acid carboxylic DS-2-079 (1.15 g, 3.50 mmol, 1 eq) and thionyl chloride (3.5 mL) and heated to reflux. After 4 h, the resulting homogeneous mixture was concentrated to dryness under reduced pressure. The solid residue obtained was then dissolved in dry dichloromethane (3 mL) and the solvent was evaporated. This process was repeated twice yielding the acyl chloride as a yellow-greenish solid.

Dry dichloromethane (2.3 mL) and 4-dimethylaminopyridine (4 mg, 0.04 mmol, 1 mol %) were introduced and the flask was cooled to 0° C. A solution of N-ethyl ethylenediamine (0.37 mL, 3.50 mmol, 1 eq) in dry dichloromethane (1.2 mL) was added dropwise over 15 min and the resulting yellow solution was slowly warmed to room temperature. After 3 h, the reaction mixture was concentrated to dryness. Purification by column chromatography on silica gel (0-10% MeOH in DCM, MeOH containing 1% NH$_3$) afforded the product (297 mg, 0.74 mmol, 21%) as a yellow solid. $^1$H NMR (400 MHz, CDCl$_3$) δ 8.63 (d, J=1.8 Hz, 1H), 7.79 (dd, J=8.6, 1.9 Hz, 1H), 7.52-7.47 (m, 2H), 7.24 (s, 1H), 7.11-7.07 (m, 2H), 6.86 (d, J=8.6 Hz, 1H), 4.76 (d, J=2.4 Hz, 2H), 3.53 (q, J=5.4 Hz, 2H), 2.91-2.84 (m, 2H), 2.69 (q, J=7.1 Hz, 2H), 2.58 (t, J=2.4 Hz, 1H), 2.29 (bs, 1H), 1.12 (t, J=7.1 Hz, 3H). $^{13}$C NMR (100 MHz, CDCl$_3$) δ 164.9, 159.4, 144.3, 144.1, 137.7, 131.8, 131.3, 128.2, 124.4, 121.7, 116.9, 77.9, 76.4, 56.1, 48.1, 43.8, 39.6, 15.2. IR (thin film): 3293, 2969, 1652, 1644, 1607, 1591, 1574, 1548, 1520, 1494, 1463, 1338, 1290, 1242, 1176, 1109, 1049, 1023, 926, 831 cm$^{-1}$. MS (ES-API) m/z: 400.1 (100%, [M+H]$^+$, C$_{20}$H$_{22}$N$_3$O$_4$S requires 400.1).

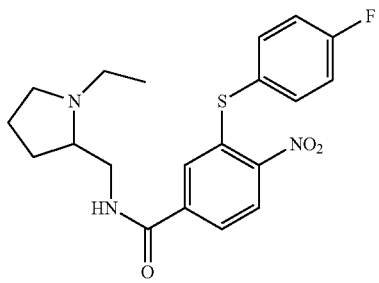 [SMILES: CCN1CCCC1CNC(=O)c1ccc([N+](=O)[O-])c(Sc2ccc(F)cc2)c1]

N-((1-ethylpyrrolidin-2-yl)methyl)-3-((4-fluorophenyl)thio)-4-nitrobenzamide (DS-2-115)

Following the general procedure B-3 using DS-2-113 and 2-(aminomethyl)-1-ethylpyrrolidine. The resulting suspension was diluted with dichloromethane (10 mL), washed with saturated sodium bicarbonate (2×5 mL), dried over anhydrous magnesium sulfate and concentrated under reduced pressure to afford the crude product. Purification by column chromatography on silica gel (0-10% MeOH in DCM, MeOH containing 1% NH$_3$). Yellow solid (85%). $^1$H NMR (400 MHz, CDCl$_3$) δ 8.21 (d, J=8.5 Hz, 1H), 7.64 (d, J=8.5 Hz, 1H), 7.56 (dd, J=8.3, 5.4 Hz, 2H), 7.36 (bs, 1H), 7.16 (t, J=8.4 Hz, 2H), 3.65-3.54 (m, 1H), 3.32-3.18 (m, 2H), 2.86-2.71 (m, 2H), 2.39-2.23 (m, 2H), 1.96-1.82 (m, 1H), 1.79-1.69 (m, 1H), 1.65-1.46 (m, 2H), 1.09 (t, J=7.2 Hz, 3H). $^{13}$C NMR (100 MHz, CDCl$_3$) δ 165.4, 164.1 (d, J$_{CF}$=252.0 Hz), 146.1, 140.0, 138.9, 138.2 (d, J$_{CF}$=8.6 Hz), 127.0, 126.3, 125.7 (d, J$_{CF}$=3.5 Hz), 123.7, 117.7 (d, J$_{CF}$=22.0 Hz), 62.9, 53.6, 48.7, 40.6, 28.1, 23.2, 13.4. IR (thin film): 3064, 2970, 2876, 2801, 1667, 1652, 1590, 1574, 1516, 1490, 1456, 1336, 1306, 1224, 1156, 1111, 1014, 837 cm$^{-1}$. MS (ES-API) m/z: 404.2 (100%, [M+H]$^+$, C$_{20}$H$_{23}$FN$_3$O$_3$S requires 404.1).

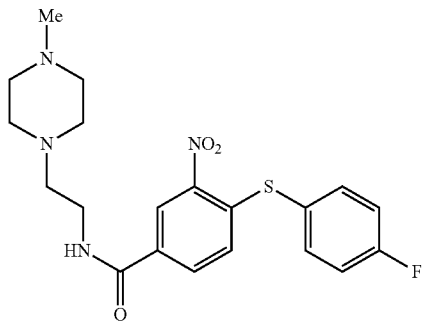 [SMILES: CN1CCN(CCNC(=O)c2ccc(Sc3ccc(F)cc3)c([N+](=O)[O-])c2)CC1]

4-(4-fluorophenyl)thio)-N-(2-(4-methylpiperazin-1-yl)ethyl)-3-nitrobenzamide (DS-2-121)

Following the general procedure B-2 using 2-(4-methylpiperazin-1-yl)-ethylamine. Yellow solid (74%). $^1$H NMR (400 MHz, CDCl$_3$) δ 8.64 (s, 1H), 7.82 (d, J=8.0 Hz, 1H), 7.62-7.54 (m, 2H), 7.22 (t, J=8.5 Hz, 2H), 7.08 (bs, 1H), 6.88 (d, J=8.5 Hz, 1H), 3.56 (q, J=5.2 Hz, 2H), 2.72-2.49 (m, 10H), 2.34 (s, 3H). $^{13}$C NMR (100 MHz, CDCl$_3$) δ 164.6, 164.3 (d, J$_{CF}$=252.3 Hz), 144.4, 143.5, 138.3 (d, J$_{CF}$=8.6 Hz), 131.9, 131.6, 128.3, 125.6 (d, J$_{CF}$=3.5 Hz), 124.4, 117.9 (d, J$_{CF}$=22.0 Hz), 56.3, 54.8, 52.7, 46.0, 36.4. IR (thin film): 3284, 2942, 2796, 1634, 1607, 1551, 1520, 1490, 1456, 1334, 1286, 1228, 1168, 1106, 1091, 1049, 1012, 841 cm$^{-1}$. MS (ES-API) m/z: 419.2 (100%, [M+H]$^+$, C$_{20}$H$_{24}$FN$_4$O$_3$S requires 419.2).

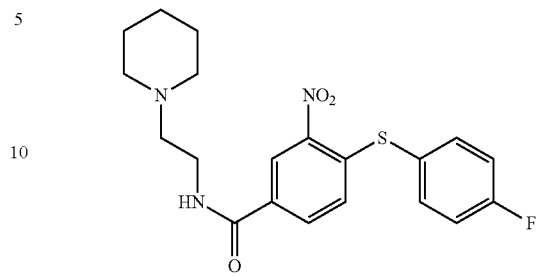

4-((4-fluorophenyl)thio)-3-nitro-N-(2-(piperidin-1-yl)ethyl)benzamide (DS-2-125)

Following the general procedure B-2 using 1-(2-aminoethyl)piperidine. Yellow solid (72%). $^1$H NMR (400 MHz, CDCl$_3$) δ 8.72 (s, 1H), 7.89 (d, J=8.0 Hz, 1H), 7.63-7.53 (m, 2H), 7.25-7.17 (m, 2H), 6.88 (d, J=8.5 Hz, 1H), 3.65-3.55 (m, 2H), 2.70 (bs, 2H), 2.60 (bs, 4H), 1.71 (bs, 4H), 1.52 (bs, 2H). $^{13}$C NMR (100 MHz, CDCl$_3$) δ 164.5, 164.2 (d, J$_{CF}$=252.3 Hz), 144.4, 143.2, 138.3 (d, J$_{CF}$=8.6 Hz), 131.8, 131.7, 128.2, 125.6 (d, J$_{CF}$=3.5 Hz), 124.5, 117.8 (d, J$_{CF}$=22.0 Hz), 56.7, 54.3, 36.6, 26.1, 24.3. IR (thin film): 2940, 2782, 1634, 1608, 1591, 1538, 1520, 1506, 1493, 1470, 1332, 1288, 1224, 1159, 1131, 1106, 1048, 834 cm$^{-1}$. MS (ES-API) m/z: 404.1 (100%, [M+H]$^+$, C$_{20}$H$_{23}$FN$_3$O$_3$S requires 404.1).

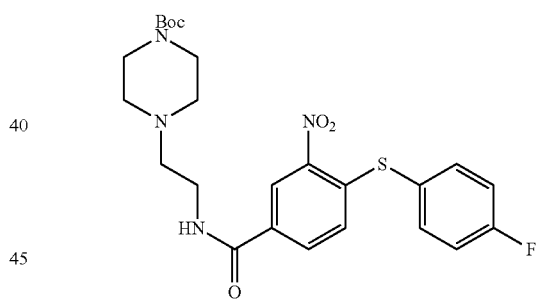

tert-butyl 4-(2-(4-((4-fluorophenyl)thio)-3-nitrobenzamido)ethyl)piperazine-1-carboxylate (DS-2-127)

Following the general procedure B-2 using 4-(2-aminoethyl)-1-boc-piperazine. Yellow solid (79%). $^1$H NMR (400 MHz, CDCl$_3$) δ 8.70 (s, 1H), 7.86 (s, 1H), 7.63-7.53 (m, 2H), 7.25-7.18 (m, 2H), 6.88 (d, J=8.5 Hz, 1H), 3.71-3.45 (m, 6H), 2.83-2.47 (m, 6H), 1.46 (s, 9H). $^{13}$C NMR (100 MHz, CDCl$_3$) δ 164.6, 164.2 (d, J$_{CF}$=252.4 Hz), 154.8, 144.3, 143.4, 138.3 (d, J$_{CF}$=8.6 Hz), 131.7, 131.6, 128.2, 125.4 (d, J$_{CF}$=3.2 Hz), 124.3, 117.8 (d, J$_{CF}$=22.0 Hz), 79.9, 56.4, 52.7, 43.6 (bs), 36.6, 28.5. IR (thin film): 3070, 2978, 2937, 2815, 1694, 1682, 1668, 1652, 1645, 1608, 1590, 1548, 1520, 1462, 1424, 1366, 1338, 1293, 1243, 1159, 1131, 1050, 1005, 837 cm$^{-1}$. MS (ES-API) m/z: 505.2 (100%, [M+H]$^+$, C$_{24}$H$_{30}$FN$_4$O$_5$S requires 505.2).

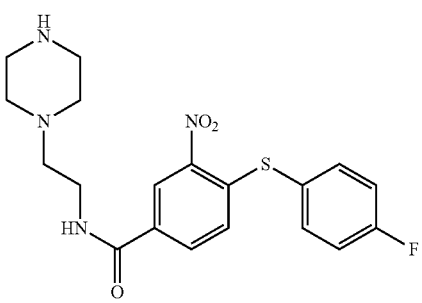 [SMILES: O=C(NCCN1CCNCC1)c1ccc(Sc2ccc(F)cc2)c([N+](=O)[O-])c1]

4-((4-fluorophenyl)thio)-3-nitro-N-(2-(piperazin-1-yl)ethyl)benzamide (DS-2-129)

A 10 mL flask was charged with DS-2-127 (505 mg, 1.00 mmol, 1 eq) and a solution of trifluoroacetic acid in dichloromethane (20%, 5 mL) was introduced. The reaction mixture was stirred overnight and concentrated to dryness under reduced pressure. The oily residue was dissolved in dichloromethane (20 mL) and saturated sodium bicarbonate (20 mL). The aqueous phase was extracted with dichloromethane (2×10 mL) and the combined organic layers were washed with brine (30 mL), dried over anhydrous magnesium sulfate and concentrated under reduced pressure to afford the crude product. Purification by column chromatography on silica gel (0-20% MeOH in DCM, MeOH containing 1% $NH_3$) afforded the product (239 mg, 0.59 mmol, 59%) as a yellow solid. $^1$H NMR (400 MHz, $CDCl_3$) δ 8.63 (d, J=1.8 Hz, 1H), 7.79 (dd, J=8.5, 1.9 Hz, 1H), 7.61-7.55 (m, 2H), 7.25-7.18 (m, 2H), 6.95 (bs, 1H), 6.88 (d, J=8.5 Hz, 1H), 3.55 (q, J=5.5 Hz, 2H), 2.98-2.93 (m, 4H), 2.62 (t, J=5.9 Hz, 2H), 2.54 (s, 4H), 2.40 (bs, 1H). $^{13}$C NMR (100 MHz, $CDCl_3$) δ 164.6, 164.2 (d, $J_{CF}$=252.4 Hz), 144.2, 143.3, 138.3 (d, $J_{CF}$=8.6 Hz), 131.8, 131.7, 128.2, 125.5 (d, $J_{CF}$=3.4 Hz), 124.4, 117.8 (d, $J_{CF}$=22.0 Hz), 56.8, 53.8, 45.9, 36.4. IR (thin film): 2945, 2821, 1652, 1634, 1608, 1590, 1548, 1520, 1490, 1464, 1338, 1226, 1158, 1049, 837 $cm^{-1}$. MS (ES-API) m/z: 405.1 (100%, [M+H]$^+$, $C_{19}H_{22}FN_4O_3S$ requires 405.1).

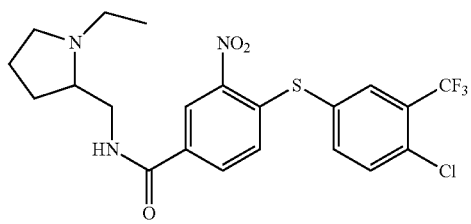 [SMILES: CCN1CCCC1CNC(=O)c1ccc(Sc2ccc(Cl)c(C(F)(F)F)c2)c([N+](=O)[O-])c1]

4-((4-chloro-3-(trifluoromethyl)phenyl)thio)-N-((1-ethylpyrrolidin-2-yl)methyl)-3-nitrobenzamide (DS-2-143)

Following the general procedure A-3 using the aryl fluoride DS-1-153 and 4-chloro-3-trifluoromethyl-benzenethiol. Pale yellow solid (78%). $^1$H NMR (400 MHz, $CDCl_3$) δ 8.64 (s, 1H), 7.91 (s, 1H), 7.80 (d, J=8.0 Hz, 1H), 7.72-7.62 (m, 2H), 7.04 (bs, 1H), 6.87 (d, J=8.2 Hz, 1H), 3.72-3.60 (m, 1H), 3.29 (d, J=13.0 Hz, 1H), 3.18 (s, 1H), 2.85-2.75 (m, 1H), 2.69 (s, 1H), 2.31-2.14 (m, 2H), 1.97-1.85 (m, 1H), 1.79-1.63 (m, 2H), 1.63-1.53 (m, 1H), 1.10 (t, J=6.5 Hz, 3H). $^{13}$C NMR (100 MHz, $CDCl_3$) δ 164.7, 144.8, 141.0, 140.1, 135.0, 134.6 (q, $J_{CF}$=5.2 Hz), 133.5, 132.6, 131.8, 130.4 (q, $J_{CF}$=32.0 Hz), 130.2, 128.3, 124.7, 122.2 (q, $J_{CF}$=274.0 Hz), 62.1, 53.6, 48.1, 41.1, 28.3, 23.0, 14.1. IR (thin film): 3096, 2970, 2801, 1644, 1607, 1522, 1469, 1396, 1338, 1307, 1254, 1178, 1144, 1110, 1037 $cm^{-1}$. MS (ES-API) m/z: 488.1 (100%, [M+H]$^+$, $C_{21}H_{22}ClF_3N_3O_3S$ requires 488.1).

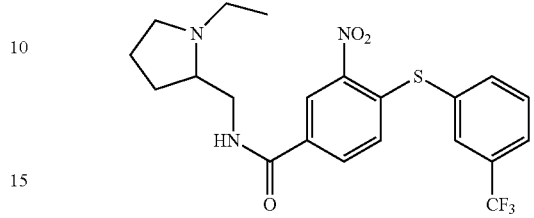

N-((1-ethylpyrrolidin-2-yl)methyl)-3-nitro-4-((3-(trifluoromethyl)phenyl)thio)benzamide (JCH-107)

Following the general procedure A-3 using the aryl fluoride DS-1-153 and 3-trifluorobenzenethiol. Light yellow solid (72%). $^1$H NMR (400 MHz, $CDCl_3$) δ 8.68 (s, 1H), 7.87 (s, 1H), 7.83-7.76 (m, 3H), 7.68-7.62 (m, 1H), 7.14 (bs, 1H), 6.87 (d, J=8.4 Hz, 1H), 3.70 (ddd, J=13.9, 6.8, 2.7 Hz, 1H), 3.36-3.30 (m, 1H), 3.22 (t, J=7.2 Hz, 1H), 2.83 (dq, J=11.8, 7.4 Hz, 1H), 2.74 (bs, 1H), 2.34-2.16 (m, 2H), 1.98-1.87 (m, 1H), 1.81-1.56 (m, 3H), 1.13 (t, J=7.2 Hz, 3H). $^{13}$C NMR (100 MHz, $CDCl_3$) δ 164.8, 144.9, 141.8, 139.3, 132.9 (q, $J_{CF}$=32.9 Hz), 132.6 (q, $J_{CF}$=3.7 Hz), 132.3, 132.1, 131.8, 130.9, 128.5, 127.3 (q, $J_{CF}$=3.6 Hz), 124.7, 123.5 (q, $J_{CF}$=271.5), 62.5, 53.7, 48.4, 40.8, 28.2, 23.1, 14.0. IR (thin film): 3073, 2971, 2877, 2805, 1644, 1608, 1548, 1523, 1338, 1323.5, 1306, 1170, 1130, 1111 $cm^{-1}$. MS (ES-API) m/z: 454.1 (100%, [M+H]$^+$, $C_{21}H_{23}F_3N_3O_3S$ requires 454.1). mp: 136° C.

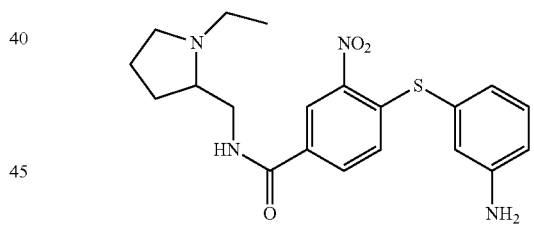

4-((3-aminophenyl)thio)-N-((1-ethylpyrrolidin-2-yl)methyl)-3-nitrobenzamide (JCH-109)

Following the general procedure A-3 using the aryl fluoride DS-1-153 and 3-aminothiophenol. The resulting biphasic mixture was diluted with dichloromethane and washed with saturated sodium bicarbonate, water and brine, dried over anhydrous magnesium sulfate and concentrated under reduced pressure. Purification by column chromatography on silica gel (5-10% MeOH in DCM, MeOH containing 1% $NH_3$). Orange solid (64%). $^1$H NMR (400 MHz, $CDCl_3$) δ 8.63 (d, J=2.0 Hz, 1H), 7.74 (dd, J=8.5, 1.8 Hz, 1H), 7.27-7.22 (m, 1H), 7.12 (bs, 1H), 7.00 (d, J=8.4 Hz, 1H), 6.93 (d, J=7.6 Hz, 1H), 6.89-6.86 (m, 1H), 6.80 (dd, J=8.0, 2.0 Hz, 1H), 3.89 (s, 2H), 3.68 (ddd, J=13.8, 7.3, 2.9 Hz, 1H), 3.31 (dt, J=14, 3.6 Hz, 1H), 3.23-3.17 (m, 1H), 2.82 (dq, J=12.1, 7.4 Hz, 1H), 2.75-2.68 (m, 1H), 2.32-2.17 (m, 2H), 1.96-1.86 (m, 1H), 1.77-1.55 (m, 3H), 1.12 (t, J=7.2 Hz, 3H). $^{13}$C NMR (100 MHz, $CDCl_3$) δ 165.1, 148.2, 144.4, 143.8, 131.5, 131.4, 131.2, 130.8, 128.7, 125.5, 124.5, 121.6, 117.0, 62.5, 53.6, 48.3, 40.9, 28.2, 23.1, 14.0. IR (thin film): 3095, 2969, 2876, 2809, 1644, 1607, 1594, 1546, 1519, 1482, 1465, 1337, 1294, 1049 cm$^{-1}$. MS (ES-API) m/z: 401.1 (38%, [M+H]$^+$, $C_{20}H_{25}N_4O_3S$ requires 401.2). mp: 56-62° C.

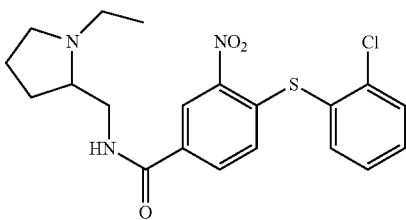 [SMILES: CCN1CCCC1CNC(=O)c1ccc(Sc2ccccc2Cl)c([N+](=O)[O-])c1]

4-((2-chlorophenyl)thio)-N-((1-ethylpyrrolidin-2-yl)methyl)-3-nitrobenzamide (JCH-111)

Following the general procedure A-3 using the aryl fluoride DS-1-153 and 2-chlorothiophenol. Purification by column chromatography on silica gel (5-10% MeOH in DCM, MeOH containing 1% NH$_3$). Yellow solid (62%). $^1$H NMR (400 MHz, CDCl$_3$) δ 8.69 (d, J=1.6 Hz, 1H), 7.80 (dd, J=7.2, 1.2 Hz, 1H), 7.72 (d, J=7.6 Hz, 1H), 7.59 (d, J=8 Hz, 1H), 7.51-7.46 (m, 1H), 7.42-7.37 (m, 1H), 7.17 (bs, 1H), 6.78 (d, J=8.4 Hz, 1H), 3.69 (ddd, J=13.8, 7.3, 3.0 Hz, 1H), 3.32 (dt, J=14.0, 3.6 Hz, 1H), 3.25-3.18 (m, 1H), 2.83 (dq, J=12.1, 7.4 Hz, 1H), 2.77-2.70 (m, 1H), 2.34-2.19 (m, 2H), 1.97-1.87 (m, 1H), 1.79-1.56 (m, 3H), 1.12 (t, J=7.2 Hz, 3H). $^{13}$C NMR (100 MHz, CDCl$_3$) δ 165.0, 144.6, 141.1, 140.2, 138.3, 132.3, 132.0, 131.7, 131.2, 129.4, 128.5, 127.9, 124.8, 62.6, 53.6, 48.4, 40.8, 28.2, 23.1, 13.9. IR (thin film): 3063, 2970, 2876, 2805, 1651, 1608, 1548, 1520, 1465, 1451, 1338, 1295, 1243, 1036, 748 cm$^{-1}$. MS (ES-API) m/z: 420.1 (100% [M+H]$^+$, $C_{20}H_{23}ClN_3O_3S$ requires 420.1). mp: 135-137° C.

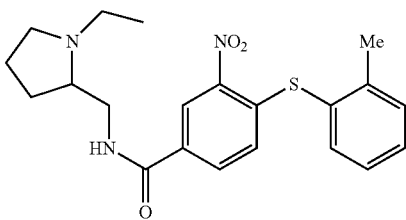 [SMILES: CCN1CCCC1CNC(=O)c1ccc(Sc2ccccc2C)c([N+](=O)[O-])c1]

N-((1-ethylpyrrolidin-2-yl)methyl)-3-nitro-4-(o-tolylthio)benzamide (JCH-114)

Following the general procedure A-3 using the aryl fluoride DS-1-153 and 2-methylthiophenol. The yellow precipitate was filtered, dissolved in dichloromethane, washed with 1M sodium hydroxide (3×), water, and brine. The organic layer was dried over anhydrous magnesium sulfate and concentrated under reduced pressure. Purification by column chromatography on silica gel (5-10% MeOH in DCM, MeOH containing 1% NH$_3$). Light yellow solid (31%). $^1$H NMR (400 MHz, CDCl$_3$) δ 8.70 (d, J=1.6 Hz, 1H), 7.76 (dd, J=8.6, 2.0 Hz, 1H), 7.57 (d, J=7.2 Hz, 1H), 7.47-7.38 (m, 2H), 7.33-7.28 (m, 1H), 7.22 (bs, 1H), 6.74 (d, J=8.4 Hz, 1H), 3.70 (ddd, J=13.9, 7.4, 3.1 Hz, 1H), 3.32 (dt, J=13.9, 3.5 Hz, 1H), 3.24-3.18 (m, 1H), 2.83 (dq, 12.0, 7.4 Hz, 1H), 2.77-2.70 (m, 1H), 2.34-2.18 (m, 2H), 2.33 (s, 3H), 1.96-1.86 (m, 1H), 1.79-1.56 (m, 3H), 1.12 (t, J=7.2 Hz, 3H). $^{13}$C NMR (100 MHz, CDCl$_3$) δ 165.1, 144.6, 143.4, 142.6, 137.3, 131.64, 131.60, 131.4, 131.2, 129.2, 127.9, 127.6, 124.8, 62.7, 53.6, 48.4, 40.8, 28.2, 23.1, 20.6, 13.9. IR (thin film): 3063, 2970, 2876, 2804, 1643, 1608, 1547, 1521, 1467, 1338, 1294, 1048, 750 cm$^{-1}$. MS (ES-API) m/z: 400.2 (100% [M+H]$^+$, $C_{21}H_{26}N_3O_3S$ requires 400.2). mp: 88-91° C.

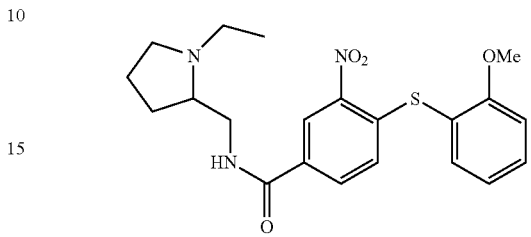

N-((1-ethylpyrrolidin-2-yl)methyl)-4-((2-methoxyphenyl)thio)-3-nitrobenzamide (JCH-117)

Following the general procedure A-3 using the aryl fluoride DS-1-153 and 2-methoxythiophenol. The yellow precipitate was filtered, dissolved in dichloromethane, washed with 1M sodium hydroxide (3×), water, and brine. The organic layer was dried over anhydrous magnesium sulfate and concentrated under reduced pressure. Purification by column chromatography on silica gel (5-10% MeOH in DCM, MeOH containing 1% NH$_3$). Light yellow solid (28%). $^1$H NMR (400 MHz, CDCl$_3$) δ 8.70 (s, 1H), 7.80 (d, J=8.4 Hz, 1H), 7.59-7.50 (m, 2H), 7.43 (s, 1H), 7.09-7.01 (m, 2H), 6.85 (d, J=8.4 Hz, 1H), 3.77 (s, 3H), 3.75-3.67 (m, 1H), 3.42-3.35 (m, 1H), 3.32-3.26 (m, 1H), 2.93-2.82 (m, 2H), 2.43-2.28 (m, 2H), 2.00-1.90 (m, 1H), 1.83-1.61 (m, 3H), 1.16 (t, J=7.2 Hz, 3H). $^{13}$C NMR (100 MHz, CDCl$_3$) δ 165.2, 160.3, 144.6, 142.8, 137.9, 132.9, 131.3, 131.1, 128.1, 124.8, 122.0, 117.6, 112.0, 63.3, 56.1, 53.7, 48.9, 40.8, 28.1, 23.2, 13.5. IR (thin film): 3272, 3068, 2969, 2803, 1638, 1608, 1549, 1521, 1476, 1341, 1295, 1276, 1250, 751 cm$^{-1}$. MS (ES-API) m/z: 416.2 (100%, [M+H]$^+$, $C_{21}H_{26}N_3O_4S$ requires 416.2). mp: 104-107° C.

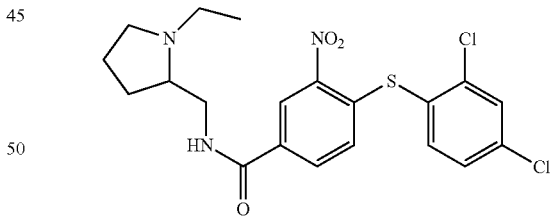

4-(2,4-dichlorophenyl)thio)-N-((1-ethylpyrrolidin-2-yl)methyl)-3-nitrobenzamide (JCH-120)

Following the general procedure A-3 using the aryl fluoride DS-1-153 and 2,4-dichlorothiophenol. Purification by column chromatography on silica gel (5-10% MeOH in DCM, MeOH containing 1% NH$_3$). Light yellow solid (44%). $^1$H NMR (400 MHz, CDCl$_3$) δ 8.67 (d, J=2.0 Hz, 1H), 7.80 (dd, J=8.5, 2.0 Hz, 1H), 7.65 (d, J=8.3 Hz, 1H), 7.61 (d, J=2.2 Hz, 1H), 7.39 (dd, J=8.2, 2.2 Hz, 1H), 7.06 (bs, 1H), 6.78 (d, J=8.4 Hz, 1H), 3.68 (ddd, J=13.8, 7.3, 2.7 Hz, 1H), 3.33-3.27 (m, 1H), 3.22-3.16 (m, 1H), 2.81 (dq, J=12.0, 7.4 Hz, 1H), 2.73-2.66 (m, 1H), 2.31-2.16 (m, 2H), 1.96-1.86 (m, 1H), 1.79-1.54 (m, 3H), 1.11 (t, J=7.2 Hz, 3H). $^{13}$C NMR (100 MHz, CDCl$_3$) δ 164.9, 144.7, 141.1, 140.4, 138.9, 138.0, 132.4, 131.8, 128.9, 128.1, 127.8, 124.8, 62.2, 53.6, 48.2, 40.9, 28.3, 23.1, 14.1. IR (thin film): 3081, 2970, 2938, 2876, 2804, 1644, 1607, 1548, 1520, 1454, 1338, 1294, 1243, 1098, 1049, 815, 737 cm$^{-1}$. MS (ES-API) m/z: 454.1 (100%, [M+H]$^+$, C$_{20}$H$_{22}$Cl$_2$N$_3$O$_3$S requires 454.1). mp: 135-137° C.

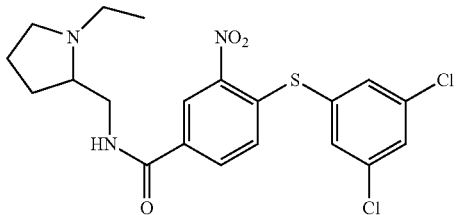 [SMILES: CCN1CCCC1CNC(=O)c1ccc(Sc2cc(Cl)cc(Cl)c2)c([N+](=O)[O-])c1]

4-((3,5-dichlorophenyl)thio)-N-((1-ethylpyrrolidin-2-yl)methyl)-3-nitrobenzamide (JCH-124)

Following the general procedure A-3 using the aryl fluoride DS-1-153 and 3,5-dichlorothiophenol. Purification by column chromatography on silica gel (5-10% MeOH in DCM, MeOH containing 1% NH$_3$). Light yellow solid (61%). $^1$H NMR (400 MHz, CDCl$_3$) δ 8.67 (d, J=2.0 Hz, 1H), 7.85 (dd, J=8.5, 2.0 Hz, 1H), 7.51-7.49 (m, 1H), 7.48-7.46 (m, 2H), 7.21 (bs, 1H), 6.95 (d, J=8.5 Hz, 1H), 3.70 (ddd, J=13.8, 7.4, 3.0 Hz, 1H), 3.35-3.29 (m, 1H), 3.23-3.17 (m, 1H), 2.88-2.78 (m, 1H), 2.76-2.70 (m, 1H), 2.33-2.19 (m, 2H), 1.97-1.87 (m, 1H), 1.79-1.56 (m, 3H), 1.12 (t, J=7.2 Hz, 3H). $^{13}$C NMR (100 MHz, CDCl$_3$) δ 164.8, 144.9, 141.0, 136.6, 133.9, 133.7, 132.6, 131.9, 130.8, 128.7, 124.7, 62.5, 53.6, 48.3, 40.8, 28.1, 23.1, 14.0. IR (thin film): 3072, 2970, 2938, 2805, 1644, 1608, 1559, 1522, 1466, 1406, 1339, 1294, 1141, 1106, 1048, 800, 736 cm$^{-1}$. MS (ES-API) m/z: 454.1 (100%, [M+H]$^+$, C$_{20}$H$_{22}$Cl$_2$N$_3$O$_3$S requires 454.1). mp: 44-47° C.

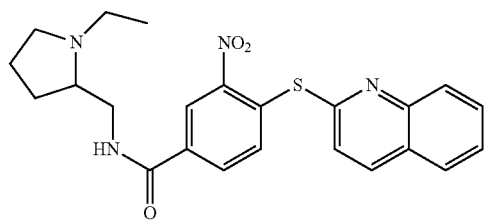 [SMILES: CCN1CCCC1CNC(=O)c1ccc(Sc2ccc3ccccc3n2)c([N+](=O)[O-])c1]

N-((1-ethylpyrrolidin-2-yl)methyl)-3-nitro-4-(quinolin-2-ylthio)benzamide (JCH-127)

Following the general procedure A-3 using the aryl fluoride DS-1-153 and 2-quinolinethiol. The reaction mixture was diluted with dichloromethane, washed with 1M sodium hydroxide (3×), water, and brine. The organic layer was dried over anhydrous magnesium sulfate and concentrated under reduced pressure. Purification by column chromatography on silica gel (0-10% MeOH in DCM, MeOH containing 1% NH$_3$). Yellow solid (41%). $^1$H NMR (400 MHz, CDCl$_3$) δ 8.60 (s, 1H), 8.16 (d, J=8.4 Hz, 1H), 8.01 (d, J=8.5 Hz, 1H), 7.89-7.82 (m, 2H), 7.77-7.72 (m, 1H), 7.59 (t, J=8 Hz, 1H), 7.52-7.47 (m, 2H), 7.18 (bs, 1H), 3.75-3.67 (m, 1H), 3.38-3.31 (m, 1H), 3.22 (t, J=7.2 Hz, 1H), 2.89-2.79 (m, 1H), 2.78-2.70 (m, 1H), 2.34-2.17 (m, 3H), 1.99-1.88 (m, 1H), 1.82-1.58 (m, 3H), 1.31 (t, J=6.8 Hz, 3H). $^{13}$C NMR (100 MHz, CDCl$_3$) δ 164.9, 155.1, 148.7, 147.5, 137.8, 136.6, 133.7, 132.1, 131.2, 130.6, 129.1, 127.8, 127.5, 127.2, 124.2 (2C), 62.4, 53.6, 48.3, 40.9, 28.1, 23.0, 14.0. IR (thin film): 3067, 2970, 2876, 2807, 1652, 1608, 1589, 1524, 1467, 1422, 1340, 1295, 1138, 1097, 910, 733 cm$^{-1}$. MS (ES-API) m/z: 437.2 (58%, [M+H]$^+$, C$_{23}$H$_{25}$N$_4$O$_3$S requires 437.2). mp: 40-43° C.

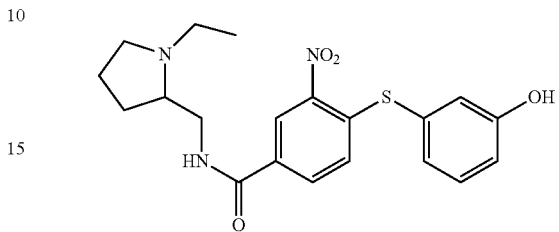

N-((1-ethylpyrrolidin-2-yl)methyl)-4-((3-hydroxyphenyl)thio)-3-nitrobenzamide (JCH-140)

Following the general procedure A-3 using the aryl fluoride DS-1-153 and 3-mercaptophenol. The reaction mixture was diluted with dichloromethane (20 mL) and methanol (5 mL), washed with saturated sodium bicarbonate (3×10 mL), water (10 mL), and brine (10 mL). The organic layer was dried over anhydrous magnesium sulfate and concentrated under reduced pressure. Purification by column chromatography on silica gel (5-10% MeOH in DCM, MeOH containing 1% NH$_3$). Orange solid (14%). $^1$H NMR (400 MHz, CDCl$_3$) δ 8.66 (d, J=1.6 Hz, 1H), 7.73 (dd, J=8.6, 1.9 Hz, 1H), 7.60 (bs, 1H), 7.32 (t, J=8.0 Hz, 1H), 7.06 (d, J=8.0 Hz, 1H), 7.03-7.00 (m, 1H), 6.98-6.94 (m, 1H), 6.89 (d, J=8.8 Hz, 1H), 4.26 (bs, 1H), 3.79-3.71 (m, 1H), 3.43 (dd, J=14.1, 3.8 Hz, 1H), 3.32-3.25 (m, 1H), 2.96-2.84 (m, 2H), 2.45-2.30 (m, 2H), 2.02-1.92 (m, 1H), 1.85-1.62 (m, 3H), 1.15 (t, J=7.2 Hz, 3H). $^{13}$C NMR (100 MHz, CDCl$_3$) δ 165.7, 158.7, 144.3, 144.0, 131.5, 131.4, 130.9, 130.7, 128.5, 126.9, 124.6, 123.1, 118.7, 63.5, 53.6, 48.9, 40.9, 27.9, 23.0, 13.4. IR (thin film): 3066, 2972, 2811, 1652, 1645, 1607, 1548, 1520, 1464, 1456, 1338, 1301, 1262, 1242, 1049, 736 cm$^{-1}$. MS (ES-API) m/z: 402.2 (100% [M+H]$^+$, C$_{20}$H$_{24}$N$_3$O$_4$S requires 402.1). mp: 77-80° C.

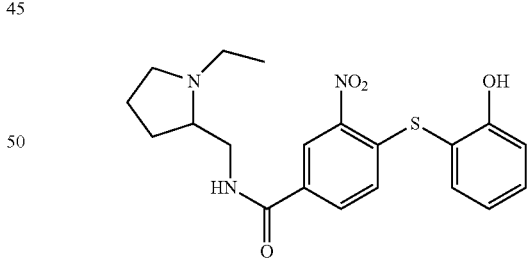

N-((1-ethylpyrrolidin-2-yl)methyl)-4-((2-hydroxyphenyl)thio)-3-nitrobenzamide (JCH-143)

Following the general procedure A-3 using the aryl fluoride DS-1-153 and 2-mercaptophenol. The reaction mixture was diluted with dichloromethane (20 mL) and methanol (5 mL), washed with saturated sodium bicarbonate (3×10 mL), water (10 mL), and brine (10 mL). The organic layer was dried over anhydrous magnesium sulfate and concentrated under reduced pressure. Purification by column chromatography on silica gel (5-10% MeOH in DCM, MeOH containing 1% NH₃). Orange solid (54%). ¹H NMR (400 MHz, CDCl₃) δ 8.60 (s, 1H), 7.88 (bs, 1H), 7.60 (d, J=8.8 Hz, 1H), 7.47 (d, J=7.6 Hz, 1H), 7.40 (t, J=7.6 Hz, 1H), 7.04 (d, J=8.2 Hz, 1H), 6.94 (t, J=7.5 Hz, 1H), 6.79 (d, J=8.5 Hz, 1H), 4.41 (bs, 1H), 3.80-3.70 (m, 1H), 3.45-3.37 (m, 1H), 3.31-3.24 (m, 1H), 2.98-2.83 (m, 2H), 2.45-2.31 (m, 2H), 1.97-1.85 (m, 1H), 1.82-1.68 (m, 2H), 1.67-1.57 (m, 1H), 1.09 (t, J=7.2 Hz, 3H). ¹³C NMR (100 MHz, CDCl₃) δ 165.1, 161.6, 144.5, 142.1, 137.5, 133.4, 131.01, 130.99, 127.7, 125.4, 119.9, 118.8, 115.5, 64.7, 53.4, 49.0, 40.1, 27.4, 22.9, 12.7. IR (thin film): 3286, 3060, 2971, 2877, 2806, 1643, 1606, 1544, 1520, 1454, 1387, 1338, 1290, 1255, 1050, 844, 753, 736 cm⁻¹. MS (ES-API) m/z: 402.2 (100%, [M+H]⁺, C₂₀H₂₄N₃O₄S requires 402.1). mp: 109-113° C.

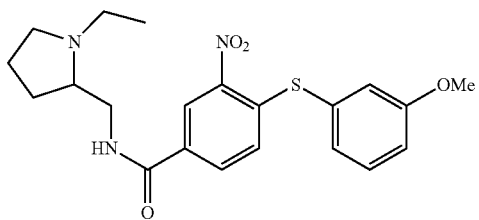 [SMILES: CCN1CCCC1CNC(=O)c1ccc(Sc2cccc(OC)c2)c([N+](=O)[O-])c1]

N-((1-ethylpyrrolidin-2-yl)methyl)-4-((3-methoxyphenyl)thio)-3-nitrobenzamide (JCH-146)

Following the general procedure A-3 using the aryl fluoride DS-1-153 and 3-methoxybenzenethiol. Orange solid (67%). ¹H NMR (400 MHz, CDCl₃) δ 8.65 (d, J=1.2 Hz, 1H), 7.77 (dd, J=8.4, 1.2 Hz, 1H), 7.41 (t, J=7.9 Hz, 1H), 7.17 (d, J=7.2 Hz, 1H), 7.13-7.03 (m, 2H), 6.96 (d, 8.8 Hz, 1H), 3.83 (s, 3H), 3.69 (ddd, J=13.8, 7.3, 3.0 Hz, 1H), 3.36-3.28 (m, 1H), 3.22 (t, J=6.8 Hz, 1H), 2.83 (dq, J=12.0, 7.4 Hz, 1H), 2.73 (bs, 1H), 2.34-2.18 (m, 3H), 1.98-1.86 (m, 1H), 1.80-1.56 (m, 3H), 1.13 (t, J=7.2 Hz, 3H). ¹³C NMR (100 MHz, CDCl₃) δ 165.1, 160.8, 144.4, 143.3, 131.7, 131.5, 131.24, 131.21, 128.5, 128.1, 124.5, 120.8, 116.6, 62.4, 55.6, 53.6, 48.3, 40.9, 28.2, 23.1, 14.0. IR (thin film): 3069, 2969, 2876, 2806, 1643, 1608, 1590, 1548, 1521, 1467, 1338, 1285, 1248, 1040, 748, 736 cm⁻¹. MS (ES-API) m/z: 416.2 (100%, [M+H]⁺, C₂₁H₂₆N₃O₄S requires 416.2). mp: 103-105° C.

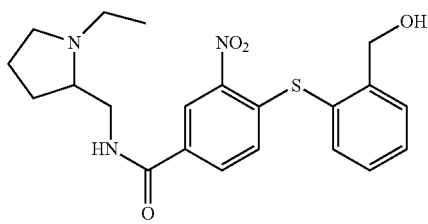 [SMILES: CCN1CCCC1CNC(=O)c1ccc(Sc2ccccc2CO)c([N+](=O)[O-])c1]

N-((1-ethylpyrrolidin-2-yl)methyl)-4-((2-(hydroxymethyl)phenyl)thio)-3-nitrobenzamide (JCH-149)

Following the general procedure A-3 using the aryl fluoride DS-1-153 and 2-mercaptobenzyl alcohol. The reaction mixture was diluted with dichloromethane (20 mL) and methanol (5 mL), washed with saturated sodium bicarbonate (3×10 mL), water (10 mL), and brine (10 mL). The organic layer was dried over anhydrous magnesium sulfate and concentrated under reduced pressure. Purification by column chromatography on silica gel (0-5% MeOH in DCM, MeOH containing 1% NH₃). Yellow solid (40%). ¹H NMR (400 MHz, CDCl₃) δ 8.72 (s, 1H), 7.77 (d, J=8.5 Hz, 1H), 7.70 (d, J=7.9 Hz, 1H), 7.60-7.55 (m, 2H), 7.46-7.31 (m, 2H), 6.73 (dd, J=8.8, 0.8 Hz, 1H), 4.75 (s, 2H), 3.76-3.69 (m, 1H), 3.40-3.32 (m, 1H), 3.29-3.21 (m, 1H), 2.92-2.77 (m, 2H), 2.60 (bs, 1H), 2.39-2.23 (m, 2H), 1.98-1.88 (m, 1H), 1.80-1.59 (m, 3H), 1.15 (t, J=6.8 Hz, 3H). ¹³C NMR (100 MHz, CDCl₃) δ 164.9, 145.5, 144.5, 142.1, 137.3, 131.52, 131.48, 131.3, 129.2, 128.8, 127.7, 127.6, 124.9, 62.8, 62.5, 53.5, 48.4, 40.5, 27.6, 22.8, 13.7. IR (thin film): 3068, 2972, 2877, 2814, 1648, 1608, 1547, 1522, 1466, 1339, 1295, 1047, 910, 733 cm⁻¹. MS (ES-API) m/z: 416.2 (100%, [M+H]⁺, C₂₁H₂₆N₃O₄S requires 416.2). mp: 59-63° C.

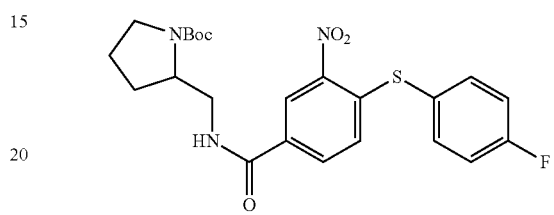

tert-butyl 2-((4-((4-fluorophenyl)thio)-3-nitrobenzamido)methyl)pyrrolidine-1-carboxylate (WW3-79)

A mixture of 4-((4-fluorophenyl)thio)-3-nitrobenzoic acid (0.7478 g, 2.55 mmol), DMAP (0.0669 g, 0.55 mmol), EDC hydrochloride (0.5371 g, 2.80 mmol) and CH₂Cl₂ (12 mL) was stirred at room temperature for 1 h. tert-Butyl 2-(aminomethyl)pyrrolidine-1-carboxylate (0.5012 g, 2.51 mmol) in CH₂Cl₂ (2 mL) was then added and the resulting solution was stirred at room temperature for 21 h. The reaction solution was diluted with CH₂Cl₂ (30 mL), and was washed sequentially with saturated aq. NaCl (30 mL) and saturated aq. NaHCO₃ solution (30 mL). The organic layer was dried over Na₂SO₄, filtered and concentrated under reduced pressure. The residue was purified through flash chromatography on silica gel (1:19 MeOH:CH₂Cl₂) to afford the entitled product (0.8348 g, 70%) as a yellow gel. ¹H NMR (400 MHz, CDCl₃) δ 8.90 (s, 1H), 8.72 (s, 1H), 7.85 (d, J=8.5 Hz, 1H), 7.54 (dd, J=8.7, 5.3 Hz, 2H), 7.17 (t, J=8.6 Hz, 2H), 6.81 (d, J=8.5 Hz, 1H), 4.15 (t, J=9.8 Hz, 1H), 3.53 (d, J=13.5 Hz, 1H), 3.47-3.20 (m, 3H), 2.05 (dt, J=17.2, 8.5 Hz, 1H), 1.96-1.80 (m, 2H), 1.71 (s, 1H), 1.44 (s, 9H). ¹³C NMR (100 MHz, CDCl₃) δ 164.3, 164.0 (d, J=252.0 Hz, 157.5, 144.4, 142.6, 138.1 (d, J=8.7 Hz) 131.8, 131.4, 127.9, 125.7 (d, J=3.7 Hz), 124.3, 117.5 (d, J=22.0 Hz), 80.7, 56.0, 47.7, 47.4, 29.6, 28.4, 24.0. MS (ESI) m/z 376.1 (100%, [M+H-Boc]⁺).

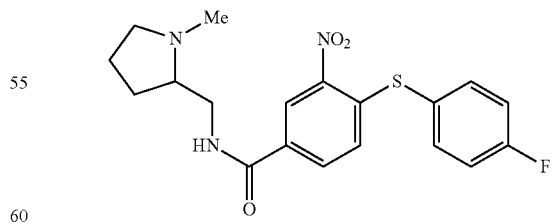

4-(4-fluorophenyl)thio)-N-((1-methylpyrrolidin-2-yl)methyl)-3-nitrobenzamide (WW3-107)

A mixture of WW3-79 (0.3116 g, 0.66 mmol) and HCl (4 M in 1,4-dioxane, 12 mL) was stirred at room temperature for 2.5 h and then was slowly poured into 4 N NaOH (35 mL) solution. The resulting solution was extracted with CH$_2$Cl$_2$ (3×35 mL). The combined organic layers were dried over Na$_2$SO$_4$, filtered and concentrated under reduced pressure to afford the deprotected amine which was used directly for next step without further purification.

A mixture of the deprotected amine above, formaldehyde (37%, 0.1914 g, 2.36 mmol), AcOH (0.05 mL, 0.87 mmol), CH$_3$OH (12 mL) and NaBH(OAc)$_3$ (0.3188 g, 1.47 mmol) was stirred at room temperate for 17 h. The reaction solution was then slowly poured into a solution of saturated aq. NaHCO$_3$ (35 mL) and extracted with DCM (3×35 mL). The combined organic layers were dried over Na$_2$SO$_4$, filtered and concentrated under reduced pressure. The residue was purified through flash chromatography on silica gel (1:19 MeOH:CH$_2$Cl$_2$) to afford the title product (0.1837 g, 72% two steps) as a yellow solid. mp 101-103° C.; $^1$H NMR (400 MHz, CDCl$_3$) δ 8.65 (s, 1H), 7.80 (dd, J=8.4, 2.1 Hz, 1H), 7.60-7.46 (m, 2H), 7.26-7.13 (m, 3H), 6.84 (d, J=8.5 Hz, 1H), 3.76 (ddd, J=14.0, 7.6, 3.1 Hz, 1H), 3.32 (d, J=13.7 Hz, 1H), 3.14 (s, 1H), 2.60 (s, 1H), 2.38 (s, 3H), 2.37-2.25 (m, 1H), 1.94 (dq, J=12.6, 8.1 Hz, 1H), 1.81-1.57 (m, 3H). $^{13}$C NMR (100 MHz, CDCl$_3$) δ 164.9, 164.06 (d, J=252.4 Hz), 144.3, 143.1, 138.2 (d, J=8.7 Hz), 131.5, 128.1, 125.4 (d, J=3.7 Hz), 124.6, 117.7 (d, J=22.0 Hz), 64.4, 57.1, 40.5, 40.0, 28.0, 22.9. MS (ESI) m/z 390.1 (100%, [M+H]$^+$).

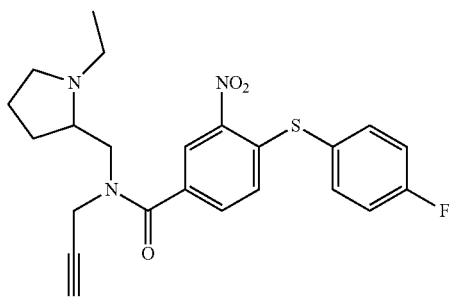 [SMILES: C#CCN(CC1CCCN1CC)C(=O)c1ccc(Sc2ccc(F)cc2)c([N+](=O)[O-])c1]

N-((1-ethylpyrrolidin-2-yl)methyl)-4-((4-fluorophenyl)thio)-3-nitro-N-(prop-2-yn-1-yl)benzamide (WW2-292)

DS-1-033 (0.1355 g, 0.34 mmol) was dissolved in anhydrous DMF (2.0 mL), followed by the addition of NaH (60%, 0.0272 g, 0.68 mmol) at 0° C. The flask was then immediately flushed with argon and sealed with a rubber septum fitted with an argon balloon. The reaction solution was stirred for 8 min at 0° C. and propargyl bromide (80% in toluene, 0.041 mL, 0.37 mmol) was added via syringe. The resulting solution was stirred for 3 h at 0° C. and the reaction was quenched by slowly adding water (25 mL) and then EtOAc (25 mL). The resulting bi-phase solution was washed by 20% LiCl solution (3×25 mL) and brine (25 mL). The organic layer was dried over Na$_2$SO$_4$, filtered and concentrated under reduced pressure. The flash chromatography on silica gel (1:19 Methanol:CH$_2$Cl$_2$) provided the desired product as a mixture of two rotamers as a brown oil (0.0722 g, 49%). The rotamers coalesced at 50° C. $^1$H NMR (400 MHz, CDCl$_3$, 50° C.) δ 8.45 (s, 1H), 7.62-7.52 (m, 2H), 7.46 (dd, J=8.4, 1.9 Hz, 1H), 7.22-7.11 (m, 2H), 6.84 (d, J=8.4 Hz, 1H), 4.30 (s, 2H), 3.49 (d, J=51.7 Hz, 2H), 3.05 (t, J=9.7 Hz, 1H), 2.91-2.64 (m, 2H), 2.43-2.23 (m, 2H), 2.18 (td, J=9.2, 7.2 Hz, 1H), 1.86 (dq, J=12.3, 8.2 Hz, 1H), 1.75-1.39 (m, 3H), 1.04 (t, J=7.2 Hz, 3H). $^{13}$C NMR (100 MHz, CDCl$_3$, 50° C.) δ 169.1, 164.0 (d, J=252.3 Hz), 144.5, 141.4, 138.0 (d, J=8.6 Hz), 132.7, 132.0, 128.1, 125.7 (d, J=3.7 Hz), 124.8, 117.5 (d, J=22.1 Hz), 78.4, 73.5, 62.8, 53.3, 49.3, 28.9, 22.7, 12.8. MS (ESI) m/z 442.2 (100%, [M+H]$^+$).

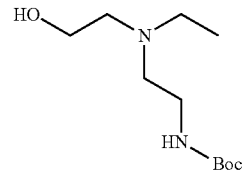

tert-butyl (2-(ethyl(2-hydroxyethyl)amino)ethyl)carbamate 2-(Ethylamino)ethanol (0.9173 g, 10.31 mmol) and tert-butyl (2-bromoethyl)carbamate (2.4964 g, 11.14 mmol) were dissolved in CH$_3$CN (12 mL), followed by addition of potassium carbonate (2.0617 g, 14.84 mmol). The formed suspension was stirred vigorously at 50° C. for 20 h and then filtered through a pad of Celite, washed by methanol. Upon removal of the solvents in vacuo, the residue was dissolved in DCM (3 mL) and purified through a short pad of silica gel, eluted with a mixture of 19:1 DCM/methanol to afford the entitled product (2.1548 g, 90%) as a colorless gel. $^1$H NMR (400 MHz, CDCl$_3$) δ 3.55 (t, J=5.3 Hz, 2H), 3.17 (q, J=5.7 Hz, 2H), 2.69-2.49 (m, 6H), 1.41 (s, 9H), 1.01 (t, J=7.1 Hz, 3H). $^{13}$C NMR (100 MHz, CDCl$_3$) δ 156.2, 58.8, 55.3, 53.0, 47.7, 40.6, 38.5, 28.3, 11.5. MS (ESI) m/z 233.2 (100%, [M+H]$^+$).

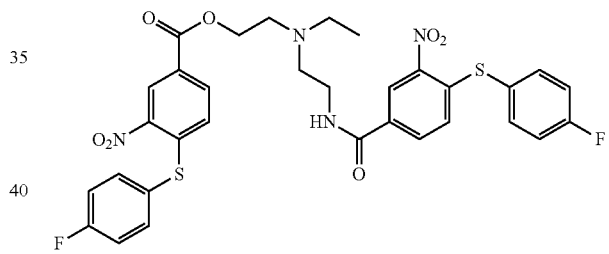

2-(ethyl(2-(4-((4-fluorophenyl)thio)-3-nitrobenzamido)ethyl)amino)ethyl 4-((4-fluorophenyl)thio)-3-nitrobenzoate A mixture of tert-butyl (2-(ethyl(2-hydroxyethyl)amino) ethyl)carbamate (0.2921 g, 1.26 mmol), HCl (37%, 2 mL) and 1,4-dioxane (6 mL) was stirred at room temperature for 4 hours. Upon removal of the excess HCl and solvents, the residue was neutralized by 2N NaOH solution, extracted with DCM (3×30 mL). The combined organic layers were dried over Na$_2$SO$_4$, filtered and concentrated under reduced pressure to about 6 mL.

To a flame-dried flask equipped with a reflux condenser were added 4-((4-fluorophenyl)thio)-3-nitrobenzoic acid (0.2970 g, 1.01 mmol) and thionyl chloride (6 mL). The resulting reaction solution was stirred at reflux for 4 h. After being cooled down to room temperature, the excess thionyl chloride was evaporated under reduced pressure to afford the acyl chloride intermediate as a yellow solid.

To the deprotected amine above in DCM solution was added Et$_3$N (0.30 mL, 2.16 mmol) at 0° C., followed by addition of the acyl chloride intermediate in portions in 5 min. The resulting solution was stirred at 0° C. for 1 h and then at room temperature for one more hour. The reaction solution was transferred to a separatory funnel and 25 mL saturated NaHCO$_3$ solution was added. The resulting bi-phase solution was extracted with DCM (3×25 mL) and the combined organic layers were dried over Na$_2$SO$_4$, filtered and concentrated under reduced pressure. The flash chromatography on silica gel (1:19 Methanol:CH$_2$Cl$_2$) provided the entitled product as a yellow gel (0.2529 g, 37%). $^1$H NMR (400 MHz, CDCl$_3$) δ 8.62 (s, 1H), 8.48 (s, 1H), 7.76 (d, J=8.6 Hz, 1H), 7.66 (d, J=8.5 Hz, 1H), 7.61-7.49 (m, 4H), 7.20-7.10 (m, 5H), 6.81-6.68 (m, 2H), 4.39 (t, J=5.3 Hz, 2H), 3.45 (q, J=5.4 Hz, 2H), 2.83 (t, J=5.3 Hz, 2H), 2.71 (t, J=5.8 Hz, 2H), 2.59 (q, J=7.1 Hz, 2H), 0.99 (t, J=7.0 Hz, 3H). $^{13}$C NMR (100 MHz, CDCl$_3$) δ 164.4, 164.3, 164.1 (d, J=252.2 Hz), 164.0 (d, J=252.4 Hz), 145.5, 145.4, 143.8, 143.1, 138.2 (d, J=8.6 Hz), 138.2 (d, J=8.7 Hz), 133.2, 131.6, 131.3, 127.8, 126.9, 126.8, 125.3 (d, J=3.4 Hz), 124.9 (d, J=3.5 Hz), 124.2, 117.8 (d, J=22.1 Hz). 117.6 (d, J=22.0 Hz), 63.7, 52.5, 52.3, 48.2, 37.6, 12.2. MS (ESI) m/z 683.2 (30%, [M+H]+).

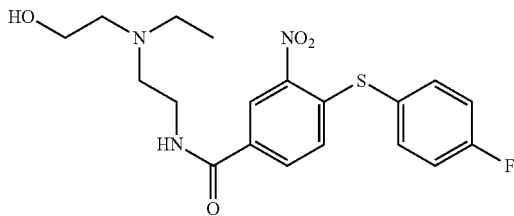 [SMILES: CCN(CCO)CCNC(=O)c1ccc(Sc2ccc(F)cc2)c([N+](=O)[O-])c1]

N-(2-(ethyl(2-hydroxyethyl)amino)ethyl)-4-((4-fluorophenyl)thio)-3-nitrobenzamide (WW3-62)

To a 15 mL flask were added 2-(ethyl(2-(4-((4-fluorophenyl)thio)-3-nitrobenzamido)ethyl)amino)ethyl 4-((4-fluorophenyl)thio)-3-nitrobenzoate (0.1262 g, 0.18 mmol), water (3 mL), NaOH (0.0905 g, 2.26 mmol), THF (1 mL) and methanol (1 mL). The reaction solution was stirred at 50° C. for 3 h and was diluted with water (20 mL), followed by extraction with DCM (3×25 mL). The combined organic layers were dried over Na$_2$SO$_4$, filtered and concentrated under reduced pressure to afford the desired product as a yellow gel (0.0507 g, 67%). $^1$H NMR (400 MHz, CDCl$_3$) δ 8.64 (d, J=1.9 Hz, 1H), 7.79 (dd, J=8.6, 2.0 Hz, 1H), 7.63-7.44 (m, 3H), 7.17 (t, J=8.6 Hz, 2H), 6.78 (d, J=8.5 Hz, 1H), 3.61 (t, J=5.2 Hz, 2H), 3.47 (q, J=5.6 Hz, 2H), 2.91 (s, 1H), 2.69 (t, J=5.8 Hz, 2H), 2.67-2.55 (m, 4H), 0.99 (t, J=7.1 Hz, 3H). $^{13}$C NMR (100 MHz, CDCl$_3$) δ 164.7, 164.0 (d, J=250.9 Hz), 144.0, 143.0, 143.0, 138.1 (d, J=8.6 Hz), 131.9, 131.5, 127.91, 125.4 (d, J=3.7 Hz), 124.3, 117.6 (d, J=22.0 Hz), 59.5, 55.1, 52.0, 48.0, 38.4, 11.6. MS (ESI) m/z 408.2 (100%, [M+H]$^+$).

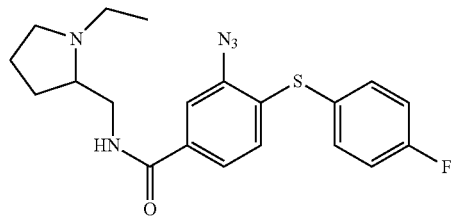 [SMILES: CCN1CCCC1CNC(=O)c1ccc(Sc2ccc(F)cc2)c(N=[N+]=[N-])c1]

3-azido-N-((1-ethylpyrrolidin-2-yl)methyl)-4-((4-fluorophenyl)thio)benzamide (WW3-57)

To a 25 mL flask containing DS-1-225 (0.1423 g, 0.38 mmol) were added 6 M HCl (1.5 ml), THF (1.5 ml) and DMF (0.8 ml). The mixture was cooled to 0° C. and NaNO$_2$ (0.0346 g, 0.50 mmol) was added. The reaction solution was stirred for 50 min at 0° C. and NaN$_3$ (0.0398 g, 0.61 mmol) in water (0.6 mL) was added. The resulting solution was then allowed to warm to room temperature and stirred overnight, followed by addition of 1 N NaOH (30 mL). The solution was extracted with CH$_2$Cl$_2$ (3×30 ml) and combined organic layers were dried over Na$_2$SO$_4$, filtered and concentrated. The residue was dissolved in EtOAc (30 mL), washed by 10% LiCl solution (30 mL) and brine (3×30 mL) to afford the entitled product (0.1298 g, 85%) as light brown gel. $^1$H NMR (400 MHz, CDCl$_3$) δ 7.91 (s, 1H), 7.75 (d, J=1.8 Hz, 1H), 7.52-7.39 (m, 3H), 7.14-7.04 (m, 2H), 6.76 (d, J=8.3 Hz, 1H), 3.73 (ddd, J=14.3, 7.1, 5.3 Hz, 1H), 3.60-3.36 (m, 2H), 3.13 (s, 1H), 3.03-2.90 (m, 1H), 2.71-2.35 (m, 2H), 2.11-1.94 (m, 1H), 1.91-1.81 (m, 2H), 1.75 (dt, J=12.6, 6.4 Hz, 1H), 1.23 (t, J=7.2 Hz, 3H). $^{13}$C NMR (100 MHz, CDCl$_3$) δ 166.2, 163.3 (d, J=250.2 Hz), 137.3, 136.7 (d, J=8.4 Hz), 133.9, 132.5, 128.0, 126.1 (d, J=3.5 Hz), 123.3, 117.0 (d, J=22.0 Hz), 116.9, 64.6, 53.7, 49.7, 40.4, 27.9, 23.3, 12.4. MS (ESI) m/z 400.2 (100%, [M+H]$^+$).

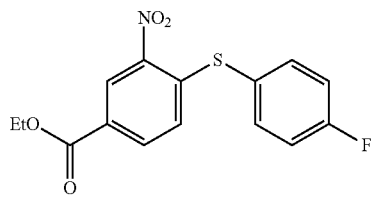 [SMILES: CCOC(=O)c1ccc(Sc2ccc(F)cc2)c([N+](=O)[O-])c1]

Ethyl 4-((4-fluorophenyl)thio)-3-nitrobenzoate

A mixture of 4-((4-fluorophenyl)thio)-3-nitrobenzoic acid (0.8795 g, 3.00 mmol), DMAP (0.0814 g, 0.67 mmol), EDC hydrochloride (0.6330 g, 3.30 mmol) and CH$_2$Cl$_2$ (7 mL) was stirred at room temperature for 30 min. Ethanol (0.7102 g, 15.44 mmol) was then added and the resulting solution was stirred at room temperature for 24 h. The reaction solution was diluted with CH$_2$Cl$_2$ (30 mL), washed by brine (30 mL) and 2 N NaOH solution (30 mL). The organic layer was dried over Na$_2$SO$_4$, filtered and concentrated under reduced pressure. The residue was purified through flash chromatography on silica gel (10:1 Hexane:EtOAc) to afford the title product as yellow solid (0.8088 g, 84%). mp 112-115° C.; $^1$H NMR (400 MHz, CDCl$_3$) δ 8.83 (d, J=1.6 Hz, 1H), 7.94 (dd, J=8.6, 1.9 Hz, 1H), 7.69-7.44 (m, 2H), 7.26-7.12 (m, 2H), 6.84 (d, J=8.6 Hz, 1H), 4.37 (q, J=7.1 Hz, 2H), 1.38 (t, J=7.1 Hz, 3H). $^{13}$C NMR (100 MHz, CDCl$_3$) δ164.3, 164.10 (d, J=252.4 Hz), 145.0, 144.3, 138.2 (d, J=8.7 Hz), 133.5, 127.8, 127.6, 127.0, 125.3 (d, J=3.6 Hz), 117.7 (d, J=22.0 Hz), 61.7, 14.2.

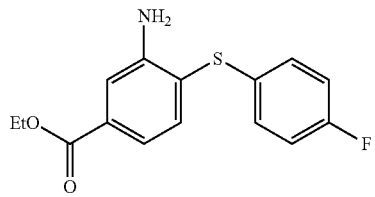

Ethyl 3-amino-4-((4-fluorophenyl)thio)benzoate

To a 50 mL flask were added ethyl 4-((4-fluorophenyl)thio)-3-nitrobenzoate (0.2132 g, 0.66 mmol), methanol (5 mL) and Pd/C (2 spatula, 10% on active carbon). The reaction flask was sealed by a septum and after the removal of air using vacuum, a hydrogen balloon was fitted on the top of the septum. The reaction suspension was then stirred at room temperature for 15 h and was filtered through a pad of Celite, washed by methanol. The filtrate was concentrated under reduced pressure to provide the desired product (0.1856 g, >95%) as a yellow gel. $^1$H NMR (400 MHz, CDCl$_3$) δ 7.45 (s, 1H), 7.38 (s, 2H), 7.15 (dd, J=8.8, 5.1 Hz, 2H), 6.96 (t, J=8.7 Hz, 2H), 4.36 (q, J=7.1 Hz, 2H), 1.38 (t, J=7.1 Hz, 3H). $^{13}$C NMR (100 MHz, CDCl$_3$) δ 166.3, 161.7 (d, J=246.3 Hz), 147.6, 135.6, 132.2, 130.1 (d, J=8.0 Hz), 129.4, 121.2, 119.3 (d, J=2.2 Hz), 116.3 (d, J=22.2 Hz), 116.1, 61.1, 14.3. MS (ESI) m/z 292.1 (100%, [M+H]$^+$).

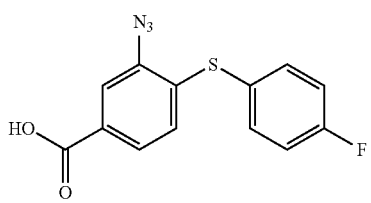 [SMILES: [N-]=[N+]=Nc1cc(C(=O)O)ccc1Sc1ccc(F)cc1]

3-azido-4-((4-fluorophenyl)thio)benzoic acid

A mixture of ethyl 3-amino-4-((4-fluorophenyl)thio)benzoate (0.1674 g, 0.58 mmol), LiOH.H$_2$O (0.1496 g, 56%, 1.99 mmol), THF (5 mL) and water (3 mL) was stirred at 72° C. for 2.5 h. The reaction solution was cooled down to room temperature and then 0° C. in an ice-water bath. The reaction solution was then acidified to pH=1 using 6 N HCl solution and NaNO$_2$ (0.0505 g, 0.73 mmol) was added at 0° C. The resulting solution was stirred for 25 min at 0° C. and NaN$_3$ (0.0623 g, 0.96 mmol) was added. The reaction solution was then allowed to warm up to room temperature gradually and stirred overnight. The reaction mixture was diluted with 15 mL water and extracted with CH$_2$Cl$_2$ (3×25 ml). The combined organic layers were dried by Na$_2$SO$_4$, filtered and concentrated to afford the entitled product (0.1322 g, 79% two steps) as orange solid. mp 156-158° C.; $^1$H NMR (400 MHz, CDCl$_3$) δ 7.82 (d, J=1.7 Hz, 1H), 7.65 (dd, J=8.3, 1.7 Hz, 1H), 7.52 (dd, J=8.6, 5.3 Hz, 2H), 7.15 (t, J=8.6 Hz, 2H), 6.73 (d, J=8.3 Hz, 1H). $^{13}$C NMR (100 MHz, CDCl$_3$) δ 170.9, 163.6 (d, J=251.5 Hz), 137.9, 137.4 (d, J=8.6 Hz), 136.5, 127.2, 126.9, 126.8, 125.1 (d, J=3.5 Hz), 119.3, 117.3 (d, J=22.0 Hz). MS (ESI) m/z 288.0 (100%, [M–H]$^-$).

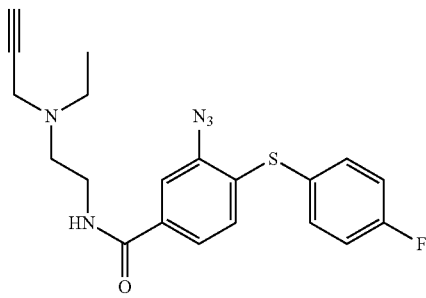 [SMILES: C#CCN(CC)CCNC(=O)c1ccc(Sc2ccc(F)cc2)c(N=[N+]=[N-])c1]

3-azido-N-(2-(ethyl(prop-2-yn-1-yl)amino)ethyl)-4-((4-fluorophenyl)thio)benzamide (WW3-77)

A mixture of 3-azido-4-((4-fluorophenyl)thio)benzoic acid (0.1231 g, 0.43 mmol), DMAP (0.0153 g, 0.13 mmol), EDC hydrochloride (0.0886 g, 0.46 mmol) and CH$_2$Cl$_2$ (3 mL) was stirred at room temperature for 20 min. N$^1$-ethyl-N$^1$-(prop-2-yn-1-yl)ethane-1,2-diamine (0.0520 g, 0.41 mmol) in DCM (1 mL) was then added and the resulting solution was stirred at room temperature for 20 h. The reaction solution was diluted with CH$_2$Cl$_2$ (25 mL), washed by brine (25 mL) and saturated NaHCO$_3$ solution (25 mL). The organic layer was dried over Na$_2$SO$_4$, filtered and concentrated under reduced pressure. The residue was purified through flash chromatography on silica gel (1:19 MeOH:CH$_2$Cl$_2$) to afford the title product as orange gel (0.1364 g, 83%). $^1$H NMR (400 MHz, CDCl$_3$) δ 7.61 (d, J=1.7 Hz, 1H), 7.45 (dd, J=8.8, 5.2 Hz, 2H), 7.25 (dd, J=8.2, 1.8 Hz, 1H), 7.10 (t, J=8.6 Hz, 2H), 6.85 (s, 1H), 6.75 (d, J=8.2 Hz, 1H), 3.48 (dd, J=11.4, 4.9 Hz, 2H), 3.40 (d, J=2.4 Hz, 2H), 2.74 (dd, J=6.4, 5.3 Hz, 2H), 2.58 (q, J=7.2 Hz, 2H), 2.19 (t, J=2.3 Hz, 1H), 1.05 (t, J=7.2 Hz, 3H). $^{13}$C NMR (100 MHz, CDCl$_3$) δ 165.9, 163.3 (d, J=250.2 Hz), 137.3, 136.6 (d, J=8.4 Hz), 133.8, 133.3, 128.1, 126.2 (d, J=3.4 Hz), 123.0, 117.5, 117.0 (d, J=22.1 Hz), 78.2, 73.3, 51.4, 47.3, 41.2, 37.1, 12.7. MS (ESI) m/z 398.2 (100%, [M+H]$^+$).

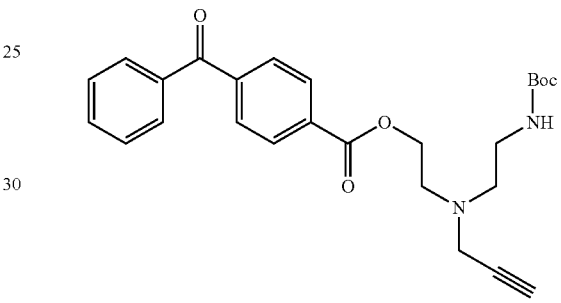

2-((2-((tert-butoxycarbonyl)amino)ethyl)(prop-2-yn-1-yl)amino)ethyl 4-benzoylbenzoate A mixture of 4-benzoylbenzoic acid (0.2009 g, 0.89 mmol), DMAP (0.0344 g, 0.28 mmol), EDC hydrochloride (0.1758 g, 0.92 mmol) and CH$_2$Cl$_2$ (5 mL) was stirred at room temperature for 1 h. tert-Butyl (2-((2-hydroxyethyl)(prop-2-yn-1-yl)amino)ethyl)carbamate (0.1952 g, 0.81 mmol) in CH$_2$Cl$_2$ (2 mL) was then added and the resulting solution was stirred at room temperature for 18.5 h. The reaction solution was diluted with CH$_2$Cl$_2$ (25 mL), washed by brine (30 mL) and saturated NaHCO$_3$ solution (30 mL). The organic layer was dried over Na$_2$SO$_4$, filtered and concentrated under reduced pressure. The residue was purified through flash chromatography on silica gel (1:19 MeOH:CH$_2$Cl$_2$) to afford the title product (0.3031 g, 83%) as colorless gel. $^1$H NMR (400 MHz, CDCl$_3$) δ 8.14 (d, J=8.3 Hz, 2H), 7.82 (d, J=8.2 Hz, 2H), 7.78 (d, J=7.1 Hz, 2H), 7.60 (t, J=7.4 Hz, 1H), 7.48 (t, J=7.7 Hz, 2H), 4.43 (t, J=5.5 Hz, 2H), 3.48 (d, J=2.4 Hz, 2H), 3.21 (q, J=5.7 Hz, 2H), 2.94 (t, J=5.6 Hz, 2H), 2.71 (t, J=5.9 Hz, 2H), 2.21 (t, J=2.3 Hz, 1H), 1.38 (s, 9H). $^{13}$C NMR (100 MHz, CDCl$_3$) δ 195.9, 165.8, 155.9, 141.3, 136.9, 133.1, 132.9, 130.1, 129.8, 129.5, 128.4, 78.1, 73.5, 63.2, 52.8, 51.9, 42.4, 37.8, 28.8, 28.4. MS (ESI) m/z 451.2 (100%, [M+H]$^+$).

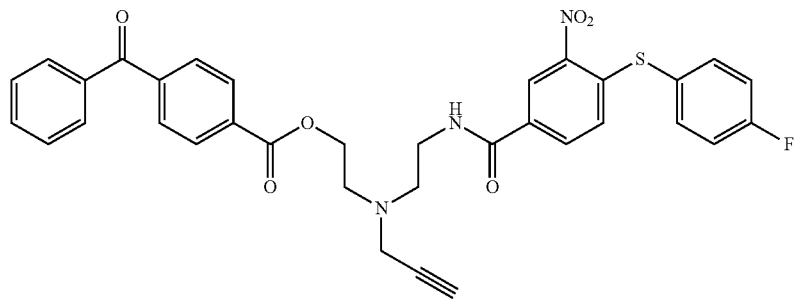 [SMILES: C#CCN(CCNC(=O)c1ccc(Sc2ccc(F)cc2)c([N+](=O)[O-])c1)CCOC(=O)c1ccc(C(=O)c2ccccc2)cc1]

2-((2-(4-((4-fluorophenyl)thio)-3-nitrobenzamido)ethyl)(prop-2-yn-1-yl)amino)ethyl 4-benzoylbenzoate (WW3-80)

2-((2-((tert-Butoxycarbonyl)amino)ethyl)(prop-2-yn-1-yl)amino)ethyl 4-benzoylbenzoate (0.1818 g, 0.40 mmol) was dissolved in anhydrous $CH_2Cl_2$ (2.5 mL), followed by addition of trifluoroacetic acid (1 mL, 13.06 mmol). The resulting solution was stirred at room temperature for 3 h and then was slowly poured into 30 mL saturated $NaHCO_3$ solution at 0° C. The bi-phasic solution was extracted with $CH_2Cl_2$ (3×30 mL). The combined organic layers were dried over $Na_2SO_4$, filtered and concentrated under reduced pressure to afford the deprotected amine which was used directly for next step without further purification.

A mixture of 4-((4-fluorophenyl)thio)-3-nitrobenzoic acid (0.1191 g, 0.41 mmol), DMAP (0.0112 g, 0.09 mmol), EDC hydrochloride (0.0900 g, 0.47 mmol) and $CH_2Cl_2$ (2 mL) was stirred at room temperature for 20 min. The deprotected amine above in $CH_2Cl_2$ (3 mL) was then added and the resulting reaction mixture was stirred at room temperature overnight and was diluted with $CH_2Cl_2$ (25 mL), washed by brine (25 mL) and saturated $NaHCO_3$ solution (25 mL). The organic layer was dried over $Na_2SO_4$, filtered and concentrated under reduced pressure. The residue was purified through flash chromatography on silica gel (1:19 MeOH:$CH_2Cl_2$) to afford the title product (0.1844 g, 73% two steps) as yellow gel. $^1H$ NMR (400 MHz, $CDCl_3$) δ 8.58 (s, 1H), 7.97 (d, J=8.3 Hz, 2H), 7.84-7.64 (m, 5H), 7.64-7.58 (m, 1H), 7.56-7.44 (m, 4H), 7.23-7.05 (m, 3H), 6.75 (d, J=8.6 Hz, 1H), 4.49 (t, J=5.2 Hz, 2H), 3.68-3.46 (m, 4H), 3.01 (t, J=5.1 Hz, 2H), 2.91 (t, J=5.7 Hz, 2H), 2.27 (t, J=2.3 Hz, 1H). $^{13}C$ NMR (100 MHz, $CDCl_3$) δ 195.7, 165.9, 164.6, 164.0 (d, J=252.4 Hz), 144.0, 143.1, 141.3, 138.1 (d, J=8.7 Hz), 136.7, 133.0, 132.8, 131.7, 131.3, 130.0, 129.7, 129.3, 128.5, 127.8, 125.3 (d, J=3.5 Hz), 124.4, 117.6 (d, J=22.1 Hz), 77.7, 74.1, 62.9, 52.5, 52.2, 43.0, 37.3. MS (ESI) m/z 626.2 (100%, [M+H]$^+$).

TABLE A

Exemplary analog compounds and their properties.

| Structure | CLogP | CLogD | TPSA (Å) | MW (g/mol) | HBD | pKa | CNS MPO | EC50 (TD-NSC) (nM) | S9 $T_{1/2}$ |
|---|---|---|---|---|---|---|---|---|---|
| DS-1-023 | 3.91 | 3.91 | 85.1 | 383 | 1 | 4.14 | 4.3 | >1000 | |
| DS-1-031 | 4.16 | 3.08 | 75.5 | 403 | 1 | 8.45 | 4.2 | 33 | 113.6 |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 $T_{1/2}$ |
|---|---|---|---|---|---|---|---|---|---|
| DS-1-033 (GBM#49) | 4.16 | 3.08 | 75.5 | 403 | 1 | 8.45 | 4.2 | 45 | 119 |
| DS-1-043 | 4.05 | 2.4 | 75.5 | 391 | 1 | 9.04 | 4.4 | 22 | 45 |
| DS-1-053 | 4.16 | 3.08 | 75.5 | 403 | 1 | 8.45 | 4.2 | 31 | 66 |
| DS-1-055 | 4.02 | 2.93 | 75.5 | 385 | 1 | 8.45 | 4.5 | 50 | 35.4 |
| DS-1-061 | 3.86 | 1.98 | 75.5 | 403 | 1 | 9.29 | 4.4 | 79 | 105.0 |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 T$_{1/2}$ |
|---|---|---|---|---|---|---|---|---|---|
| DS-1-063 | 3.74 | 2.9 | 75.5 | 389 | 1 | 8.17 | 4.7 | 52 | 187.3 |
| DS-1-065 | 4.90 | 3.81 | 75.5 | 453 | 1 | 8.45 | 3.1 | 86 | |
| DS-1-067 | 4.3 | 3.22 | 75.5 | 421 | 1 | 8.45 | 3.9 | 118 | |
| DS-1-069 | 4.16 | 3.08 | 75.5 | 403 | 1 | 8.45 | 4.2 | 88 | 35.2 |
| DS-1-071 | 3.39 | 2.31 | 88.4 | 386 | 1 | 8.44 | 5.1 | 419 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 T$_{1/2}$ |
|---|---|---|---|---|---|---|---|---|---|
| DS-1-075 | 4.16 | 3.08 | 75.5 | 403 | 1 | 8.45 | 4.2 | 102 | |
| DS-1-077 | 3.26 | 2.17 | 204.6 | 443 | 2 | 8.45 | 4.0 | >1000 | |
| DS-1-079 | 4.64 | 2.67 | 58.4 | 389 | 1 | 9.30 | 3.8 | 36 | 21.4 |
| DS-1-085 | 3.42 | 0.18 | 84.3 | 375 | 2 | 10.56 | 4.2 | 132 | .240 |
| DS-1-089 | 3.12 | 3.11 | 84.7 | 405 | 1 | 5.85 | 4.9 | 25 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 $T_{1/2}$ |
|---|---|---|---|---|---|---|---|---|---|
| DS-1-103 | 3.47 | 2.39 | 84.7 | 387 | 1 | 8.45 | 5.0 | 36 | |
| DS-1-105 | 4.71 | 3.58 | 87.5 | 386 | 2 | 8.50 | 3.4 | 255 | |
| DS-1-117 | 4.22 | 2.97 | 32.3 | 358 | 1 | 8.62 | 4.0 | 394 | |
| DS-1-119 | 2.02 | / | 72.2 | 419 | 1 | −1.23 | 4.4 | >1000 | |
| DS-1-123 | 5.26 | 4.18 | 75.5 | 428 | 1 | 8.45 | 3.1 | 516 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 $T_{1/2}$ |
|---|---|---|---|---|---|---|---|---|---|
| DS-1-125 | 4.30 | 3.22 | 75.5 | 421 | 1 | 8.45 | 3.9 | 51 | 87.7 |
| DS-1-129 | 2.80 | 1.71 | 88.4 | 386 | 1 | 8.45 | 5.4 | 150 | 92.4 |
| DS-1-131 | 4.22 | 3.13 | 75.5 | 418 | 1 | 8.45 | 4.0 | 35 | 96.3 |
| DS-1-133 | 3.86 | 2.78 | 84.7 | 416 | 1 | 8.45 | 4.4 | 62 | 48.1 |
| DS-1-135 | 2.79 | 2.29 | 92.6 | 419 | 1 | 7.73 | 5.2 | >1000 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 $T_{1/2}$ |
|---|---|---|---|---|---|---|---|---|---|
| DS-1-137 | 3.96 | 2.87 | 118.6 | 430 | 1 | 8.45 | 3.2 | 69 | |
| DS-1-139 | 4.05 | 2.96 | 75.5 | 392 | 1 | 8.45 | 4.4 | 192 | |
| DS-1-163 | 4.62 | 3.54 | 75.5 | 420 | 1 | 8.45 | 3.6 | 51 | 88.8 |
| DS-1-177 | 3.19 | 2.10 | 101.5 | 400 | 2 | 8.45 | 4.5 | 340 | |
| DS-1-179 | 0.95 | 0.91 | 112.0 | 429 | 2 | 8.45 | 4.0 | >1000 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 T$_{1/2}$ |
|---|---|---|---|---|---|---|---|---|---|
| DS-1-181 | 3.62 | 2.52 | 75.5 | 371 | 1 | 8.47 | 4.9 | >1000 | |
| DS-1-183 | 3.62 | 2.52 | 75.5 | 371 | 1 | 8.46 | 5.0 | >1000 | |
| DS-1-185 | 4.79 | 3.70 | 75.5 | 464 | 1 | 8.45 | 3.1 | 62 | |
| DS-1-191 | 4.16 | 3.08 | 75.5 | 403 | 1 | 8.45 | 4.2 | 95 | |
| DS-1-195 | 2.54 | 0.53 | 101.5 | 392 | 2 | 9.51 | 4.2 | >1000 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 T$_{1/2}$ |
|---|---|---|---|---|---|---|---|---|---|
| DS-1-205 | 2.90 | 1.13 | 147.7 | 619 | 4 | 7.70 | 3.0 | ≈40000 | |
| DS-1-209 | 3.60 | 2.46 | 45.2 | 359 | 1 | 8.50 | 5.1 | >1000 | |
| DS-1-213 | 1.12 | 1.18 | 121.7 | 450 | 2 | 8.46 | 3.6 | >1000 | |
| DS-1-217 | 3.39 | 2.63 | 95.7 | 401 | 2 | 8.37 | 4.3 | 485 | |
|  | 3.39 | 2.09 | 58.4 | 373 | 2 | 8.68 | 4.8 | 192 | |
|  | 4.08 | 2.89 | 56.1 | 383 | 1 | 8.56 | 4.4 | 53 | 65 |
|  | 3.07 | 1.89 | 75.4 | 402 | 2 | 8.55 | 4.9 | >1000 | |
|  | 4.05 | 2.40 | 75.5 | 391 | 1 | 9.04 | 4.4 | 59 | |
|  | 3.12 | 3.11 | 84.7 | 405 | 1 | 5.85 | 4.9 | 44 | |
|  | 4.09 | 3.00 | 84.7 | 440 | 1 | 8.45 | 4.0 | 269 | |
|  | 4.52 | 3.44 | 101.8 | 476 | 1 | 8.45 | 2.9 | >1000 | |
| DS-1-269 | 4.17 | 3.09 | 88.4 | 437 | 1 | 8.45 | 3.9 | 535 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 T$_{1/2}$ |
|---|---|---|---|---|---|---|---|---|---|
| DS-1-271 | 4.53 | 3.45 | 75.5 | 400 | 1 | 8.45 | 3.8 | 55 | |
| DS-1-275 | 3.74 | 3.74 | 81.5 | 376 | 1 | −1.07 | 4.5 | >1000 | |
| DS-1-279 | 4.27 | 2.92 | 66.7 | 415 | 0 | 8.73 | 4.1 | 58 | 26.7 |
|  | 3.18 | 3.05 | 84.7 | 419 | 1 | 6.95 | 4.8 | 42 | 93.6 |
|  | 5.09 | 4.06 | 72.7 | 404 | 0 | 8.39 | 3.5 | >1000 | |
|  | 5.23 | 4.14 | 75.5 | 454 | 1 | 8.45 | 2.9 | 93 | |
|  | 4.62 | 3.54 | 75.5 | 420 | 1 | 8.45 | 3.6 | 70 | |
|  | 5.04 | 3.96 | 75.5 | 414 | 1 | 8.45 | 3.2 | 169 | |
| DS-1-301 | 3.06 | 2.89 | 66.5 | 437 | 1 | 7.09 | 4.8 | 236 | >240 |
| DS-1-305 | 4.53 | 3.45 | 75.5 | 400 | 1 | 8.45 | 3.8 | 86 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 T$_{1/2}$ |
|---|---|---|---|---|---|---|---|---|---|
| DS-1-311 | 3.39 | 2.20 | 65.4 | 367 | 1 | 8.56 | 5.2 | | 117.5 |
| DS-2-027 | 3.04 | 3.02 | 65.4 | 386 | 1 | 5.96 | 5.1 | | 40.1 |
| DS-2-035 | 3.92 | 3.33 | 78.2 | 401 | 1 | 7.90 | 4.4 | 49 | |
| | 2.35 | 2.33 | 74.6 | 369 | 1 | 5.96 | 5.6 | 74 | 99 |
| | 2.99 | 1.91 | 104.4 | 401 | 2 | 8.45 | 4.5 | 564 | |
| | 4.36 | 3.18 | 32.3 | 376 | 1 | 8.56 | 3.8 | 87 | 41 |
| DS-2-055 | 3.92 | 3.50 | 101.2 | 440 | 1 | 7.60 | 3.7 | 155 | |
| DS-2-057 | 3.43 | 2.94 | 101.2 | 399 | 1 | 7.72 | 4.5 | 233 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 T₁/₂ |
|---|---|---|---|---|---|---|---|---|---|
| DS-2-061 | 4.38 | 3.15 | 75.4 | 418 | 0 | 8.61 | 4.0 | 15 | |
| DS-2-091 | 4.09 | 3.47 | 132.9 | 424 | 1 | 7.90 | 3.1 | >1000 | |
| DS-2-093 | 6.81 | 6.47 | 110.5 | 594 | 1 | 7.47 | 2.2 | >1000 | |
| DS-2-097 | 4.55 | 3.93 | 110.5 | 472 | 1 | 7.90 | 2.6 | >1000 | |
| DS-2-101 | 4.55 | 3.93 | 110.5 | 472 | 1 | 7.90 | 2.6 | >1000 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 $T_{1/2}$ |
|---|---|---|---|---|---|---|---|---|---|
| DS-2-107 | 3.19 | 2.98 | 101.2 | 397 | 1 | 7.20 | 4.6 | >1000 | |
| DS-2-111 | 3.24 | 1.02 | 102.2 | 399 | 2 | 9.66 | 3.9 | >1000 | |
|  | 4.16 | 3.04 | 84.2 | 403 | 1 | 8.49 | 4.2 | 60 | |
| DS-2-121 | 3.18 | 2.32 | 87.4 | 418 | 1 | 8.20 | 5.1 | 287 | |
| DS-2-125 | 4.19 | 3.44 | 84.2 | 404 | 1 | 8.06 | 4.2 | 50 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 $T_{1/2}$ |
|---|---|---|---|---|---|---|---|---|---|
| DS-2-127 | 4.08 | 4.07 | 113.7 | 505 | 1 | 5.78 | 2.5 | Not active | |
| DS-2-129 | 2.80 | 0.99 | 96.2 | 404 | 2 | 9.22 | 4.4 | 141 | |
| DS-2-143 | 5.50 | 4.41 | 84.2 | 488 | 1 | 8.45 | 2.7 | 129 | |
| JCH-107 | 4.90 | 3.79 | 84.2 | 454 | 1 | 8.47 | 3.1 | | |
| JCH-109 | 3.19 | 2.09 | 110.2 | 401 | 2 | 8.47 | 4.2 | 301 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 T$_{1/2}$ |
|---|---|---|---|---|---|---|---|---|---|
| JCH-113 | 4.62 | 3.54 | 84.2 | 420 | 1 | 8.45 | 3.6 | 119 | |
| JCH-114 | 4.53 | 3.45 | 84.2 | 400 | 1 | 8.45 | 3.8 | 78 | |
| JCH-117 | 3.86 | 2.78 | 93.4 | 416 | 1 | 8.45 | 4.3 | 119 | |
| JCH-120 | 5.23 | 4.14 | 84.2 | 454 | 1 | 8.45 | 2.9 | 68 | |
| JCH-124 | 5.23 | 4.14 | 84.2 | 454 | 1 | 8.45 | 2.9 | 510 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 T$_{1/2}$ |
|---|---|---|---|---|---|---|---|---|---|
| JCH-127 | 4.77 | 3.69 | 96.5 | 437 | 1 | 8.44 | 3.1 | 125 | |
| JCH-140 | 3.71 | 2.66 | 104.4 | 401 | 2 | 8.73 | 3.7 | 139 | |
| JCH-143 | 3.71 | 2.66 | 104.4 | 401 | 2 | 8.23 | 3.9 | 160 | |
| JCH-146 | 3.86 | 2.78 | 93.4 | 415.5 | 1 | 8.45 | 4.3 | 185 | |
| JCH-149 | 3.25 | 2.17 | 104.4 | 415.5 | 2 | 8.45 | 4.2 | 154 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 $T_{1/2}$ |
|---|---|---|---|---|---|---|---|---|---|
| ww2-292 | 5.47 | 3.45 | 75.4 | 441.5 | 0 | 8.54 | 3.4 | 531 | |
| ww3-13 | 6.07 | 3.57 | 118.1 | 491.5 | 1 | 8.48 | 1.9 | >1000 | |
| ww3-57 | 5.65 | 3.35 | 81.1 | 399.5 | 1 | 8.55 | 3.6 | 63 | |
| ww3-62 | 4.11 | 1.90 | 104.4 | 407.5 | 2 | 8.48 | 3.9 | 57 | |

TABLE A-continued

Exemplary analog compounds and their properties.

| Structure | CLogP | CLogD | TPSA (Å) | MW (g/mol) | HBD | pKa | CNS MPO | EC50 (TD-NSC) (nM) | S9 $T_{1/2}$ |
|---|---|---|---|---|---|---|---|---|---|
| ww3-77 | 5.62 | 3.67 | 81.1 | 397.5 | 1 | 7.90 | 3.7 | 239 | |
| ww3-80 | 7.95 | 6.81 | 127.5 | 625.7 | 1 | 6.10 | 1.8 | 161 | |

Plasma Stability

Compounds were diluted to a final concentration of 2 μM in commercial plasma (Bioreclamation, Westbury, N.Y.) and 200 μl aliquoted into multiple Eppendorf vials. One vial was immediately extracted with the addition of an equal volume of methanol containing 0.2% formic acid and 200 ng/ml of an internal standard (either n-benzylbenzamide or tolbutamide, Sigma, St. Louis, Mo.). The vial was vortexed for 15 seconds, incubated 10 min at RT and centrifuged at 16,100×g for 5 min. The supernatant was re-centrifuged 5 min 16,100×g and the secondary supernatant placed in an HPLC vial and analyze by LC-MS/MS as described above. The remaining aliquots were incubated in a 37° C. water bath for up to 24 hours. At various points, samples were removed and processed as described above. LC-MS/MS analyses was as described for the S9 and hepatocyte stability analyses.

Metabolic Stability Data Analysis

The method described in McNaney, et al (McNaney, C A, D M Drexler, S Hnatyshyn, T A Zvyaga, J O Knipe, J V Belcastro, and M Sanders. 2008. An automated liquid chromatography-mass spectrometry process to determine metabolic stability half-life and intrinsic clearance of drug candidates by substrate depletion. Assay and Drug Development Technologies 6:121-129. Determination of Plasma and Brain Pharmacokinetics) was used with modification for determination of metabolic stability half-life by substrate depletion. A "% remaining" value was used to assess metabolic stability of a compound over time. The LC/MS/MS peak area of the incubated sample at each time point was divided by the LC/MS/MS peak area of the time 0 (T0) sample and multiplied by 100. The natural Log (LN) of the % remaining of compound was then plotted versus time (in min) and a linear regression curve plotted going through y-intercept at LN(100). The metabolism of some compounds failed to show linear kinetics at later time point, so those time points were excluded. The half-life (T½) was calculated as T½=0.693/slope.

Determination of Plasma and Brain Pharmacokinetics

Compounds were prepared for dosing by dissolving in DMSO at 25-50 mg/ml. The compounds were diluted to the final formulation as listed in the individual Excel data files (most often 10% DMSO/10% cremophor EL/80% D5W (5% dextrose in water, pH 7.4).) Adult CD-1 female mice were dosed IP in a total volume of 0.2 ml and at varying times post-dose were sacrificed by inhalation overdose of CO2. Whole blood was collected by cardiac puncture with an ACD solution (sodium citrate) coated syringe and needle. The blood was subsequently centrifuged at 9300×g for 10' to isolate plasma. Plasma was stored at −80° C. until analysis. Brains were isolated from mice immediately after sacrifice, rinsed three times with PBS and blotted gently to remove any surface adhering blood, weighed, and snap frozen in liquid nitrogen. Lysates were prepared by homogenizing the brain tissue in a 3-fold volume of PBS (weight of brain in g X=volume of PBS in ml added). Total lysate volume was estimated as volume of PBS added+volume of brain in ml. One hundred μl of either plasma or brain was processed by addition of 200 μl of acetonitrile or methanol containing 0.15% formic acid and 150 ng/ml internal standard (n-benzyl benzamide or tolbutamide) to precipitate plasma or tissue protein and release bound drug. This mixture was centrifuged at 16,100×g for 5 min, the supernatant was re-centrifuged and analyzed directly by LC-MS/MS Compound levels were monitored by LC-MS/MS using an AB/Sciex (Applied Biosystems, Foster City, Calif.) 4000 Qtrap mass spectrometer coupled to a Shimadzu Prominence LC. The compound was detected with the mass spectrometer in MRM (multiple reaction monitoring) mode by following the precursor to fragment ion transitions indicated in the Methods box for individual data files. Standard curves were prepared by addition of compound to blank plasma or blank brain lysate. A value of 3× above the signal obtained from blank plasma or brain lysate was designated the limit of detection (LOD). The limit of quantitation (LOQ) was defined as the lowest concentration at which back calculation yielded a concentration within 20% of theoretical. In general back calculation of points on both curves yielded values within 15% of theoretical over 4 orders of magnitude (1000 to 1 ng/ml). Pharmacokinetic parameters were calculated using the noncompartmental analysis tool of Phoenix WinNonLin (Certara, Corporation, Princeton, N.J.). The amount of compound in the vasculature of the brain was subtracted using reference values for the amount of blood in the brain (30 µl/g brain tissue) and the measured plasma concentration (Kwon, Y. (2001). The Handbook of Essential Pharmacokinetics, Pharmacodynamics, and Drug Metabolism for Industrial Scientists. Kluwer Academic/Plenum Publishers, pp 231-232).

Compound was assumed to partition equally between plasma and blood for this determination. The Brain:Blood ratio was calculated using the subtracted brain AUC and the plasma AUC.

terol, a core of cholesteryl esters and triglycerides. Id. at 1072. Triglycerides consist of a three-carbon glycerol backbone covalently linked to three fatty acids. Their fatty acid composition varies in terms of chain length and degree of saturation. Triglyceride molecules are nonpolar and hydrophobic, and are transported in the core of the lipoprotein. Hydrolysis of triglycerides by lipases generates free fatty acids (FFAs) used for energy. Id. Phospholipids, constituents of all cellular membranes, consist of a glycerol molecule linked to two fatty acids. The fatty acids differ in length and in the presence of a single or multiple double bonds. The third carbon of the glycerol moiety carries a phosphate group to which one of four molecules is linked: choline (phosphatidylcholine or lecithin), ethanolamine (phosphatidylethanolamine), serine (phosphatidylserine), or inositol (phosphatidylinositol). Phospholipids, which are polar molecules, more soluble than triglycerides or cholesterol or its esters, participate in signal transduction pathways. Hydrolysis by membrane-associated phospholipases generates second messengers such as diacyl glycerols, lysophospholipids, phoshatidic acids and free fatty acids (FFAs) such as arachidonate that can regulate many cell functions. Id.

The apolipoproteins, which comprise the protein moiety of lipoproteins, vary in size, density in the aqueous environment of plasma, and lipid and apolipoprotein content. The classification of lipoproteins reflects their density in plasma (1.006 gm/mL) as gauged by flotation in the ultracentrifuge. For example, triglyceride-rich lipoproteins consisting of chylomicrons (meaning a class of lipoproteins that

TABLE B pharmacokinetic parameters for exemplary compounds.

| | Bioavailability (IP) in Plasma | | | | Bioavailability (IP) in Brain | | | |
| --- | --- | --- | --- | --- | --- | --- | --- | --- |
| Compound | Cmax (ng/ml) | $T_{1/2}$ (min) | AUC min * ng/mL (10 mg/kg IP) | Cl mil/min (10 mg/kg IP) | Cmax (ng/ml) | $T_{1/2}$ (min) | AUC min * ng/mL (10 mg/kg IP) | Cl ml/min (10 mg/kg IP) |
| A | 7946.67 | 101.97 | 513,117.5 | — | 52.08 | 175.36 | 17,465.9 | |
| B | 1387 | 52 | 139,721 | 1.66 | 646 | 62 | 95,916 | 2.38 |
| C | 7946.67 | 101.97 | 513,117.49 | 0.47 | 52.08 | 175.36 | 17,465.90 | 13.85 |
| D | 2160 | 137 | 309,840 | 0.75 | 503 | 240 | 130,384 | 1.75 |
| E | 2833.33 | 83.6 | 163.543 | 1.47 | 1035.00 | 118.4 | 49,878 | 4.68 |
| F | 1103 | 52 | 50,857 | 4.51 | 1701 | 56 | 206,079 | 1.11 |

Example 2. Deregulators of Cholesterol Biosynthesis Pathways

Microarray analysis was conducted to identify overrepresented pathways associated with treatment with compound 4C12 for 48 hr. The results, which are shown in FIG. 9, suggest that compound 4C12 deregulates the cholesterol biosynthesis pathway.

Cholesterol Pathways

The major types of lipids that circulate in plasma include cholesterol and cholesteryl esters, phospholipids and triglycerides. Braunwald's Heart Disease, P. Libby, R. Bonow, D. Mann and D. Zipes, Eds., 8$^{th}$ Edition, Saunders Elsevier, Philadelphia, Pa. (2008) at 1071. Cholesterol contributes an essential component of mammalian cell membranes and furnishes substrate for steroid hormones and bile acids. Many cell functions depend critically on membrane cholesterol, and cells tightly regulate cholesterol content. Most of the cholesterol in plasma circulates in the form of cholesteryl esters in the core of lipoprotein particles. The enzyme lecithin cholesterol acyl transferase (LCAT) forms cholesteryl esters in the blood compartment by transferring a fatty acyl chain from phosphatidylcholine to cholesterol. Id.

Lipoproteins are complex macromolecular structures composed of an envelope of phospholipids and free cholestransport dietary cholesterol and triglycerides after meals from the small intestine to tissues for degradation) and very low density lipoprotein (VLDL) have a density less than 1.06 gm/mL. Id.

Apolipoproteins have four major roles: (1) assembly and secretion of the lipoprotein (apo B100 and B48); (2) structural integrity of the lipoprotein (apo B, apo E, apo A1, apo AII); (3) coactivators or inhibitors of enzymes (apo A1, C1, CII, CIII); and (4) binding or docking to specific receptors and proteins for cellular uptake of the entire particle or selective uptake of a lipid component (apoA1, B100, E). Id. The role of several apolipoproteins (AIV, AV, D, and J) remain incompletely understood. Id.

Low density lipoprotein (or LDL cholesterol) particles carry cholesterol throughout the body, delivering it to different organs and tissues. The excess keeps circulating in blood. LDL particles contain predominantly cholesteryl esters packaged with the protein moiety apoB100. Id. at 1076.

High density lipoproteins (or HDL cholesterol) act as cholesterol scavengers, picking up excess cholesterol in the blood and taking it back to the liver where it is broken down. Apolipoprotein A1, the main protein of HDL, is synthesized in the intestine and liver. Lipid-free Apo A1 acquires phospholipids from cell membranes and from redundant phospholipids shed during hydrolysis of triglceride-rich lipoproteins. Lipid-free apo A1 binds to ABCA1 and promotes its phosphorylation via cAMP, which increases the net efflux of phospholipids and cholesterol onto apo A1 to form a nascent HDL particle. Id. These nascent HDL particles will mediate further cellular cholesterol efflux. Id.

The scavenger receptor class B (SR-B1; also named CLA-1 in humans (Id., citing Acton, S. et al, "Identification of scavenger receptor SR-B1 as a high density lipoprotein receptor," Science 271: 518 (1996)) and the adenosine triphosphate binding cassette transporter A1 (ABCA1) (Id., citing Krinbou, L. et al, "Biogenesis and speciation of nascent apo A1-containing particles in various cell lines," J. Lipid Res. 46: 1668 (2005)) bind HDL particles. SR-B1, a receptor for HDL (also for LDL and VLDL, but with less affinity), mediates the selective uptake of HDL cholesteryl esters in steroidogenic tissues, hepatocytes and endothelium. ABCA1 mediates cellular phospholipid (and possibly cholesterol) efflux and is necessary and essential for HDL biogenesis. Id.

Figure 11:
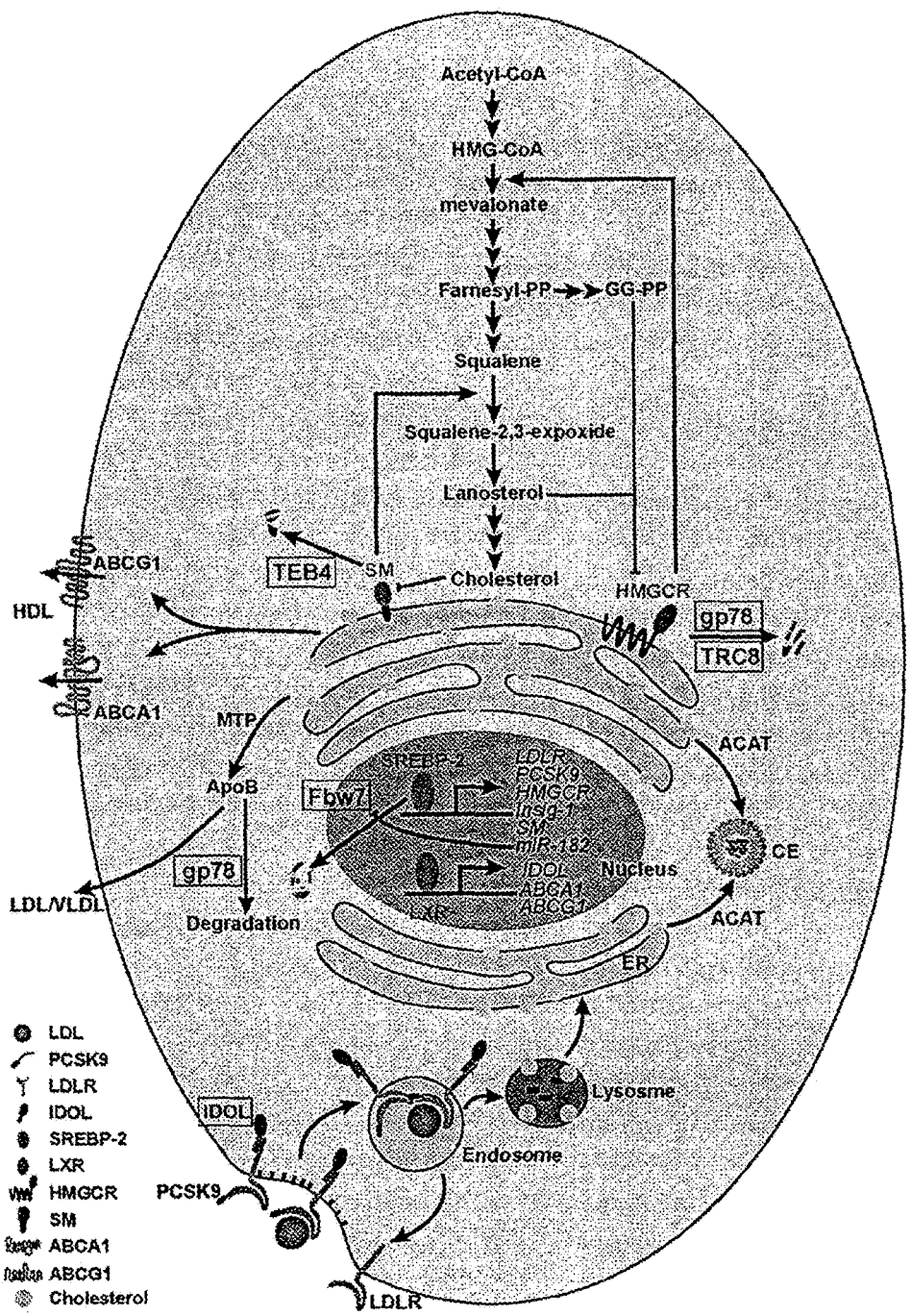
FIG. 11 is an illustration showing that cholesterol homeostasis in a typical mammalian cell is achieved via at least four major routes (taken from Jiang W and Song, B L, "Ubiquitin ligases in cholesterol metabolism," Diabetes Metab. J. 38: 171-180 (2014).

Cellular cholesterol homeostasis is achieved via at least four major routes: (1) cholesterol de novo biosynthesis from acetyl-CoA in the endoplasmic reticulum; (2) cholesterol uptake by low density lipoprotein (LDL) receptor-mediated endocytosis of LDL-derived cholesterol from plasma; 3) cholesterol efflux mediated by ABC family transporters such as ATP-binding cassette, sub-family A (ABC1), member 1 (ABCA1)/ATP-binding cassette, sub-family G, member 1 (ABCG1), and secretion mediated by apolipoprotein B (ApoB); and (4) cholesterol esterification with fatty acids to cholesterol esters (CE) by acyl-coenzyme A:cholesterol acyltransferase (ACAT) (see FIG. 11 (Jiang, W. and Song, B-L, "Ubiquitin Ligases in Cholesterol Metabolism," Diabetes Metab. 38: 171-80 (2014)).

Cholesterol Biosynthetic Pathways

Cholesterol synthesis takes place in four stages: (1) condensation of three acetate units to form a six-carbon intermediate, mevalonate; (2) conversion of mevalonate to activated isoprene units; (3) polymerization of six 5-carbon isoprene units to form the 30-carbon linear squalene; and (4) cyclization of squalene to form the steroid nucleus, with a further series of changes to produce cholesterol. (Endo, A., "A historical perspective on the discovery of statins," Proc. Jpn Acad, Ser. B Phys. Biol. Sci 86(5): 484-93 (2010)).

The mevalonate arm of the cholesterol biosynthesis pathway, which includes enzymatic activity in the mitochondria, peroxisome, cytoplasm and endoplasmic reticulum, starts with the consumption of acetyl-CoA, which occurs in parallel in three cell compartments (the mitochondria, cytoplasm, and peroxisome) and terminates with the production of squalene in the endoplasmic reticulum (Mazein, A. et al., "A comprehensive machine-readable view of the mammalian cholesterol biosynthesis pathway," Biochemical Pharmacol. 86: 56-66 (2013)). The following are enzymes of the mevalonate arm:

Acetyl-CoA acetyltransferase (ACAT1; ACAT2; acetoacetyl-CoA thiolase; EC 2.3.1.9) catalyzes the reversible condensation of two molecules of acetylcoA and forms acetoacetyl-CoA. Id.

Hydroxymethylglutaryl-CoA synthase (HMGCS1 (cytoplasmic); HMGCS2 (mitochondria and peroxisome); EC 2.3.3.10 catalyzes the formation of 3-hydroxy-3-methylglutaryl CoA (3HMG-CoA) from acetyl CoA and acetoacetyl Co A. Id.

Hydroxymethylglutaryl-CoA lysase (mitochondrial, HMGCL; EC 4.1.3.4) transforms HMG-CoA into Acetyl-CoA and acetoacetate (HMGCR; EC 1.1.34) catalyzes the conversion of 3HMG-CoA into mevalonic acid. This step is the committed step in cholesterol formation. HMGCR is highly regulated by signaling pathways, including the SREBP pathway.Id.

Mevalonate kinase (MVK; ATP:mevalonate 5-phosphotransferase; EC 2.7.1.36) catalyzes conversion of mevalonate into phosphomevalonate. Id.

Phosphomevalonate kinase (PMVK; EC 2.7.4.2) catalyzes formation of mevalonate 5-diphosphate from mevalonate 5-phosphate. Id.

Diphosphomevalonate decarboxylase (MVD; mevalonate (diphospho) decarboxylase; EC 4.1.1.33) decarboxylates mevalonate 5-diphosphate, forming isopentenyldiphosphate while hydrolyzing ATP. Id.

Isopentenyl-diphosphate delta-isomerases (ID11; ID12; EC 5.3.3.2) isomerize isopentenyl diphosphate into dimethylallyl diphosphate, the fundamental building blocks of isoprenoids. Id.

Farnesyl diphosphate synthase (FDPS; EC2.5.1.10; EC 2.5.1.1; dimethylallyltranstransferase) catalyzes two reactions that lead to farnesyl diphosphate formation. In the first (EC 2.5.1.1 activity), isopentyl diphosphate and dimethylallyl diphosphate are condensed to form geranyl disphosphate. Next, geranyl diphosphate and isopentenyl diphosphate are condensed to form farnesyl diphosphate (EC 2.5.1.10 activity). Id.

Geranylgeranyl pyrophosphate synthase (GGPS1; EC 1.5.1.29; EC 2.5.1.10; farnesyl diphosphate synthase; EC 2.5.1.1; dimethylallyltranstransferase) catalyzes the two reactions of farnesyl diphosphate formation and the addition of three molecules of isopentenyl diphosphate to dimethylallyl diphosphate to form geranylgeranyl diphosphate. Id.

Farnesyl-diphosphate farnesyltransferase 1 (FDFT1; EC 2.5.1.21; squalene synthase) catalyzes a two-step reductive dimerization of two farnesyl diphosphate molecules (C15) to form squalene (C30). The FDFT1 expression level is regulated by cholesterol status; the human FDFT1 gene has a complex promoter with multiple binding sites for SREBP-1a and SREBP-2. Id.

The sterols arms of the pathway start with Squalene and terminate with cholesterol production on the Bloch and Kandutsch-Russell pathways and with 24 (S),25-epoxycholesterol on the shunt pathway. Id. The following are enzymes of the sterol arms:

Squalene epoxidase (SQLE; EC 1.14.13.132, squalene monooxygenase) catalyzes the conversion of squalene into squalene-2,3-epoxide and the conversion of squalene-2,3-epoxide (2,3-oxidosqualene) into 2,3:22,23-diepoxysqualene (2,3:22,23-dioxidosqualene). The first reaction is the first oxygenation step in the cholesterol biosynthesis pathway. The second is the first step in 24(S),25-epoxycholesterol formation from squalene 2,3-epoxide. Id.

Lanosterol synthase (LSS; OLC; OSC; 2,3-oxidosqualene:lanosterol cyclase; EC 5.4.99.7) catalyzes cyclization of squalene-2,3-epoxide to lanosterol and 2,3:22,23-depoxysqualene to 24(S),25-epoxylanosterol. Id.

Delta(24)-sterol reductase (DHCR24; 24-dehydrocholesterol reductase; EC 1.3.1.72) catalyzes the reduction of the delta-24 double bond of intermediate metabolites. In particular it converts lanosterol into 24, 25-dihydrolanosterol, the initial metabolite of the Kandutsch-Russel pathway and also provides the last step of the Bloch pathway converting desmosterol into cholesterol. Intermediates of the Bloch pathway are converted by DHCR24 into intermediates of the Kandutsch-Russell pathway. Id.

Lanosterol 14-alpha demethylase (CYP51A1; cytochrome P450, family 51, subfamily A, polypeptide 1; EC 1.14.13.70) converts lanosterol into 4,4-dimethyl-5α-cholesta-8,14,24-trien-3β-ol and 24,25-dihydrolanosterol into 4,4-dimethyl-5α-cholesta-8,14-dien-3β-ol in three steps. Id.

Delta (14)-sterol reductase (TM7F2; transmembrane 7 superfamily member 2, EC 1.3.1.70) catalyzes reactions on the three branches of the cholesterol and 24(S),25-epoxycholesterol pathways. Id.

Methylsterol monooxygenase 1 (MSM01; SC4MOL; C-4 methylsterol oxidase; EC 1.14.13.72) catalyzes demethylation of C4 methylsterols. Id.

Sterol-4-alpha-carboxylate 3-dehydrogenase, decarboxylating (NSDHL; NAD(P) dependent steroid dehydrogenase-like; EC 1.1.1.170) participates in several steps of post-squalene cholesterol and 24(S),25-epoxycholeseterol synthesis. Id.

3-keto-steroid reductase (HSD17B7; 17-beta-hydroxysteroid dehydrogenase 7; EC 1.1.1.270) converts zymosterone into zymosterol in the Bloch pathway. Id.

3-Beta-hydroxysteroid-delta(8),delta(7)-isomerase (EBP; emopamil-binding protein; EC5.3.3.5) catalyzes the conversion of delta(8)-sterols into delta(7)-sterols. Id.

Lathosterol oxidase (SC5DL; sterol-C5-desaturase (ERG3 delta-5-desaturase homolog, S. cerevisiae-like; EC 1.14.21.6) catalyzes the production of 7-dehydrocholesterol, 7-dehydrodesmosterol and 24(S),25-epoxy-7-dehydrocholesterol. Id.

7-dehydrocholesterol reductase (DHCR7; EC 1.3.1.21) catalyzes reduction of the C7-C8 double bond of 7-dehydrocholesterol and formation of cholesterol, and produces desmosterol from 7-dehydrodesmosterol and 24(S),25-epoxycholesterol from 24(S),25-epoxy-7-dehydrocholesterol. Id.

Cytochrome P450, family 3, subfamily A, polypeptide 4 (CYP3A4; 1,8-cineole 2-exo-monooxygenase; taurochenodeoxycholate 6α-hydroxylase; EC 1.14.13.97)) catalyzes the hydroxylation of cholesterol leading to 25-hydroxycholesterol and 4β-hydroxycholesterol. Id.

Cholesterol 25-hydroxylase (CH25H; cholesterol 25-monooxygenase; EC 1.14.99.38) uses di-iron cofactors to catalyze the hydroxylation of cholesterol to produce 25-hydroxycholesterol, and has the capacity to catalyze the transition of 24-hydroxycholesterol to 24, 25-dihydroxycholesterol. Id.

Cytochrome P450, family 7, subfamily A, polypeptide 1 (CYP7A1; cholesterol 7-alpha-hydroxylase; EC 1.14.13.17) is responsible for introducing a hydrophilic moiety at position 7 of cholesterol to form 7α-hydroxycholesterol. Id.

Cytochrome P450, family 27, subfamily A, polypeptide 1 (CYP27A1; Sterol 27-hydroxylase; EC 1.14.13.15) catalyzes the transition of mitochondrial cholesterol to 27-hydroxycholesterol and 25-hydroxycholesterol. Id.

Cytochrome P450 46A1 (CYP46A1, cholesterol 24-hydroxylase, EC 1.14.13.98) catalyzes transformation of cholesterol into 24(S)-hydroxycholesterol. Id.

Intermediates in Cholesterol Synthesis as Physiological Regulators

Intermediates in cholesterol synthesis, mostly sterols (e.g., 7-dehydrocholesterol, which is converted to cholesterol by DHCR7 (7-dehydrocholesterol reductase), but which also is a precursor for vitamin D), have been credited with having regulatory functions distinct from those of cholesterol. (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013)).

C4-methylsterols are produced by lanosterol 14α-demethylase (encoded by CYP51A1 (cytochrome P450, family 51, subfamily A, polypeptide 1) and demethylated by SC4MOL (sterol-C4-methyl oxidase like 1; methylsterol monooxygenase 1) and its partner, NSDHL (NAD(P)-dependent steroid dehydrogenase-like; sterol-4-α-carboxylate 3-dehydrogenase, decarboxylating),Id.

24, 25-dihydrolanosterol purportedly is the primary degradation signal for 3-hydroxy-3-methylglutaryl-CoA reductase (HMGCR) (Id., citing Song, B L, et al, "Insig-mediated degradation of HMG-CoA reductase stimulated by lanosterol, an intermediate in the synthesis of cholesterol," Cell Meta. 1: 179-89 (2005); Lange, Y. et al, "Effectors of rapid homeostatic responses of endoplasmic reticulum cholesterol and 3-hydroxy-3-methylglutaryl-CoA reductase," J. Biol. Chem. 283: 1445-55 (2008)).

The nonsterol intermediate squalene has been implicated in stimulating HMGCR degradation (Id., citing Leichner, G S, et al, "Metabolically regulated endoplasmic reticulum-associated degradation of 3-hydroxy-3-methylglutaryl-CoA reductase. Evidence for requirement of a geranylgeranylated protein," J. Biol. Chem. 286: 32150-61 (2011)).

A number of cholesterol synthesis intermediates can serve as activating ligands of the nuclear liver X receptor (LXR), which up-regulates cholesterol export genes and represses inflammatory genes. These sterols include 24,25-dihydrolanosterol (Id., citing Zhu, J. et al, "Effects of FoxO4 overexpression on cholesterol biosynthesis, triacylglycerol accumulation, and glucose uptake," J. Lipid Res. 51: 1312-24 (2010)), meiosis-activating sterols (MASs) (Id., citing He, M, et al, "Mutations in the human SC4MOL gene encoding a methyl sterol oxidase cause psoriasiform dermatitis, microcephaly, and developmental delay," J. Clin. Invest. 121: 97 6-984 (2011)) and desmosterol (Id., citing Yang, C. et al, "Sterol intermediates from choleseterol biosynthetic pathway as liver X receptor ligands," J. Biol. Chem. 281: 27816-826 (2006); Spann, N J et al, "Regulated accumulation of desmosterol integrates macrophage lipid metabolism and inflammatory responses," Cell 151: 138-52 (2012)).

The oxysterol 24(S),25-epoxycholesterol (24,25-EC), a potent LXR agonist (Id., citing Lehmann, J M et al, "Activation of the nuclear receptor LXR by oxysterols defines a new hormone response pathway," J. Biol. Chem. 272: 3137-40 (1997)), is produced in a shunt pathway in sterol synthesis (Id., citing Spencer, T A, et al, "24(S),25-epoxyscholesterol. Evidence consistent with a role in the regulation of hepatic cholestrogenesis," J. Biol. Chem. 260: 13391-94 (1985)), and its production is determined by the relative activities of squalene monooxygenase (SM) and lanosterol synthase (LS). Partial inhibition or knockdown of LS diverts more flux into the shunt pathway, producing more 14,15-epoxycholesterol (14,15-EC) (Id., citing Dang, H. et al, "Suppression of 2,3-oxidosqualene cyclase by high fat diet contributes to liver X receptor-α-mediated improvement of hepatic lipid profile," J. Biol. Chem. 284: 6218-26 (2009)), whereas overexpression of LS abolishes 24,25-EC production (Id., citing Wong, J. et al, "Endogenous 24(S),25-epoxycholesterol fine-tunes acute control of cellular cholesterol homeostasis," J. Biol. Chem. 283: 700-707 (2008)). Conversely, overexpression of SM increases 24,25-EC production (Id., citing Zerenturk, E J et al, "The endogenous regulator 24(S),25-epoxycholesterol inhibits choleseterol synthesis at DHCR24 (Seladin-1)," Biochim. Biophys. Acta 1821: 1269-77 (2012)). The extent to which SM and LS are differentially regulated to alter 14,15-EC production is not known.

Cholesterol Uptake by Low Density Lipoprotein (LDL) Receptor-Mediated Endocytosis of LDL-Derived Cholesterol from Plasma The LDL receptor regulates the entry of cholesterol into cells; tight control mechanisms alter its expression on the cell surface, depending on need. Braunwald's Heart Disease, P. Libby, R. Bonow, D. Mann and D. Zipes, Eds., 8th Edition, Saunders Elsevier, Philadelphia, Pa. (2008) at 1072. Other receptors for lipoproteins include several that bind VLDL, but not LDL. Id. The LDL receptor-related peptide, which mediates the uptake of chylomicron remnants and VLDL, preferentially recognizes apolipoprotein E (apo E) (Id., citing Hiltunen, T P et al, Expression of LDL receptor, VLDL receptor, LDL receptor-related protein, and scavenger receptor in rabbit atherosclerotic lesions: Marked induction of scavenger receptor and VLDL receptor expression during lesion development," Circulation 97: 1079 (1998)). The LDL receptor-related peptide interacts with hepatic lipase. A specific VLDL receptor also exists (Id., citing Nimph, J, and Schneider, W J, "The VLDL receptor: an LDL receptor relative with eight ligand binding repeats, LR8. Atherosclerosis 141: 191-202 (1998)). The interaction between hepatocytes and the various lipoproteins containing apo E is complex and involves cell surface proteoglycans that provide a scaffolding for lipolytic enzymes (lipoprotein lipase and hepatic lipase) involved in remnant lipoprotein recognition (Id., citing Mahley, R W, Ji, Zs, "Remnant lipoprotein metabolism: key pathways involving cell-surface heparin sulfate proteoglycans and apolipoprotein E," J. Lipid Res. 40: 1-(1999); Barown M I et al, "A macrophage receptor for apolipoprotein B48: cloning, expression and atherosclerosis, Proc. Natl Acad. Sci. USA 97: 7488 (2000); de Man, F H et al, "Lipolysis of very low density lipoproteins by heparin sulfate proteoglycan-bound lipoprotein lipase," J. Lipid Res. 38: 2465 (1997)).

Macrophages express receptors that bind modified (especially oxidized) lipoproteins. These scavenger lipoprotein receptors mediate the uptake of oxidized LDL into macrophages. In contrast to the regulated LDL receptor, high cellular cholesterol content does not suppress scavenger receptors, enabling the intimal macrophages to accumulate abundant cholesterol, become foam cells, and form fatty streaks. Endothelial cells also can take up modified lipoproteins through a specific receptor, such as Lox-1 (Sawamura, T. et al, "an endothelial receptor for oxidized low-density lipoprotein," Nature 386: 73 (1997)).

Cholesterol Efflux is Mediated by ABC Family Transporters Such as ATP-Binding Cassette, Sub-Family A (ABC1), Member 1 (ABCA1)/ATP-Binding Cassette, Sub-Family G, Member 1 (ABCG1), and Secretion Mediated by Apolipoprotein B (ApoB);

Because most cells in the body do not express pathways for catabolizing cholesterol, efflux of cholesterol is critical for maintaining homeostasis. (Phillips, M C, "Molecular Mechanisms of Cellular Cholesterol Efflux," J. Biol. Chem. 289 (35): 24020-29 (2014)). High density lipoprotein (HDL) comprises a heterogeneous population of microemulsion particles 7-12 nm in diameter containing a core of cholesterol ester (CE) and triglyceride (TG) molecules stabilized by a monomolecular layer of phospholipid (PL) and apolipoprotein (apo), of which apo1 is the principal component (Id. citing Phillips, M C, "New insights into the determination of HDL structure by apolipoproteins," J. Lipid Res. 54: 2034-48 (2013)). The presence of PL in the particles enables HDL to solubilize and transport unesterified (free) cholesterol (FC) released from cells, thereby mediating removal of cholesterol from cholesterol-loaded arterial macrophages and transport to the liver for catabolism and elimination from the body ("reverse cholesterol transport") (Id., citing Rothblat, G H and Phillips, M C, "High-density lipoprotein heterogeneity and function in reverse cholesterol transport," Curr. Opin. Lipidol. 21: 229-38 (2010); Rosenson, R S et al, "Cholesterol efflux and atheroprotection: advancing the concept of reverse cholesterol transport," Circulation 125: 1905-19 (2012)).

The first step in reverse cholesterol transport is efflux of FC from the cell plasma membrane to HDL. Id. In the case of macrophages, four efflux pathways have been identified: the aqueous diffusion efflux pathway, the scavenger receptor class B, type 1 (SR-B1) pathway; the ATP binding cassette transporter G1 (ABCG1) pathway and the ATP-binding cassette transporter A1 (ABCA1) pathway. Id. The first two processes, which are passive, involve simple diffusion (aqueous diffusion pathway) and facilitated diffusion (SR-B1-mediated pathway). Id. The two active processes involve members of the ATP-binding cassette (ABC) family of transmembrane transporters, namely ABCA1 and ABCG1. Id. The efficiency of an individual serum sample in accepting cellular cholesterol depends upon both the distribution of HDL particles present and the levels of cholesterol transporters expressed in the donor cells. Id.

Aqueous Diffusion Efflux Pathway

HDL is the component of serum responsible for mediating FC efflux from monolayers of mouse L-cell fibroblasts. Id. Transfer occurs by an aqueous phase intermediate where monomeric FC molecules desorb from a donor particle and diffuse until they are absorbed by an acceptor particle. The rate of transfer of the highly hydrophobic cholesterol molecule from donor to acceptor is limited by the rate of desorption into the aqueous phase, which is sensitive to the physical state of the phospholipid (PL) milieu in which the transferring FC molecules are located. The net mass FC efflux from cells to HDL in the extracellular medium is promoted by metabolic trapping in which return of released FC to the cell is prevented by esterification, when lecithin-cholesterol aceyltransferase acts on HDL (Id., citing Czarnecka, H. and Yokoyama, S., "Regulation of cellular cholesterol efflux by lecithin: cholesterol acyltransferase reaction through nonspecific lipid exchange," J. Biol. Chem. 271: 1023-27 (1996)).

SR-B1 Efflux Pathway

SR-B1 is a member of the CD36 superfamily of scavenger receptor proteins that also includes lysosomal integral membrane protein-2 (LIMP-2). Id. The receptor is most abundantly expressed in liver, where it functions in the reverse cholesterol transport pathway and in steroidogenic tissue, where it mediates cholesterol delivery (Id., citing Zannis, V. et al, "Role of apoA-1, ABCA1, LCAT and SR-B1 in the biogenesis of HDL," J. Mol. Med. 84: 276-94 (2006)). It is a homo-oligomeric glycoprotein located in the plasma membrane with two N- and C-terminal transmembrane domains and a large central extracellular domain (Id., citing Williams, D L, et al, "Scavenger receptor B1 and cholesterol trafficking," Curr. Opin. Lipidol. 10: 329-39 (1999); Meyer, J M et al, "New developments in selective cholesteryl ester uptake," Curr. Opin. Lipidol. 24: 386-92 (2013)). In 1996, it was established that SR-B1 is an HDL receptor that mediates cholesterol uptake into cells. This process involves selective transfer of the cholesterol ester (CE) in an HDL particle into the cell without endocytic uptake and degradation of the HDL particle itself. In addition to promoting delivery of HDL cholesterol to cells, SR-B1 also enhances efflux of cellular cholesterol to HDL (Id., citing Ji, Y et al, "Scavenger receptor B1 promotes high density lipoprotein-mediated cellular cholesterol efflux," J. Biol. Chem. 272: 20982-985 (1997); Jian, B. et al, "Scavenger receptor class B type 1 as a mediator of cellular cholesterol efflux to lipoproteins and phospholipid acceptors," J. Biol. Chem. 273: 5599-5606 (1998)) with the two processes being related (Id., citing Gu, X et al, "Scavenger receptor class B, type 1-mediated [3H]cholesterol efflux to high and alow density lipoproteins is dependent on lipoprotein binding to the receptor," J. Biol. Chem. 275: 29993-30001 (2000)). For CE selective uptake via SR-B1, HDL binding and CE uptake are tightly coupled. The mechanism for CE uptake from HDL involves a two-step process in which HDL first binds to the receptor and then CE molecules transfer from the bound HDL particle into the cell plasma membrane, with enhanced binding of larger HDL particles to SR-B1 increasing the selective delivery of CE (Id., citing Thuahnai, S T, et al, "SR-B1-mediated cholesteryl ester selective uptake and efflux of unesterified cholesterol: influence of HDL size and structure, "" J. Biol. Chem. 279: 12448-455 (2004)). The binding of HDL to the extracellular domain of SR-B1 involves direct protein-protein contact with a recognition motif being the amphipathic α helix characteristic of HDL apolipoproteins (Id., citing Williams, D L et al, "Binding and cross-linking studies show that scavenger receptor B1 interacts with multiple sites in apolipoprotein A-1 and identify the class A amphipathic α helix as a recognition motif," J. Biol. Chem. 275: 18897-18904 (2000). Consistent with CE selective uptake being a passive process, the rate of uptake is proportional to the amount of CE initially present in the HDL particles.

FC efflux and HDL binding are not completely coupled, and the FC efflux mechanism proceeds by different pathways at low and high extracellular HDL concentrations (Id., citing Thuahnai, S T, et al, "SR-B1-mediated cholesteryl ester selective uptake and efflux of unesterified cholesterol: influence of HDL size and structure,"" J. Biol. Chem. 279: 12448-455 (2004); de la Llera-Moya, M. et al, "Scavenger receptor B1 (SR-B1) mediates free cholesterol flux independently of HDL tethering to the cell surface," J. Lipid Res. 40: 575-80 (1999)). At low HDL concentrations, binding of HDL to SR-B1 is critical, allowing bidirectional FC transit through the hydrophobic tunnel present in the extracellular domain of the receptor. Because the FC concentration gradient between the bound HDL particle and the cell plasma membrane is opposite to that of CE, the relatively high FC/PL ratio in the plasma membrane causes the direction of net mass FC transport to be out of the cell. Consistent with this concept, enhancing the PL content of HDL promotes FC efflux from cells (Id., citing Yancey, P G, et al, "High density lipoprotein phospholipid composition is a major determinant of the bi-directional flux and net movement of cellular free cholesterol mediated by scavenger receptor B1," J. Biol. Chem. 275: 36596-36604 (2000)). Larger HDL particles promote more FC efflux than smaller HDL, because they bind better to SR-B1 (Id., citing Thuahnai, S T, et al, "SR-B1-mediated cholesteryl ester selective uptake and efflux of unesterified cholesterol: influence of HDL size and structure,"" J. Biol. Chem. 279: 12448-455 (2004)). At higher HDL concentrations where binding to the receptor is saturated, FC efflux still increases with increasing HDL concentration (Id., citing Thuahnai, S T, et al, "SR-B1-mediated cholesteryl ester selective uptake and efflux of unesterified cholesterol: influence of HDL size and structure, "" J. Biol. Chem. 279: 12448-455 (2004)), because SR-B1 induces reorganization of the FC in the cell plasma membrane.

ABCG1 Efflux Pathway

ABCG1 functions as a homodimer, and is expressed in several types, where it mediates cholesterol transport through its ability to translocate cholesterol and oxysterols across membranes. Id. Expression of ABCG1 enhances FC and PL efflux to HDL (Id., citing Wang, N. et al, "ATP-binding cassette transporters G1 and G4 mediate cellular cholesterol efflux to high-density lipoproteins," Proc. Natl Acad. Sci. USA 101: 9774-79 (2004); Kennedy, M A et al, "ABCG1 has a critical role in mediating cholesterol efflux to HDL and preventing cellular lipid accumulation," Cell Metab. 1: 121-31 (2005)), but not to lipid-free apoA-1 (Id., citing Vaughan, A M and Oram, J F, "ABCG1 redistributes cell cholesterol to domains removable by high density lipoprotein but not by lipid-depleted apolipoproteins," J. Biol. Chem. 280: 20150-57 (2005); Sankaranarayanan, S. et al., "Effects of acceptor composition and mechanism of ABCG1-mediated cellular free cholesterol efflux," J. Lipid Res. 50: 275-84 (2009)). The presence of the transporter induces reorganization of plasma membrane cholesterol so that it becomes accessible to cholesterol oxidase (Id., citing Vaughan, A M and Oram, J F, "ABCG1 redistributes cell cholesterol to domains removable by high density lipoprotein but not by lipid-depleted apolipoproteins," J. Biol. Chem. 280: 20150-57 (2005)), creating an activated pool of plasma membrane FC, and desorption of FC molecules from this environment into the extracellular medium is facilitated. Increased expression of ABCG1 enhances FC efflux to HDL2 and HDL3 similarly, but has no effect on the influx of FC from these lipoprotein particles.

ABCA1 Efflux Pathway

ABCA1 is a full transporter whose expression is up-regulated by cholesterol loading, which leads to enhanced FC efflux. Id. Binding and hydrolysis of ATP by the two cytoplasmic, nucleotide-binding domains control the conformation of the transmembrane domains so that the extrusion pocket is available to translocate substrate from the cytoplasmic leaflet to the exofacial leaflet of the bilayer membrane. Id. ABCA1 actively transports phosphatidylcholine, phosphatidylserine, and sphingomyelin with a preference for phosphatidylcholine (Id., citing Quazi, F and Molday, R S, "Differential phospholipid substrates and directional transport by ATP-binding cassette proteins ABCA, ABCA7, and ABCA4 and disease-causing mutants," J. Biol. Chem. 288: 34414-26 (2013)). This PL translocase activity leads to the simultaneous efflux of PL and FC (Id., citing Gillotte, K L, et al, "Removal of cellular cholesterol by pre-β-HDL involves plasma membrane microsolubilization," J. Lipid Res. 39: 1918-28 (1998); Smith, J D et al, "ABCA1 mediates concurrent cholesterol and phospholipid efflux to apolipoprotein A-1," J. Lipid Res. 45: 635-44 (2004)) to lipid-free apoA-1 (plasma pre-β1-HDL). The cellular FC released to apoA-1 originates from both the plasma membrane and the endosomal compartment (Id., citing Chen, W. et al, "Preferential ATP-binding cassette transporter A1-mediated cholesterol efflux from late endosomes/lysosomes," J. Biol. Chem. 276: 43564-69 (2001)).

The PL translocase activity of ABCA1 induces reorganization of lipid domains in the plasma membrane (Id., citing Landry, Y D, et al, "ATP-binding cassette transporter A1 expression disruptsraft membrane microdomains through its ATPase-related functions," J. Biol. Chem. 281: 36091-101 (2006)). ABCA1 exports PL and FC to various plasma apolipoproteins. Besides FC efflux, intracellular signaling pathways are activated by the interaction of apoA-1 with ABCA1 (Id., citing Mineo, C. and Shaul, P W, "Regulation of signal transduction by HDL," J. Lipid Res. 54: 2315-24 (2013); Liu, Y, and Tang, C., "Regulation of ABCA1 functions by signaling pathways," Biochim. Biophys. Acta, 1821: 522-29 (2012)).

It is well established that the activity of ABCA1 in the plasma membrane enhances binding of apoA-1 to the cell surface, but there has been controversy about the role of this binding in the acquisition of membrane PL by apo-A1. Id. It has been proposed that apoA-1 acquires PL either directly from ABCA1 while it is bound to the transporter, or indirectly at a membrane lipid-binding site created by ABCA1 activity. Id.

The ABCA1-mediated assembly of nascent HDL particles occurs primarily at the cell surface (Id., citing Faulkner, L E, et al, "An analysis of the role of a retroendocytosis pathway in ABCA1-mediated cholesterol efflux from macrophages," J. Lipid Res. 49: 1322-32 (2008); Denis, M. et al, "ATP-binding cassette A-1-mediated lipidation of apolipoprotein A-1 occurs at the plasma membrane and not in the endocytic compartments," J. Biol. Chem. 283: 16178-186 (2008)), where extracellular apoA-1 for HDL particle formation is available. The FC/PL ratio in nascent HDL particles created by ABCA1 activity is dependent upon the cell type and metabolic status of the cell, but the population of larger particles is always relatively FC-rich as compared with the smaller particles.

Regulation of cholesterol efflux depends in part on the ABCA1 pathway, controlled in turn by hydroxysterols (especially 24 and 27-OH cholesterol, which act as ligands for the liver-specific receptor (LXR) family of transcriptional regulatory factors. Braunwald's Heart Disease, P. Libby, R. Bonow, D. Mann and D. Zipes, Eds., $8^{th}$ Edition, Saunders Elsevier, Philadelphia, Pa. (2008) at 1076.

It has been demonstrated by in vivo genetic evidence that ABCA1 efflux function has anti-cancer activity, which is compromised following inhibition of ABCA1 gene expression by oncogenic mutations or cancer-specific ABCA1 loss-of-function mutations. Smith, B. and Land, H., "Anti-cancer activity of the cholesterol exporter ABCA1 gene,"

Cell Rep. 22(3): 580-90 (2012), It has been suggested that loss of ABCA1-mediated efflux is a key step in allowing the accumulation of mitochondrial cholesterol levels that support cancer survival. Id. They interpreted their data as supporting a causal role for elevated mitochondrial cholesterol in cancer cells, and hypothesized that in concert with elevated cholesterol synthesis found in cancer cells, deficiency of ABCA1 allows for increased mitochondrial cholesterol, inhibits release of mitochondrial cell death-promoting molecules, and thus facilitates cancer cell survival. Id.

Cholesterol Esterification with Fatty Acids to Cholesterol Esters (CE) by Acyl-Coenzyme A:Cholesterol Acyltransferase (ACAT)

Cholesterol content in membranes regulates the cholesterol acyltransferase (CAT) pathway at the level of protein regulation. (Braunwald's Heart Disease, P. Libby, R. Bonow, D. Mann and D. Zipes, Eds., 8th Edition, Saunders Elsevier, Philadelphia, Pa. (2008) at 1076, citing Willner, E. et al, "Deficiency of acyl CoA:cholesterol aceyltransferase 2 prevents atherosclerosis in apolipoprotein E-deficient mice., Proc. Natl Acad. Sci. USA 100: 1262 (2003). Humans express two separate forms of ACAT (ACT1 and ACAT2), which derive from different genes and mediate cholesterol esterification in cytoplasm and in the endoplasmic reticulum lumen for lipoprotein assembly and secretion.

Regulation of Cholesterol Content

Under conditions of cell cholesterol sufficiency, the cell can decrease its input of cholesterol by decreasing the de novo synthesis of cholesterol. The cell can also decrease the amount of cholesterol that enters the cell via the LDL-R, increase the amount stored as cholesteryl esters, and promote the removal of cholesterol by increasing its movement to the plasma membrane for efflux.

The regulation of HMG CoA reductase, the rate limiting step in cholesterol biosynthesis, has been investigated in detail. However, this enzyme acts very early in the cholesterol synthesis pathway. There is accumulating evidence that enzymes beyond HMG CoA reductase serve as flux controlling points, and that regulation of cholesterol synthesis can occur at multiple levels throughout the pathway. (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013)).

Transcriptional Regulation

Sterol Regulatory Element-Binding Proteins (SREBPs)

SREBPs, membrane bound transcription factors that coordinate the synthesis of fatty acids and cholesterol, the two major building blocks of membranes (Brown, M S & Goldstein, J L, "The SREBP pathway: regulation of cholesterol metabolism by proteolysis of a membrane-bound transcription factor," Cell 89: 331-40 (1997)), belong to the basic helix-loop-helix-leucine zipper (bHLH-Zip) family of transcription factors. There are three SREBP proteins (SREB-1a, SREBP-1c, and SREBP-2) from two srebp genes designated srebp1 and srebp2. Id. The SREBP2 isoform plays a major role in regulating cholesterol synthetic genes.

As shown in Table 1, nearly all of the genes encoding cholesterol synthesis enzymes are SREBP targets.

| Gene Name | Gene Symbol | SREBP Target |
|---|---|---|
| Acetyl-CoA acetyltransferase, cytosolic | ACAT2 | Yes |
| 3-hydroxy-3-methylglutaryl-CoA synthase 1 (soluble) | MHGCS1 | Yes |
| 3-hydroxy-3-methylglutaryl-CoA reductase | HMGCR | Yes |
| Mevalonate kinase | MVK | Yes |
| Phosphomevalonate kinase | PMVK | Yes |
| Mevalonate (diphospho)decarboxylase | MVD | Yes |
| Isopentenyl-diphosphate Δ-isomerase ½ | ID11/ID12 | Yes |
| Farnesyl-diphosphate synthase | FDFS | Yes |
| Geranylgeranyl-diphosphate synthase 1 | GGPS1 | Yes |
| Farnesyl-diphosphate farnesyltransferase 1 | FDFT1 | Yes |
| Squalene epoxidase | SQLE | Yes |
| Lanosterol synthase (2,3-oxidosqualene-lanosterol cyclase) | LSS | Yes |
| Cytochrome P450, family 51, subfamily A, polypeptide 1 | CYPS1A1 | Yes |
| Transmembrane 7 superfamily member 2 | TM75F2 | Yes |
| Lamin B receptor | LBR | No |
| Methylsterol monooxygenase 1 | SCAMOL | Yes |
| NAD(P)-dependent steroid dehydrogenase-like | NSDHL | Yes |
| Hydroxysteroid 17β-dehydrogenase 7 | HSD17B7 | Yes |
| Emopamil-binding protein (sterol isomerase) | EBP | Yes |
| Sterol C5-desaturase | SC5D | Yes |
| 7-Dehydrocholesterol reductase | DHCR7 | Yes |
| 24 Dehydrocholesterol reductase | DHCR24 | Yes |

Taken from Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013))

SREBPs coordinately regulate the cholesterol biosynthetic pathway and receptor-mediated endocytosis of LDL at the level of gene transcription. (Brown, M S and Goldstein, J L, "A proteolytic pathway that controls the cholesterol content of membranes, cells and blood," Proc. Natl Acad. Sci. USA 96: 11041-48 (1999)). In the cholesterol biosynthetic pathway, SREBPs regulate transcription of HMG CoA reductase as well as transcription of genes encoding many other enzymes in the cholesterol biosynthetic pathway, including HMG CoA synthase, farnesyl diphosphate synthase and squalene synthase. Id. Studies investigating regulation of the DHCR24 promoter provided evidence of binding sites for SREBP-2 [Daimiel, L A, et al, "Promoter analysis of the DHCR24 (3β-hydroxysterol 424-reductase) gene: characterization of SREBP (sterol-regulatory element-binding-protein)-mediated activation," Biosci. Rep. (2013)/art:e000/doi 10.1042/BSR20120095); Zerenturk, E J, et al, "Sterols regulate 3β-hydroxysterolΔ24-reductase (DHCR24) via dual sterol regulatory elements: cooperative induction of key enzymes in lipid synthesis by sterol regulatory element binding proteins," Biochim. Et Biophys. Acta 1821 (10): 1350-60 (2012)). The SREBPs also regulate the LDL receptor, which supplies cholesterol through receptor mediated endocytosis, and modulate transcription of genes encoding enzymes of fatty acid synthesis and uptake, including acetyl CoA carboxylase, fatty acid synthase, stearoyl CoA desaturase-1 and lipoprotein lipase. (Brown, M S & Goldstein, J L, "The SREBP pathway: regulation of cholesterol metabolism by proteolysis of a membrane-bound transcription factor," Cell 89: 331-40 (1997)).

Nascent SREBPs are targeted to the endoplasmic reticulum (ER) membrane without any transcription activity, because they are not available for their target genes, which are located in the nucleus. (Brown, M S & Goldstein, J L, "The SREBP pathway: regulation of cholesterol metabolism by proteolysis of a membrane-bound transcription factor,"

Cell 89: 331-40 (1997)). To enhance transcription when cellular sterol is low, the active $NH_2$-terminal domains of SREBPs are released from endoplasmic reticulum membranes by two sequential cleavages that must occur in the proper order. The first is catalyzed by Site-1 protease (S1P), a membrane bound subtilisin-related serine protease that cleaves the hydrophilic loop of SREBP that projects into the endoplasmic reticulum lumen. (Brown, M S and Goldstein, J L, "A proteolytic pathway that controls the cholesterol content of membranes, cells and blood," Proc. Natl Acad. Sci. USA 96: 11041-48 (1999)). The second cleavage, at Site-2, requires the action of S2P, a hydrophobic protein that appears to be a zinc metalloprotease, and takes place within a membrane-spanning domain of SREBP. Id. Sterols block SREBP processing by inhibiting S1P. Id. Sterols block the proteolytic release process by selectively inhibiting cleavage by S1P; S2P is regulated indirectly because it cannot act until SREBP has been processed by S1P. Id.

SREBP cleavage-activating protein (SCAP), an integral ER membrane regulatory protein, is required for cleavage at Site 1 and is the target for sterol suppression of this cleavage, i.e., SCAP loses its activity when sterols overaccumulate in cells. Id. Within cells, SCAP is found in a tight complex with SREBPs. Id. SCAP contains two distinct domains: a hydrophobic N-terminal domain that spans the membrane eight times and a hydrophilic C-terminal domain that projects into the cytosol. (DeBose-Boyd, R. A. "Feedback Regulation of Cholesterol Synthesis: Sterol-accelerated ubiquitination and degradation of HMG CoA Reductase," Cell Res. 18 (6): 609-21 (2008)) A 160 amino acid segment of the membrane domain of SCAP has been termed the sterol-sensing domain. (Brown, M S and Goldstein, J L, "A proteolytic pathway that controls the cholesterol content of membranes, cells and blood," Proc. Natl Acad. Sci. USA 96: 11041-48 (1999)). The C-terminal domain of SCAP mediates a constitutive association with SREBPs, which is required for SCAP-dependent translocation of SREBPs from the ER to Golgi in sterol-deprived cells. (DeBose-Boyd, R. A. "Feedback Regulation of Cholesterol Synthesis: Sterol-accelerated ubiquitination and degradation of HMG CoA Reductase," Cell Res. 18 (6): 609-21 (2008)). The $NH_2$-terminal bHL-Zip domain with full transcription activity is released from the membrane to reach the nucleus and act as a transcription factor to activate genes responsible for cholesterol and fatty acid biosynthesis and LDL uptake (Brown, M S and Goldstein, J L, "A proteolytic pathway that controls the cholesterol content of membranes, cells and blood," Proc. Natl Acad. Sci. USA 96: 11041-48 (1999)).

When sterols build up within cells, the proteolytic release of SREBPs from ER membranes is blocked, the $NH_2$-terminal domains that have already entered the nucleus are rapidly degraded, and, as a result, transcription of all of the target genes declines. (Id). This decline is complete for the cholesterol biosynthetic enzymes whose transcription is entirely dependent on SREBPs, but less complete for the fatty acid biosynthetic enzymes whose basal transcription can be maintained by other factors.

Other Factors

Besides SREBP, numerous other transcription factors have been implicated in the transcriptional control of the various enzymes in cholesterol biosynthesis. (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013)).

Liver X Receptors (LXRs)

Liver X receptors (LXRs) are ligand-activated transcription factors of the nuclear receptor superfamily. (Baranowski, M., "Biological role of liver X receptors," J. Physiol. Pharmacology. 59 Suppl. 7: 31-55 (2008)). There are two LXR isoforms (termed alpha and beta), which, upon activation, form heterodimers with retinoid X receptor and bind to LXR response elements found in the promoter region of the target genes. Id. High expression levels of LXRα in metabolically active tissues fit with a central role of the receptor in lipid metabolism, while LXRβ is more ubiquitously expressed. (Pehkonen, P. et al., "Genome-wide landscape of liver X receptor chromatin binding and gene regulation in human macrophages," BMC Genomics 13: 50 (2012)). Both LXRs are found in various cells of the immune system, such as macrophages, dendritic cells and lymphocytes. Id. In macrophages, the accumulation of excess lipoprotein-derived cholesterol activates LXR and triggers the induction of a transcriptional program for cholesterol efflux, such as ATP-binding cassette transporter (ABC) A1 (ABCA1) and ABCG1, while in parallel the receptor transrepresses inflammatory genes, such as inducible nitric oxide synthase, interleukin 1β, and monocyte chemotactic protein-1. Id. LXR has been reported to regulate cholesterol biosynthesis by directly silencing the gene expression of two cholesterogenic enzymes (FDFT1 and CYP51A1). (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013), citing Wang, Y. et al, "Regulation of cholesterologenesis by the oxysterol receptor, LXRα," J. Biol. Chem. 283: 26332-339 (2008)).

Endogenous agonists of the LXRs include oxysterols, which are oxidized cholesterol derivatives. (Baranowski, M., "Biological role of liver X receptors," J. Physiol. Pharmacol. 59 Suppl. 7: 31-55 (2008)). LXRs have been characterized as key transcriptional regulators of lipid and carbohydrate metabolism, and were shown to function as sterol sensors protecting the cells from cholesterol overload by stimulating reverse cholesterol transport and activating its conversion to bile acids in the liver. Id. This finding led to identification of LXR agonists as potent anti-atherogenic agents in rodent models of atherosclerosis. Id. However, first-generation LXR activators were also shown to stimulate lipogenesis via SREBP1c leading to liver steatosis and hypertriglyceridemia. Id.

Despite their lipogenic action, LXR agonists possess antidiabetic properties. Id. LXR activation normalizes glycemia and improves insulin sensitivity in rodent models of type 2 diabetes and insulin resistance. Id. Although antidiabetic action of LXR agonists is thought to result predominantly from suppression of hepatic gluconeogenesis, some studies suggest that LXR activation may also enhance peripheral glucose uptake. Id.

Published reports of anti-proliferative effects of synthetic LXR ligands on breast, prostate, ovarian, lung, skin, and colorectal cancer cells suggest that LXRs are potential targets in cancer prevention and treatment. Nguyen-Vu, T. et al, "Liver x receptor ligands disrupt breast cancer cell proliferation through an E2F-mediated mechanism," Breast Cancer Res. 15: R51 (2013). Cell line-specific transcriptional responses and a set of common responsive genes were shown by microarray analysis of gene expression in four breast cell lines [MCF-7 (ER+), T-47D (ER+), SK-BR-3 (ER-), and MDA-MB-231] following treatment with the synthetic LXR ligand GW3965. Id. In the common responsive gene set, upregulated genes tend to function in the known metabolic effects of LXR ligands and LXRs whereas the downregulated genes mostly include those which function in cell cycle regulation, DNA replication, and other cell proliferation-related processes. Id. Transcription factor binding site analysis of the downregulated genes revealed an enrichment of E2F binding site sequence motifs. Id. Correspondingly, E2F2 transcript levels are downregulated following LXR ligand treatment. Id. Knockdown of E2F2 expression, similar to LXR ligand treatment, resulted in a significant disruption of estrogen receptor positive breast cancer cell proliferation. Id. Ligand treatment also decreased E2F2 binding to cis-regulatory regions of target genes.

Expression of activated LXRα blocks proliferation of human colorectal cancer cells and slows the growth of xenograft tumors in mice, and reduces intestinal tumor formation after administration of chemical carcinogens in Apc(min/+) mice. Lo Sasso, G. et al., "Liver X receptors inhibit proliferation of human colorectal cancer cells and growth of intestinal tumors in mice," Gastroenterology 144(7): 1497-507 (2013). A link of LXRs to apoptosis has been reported. (Pehkonen, P. et al, "Genome-wide landscape of liver X receptor chromatin binding and gene regulation in human macrophages," BMC Genomics 13: 50 (2012)).

MicroRNAs and Alternative Splicing

Overall, relatively little has been reported on miRNAs in the context of cholesterol synthesis. (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013)) In the context of cholesterol metabolism, perhaps the best studied microRNA (miRNA) is miR-33, an intronic miRNA encoded in the SREBP genes that controls cellular cholesterol export, whereas its SREBP host genes stimulate cholesterol synthesis (Id., citing Fernandez-Hernando, et al, "MicroRNAs in metabolic disease," Arterioscl. Thromb. Vasc. Biol. 33: 178-85 (2013)).

Alternative splicing of HMGCR is regulated by sterols, with proportionally less of an unproductive transcript present when sterol levels are low and more when sterol levels are higher (Id., citing Medina, M. W., et al, "Coordinately regulated alternative splicing of genes involved in cholesterol biosynthesis and uptake," PLosONE 6: e19420 (2011)). This effect also extends to other cholesterogenic genes, including HMGSC1 and MVK (Id citing Medina, M. W., et al, "Coordinately regulated alternative splicing of genes involved in cholesterol biosynthesis and uptake," PLosONE 6: e19420 (2011)). Because the effect is mediated via SREBP-2 and alternative transcripts occur for all cholesterol synthesis enzymes beyond HMGCR (Id., citing de la Grange, P., et al, "a new advance in alternative splicing databases from catalogue to detailed analysis of regulation of expression and function of human alternative splicing variants," BMC Bioinformatics 8: 180 (2007)), this effect may involve the entire cholesterol synthesis pathway.

Post-Translational Regulation

Because transcriptional down-regulation via the SREBP pathway is relatively slow, with mRNA of target genes decreasing only after several hours, rapid shutdown of cholesterol synthesis requires post-transcriptional control. Turnover of 3-hydroxy-3-methylglutaryl-CoA reductase (HMGCR) is accelerated by non-sterol and sterol products of the mevalonate pathways (Id., citing Roitelman, J. and Simoni, RD, "Distinct sterol and nonsterol signals for the regulated degradation of 3-hyudroxy-3-methylglutaryl-CoA reductase," J. Biol. Chem. 267: 25264-273 (1992)), with physiological sterol degradation signals, such as 24,25-dihydrolanosterol, and side chain oxysterols, such as 24,25-EC and 27-hydroxycholeseterol (generated from cholesterol itself (Id., citing Lange, Y. et al, "Effectors of rapid homeostatic responses of endoplasmic reticulum cholesterol and 3-hydroxy-3-methylglutaryl-CoA reductase," J. Biol. Chem. 283: 1445-55 (2008); Nguyen, A D et al, "Hypoxyia stimulates degradation of 3-hydroxy-3-methylglutaryl-coenzyme A reductase through accumulation of lanosterol and hypoxia-inducible factor-mediated induction of Insigs," J. Biol. Chem. 282: 27436-446 (2007)). The regulated turnover is proteosomal, and requires the Insig proteins, which also act to suppress SREBP activation (Jo, Y and Debose-Boyd, R A, "Control of cholesterol synthesis through regulated ER-associated degradation of HMG CoA reductase," Crit. Rev. Biochem. Mol. Bio. 445: 185-198 (2010); Burg, J S and Espenshade, P J, "Regulation of HMG-CoA reductase in mammals and yeast," Prog. Lipid Res. 50: 403-410 (2011)).

Regulated ER-associated degradation also occurs for a later step in cholesterol synthesis, catalyzed by squalene monooxygenase (SM), albeit by a mechanism distinct from HMGCR. Squalene monooxygenase has been proposed as a second rate-limiting enzyme in cholesterol synthesis (Id., citing Gonzalez, R. et al, "Two major regulatory steps in cholesterol synthesis by human renal cancer cells," Arch. Biochem. Biophys. 196: 574-80 (1979); Hidaka, Y, et al, "Regulation of squalene epoxidase in HepG2 cells," J. Lipid Res. 31: 2087-94 (1990)). Cholesterol itself accelerates SM degradation, an example of end product inhibition (Id., citing Gill, S. et al, "Cholesterol-dependent degradation of squalene monooxygenase, a control point in cholesterol synthesis beyond HMG-CoA reductase," Cell Metab. 13: 260-73 (2011)), and unlike HMGCR, SM turnover does not require the Insig proteins.

Feedback Regulation of Cholesterol Synthesis

Cholesterol accumulation lowers the activity of HMG CoA reductase and several other enzymes in the cholesterol biosynthetic pathway, thereby limiting the production of cholesterol.

HMG CoA reductase, the rate-limiting enzyme in cholesterol synthesis, and the target of statins, is subject to feedback control through multiple mechanisms that are mediated by sterol and nonsterol end-products of mevalonate metabolism such that essential nonsterol isoprenoids can be constantly supplied without risking the potentially toxic overproduction of cholesterol or one of its sterol precursors. (DeBose-Boyd, R. A. "Feedback Regulation of Cholesterol Synthesis: Sterol-accelerated ubiquitination and degradation of HMG CoA Reductase," Cell Res. 18 (6): 609-21 (2008)). For example, treatment of cultured cells with the statin Compactin, a competitive inhibitor of HMG-CoA reductase, blocks production of mevalonate, thereby reducing levels of sterol and nonsterol isoprenoids that normally govern this feedback regulation. Id. Cells respond to the inhibition of HMG-CoA reductase with a compensatory increase in the reductase due to the combined effects of enhanced transcription of the reductase gene, efficient translation of mRNA, and extended half-life of reductase protein. Id. Complete reversal of this compensatory increase in reductase requires regulatory actions of both sterol and nonsterol end-products of mevalonate metabolism. Id.

Sterols inhibit the activity of sterol regulatory element-binding proteins (SREBPs) and the low density lipoprotein (LDL)-receptor (Id., citing Horton, J D, et al, "SREBPs: activators of the complete program of cholesterol and fatty acid synthesis in the liver," J. Clin. Invest. 109: 1125-31 (2002)). A nonsterol mevalonate-derived product(s) control(s) the translational effects through a poorly understood mechanism that may be mediated by the complex 5'-untranslated region of the reductase mRNA (Id., citing Nakanishi, M. et al, "Multivalent control of 3-hydroxy-3-methyl-glutaryl coenzyme A reductase. Mevalonate-derived product inhibits translation of mRNA and accelerates degradation of enzyme," J. Biol. Chem. 263: 8929-37 (1988)). Both sterol and nonsterol end-products of mevalonate metabolism combine to accelerate degradation of reductase protein through a mechanism mediated by the ubiquitin-proteosome pathway (Id., citing Roitelman, J. and Simoni, RD, "Distinct sterol and nonsterol signals for the regulated degradation of 3-hydroxy-3-methylglutaryl-CoA reductase," J. Biol. Che. 267: 25264-273 (1992); McGee, T P et al, "Degradation of 3-hydroxy-3-methylglutaryl-CoA reductase in endoplasmic reticulum membranes is accelerated as a result of increased susceptibility to proteolysis," J. Biol. Chem. 271: 25630-638 (1996); Ravid, T. et al, "The ubiquitin proteasome pathway mediates the regulated degradation of mammalian 3-hydroxy-3-methylglutaryl-Coenzyme A reductase," J. Biol. Chem. 275: 35840-47 (2000)).

Inhibition of ER to Golgi transport of SREBPs results from sterol-induced binding of SCAP to ER retention proteins called insulin-induced gene 1 and 2 proteins (Insig-1 and Insig-2) (DeBose-Boyd, R. A. "Feedback Regulation of Cholesterol Synthesis: Sterol-accelerated ubiquitination and degradation of HMG CoA Reductase," Cell Res. 18 (6): 609-21 (2008., citing Yang, T. et al, "Crucial step in cholesterol homeostasis: sterols promote binding of SCAP to INSIG-1, a membrane protein that facilitates retention of SREBPs in ER," Cell 110: 489-500 (2002); Yabe, D. et al, "Insig-2, a second endoplasmic reticulum protein that binds SCAP and blocks export of sterol regulatory element-binding proteins," Proc. Natl. Acad. Sci. USA 99: 12753-758 (2002)). Insig binding occludes a cytosolic binding site in SCAP recognized by COPII proteins, which incorporate cargo molecules into vesicles that deliver ER-derived proteins to the Golgi (Id., citing Sun L P et al, "From the Cover: Sterol-regulated transport of SREBPs from endoplasmic reticulum to Golgi: Insig renders sorting signal in Scap inaccessible to COPII proteins," Proc. Natl Acad. Sci. USA 104: 6519-26 (2007)). SCAP-Insig binding is mediated by a segment of SCAP's membrane domain that includes transmembrane helices 2-6 (Id., citing Hua, X et al, "Sterol resistance in CHO cells traced to point mutation in SREBP cleavage-activating protein," Cell 87: 415-26 (1996); Yang, T. et al, "Crucial step in cholesterol homeostasis: sterols promote binding of SCAP to INSIG-1, a membrane protein that facilitates retention of SREBPs in ER," Cell 110: 489-500 (2002)), i.e., the sterol-sensing domain (Id., citing Kuwabara, PE, "The sterol-sensing domain: multiple families, a unique role," Trends Genet. 18: 193-201 (2002)), since a similar stretch of transmembrane helices is found in at least four other polytopic proteins, including the Niemann Pick C1 protein (part of an intestinal cholesterol transporter complex), Patched, Dispatched and reductase) that have been postulated to interact with sterols. Point mutations within this region disrupt Insig binding, which relieves sterol-mediated retention of mutant SCAP-SREBP complexes in the ER (Id., citing Yang, T. et al, "Crucial step in cholesterol homeostasis: sterols promote binding of SCAP to INSIG-1, a membrane protein that facilitates retention of SREBPs in ER," Cell 110: 489-500 (2002); Yabe, D., "Insig-2, a second endoplasmic reticulum protein that binds SCAP and blocks export of sterol regulatory element-binding proteins," Proc. Natl. Acad. Sci. USA 99: 12753-758 (2002); Yabe, D. et al, "Three mutations in sterol-sensing domain of SCAP block interaction with insig and render SREBP cleavage insensitive to sterols," Proc. Natl Acad. Sci. USA 99: 16672-77 (2002); Nohturfft, A. et al, "A substitution in a single codon of SREBP cleavage-activating protein causes sterol resistance in three mutant Chinese hamster ovary cell lines," Proc. Natl Acad. Sci. USA 93: 13709-714 (1996); Nohturfft, A. et al, "Sterols regulate processing of carbohydrate chains of wild-type SREBP cleavage-activating protein (SCAP), but not sterol-resistant mutants Y298C o D443N," Proc. Natl Acad. Sci. USA 95: 12848-853 (1998)).

The following observations suggest that Insigs may play a role in degradation of HMG CoA reductase. First, when Insigs are overexpressed by transfection in Chinese hamster ovary (CHO) cells, HMG CoA reductase cannot be degraded when the cells are treated with sterols (Id., citing Sever, N. et al, "Accelerated degradation of HMG CoA reductase mediated by binding of insig-1 to its sterol-sensing domain," Mol. Cell 11: 25-33 (2003)). Co-expression of Insig-2 restores sterol-accelerated degradation of HMG CoA reductase, suggesting the saturation of endogenous Insigs by the overexpressed reductase. Id. Second, reduction of both Insig-1 and Insig-2 by RNA interference (RNAi) abolishes sterol-accelerated degradation of endogenous HMG CoA reductase (Id., citing Sever, N. et al, "Insig-dependent ubiquitination and degradation of mammalian 3-hydroxy-3-methylglutaryl CoA reductase stimulated by sterols and geranylgeraniol," J. Biol. Chem. 278: 52479-90 (2003)).

Third, mutant CHO cells lacking both Insigs are impervious to sterol-stimulated degradation of HMG CoA reductase as well as sterol-mediated inhibition of SREBP processing (Id., citing Lee, P. C. et al, "Isolation of sterol-resistant Chinese hamster ovary cells with genetic deficiencies in both Insig-1 and Insig-2," J. Biol. Chem. 280: 25242-249 (2005)).

Degradation of HMG CoA reductase coincides with sterol-induced binding of its membrane domain to Insigs (Id., citing Sever, N. et al, "Accelerated degradation of HMG CoA reductase mediated by binding of insig-1 to its sterol-sensing domain," Mol. Cell 11: 25-33 (2003)), an action that requires a tetrapeptide sequence (YIYF) located in the second transmembrane segment of HMG CoA reductase. A mutant form of HMG CoA reductase in which the YIYF sequence is mutated to alanine residues no longer binds to Insigs, and the enzyme is not subject to rapid degradation. The YIYF sequence is also present in the second transmembrane domain of SCAP, where it mediates sterol-dependent formation of SCAP-Insig complexes (Id., citing Yang, T. et al, "Crucial step in cholesterol homeostasis: sterols promote binding of SCAP to INSIG-1, a membrane protein that facilitates retention of SREBPs in ER," Cell 110: 489-500 (2002); Yabe, D., "Insig-2, a second endoplasmic reticulum protein that binds SCAP and blocks export of sterol regulatory element-binding proteins," Proc. Natl. Acad. Sci. USA 99: 12753-758 (2002)). Overexpressing the sterol-sensing domain of SCAP in cells blocks Insig-mediated, sterol-accelerated degradation of HMG CoA reductase; mutation of the YIYF sequence in the SCAP sterol-sensing domain ablates this inhibition, suggesting that SCAP and HMG CoA reductase bind to the same site on Insigs and that the two proteins compete for limiting amounts of Insigs when intracellular sterol levels rise. Id.

Glycoprotein 78 (Gp78), an E3 ubiquitin ligase, mediates ubiquitination of ApoB-100, Insig 1 and 2 proteins, and HMG-CoA reductase (Jiang, W., Song, B-L, "Ubiquitin Ligases in Cholesterol Metabolism," Diabetes Metab. 38: 171-80 (2014)). High concentration of sterol (lanosterol) promote the $NH_2$-terminal transmembrane domain of 3-hydroxy-3-methylglutaryl CoA reductase to interact with Insigs (Id., citing Sever, N. et al, "Accelerated degradation of HMG CoA reductase mediated by binding of insig-1 to its sterol-sensing domain," Mol. Cell 11: 25-33 (2003); Song, B L, et al, "Insig-mediated degradation of HMG CoA reductase stimulated by lanosterol, an intermediate in the synthesis of choleseterol," Cell Metab. 1: 179-89 (2005)), and sterol-dependent Insig binding results in recruitment of ubiquitin ligase.

Gp78 binds Insig-1 constitutively in the ER membrane. Id. When the cellular sterol level is high, the insig-1/gp78 complex binds the transmembrane domain of 3-hydroxy-3-methylglutaryl CoA reductase. Id. With the assistance of at least two proteins associated with gp78, p97/VCP and Aup1 (Id., citing Song, B L et al, "Gp8, a membrane-anchored ubiquitin ligase, associates with Insig-1 and couples sterol-regulated ubiquitination to degradation of HMG CoA reductase," Mol. Cell 19: 829-40 (2005); Jo, Y et al, "ancient ubiquitous protein 1 mediates sterol-induced ubiquitination of 3-hydroxy-3-methylglutaryl CoA reductase in lipid droplet-associated endoplasmic reticulum membranes," Mol. Biol. Cell 24: 169-83 (2013)), the ubiquitinated reductase is translocated to lipid droplet-associated ER membrane and dislocated from membrane into cytosol for proteosomal degradation (Id., citing Jo, Y et al, "ancient ubiquitous protein 1 mediates sterol-induced ubiquitination of 3-hydroxy-3-methylglutaryl CoA reductase in lipid droplet-associated endoplasmic reticulum membranes," Mol. Biol. Cell 24: 169-83 (2013); Hartman I Z, et al, "Sterol-induced dislocation of 3-hydroxy-3-methylglutaryl coenzyme A reductase from endoplasmic reticulum membranes into the cytosol through a subcellular compartment resembling lipi droplets," J. Biol. Chem. 285: 19288-98 (2010)). This post-ubiquitination process can be promoted by geranylgeraniol or its metabolically active geranyl-geranyl-pyrophosphate (Id., citing Sever, N. et al, "Insig-dependent ubiquitination and degradation of mammalian 3-hydroxy-3-methylglutaryl CoA reductase stimulated by sterols and geranylgeraniol," J. Biol. Chem. 278: 52479-90 (2003)).

In short, the ubiquitination of Insig-1 is mediated by gp78 and regulated by sterols. Id. Insig-1 is modified by gp78 under low sterol conditions. Id. High sterol promotes SCAP to bind Insig and gp78 is competed off, thereby stabilizing Insig-1. Id.

Gp78-mediated ubiquitination and degradation of Insig-1 provides a mechanism for convergent feedback inhibition, whereby inhibition of SREBP processing requires convergence of newly synthesized Insig-1 and newly acquired sterols. (DeBose-Boyd, R. A. "Feedback Regulation of Cholesterol Synthesis: Sterol-accelerated ubiquitination and degradation of HMG CoA Reductase," Cell Res. 18 (6): 609-21 (2008); citing Gong, Y. et al, "Sterol-regulated ubiquitination and degradation of Insig-1 creates a convergent mechanism for feedback control of cholesterol synthesis and uptake," Cell Metab. 3: 15-24 (2006)). In sterol-depleted cells, SCAP-SREBP complexes no longer bind Insig-1, which in turn becomes ubiquitinated and degraded. Id. These SCAP-SREBP complexes are free to exit the ER and translocate to the Golgi, where the SREBPs are processed to the nuclear form that stimulates transcription of target genes, including the Insig-1 gene. Id. Increased transcription of the Insig-1 gene leads to increased synthesis of Insig-1 protein, but the protein is ubiquitinated and degraded until sterols build up to levels sufficient to trigger SCAP binding. Id.

Insig-2 has been defined as a membrane-bound oxysterol binding protein with binding specificity that correlates with the ability of oxysterols to inhibit SREBP processing (Id., citing Sun, L P, et al, "Sterol-regulated transport of SREBPs from endoplasmic reticulum to Golgi: Insig renders sorting signal in Scap inaccessible to COPII proteins," Proc. Natl Acad. Sci. USA 104: 6519-26 (2007); Radhakrishnan, A. et al, "From the Cover: Sterol-regulated transport of SREBPs from endoplasmic reticulum to Golgi: Oxysterols block transport by binding to Insig," Proc. Natl Acad. Sci. USA 104: 6511-18 (2007)). Oxysterols, cholesterol derivatives that contain hydroxyl groups at various positions in the iso-octyl side chain (e.g., 24-hydroxycholesterol, 25-hydroxycholesterol, 27-hydroxycholesterol), are synthesized in many tissues by specific hydrolases; oxysterols play key roles in cholesterol export, and are intermediates in the synthesis of bile acids (Id., citing Russell, D W, "Oxsterol biosynthetic enzymes," Biochim. Biophys. Acta—Molec. Cell Biol. Lipids 1529: 126-135 (2000)). Oxysterols, which are significantly more soluble than cholesterol in aqueous solution, can readily pass across the plasma membrane and enter cells, and are extremely potent in inhibiting cholesterol synthesis by stimulating binding of both HMG Co A reductase and SCAP to Insigs. Id. Thus, formation of the SCAP-Insig complex can be initiated by either binding of cholesterol to the membrane domain of SCAP or by binding of oxysterols to Insigs, both of which prevent incorporation of SCAP-SREBP into vesicles that bud from the ER en route to the Golgi. Id.

Insig-mediated regulation of HMG Co A reductase is controlled by three classes of sterols: oxysterols, cholesterol, and methylated sterols (e.g., lanosterol and 24, 25-dihydrolanosterol). Id. Oxysterols both accelerate degradation of HMG Co A reductase and block ER to Golgi transport of SCAP-SREBP through their direct binding to Insigs. Id. Cholesterol does not regulate HMG Co A reductase stability directly, but binds to SCAP and triggers Insig binding, thereby preventing escape of SCAP-SREBP from the ER.Id. Lanosterol selectively accelerates degradation of HMG Co A reductase without an effect on ER to Golgi transport of SCAP-SREBP. Id. However, the demethylation of lanosterol has been implicated as a rate-limiting step in the post-squalene portion of cholesterol synthesis (Id., citing Gaylor, J L, "Membrane bound enzymes of cholesterol synthesis from lanosterol," Biochem. Biophys. Res. Communic., 292: 1139-46 (2002); Williams, M T, et al, "Investigation of the rate-determining microsomal reaction of cholesterol biosynthesis from lanosterol in Morris hepatomas and liver," Cancer Res. 37: 1377-83 (1977)). The accumulation of lanosterol is avoided; its inability to block SREBP processing through SCAP assures that mRNAs encoding enzymes catalyzing reactions subsequent to lanosterol remain elevated, and lanosterol is metabolized to cholesterol.

It is a paradox that gp78 deficiency increases both the 3-hydroxy-3-methylglutaryl CoA reductase and Insig protein levels in mouse liver, because Insigs not only negatively regulate 3-hydroxy-3-methylglutaryl CoA reductase post-transcriptionally, but also inhibit SREBPs processing through binding to SCAP (Jiang, W. and Song, B-L, "Ubiquitin Ligases in Cholesterol Metabolism," Diabetes Metab. 38: 171-80 (2014) citing Nohturfft, A. et al., "Topology of SREBP cleavage-activating protein, a polytopic membrane protein with a sterol sensing domain," J. Biol. Chem. 273: 17243-250 (1998)). These two outcomes are contradictory regarding cholesterol biosynthesis. Studies from L-gp78+ mice have shown that the biosynthesis of cholesterol and fatty acids is decreased in gp78-deficient mouse liver (Id., citing Edwards, P A et al, "Purification and properties of rat liver 3-hydroxy-3-methylglutaryl coenzyme A reductase," Biochim. Biophys. Acta 574: 123-35 (1979)). This has been interpreted to mean that the Insig-SCAP-SREBP axis dominates, even though 3-hydroxy-3-methylglutaryl CoA (HMG CoA) reductase is elevated. Id.

ApoB-100, an essential protein component of very low density lipoproteins (VLDL) and low density lipoproteins (LDL), which plays critical roles in plasma cholesterol transportation, is another substrate of g78. Id. Under normal conditions, ApoB-100 is one of the committed secretory proteins. Id. However, when the cellular lipid availability is limited (e.g., the new synthesized core lipids (triglyceride, cholesterol ester) or microsomal triglyceride transfer protein activity is decreased), the nascent ApoB-100 is subjected to ER-associated degradation mediated by gp78. Id. When gp78 is overexpressed, ubiquitination and degradation through the 26S proteosome of apoB-100 is decreased (Id., citing Ravid, T. et al, "The ubiquitin-proteasome pathway mediates the regulated degradation of mammalian 3-hydroxy-3-methylglutaryl-coenzyme A reductase," J. Biol. Chem. 275: 35840-847 (2000)). When gp78 is knocked down, the secretion of apoB-100 and the assembly of VLDL are increased in HepG2 cells (Id., citing Hua, X., et al, "Sterol resistance in CHO cells traced to point mutation in SREBP cleavage-activating protein," Cell 87: 415-426 (1996)). The retrotranslocation of ApoB-100 also requires p97/VCP, similar to HMG CoA reductase (Id, citing Nakanishi, M. et al, "multivalent control of 3-hydroxy-3-methylglutaryl coenzyme A reductase. Mevalonate-derived product inhibits translation of mRNA and accelerates degradation of enzyme," J. Biol. Chem. 263: 8929-37 (1988); Hua, X., et al, "Sterol resistance in CHO cells traced to point mutation in SREBP cleavage-activating protein," Cell 87: 415-426 (1996)).

TRC8

Human TRC8 is a multi-pass membrane protein located in the ER membrane that binds both Insig-1 and Insig-2. (Id., citing Inoue, S. et al, "Inhibition of degradation of 3-hydroxyl-3-methylglutaryl-coenzyme A reductase in vivo by cysteine protease inhibitors," J. Biol. Chem. 266: 13311-17 (1991)). It contains a conserved sterol sensing domain and C-terminal RING domain with ubiquitin ligase activity (Id., citing Yabe, D. et al, "Insig-2, a second endoplasmic reticulum protein that binds SCAP and blocks export of sterol regulatory element-binding proteins," Proc. Natl. Acad. Sci. USA 99: 12753-758 (2002); Sun L P et al, "From the Cover: Sterol-regulated transport of SREBPs from endoplasmic reticulum to Golgi: Insig renders sorting signal in Scap inaccessible to COPII proteins," Proc. Natl Acad. Sci. USA 104: 6519-26 (2007)). RNAi studies in SV-589 cells showed that knockdown of TRC8 combined with gp78 can dramatically decrease the sterol-regulated ubiquitination as well as degradation of HMG CoA reductase, suggesting that both gp78 and TRC8 are involved in the sterol-accelerated ubiquitination of HMG CoA reductase in CHO-7 and SV-589 cells. (Id., citing Inoue, S. et al, "Inhibition of degradation of 3-hydroxyl-3-methylglutaryl-coenzyme A reductase in vivo by cysteine protease inhibitors," J. Biol. Chem. 266: 13311-17 (1991)).

TEB4

Human TEB4 is a 910 amino acid ER membrane-resident ubiquitin ligase. In mammalian cells, cholesterol stimulates the degradation of squalene monooxygenase (SM), the enzyme that catalyzes the first oxygenation step in cholesterol synthesis by which squalene is converted to the squalene-2,3-epoxide (37) mediated by TEB4 (Id., citing Sever, N. et al, "Accelerated degradation of HMG CoA reductase mediated by binding of insig-1 to its sterol-sensing domain," Mol. Cell 11: 25-33 (2003)). As one of the target genes of SREBP-2, both the transcription of SM and the stability of SM protein are regulated by sterols (Id., citing Sever, N. et al, Insig-dependent ubiquitination and degradation of mammalin 3-hydroxy-3-methylglutaryl-CoA reductase stimulated by sterols and geranylgeraniol," J. Biol. Chem. 278: 52479-490 (2003)). SM protein level is negatively regulated by cholesterol in mammalian cells (Id., citing Lee, P C, et al, "Isolation of sterol-resistant Chinese hamster ovary cells with genetic deficiencies in both Insig-1 and Insig-2," J. Biol. Chem. 280: 25242-249 (2005)). When cholesterol, but not 24, 25-dihydrolanosterol, or side chain oxysterols, such as 27-hydroxycholesterol, is/are present, SM is ubiquitinated by TEB4 (Id., citing Sever, N. et al, "Accelerated degradation of HMG CoA reductase mediated by binding of insig-1 to its sterol-sensing domain," Mol. Cell 11: 25-33 (2003); Lee, P C, et al, "Isolation of sterol-resistant Chinese hamster ovary cells with genetic deficiencies in both Insig-1 and Insig-2," J. Biol. Chem. 280: 25242-249 (2005)).

IDOL

The low density lipoprotein receptor (LDL-R) gene family consists of cell surface proteins involved in receptor-mediated endocytosis of specific ligands. Low density lipoprotein (LDL) is normally bound at the cell membrane and taken into the cell, ending up in lysosomes where the protein is degraded and the cholesterol is made available for repression of microsomal enzyme HMG CoA reductase. At the same time, a reciprocal stimulation of cholesterol ester synthesis takes place.

Inducible degrader of LDL-R (IDOL) moderates the degradation of LDL-R and requires the E2 enzyme UBE2D (Id., citing Schroepfer, G J, Jr., "Oxysterols: modulators of cholesterol metabolism and other processes," Physiol. Rev. 80: 361-554 (2000); Bjorkhem, I., "Do oxysterols control choleseterol homeostasis," J. Clin. Invest. 110: 725-30 (2002)).

Transcription of the LDL-R gene is regulated primarily by SREBP in a sterol responsive manner. (Id.) The LDL-R is also regulated at the posttranscriptional level by protoprotein convertase subtilisin/kexin type 9 (PCSK9)-mediated degradation of LDLR in the lysosome. (Id., citing Radhakrishnan, A. et al, "Direct binding of cholesterol to the purified membrane region of SCAP: Mechanism for a sterol-sensing domain," Mol. Cell 15: 259-68 (2004)). PCSK9 is synthesized as an about 74 kD soluble zymogen in the endoplasmic reticulum (ER), where it undergoes autocatalytic processing to release a processing enzyme of about 60 kDa to secrete from cells. (Id.) PCSK9 binds the extracellular domain of LDLR, which leads to lysosomal degradation of LDLR. (Id.)

IDOL also is a post-transcriptional regulator of LDL-R (Id., citing Schroepfer, G J, Jr., "Oxysterols: modulators of cholesterol metabolism and other processes," Physiol. Rev. 80: 361-554 (2000)). Activation of LXR can decrease the abundance of LDLR without changing its mRNA level and subsequently inhibited uptake of LDL in different cells (Id., citing Schroepfer, G J, Jr., "Oxysterols: modulators of cholesterol metabolism and other processes," Physiol. Rev. 80: 361-554 (2000)). IDOL can increase plasma cholesterol level by ubiquitination and degradation of LDL-R dependent on its cytosolic domain. The decrease or ablation of IDOL can elevate the LDL-R protein level and promote LDL uptake. The expression of Idol in liver is relatively low, and it is not regulated by LXR, while the LXR-IDOL pathway seems to be more active in peripheral cells, e.g., macrophages, small intestine, adrenals.

Cholesterol Biosynthesis Pathway Inhibitors as Antitumor Agents

Statins, which were developed as lipid-lowering drugs to control hypercholesterolemia, competitively inhibit HMG-CoA reductase, and have been proposed as anticancer agents, because of their ability to trigger apoptosis in a variety of tumor cells in a manner that is sensitive and specific to the inhibition of HMG-CoA reductase (Thumher, M., et al., "Novel aspects of mevalonate pathway inhibitors as antitumor agents," Clin. Cancer Res. 18: 3524-31 (2012) citing Wong, W W et al, "HMG-CoA reductase inhibitors and the malignant cell: the statin family of drugs as triggers of tumor-specific apoptosis," Leukemia 16: 508-19 (2002)). This apoptotic response is in part due to the downstream depletion of geranylgeranyl pyrophosphate (GGPP), and thus due to inhibition of protein prenylation. Protein prenylation creates a lipidated hydrophobic domain and plays a role in membrane attachment or protein-protein interactions. Prenylation occurs on many members of the Ras and Rho family of small guanosine triphosphatases (GTPases). Three enzymes (farnesyltransferase (FTase), geranylgeranyltransferase (GGTase) I and GGTase II can catalyze protein prenylation.

While statin therapy blocks the intracellular synthesis of cholesterol, it also alters the cholesterol content of tumor cell membranes, interfering with key signaling pathways. (Cruz, P M R, et al, "The role of cholesterol metabolism and cholesterol transport in carcinogenesis: a review of scientific findings, relevant to future cancer therapeutics," Frontiers in Pharmacol. 4(119): doi:10.3369/phar.2013.00119, citing Zhuang, L. et al, "Cholesterol targeting alters lipid raft composition and cell survival in prostate cancer cells and zenografts," J. Clin. Invest. 115: 959-68 (2005)).

Statins have been shown to have immunomodulatory activity (Thumher, M., et al., "Novel aspects of mevalonate pathway inhibitors as antitumor agents," Clin. Cancer Res. 18: 3524-31 (2012), citing Greenwood, J et al, Statin therapy and autoimmune disease: from protein prenylation to immunomodulation," Nat. Rev. Immunol. 6: 358-70 (2006)), and to induce the depletion of prenyl pyrophosphates in human dendritic cells [Gruenbacher, G. et al., "CD56+ human blood dendritic cells effectively promote TH1-type gammadelta T cell responses," Blood 114: 4422-31 (2009); Steinman, R M, Banchereau, J., "Taking dendritic cells into medicine," Nature 449: 419-26 (2007)). Prenyl pyrophosphate deprivation translated into activation of caspase I, which cleaved the preforms of IL-1β and IL-18 and enabled the release of bioactive cytokines. The statin-treated dendritic cells (DCs) thus acquired the capability to potentially activate IL-2 primed natural killer (NK) cells (Id., citing Gruenbacher, G. et al., "IL-2 costimulation enables statin-mediated activation of human NK cells, preferentially through a mechanism involving CD56+ dendritic cells," Cancer Res. 70: 9611-20 (2010)). NK cells, which recognize and attack tumor cells that lack MHC class I molecules (Id., citing Munz, C. et al, "Dendritic cell maturation by innate lymphocytes: coordinated stimulation of innate and adaptive immunity," J. Exptl Med. 202: 203-7 (2005); Maniar, A. et al, "Human gammadelta T lymphocytes induce robust NK cell-mediated antitumor cytotoxicity through CD137 engagement," Blood 116: 1726-33 (2010)) contribute to innate immune responses against neoplastic cells. The statin-induced response of IL-2-primed NK cells could be abolished completely when cell cultures were reconstituted with the isoprenoid pyrophosphate GGPP, which allows protein geranylgeranylation to occur despite statin-mediated inhibition of HMB-CoA reductase. Statins also acted directly on human carcinoma cells to induce apoptosis, and IFN-γ produced by NK cells cooperated with statins to enhance tumor cell death synergistically (Id., citing Gruenbacher, G. et al., "IL-2 costimulation enables statin-mediated activation of human NK cells, preferentially through a mechanism involving CD56+ dendritic cells," Cancer Res. 70: 9611-20 (2010)).

Mutant p53, which is present in more than half of all human cancers, can significantly upregulate mevalonate pathway activity in cancer cells, which contributes to maintenance of the malignant phenotype. (Id., citing Freed-Pastor, W A, et al, "Mutant p53 disrupts mammary tissue architecture via the mevalonate pathway," Cell 148: 244-58 (2012)). Simvastatin was shown to reduce 3-dimensional growth of cancer cells expressing a single mutant p53 allele, and was able to induce extensive cancer cell death and a significant reduction of their invasive phenotype. In isoprenoid add-back experiments, supplementation with GGPP was sufficient to restore the invasive phenotype in the presence of HMG-CoA reductase inhibition, showing that upregulation of protein geranylgeranylation is an important effect of mutant p53 (Id., citing Freed-Pastor, W A, et al, "Mutant p53 disrupts mammary tissue architecture via the mevalonate pathway," Cell 148: 244-58 (2012)).

Bisphosphonates, drugs that prevent bone resorption, act downstream of HMG-CoA reductase to inhibit farnesyl pyrophosphate (FPP) synthase. Both bisphosphonates and statins eventually cause FPP and GGPP deprivation and thus failure to perform farnesylation and geranylgeranylation of small GTPases of the Ras superfamily. With regard to bisphosphonates, the inhibition of Ras signaling due to the disruption of membrane anchoring of these GTPases eventually stops osteoclast-mediated bone resorption (Id., citing Konstantinopoulos, P A, et al, "Post translational modifications and regulation of the RAS superfamily of GTPases as anticancer targets," Nat. Rev. Drug Discov. 6: 541-55 (2007)).

Suppressors of the mevalonate pathway also include the diverse isoprenoids (Cruz, P M R, et al, "The role of cholesterol metabolism and cholesterol transport in carcinogenesis: a review of scientific findings, relevant to future cancer therapeutics," Frontiers in Pharmacol. 4(119): doi: 10.3369/phar.2013.00119, Id., citing Mo, H and Elson, C E, "Studies of the isopreoid-mediated inhibition of mevalonate synthesis applied to cancer chemotherapy and chemoprevention," Exp. Biol. Med. (Maywood) 229: 567-85 (2004)), mevalonate-derived secondary metabolites of plants (Bach, T J, "Some new aspects of isoprenoid biosynthesis in plants—a review," Lipids 30: 191-202 (1995)). The potencies of isoprenoids in suppressing hepatic HMG-CoA reductase activity was found to be strongly correlated to their potencies in tumor suppression (Id., citing Elson, C E and Quereshi, A A, "Coupling the cholesterol—and tumor-suppressive actions of palm oil to the impact of its minor constituents on 3-hydroxy-3-methylglutaryl coenzyme A reductase activity," Prostaglandins Leukot. Essent. Fatty Acids 52: 205-207 (1995)). The tocotrienols, vitamin E molecules, and "mixed isoprenoids" with a farnesol side chain, down-regulate HMG-CoA reductase activity in tumors and consequently induce cell cycle arrest and apoptosis (Id., citing Mo H and Elfakhani, C E, "Mevalonate-suppressive tocotrienols for cancer chemoprevention and adjuvant therapy, in Tocotrienols: Vitamin E beyond tocopherols, eds. RR. Wilson et al (Boca Raton: CRC Press), 135-149 (2013)). The growth-suppressive effect of tocotrienols was attenuated by supplemental mevalonate (Id., citing Hussein, D and Mo, H, "d-δ-tocotrienol-mediated suppression of the proliferation of human PANC-1, M1A PaCa2 and BxPC-3 pancreatic carcinoma cells," Pancreas 38: e124-e136 (2009)).

Activity of azole antifungal compounds, such as ketoconazole, to block the function of several cytochrome P450 enzymes involved in cholesterol biosynthesis (e.g., CYP51A1, which catalyzes demethylation of lanosterol) and CYP17A1 (which mediates a step in the synthesis of androgens) has been utilized clinically to treat hormone refractory prostate cancer, and recently has been surpassed by abiraterone, a CYP17A1 antagonist. Gorin, A. et al., "Regulation of cholesterol biosynthesis and cancer signaling," Curr. Op. Pharmcol. 12(6) 710-16 (2012); citing (4). Itraconazole has shown activity against medulloblastoma, via its inhibitory effects on Smoothened in the hedgehog pathway. (Id., citing Kim, J. et al, "Itraconazole, a commonly used antifungal that inhibits Hedgehog pathway activity and cancer growth," Cancer Cell. 17(4): 388-99 (2010)), and suppression of angiogenesis via its interference with lysosomal cholesterol trafficking (Id., citing Xu, J. et al, "Cholesterol trafficking is required for mTPOR activation in endothelial cells," Proc. Natl Acad. Sci. USA 107(10): 4764-69 (2010)). The antiangiogenic effect of itraconazole, a well-established CYP51/ERG11 antifungal antibiotic, is exerted via inhibition of endosomal cholesterol trafficking and suppression of mTOR signaling (Id.).

In tumor cells, increased signaling activity of growth factor or steroid hormone receptors via PI3K/AKT and MAPK/ERK1/2 (Gorin, A. et al., Regulation of choletrol biosynthesis and cancer signaling, Curr. Opin. Pharmacol. 12(6): 710-16 (2012), citing Menendez, J A and Lupu, R., Fatty acid synthase and the lipogenic phenotype in cancer pathogenesis," Nat. Rev. Cancer 7(10): 763-77 (2007)), HIF-1α, p53 (Id., citing Oliverase, G. et al, "Novel anti-fatty acid synthase compounds with anti-cancer activity in Her2+ breast cancer," Ann. N.Y. Acad. Sci. 1210: 86-92 (2010)) and sonic hedgehog (SHH) (Id., citing Bhatia, B. et al, "Sonic hedgehog signaling and malignant transformation of the cerebellar granule neuron precursor cells," Oncogene 30(4): 410-22 (2011)) pathways modulate and activate SREBP-1, the main regulatory component of lipogenesis. It has been reported that inhibiting mTORC1 using rapamycin has little effect on SREBP-1 nuclear localization and its abundance, but inhibiting its upstream factors, like EGFR, PI3K and Akt, significantly decreases SREBP-1 N-terminal levels and diminishes its abundance in the nucleus (Guo, D et al, "Targeting SREBP-1 driven lipid metabolism to treat cancer," Curr. Pharm Des. 20(15): 2619-26 (2014) citing Guo, D. et al, "EGFR signaling through han Akt-SREBP-1-dependent, rapamycin-resistant pathway sensitizes glioblastomas to antilipogenic therapy," Science Signaling 2: ra82 (2009)). mTOR kinase inhibitor Torin-1 (Id., citing Peterson, T R et al, "DEPTOR is an mTOR inhibitor frequently overexpressed in multiple myeloma cells and required for their survival," Cell 137: 873-86 (2009)), which inhibits both mTORC1 and mTORC2 activity (Id., citing Sabatini, D M, "mTOR and cancer: insights into a complex relationship," Nat. Rev. Cancer 6: 729-34 (2006)), significantly decreased SREBP-1 abundance in the nucleus compared to the inhibition of mTORC1 alone by rapamycin (Id., citing Peterson, T R, et al, "mTOR complex I regulates lipin 1 localization to control the SREBP pathway," Cell 146: 408-20 (2011), Hagiwara, et al, "Hepatic mTORC2 activates glycolysis and lipogenesis through Akt, glucokinase and SREBP1c," Cell Metab. 15: 725-38 (2012)).

Overexpression of lipogenic enzymes has been observed in a number of carcinomas (Gorin, A. et al., Regulation of cholesterol biosynthesis and cancer signaling, Curr. Opin. Pharmacol. 12(6): 710-16 (2012), citing Nagahashi, M. et al, "Sphingosine-1-phosphate produced by sphingosine kinase 1 promotes breast cancer progression by stimulating angiogenesis and lymphangiogenesis," Cancer Res. 72(3): 726-35 (2012)) and has been described to correlate with disease severity, increased risk of recurrence and a lower chance of survival (Id., citing Uddin, S. et al, "High prevalence of fatty acid synthase expression in colorectal cancers in Middle Eastern patients and its potential role as a therapeutic target," Am. J. Gastroenterol. 104(7): 1790-1801 (2009; Mashima, T. et al, "De novo fatty-acid synthesis and related pathways as molecular targets for cancer therapy," Br. J. Cancer 100 (9): 1369-72 (2009)).

Accelerated synthesis of lipids and sterols also is an essential mechanistic component of malignant transformation. Oxidized LDL receptor 1 (OLR1) is required for Src kinase transformation of immortalized MCF10A mammary epithelial cells (Id., citing Hirsch, H A et al, "A transcriptional signature and common gene networks link cancer with lipid metabolism and diverse human diseases," Cancer Cell. 17(4): 348-61 (2010)). OLR1 is significantly induced during transformation, and depletion of OLR1 by siRNA blocks morphological transformation and inhibits cell migration and invasion, and results in reduction of tumor growth in vivo (Id.). Conversely, overexpression of ORL1 protein in MCF10A and HCC1143 mammary epithelial cells leads to significant upregulating of BCL2, a negative regulator of apoptosis (Id., citing Khaidakov, M., et al., "Oxidized LDL receptor 1 (OLR1) as a possible link between obesity, dyslipidemia and cancer," PLoS One 6(5): e20277 (2011)).

EBP in complex with dihydrocholesterol-7 reductase (DHCR7) catalyzes isomerization of the double-bond between C7 and C8 in the second cholesterol ring. (Gabitova, L. et al., "Molecular Pathways: Sterols and receptor signaling in Cancer," Clin. Cancer Res. 19(23): 6344-50 (2013)). This complex mediates the activity of cholesterol epoxide hydrolase (Id., citing de Medina, P. et al, "Identification and pharmacological characterization of cholesterol-5,6-epoxide hydrolase as a target for tamoxifen and AEBS ligands," Proc. Natl. Acad. Sci. USA 107: 13520-5 (2010)).

There are several known inhibitors of EBP, and some have been described as anti-cancer agents. For example, a sterol conjugate of a naturally occurring steroidal alkaloid, 5alpha-hydroxy-6beta-[2-(1H-imidazol-4-yl)ethylamino]cholestan-3beta-ol (dendrogenin A) which is produced in normal, but not in cancer cells, and 5,6 alpha-epoxy-cholesterol and histamine (Id., citing de Medina, P. et al, "Dendrogenin A arises from cholesterol and histamine metabolism and shows cell differentiation and anti-tumour properties," Nature Communic. 4: 1840 (2013); de Medina, P. et al, "Synthesis of new alkylaminooxysterols with potent cell differentiating activities: identification of leads for the treatment of cancer and neurodegenerative diseases," J. Med. Chem. 52: 7765-77 (2009)), has been shown to suppress cancer cell growth and to induce differentiation in vitro in various tumor cell lines of different types of cancers (Id., citing de Medina, P. et al, "Synthesis of new alkylaminooxysterols with potent cell differentiating activities: identification of leads for the treatment of cancer and neurodegenerative diseases," J. Med. Chem. 52: 7765-77 (2009)). It also inhibited tumor growth in melanoma xenograft studies in vivo and prolonged animal survival. (Id., citing de Medina, P. et al, "Dendrogenin A arises from cholesterol and histamine metabolism and shows cell differentiation and anti-tumour properties," Nature Communic. 4: 1840 (2013);).

SR31747A (cis-N-cyclohexyl-N-ethyl-3-(3-choloro-4-cyclohexyl-phenyl)propen-2-ylamine hydrochloride), a selective peripheral sigma binding site ligand whose biological activities include immunoregulation and inhibition of cell proliferation, binds to SR31747A-binding protein 1 (SR-BP) and EBP with nanomolar affinity. Berthois, Y. et all., "SR31747A is a sigma receptor ligand exhibiting antitumoural activity both in vitro and in vivo," Br. J. Cancer 88: 438-46 (2003). The effect of SR31747A on proliferative activity was evaluated in vitro on the following breast and prostate cancer cell lines: breast (hormone responsive MCF-7 cells from a breast adenocarcinoma pleural effusion; MCF-7AZ; Hormone independent MCF-7/LCC1 cells derived from MCF-7 cell lines; MCF-7LY2, resistant to the growth-inhibitory effects of the antiestrogen LY117018; Hormone unresponsive MDA-MB-321 and BT20 established from a metastatic human breast cancer tumor); and prostate (Hormone responsive prostate cancer cell line LNCaP; hormone-unresponsive PC3 cell line established from bone marrow metastasis; hormone-unresponsive DU145 established from brain metastasis). Id. SR31747A induced concentration-dependent inhibition of cell proliferation, regardless of whether the cells were hormone responsive or unresponsive. Id. The antiproliferative effect of SR31747A was partially reduced by adding cholesterol (Id.; Labit-Le Bouteiller, C. et al., "Antiproliferative effects of SR31747A in animal cell lines are mediated by inhibition of cholesterol biosynthesis at the sterol isomerase step," Eur. J. Biochem. 256: 342-49 (1998)), thus demonstrating the involvement of EBP. Sensitivity to SR31747A did not correlate with cellular levels of EBP. Berthois, Y. et all., "SR31747A is a sigma receptor ligand exhibiting antitumoural activity both in vitro and in vivo," Br. J. Cancer 88: 438-46 (2003).SR31747A also inhibited proliferation in vivo in the mouse xenograft model. Id. Murine EBP cDNA overexpression in CHO cells increased resistance of these cells to SR31747A-induced inhibition of proliferation. Labit-Le Bouteiller, C. et al., "Antiprolifertive effects of SR31747A in animal cell lines are mediated by inhibition of cholesterol biosynthesis at the sterol isomerase step," Eur. J. Biochem. 256: 342-49 (1998)), Tamoxifen, inhibited SR31747 binding in a competitive manner and induced the accumulation of Δ8-sterols, while Emopamil, a high affinity ligand of human sterol isomerase, and verapamil, another calcium channel-blocking agent, are inefficient in inhibiting SR31747 binding to its mammalian target, suggesting that their binding sites do not overlap. Paul, R. et al., "Both the immunosuppressant SR31747 and the antiestrogen tamoxifen bind to an emopamil-insensitive site of Mammalian Δ8-Δ7 sterol isomerase," J. Pharmacol. Exptl Thera. 285(3): 1296-1302 (1998)). Some drugs, e.g., cis-flupentixol, trifluoroperazine, 7-=ketocholestanol and tamoxifen, inhibit SR31747 binding only with mammalian EBP enzymes, whereas other drugs, e.g., haloperidol and fenpropimorph, are more effective with the yeast enzyme than with the mammalian ones. Id.

Example 3. Experiments Showing that Cholesterol Synthesis Enzymes are Downregulated by 4C12

FIG. 12A is a bar graph showing cholesterol (pg/cell), and triglyceride (pg/cell) levels in Mut6 cells treated with compound 4C12 for 24 hours and 48 hours, versus a negative control (vehicle only). The figures show that in the presence of compound 4C12, cholesterol level decreases, and triglyceride level increases. FIG. 12B is a bar graph of relative mRNA vs. enzymes of cholesterol synthesis showing that genes for cholesterol synthesis enzymes are down-regulated by 4C12. Mut6 cells were treated with compound 4C12 for 24 hours and then mRNA levels for Hydroxymethylglutaryl-CoA synthase(Hmgcs); 3-hydroxy-3-methylglutaryl-coenzyme A reductase (Hmgcr); acetoacetyl-CoA synthetase (AACS); Delta(24)-sterol reductase (Dhcr24); 7-dehydrocholesterol reductase (Dhcr7), Sterol C5-desaturase (Sc5d);

Squalene synthase (SS); and farnesyl pyrophosphate (FPP) synthase (FPPS) were determined.

In FIG. 13(a)-(e) Mut6 cells were treated with compound 4C12 for 2, 9, 16, 24, and 48 hr, respectively, and their cholesterol gene profile compared to a DMSO control. The data shows that compound 4C12 inhibits Srebp2 target genes, and not Srebp1 target genes. (f) Western blot. Mut6 cells were treated with vehicle only (−) or with compound 4C12 (+) for 7 hr, 13 hr and 23 hr. Cells were collected, lysed in SDS buffer, subjected to SDS PAGE, and cell proteins transferred to a membrane by a standard protocol. The membrane was washed, treated with antibodies to SREBP1, SREBP2 and a positive control (Cadherin), rewashed and bound antibodies then revealed. The blots showed that compound 4C12 was effective to decrease SREBP2 protein.

Figure 13:
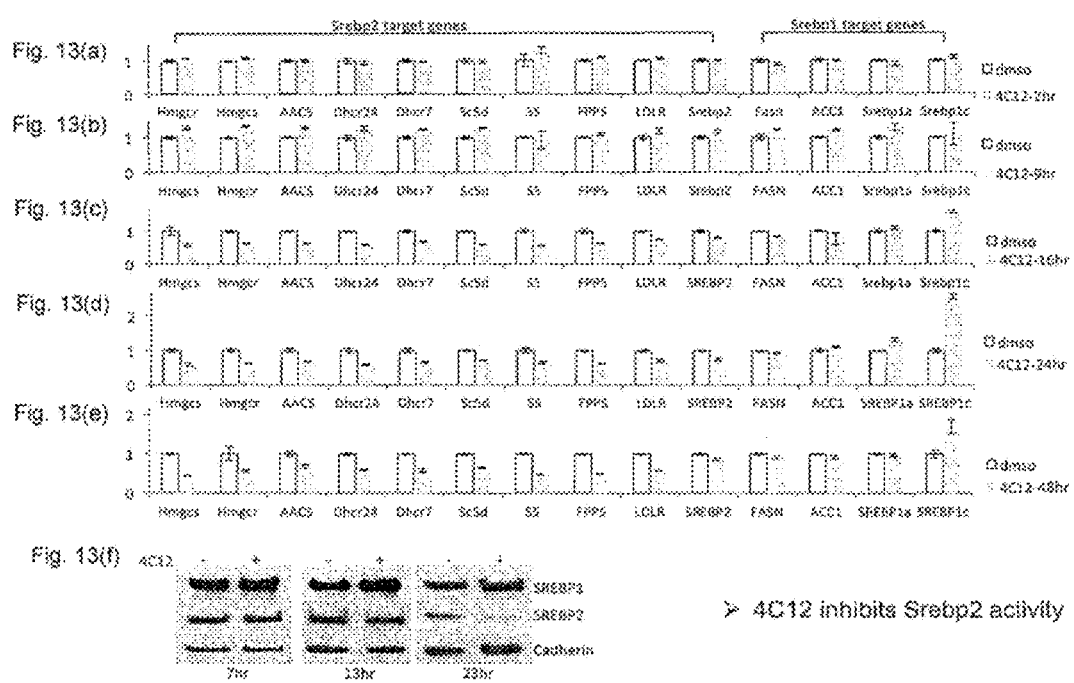
FIG. 13 comprising FIG. 13(a), FIG. 13(b), FIG. 13(c), FIG. 13(d), FIG. 13(e)
Figure 14:
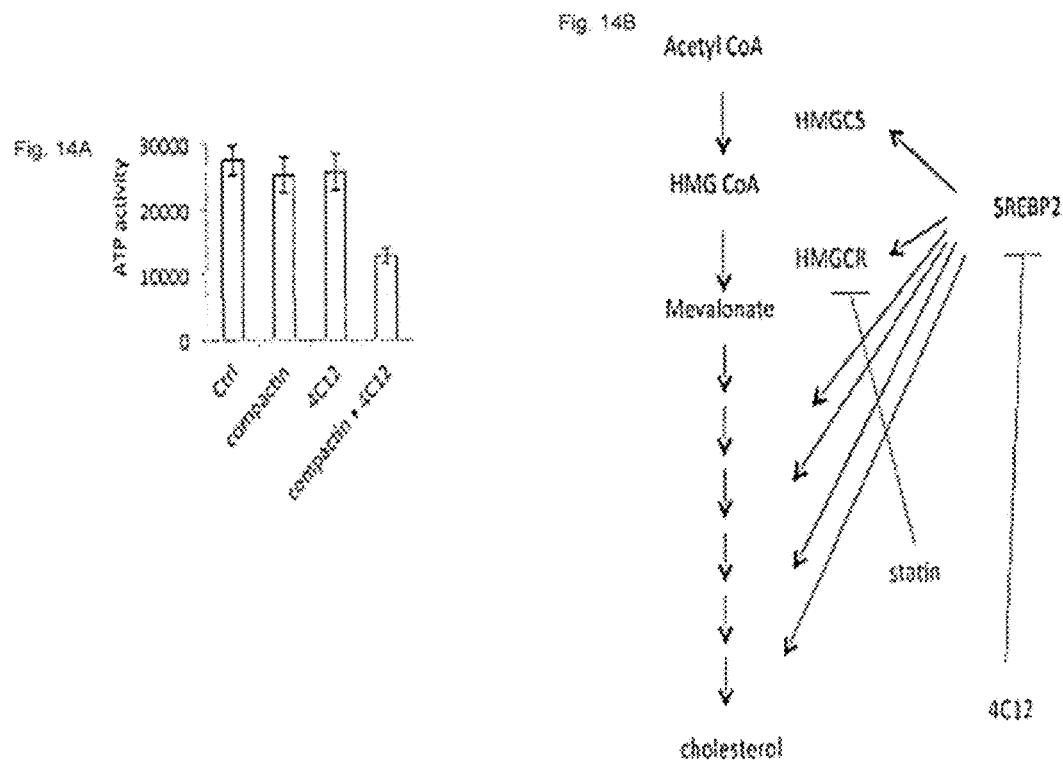
FIG. 14 comprising FIG. 14A

Example 4: Experiments to Determine Whether Decrease of Cholesterol is Functionally Important in Compound 4C12-Induced Cell Death FIGS. 14A and 15(a) are a bar graph plotting ATP activity (a measure of viability) for Mut6 cells treated with compactin/mevastatin, compound 4C12, and the combination of compactin/mevastatin+compound 4C12, versus a negative control (vehicle only). The results show that the combination of compactin/mevastatin and compound 4C12 exert an effect greater than each does alone. FIG. 13B illustrates statins' inhibitory effect on the mevalonate arm of the cholesterol biosynthesis pathway.

FIG. 15(b) is a bar graph showing ATP activity (a measure of viability) vs. concentration of cholesterol (μM)—Mut6 cells were treated with compound 4C12 versus a cells treated with DMSO (negative control). Addition of cholesterol inhibits compound 4C12-induced cell-death. 15(c) shows relative ATP activity (y-axis, a measure of viability) vs. compound 4C12 concentration (nM (x axis). Addition of SREBP2 by knock-down of Insig1/Insig2 makes Mut6 cells less sensitive to compound 4C12.

FIG. 16 is a bar graph of relative mRNA level for cholesterol biosynthesis pathway target genes Hmgcs, Hmgcr, FPPS, LDLR; and SREBP1c in mouse embryo fibroblasts (left) and astrocytes (right) treated with compound 4C12 or dmso (negative control). The figure shows that Srebp2 target genes were not decreased by compound 4C12 in MEFs and Astrocytes.

FIG. 17 compares cholesterol level (pg/cell) (Left) and triglyceride level (pg/cell) (Right) in Mut6 cells and in MEF cells treated with compound 4C12 for 24 hours and 48 hours to a negative control (vehicle). The results show that the observed decrease in cholesterol by compound 4C12 is specific to Mut6 tumor cells, and that Mut6 cells have a much lower basal level of cholesterol and triglycerides.

Figure 18:
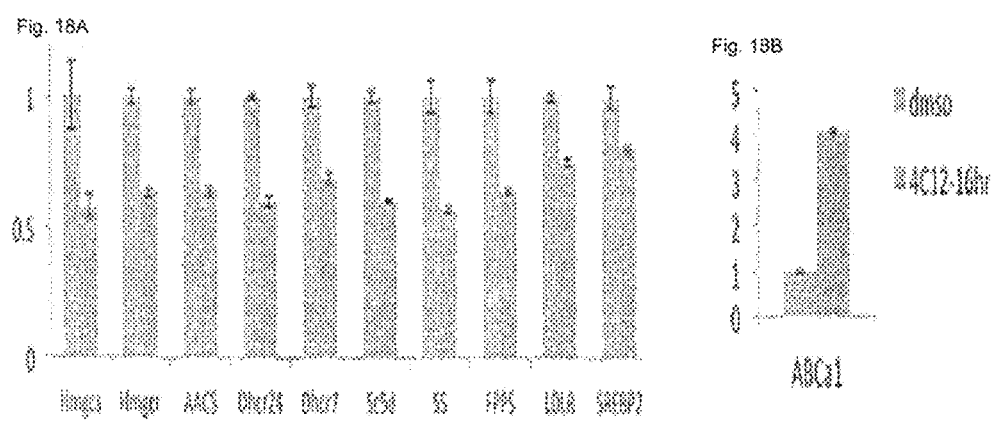
FIG. 18 comprising FIG. 18A

FIG. 18A is a bar graph showing the effect of inhibition of cholesterol biosynthesis pathway genes Hmgcs; Hmgcr, AACS, Dhcr24, Dhcr7, Sc5d, SS, FPPS, LDLR; and SREBP2 in Mut6 cells treated with DMSO or with compound 4C12 for 16 hours. FIG. 18B is a bar graph showing effect on level of ABCa1 of treating Mut6 cells with compound 4C12 for 16 hours versus a DMSO negative control.

FIG. 19 shows relative ATP level (y-axis, a measure of viability) vs. concentration of compound 4C12 (nM) for various primary patient derived glioblastoma cell lines (top left and top right), and for HeLa (cervical), HT-29 (colon), 435 (breast), 549 (lung), MCF7 (breast), HCC38 (breast), Daoy (medulloblastoma (brain)) cancer cell lines, and mouse embryonic fibroblast (MEF) cells in the presence (bottom left) and absence (bottom right) of serum.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A compound according to Formula I-g

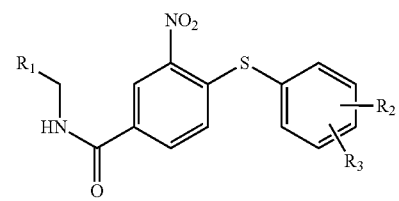

Formula I-g wherein $R_1$ is selected from the group consisting of

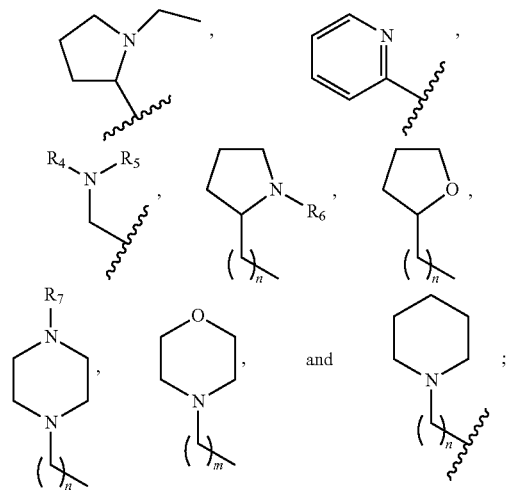

n=0, 1, or 2;

m=0 or 1;

$R_2$ and $R_3$ can be attached at any available position on the aromatic ring and are independently selected from the group consisting of H, D, F, Cl, $CF_3$, $C_1$-$C_6$ alkyl, $C_2$-$C_6$ alkenyl, $C_2$-$C_6$ alkynyl, $C_1$-$C_6$ hydroxyalkyl, cycloalkyl, OR, $N(R)_2$, $NO_2$, $N_3$, NH—C(O)—R, CN, C(O)R, C(O)OR, C(O)N(R)$_2$, SR, alkylacyl, and arylacyl;

Each R is independently selected from the group consisting of H, $C_{1-3}$ alkyl, propargyl, and phenyl;

$R_4$ and $R_5$ are independently selected from the group consisting of H, $C_{1-6}$ alkyl optionally substituted with $N(R)_2$, $C_2$-$C_6$ alkenyl, $C_2$-$C_6$ alkynyl, $C_1$-$C_6$ hydroxyalkyl, phenyl optionally substituted with $R_3$, and $CH_2OC(O)$-phenyl optionally substituted with $R_3$;

$R_6$ and $R_7$ are independently selected from the group consisting of H, $C_{1-3}$ alkyl, and $C(O)OMe_3$;

such that all possible stereoisomers, including optically active isomers, are included whenever stereogenic centers are present;

or a pharmaceutically acceptable salt, prodrug, active metabolite, or solvate thereof.

2. A compound of claim 1 according to Formula I-g

Formula I-h

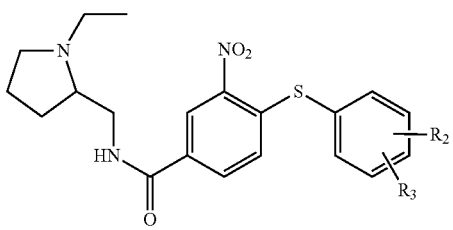

wherein $R_2$ and $R_3$ can be attached at any available position on the aromatic ring and are independently selected from the group consisting of H, D, F, Cl, $CF_3$, $C_1$-$C_3$ alkyl, $C_2$-$C_3$ alkenyl, $C_2$-$C_3$ alkynyl, $C_1$-$C_3$ hydroxyalkyl, $C_4$-$C_6$ cycloalkyl, OR, $N(R)_2$, $NO_2$, $N_3$, NH—C(O)—R, CN, C(O)R, C(O)OR, C(O)N(R)$_2$, and SR;

Each R is independently selected from the group consisting of H, $C_{1-3}$ alkyl, propargyl, and phenyl;

such that all possible stereoisomers, including optically active isomers, are included whenever stereogenic centers are present;

or a pharmaceutically acceptable salt, prodrug, active metabolite, or solvate thereof.

3. A pharmaceutical composition comprising a therapeutic amount of the compound according to claim 1, and a pharmaceutically acceptable carrier.

4. A compound selected from the group consisting of:

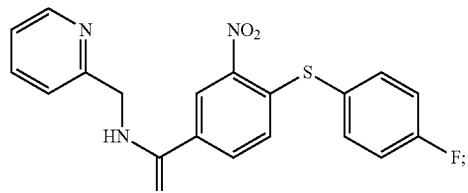

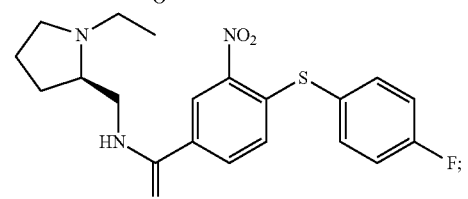

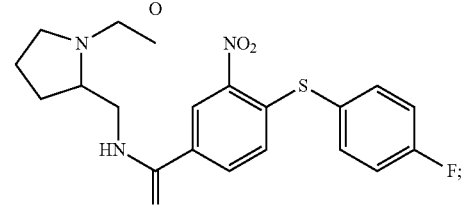

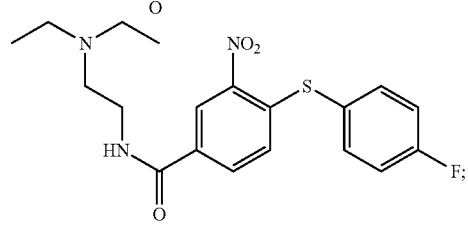

-continued

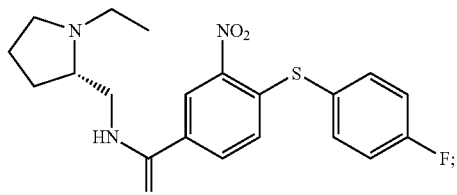

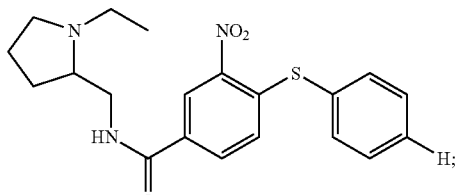

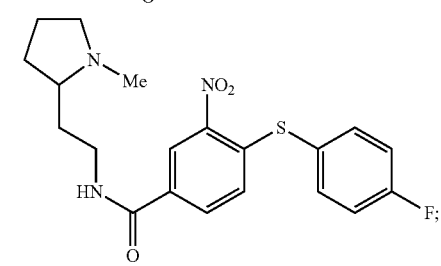

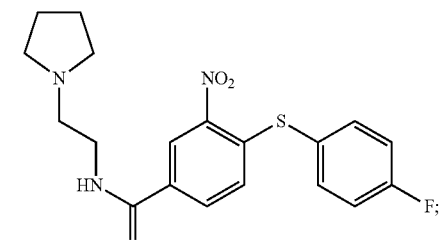

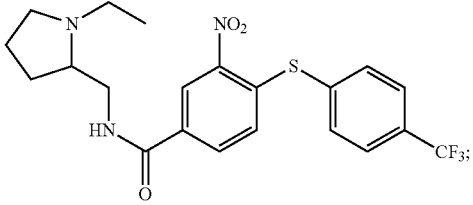

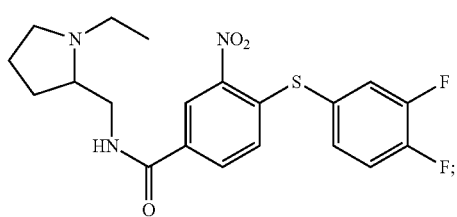

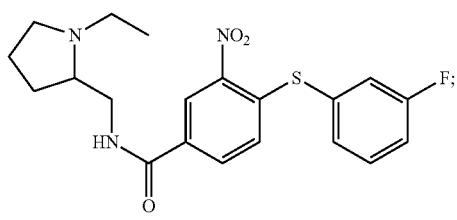

221
-continued
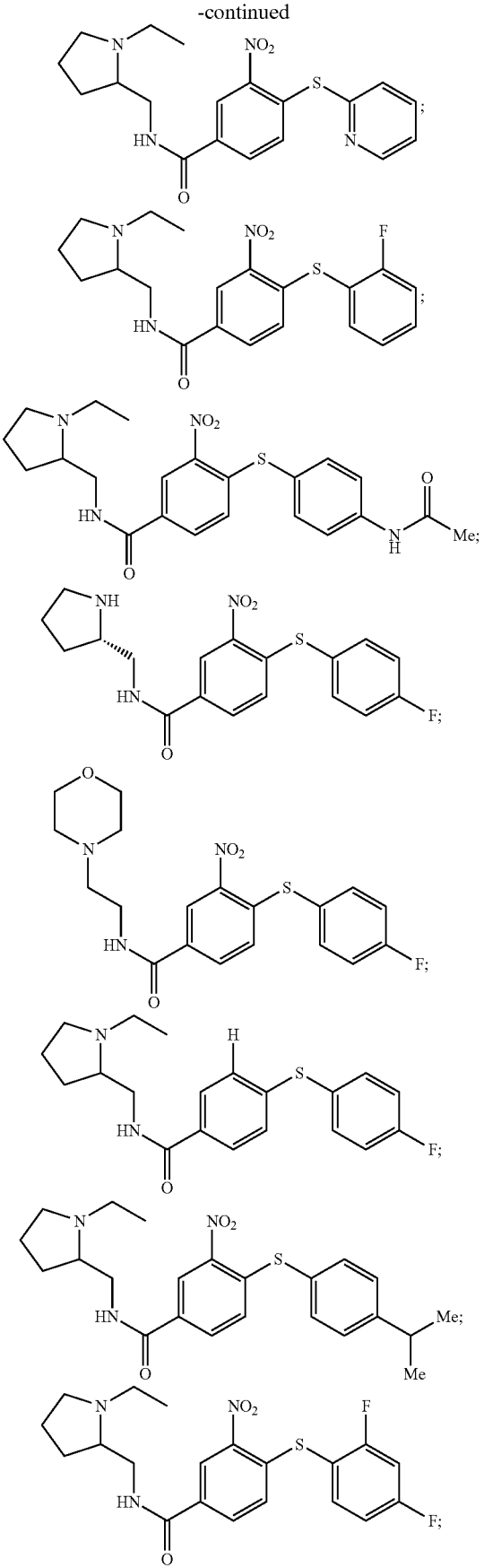
222
-continued
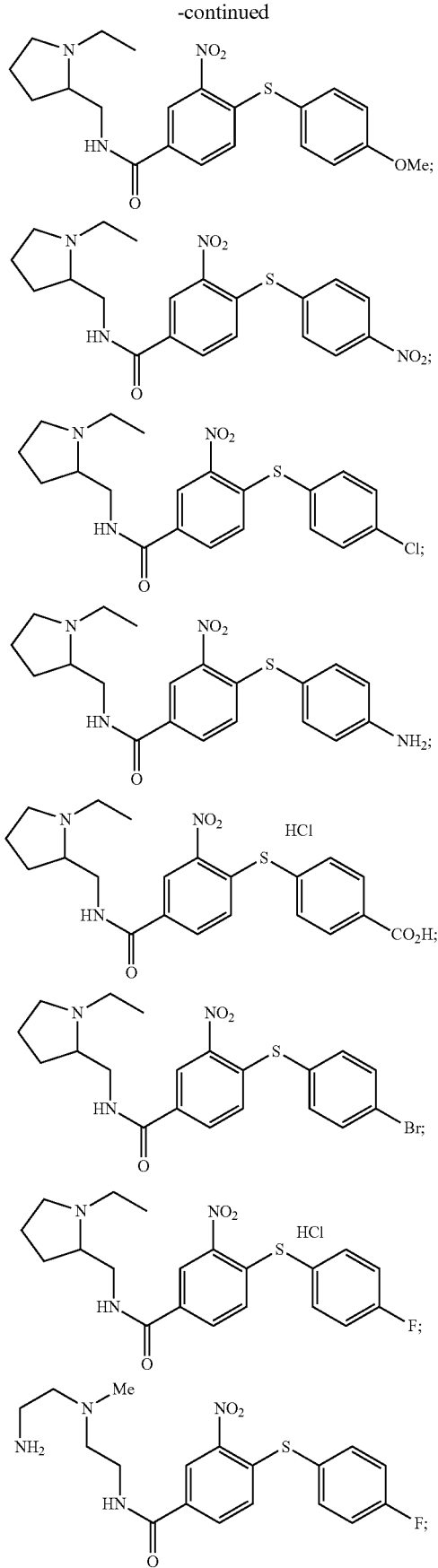

-continued
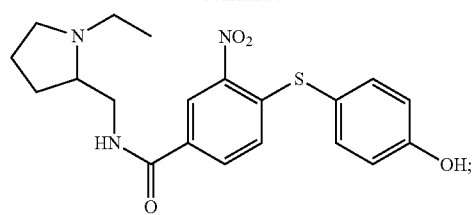
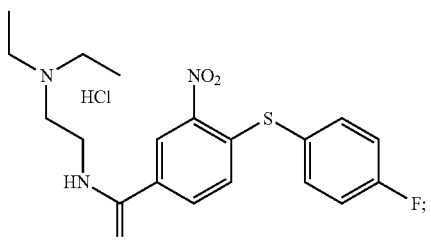
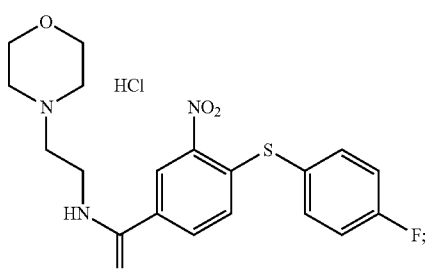
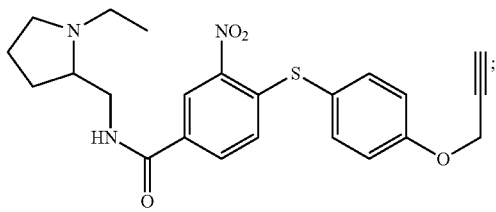
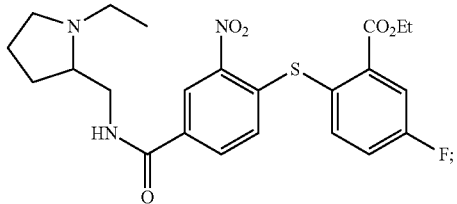
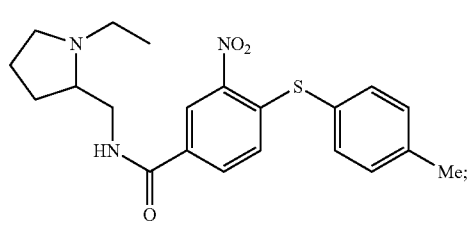
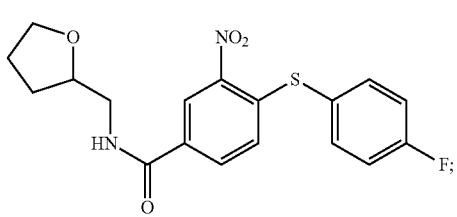
-continued
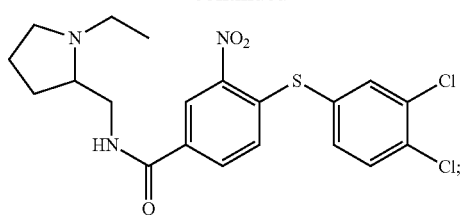
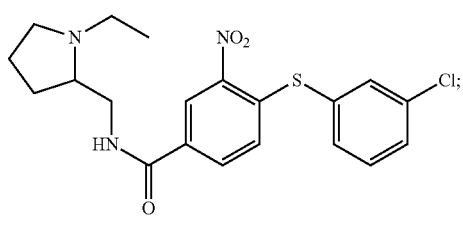
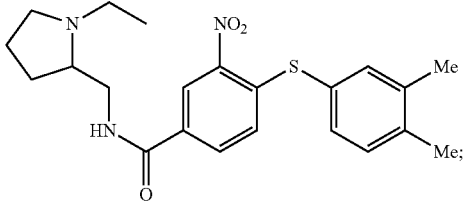
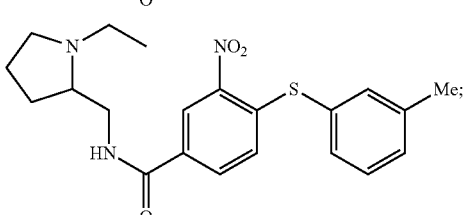
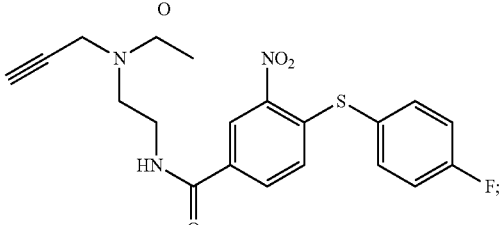
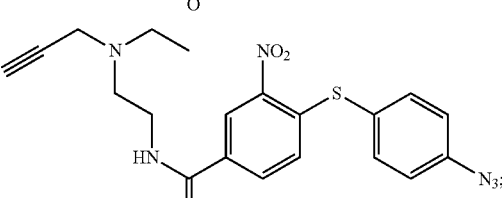
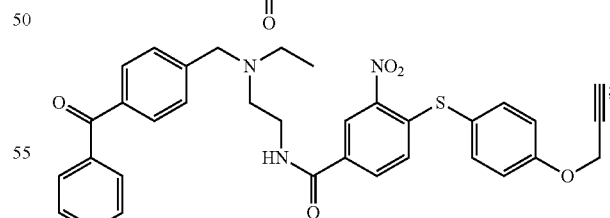
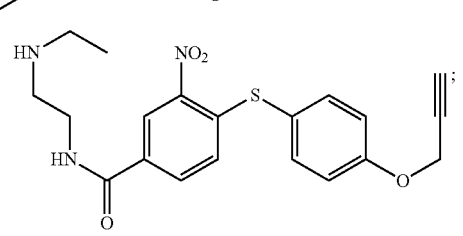

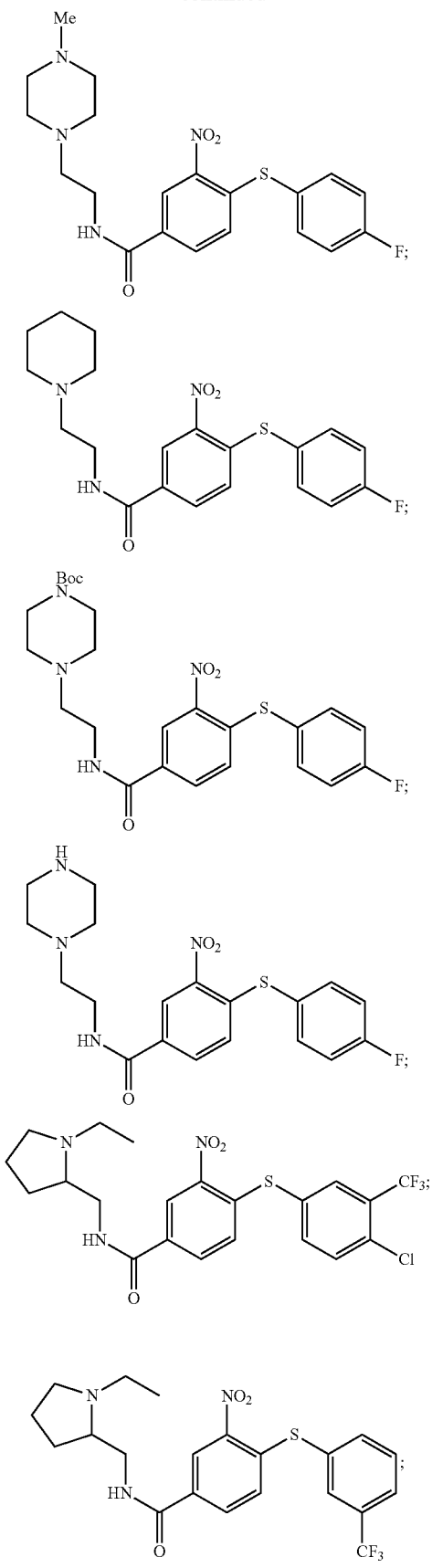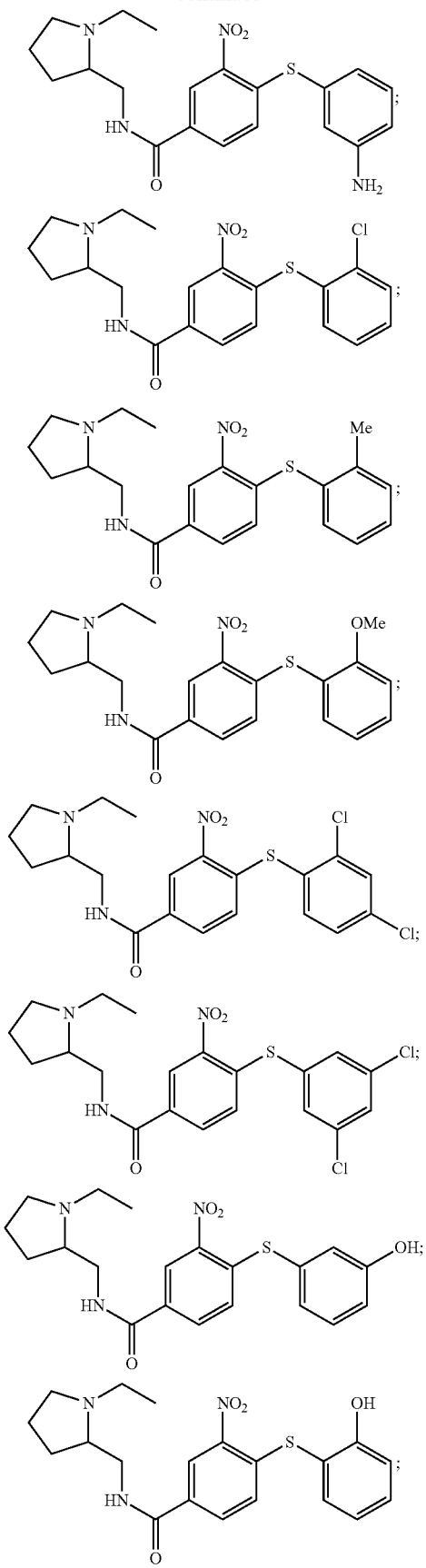

-continued
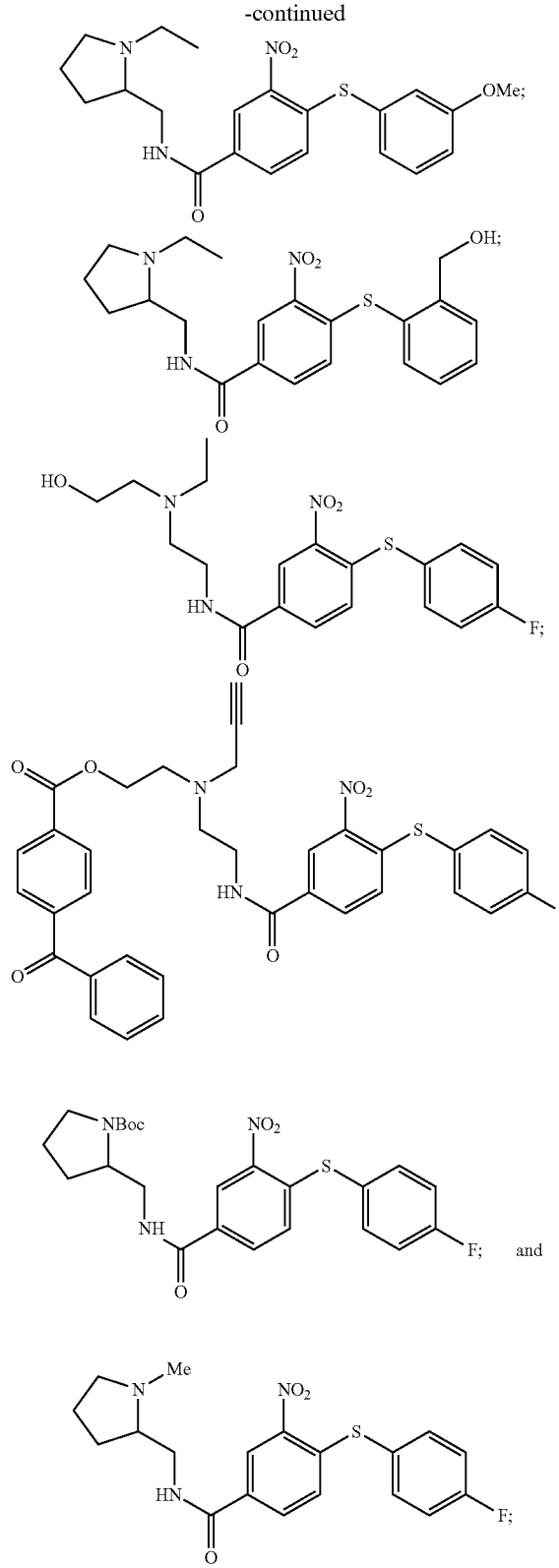
such that all possible stereoisomers, including optically active isomers, are included whenever stereogenic centers are present;
or a pharmaceutically acceptable salt, prodrug, active metabolite, or solvate thereof.
5. A compound selected from the group consisting of
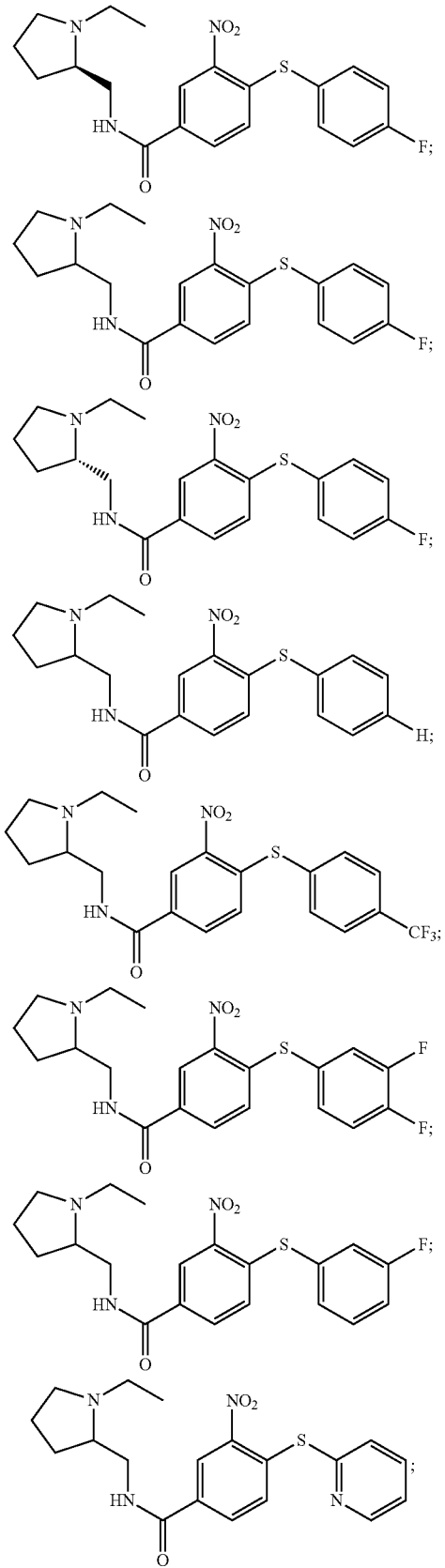

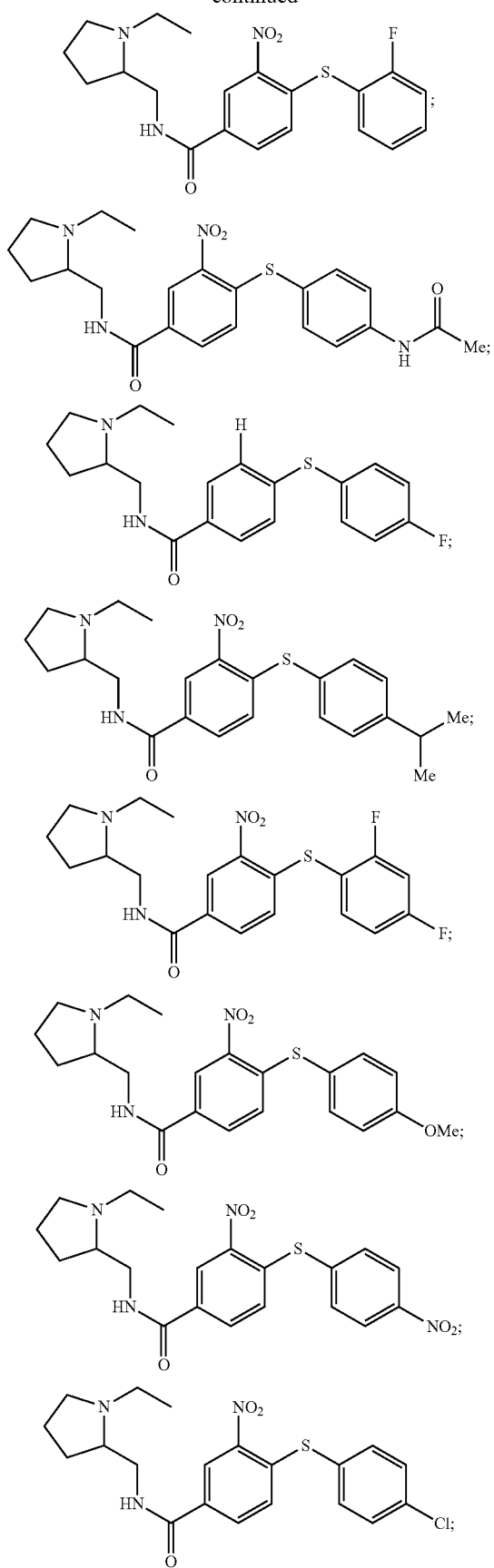
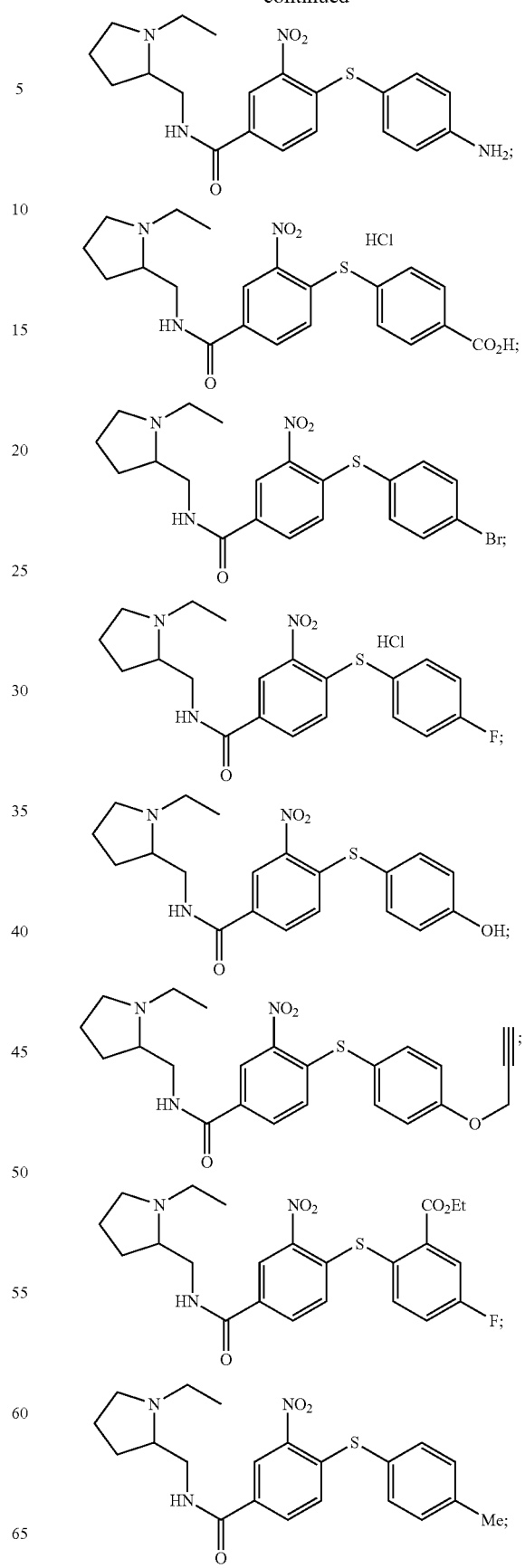

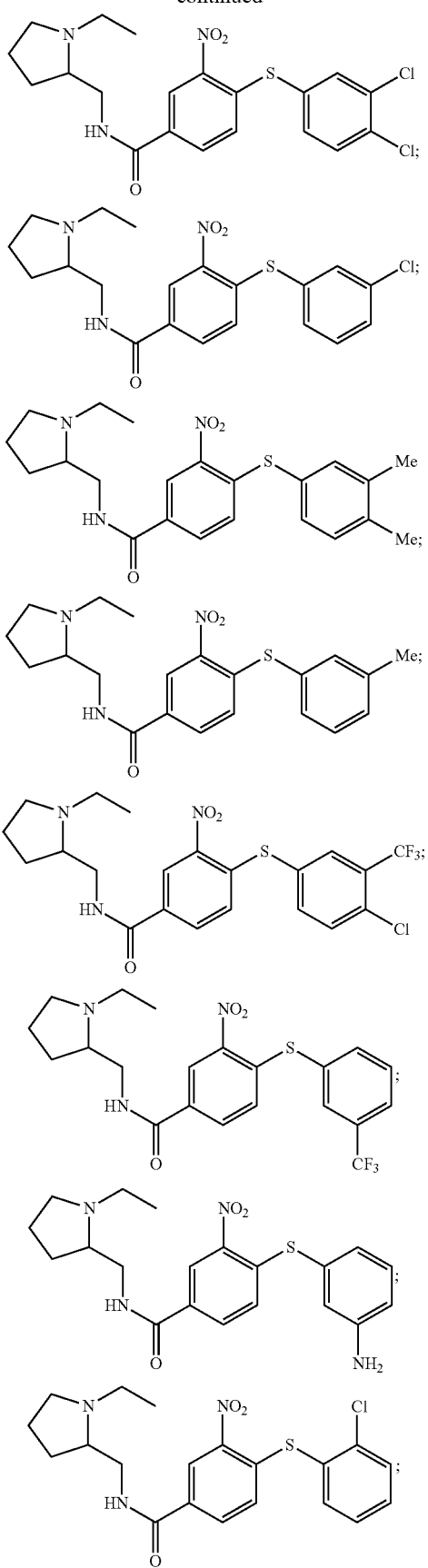
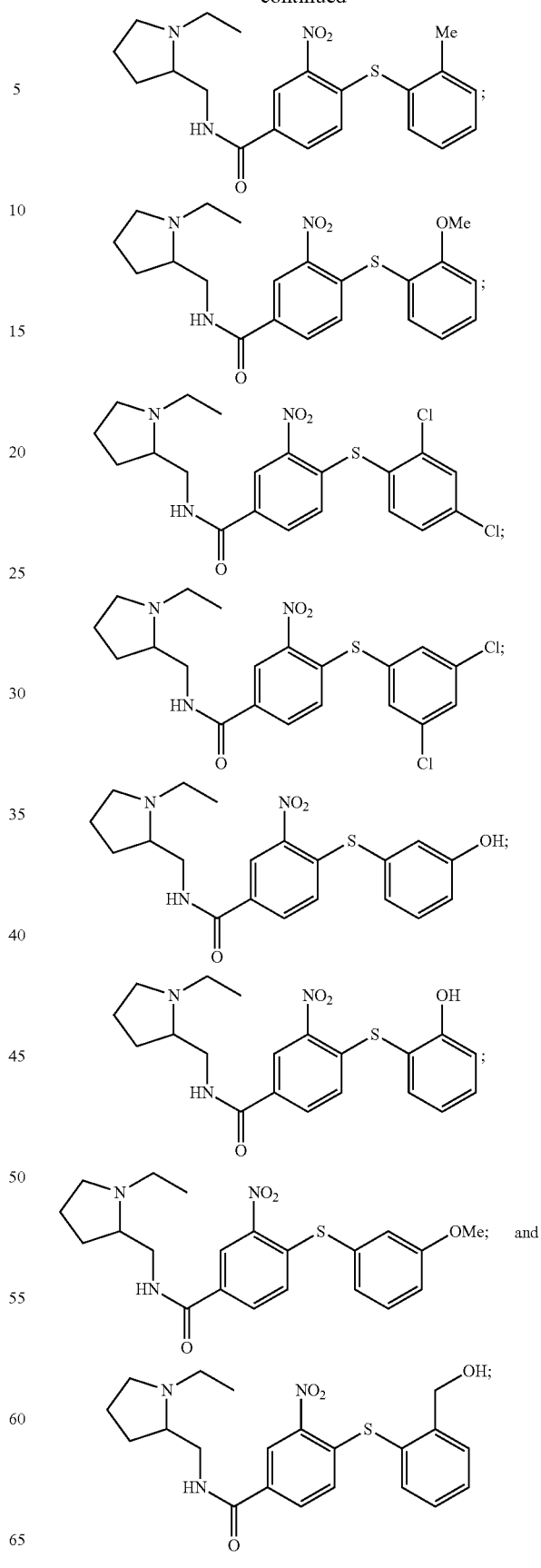

such that all possible stereoisomers, including optically active isomers, are included whenever stereogenic centers are present;
or a pharmaceutically acceptable salt, prodrug, active metabolite, or solvate thereof.
6. A compound selected from the group consisting of:
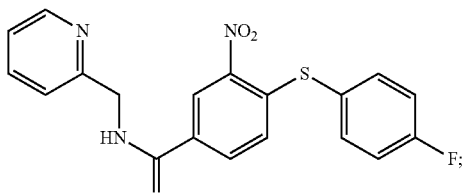
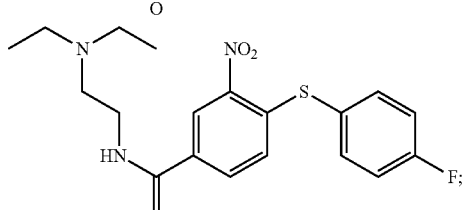
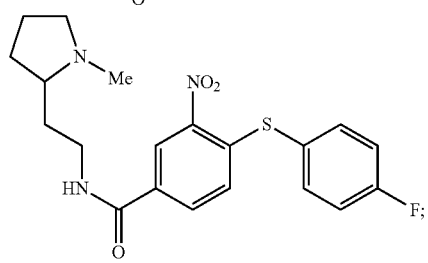
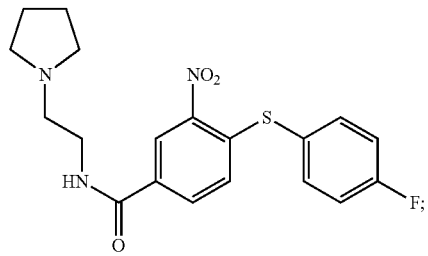
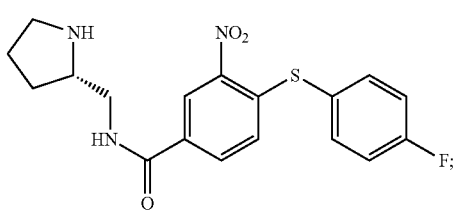
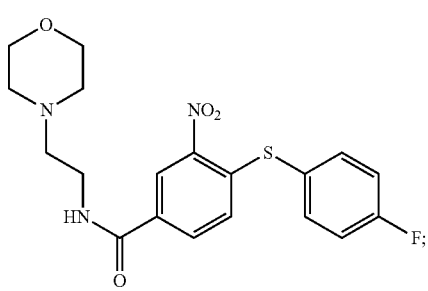
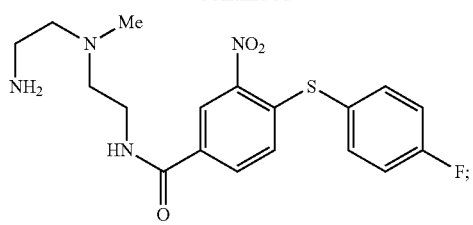
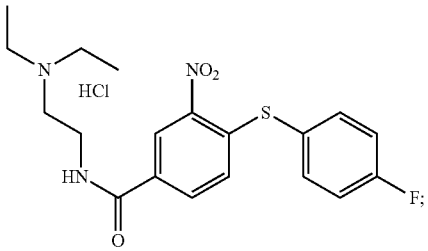
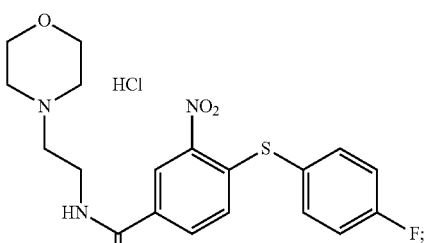
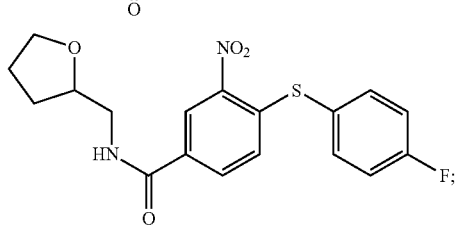
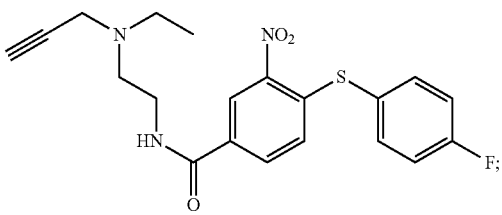
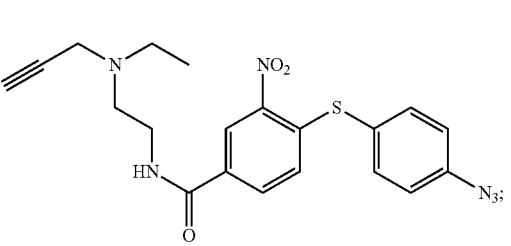
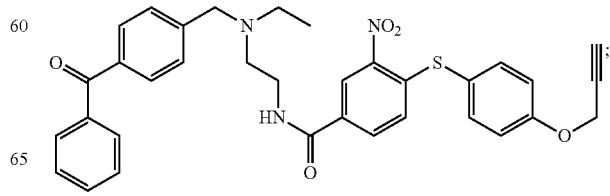

-continued

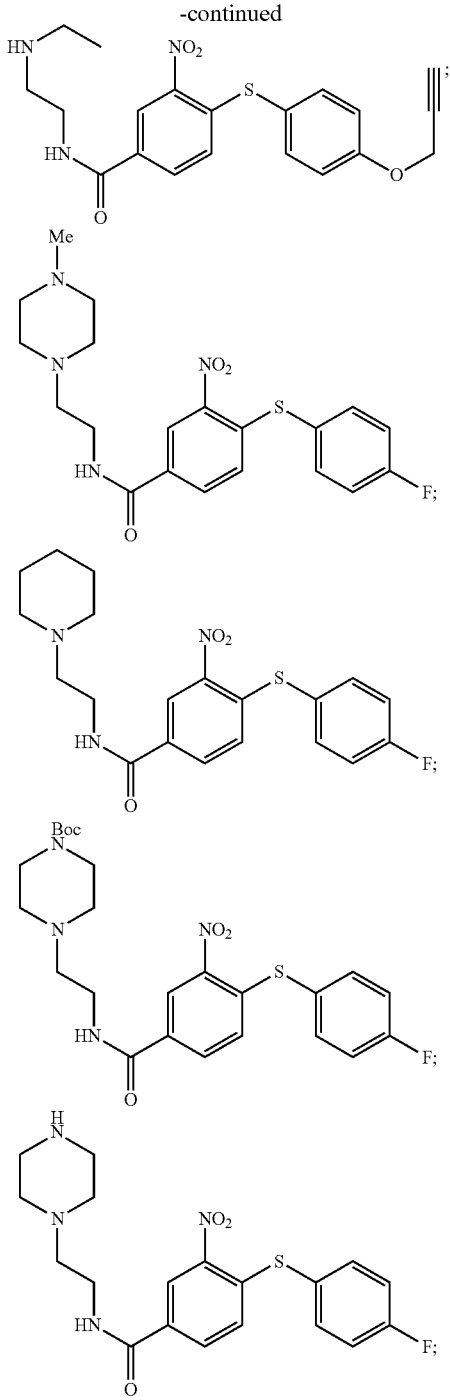

-continued

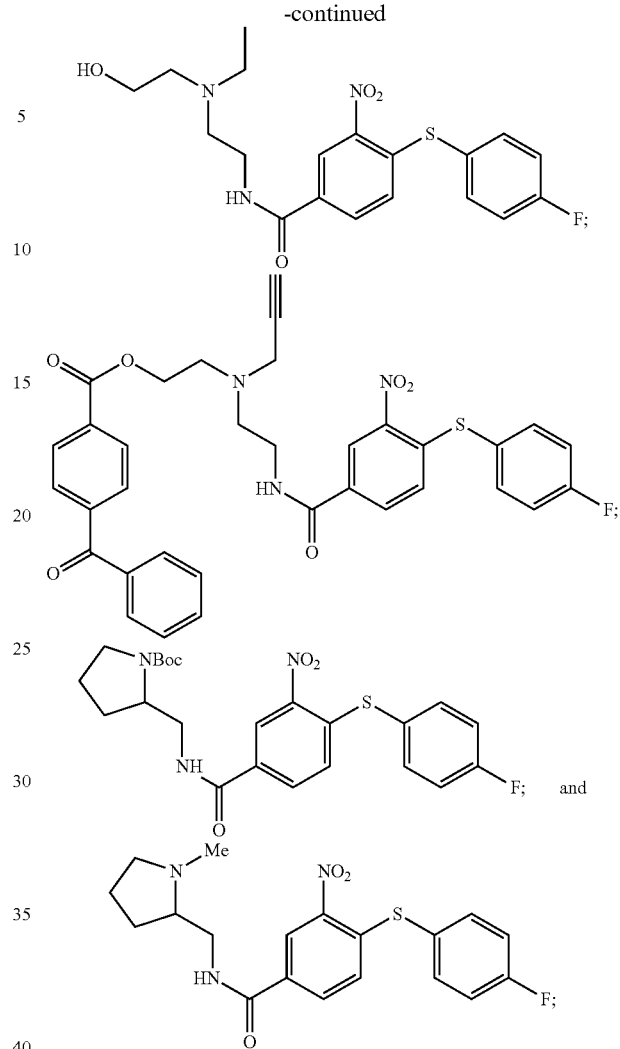

such that all possible stereoisomers, including optically active isomers, are included whenever stereogenic centers are present;

or a pharmaceutically acceptable salt, prodrug, active metabolite, or solvate thereof.

7. A pharmaceutical composition comprising a therapeutic amount of the compound according to any one of claims 4-6 and a pharmaceutically acceptable carrier.

* * * * *

UNITED STATES PATENT AND TRADEMARK OFFICE
CERTIFICATE OF CORRECTION

PATENT NO. : 10,112,948 B2
APPLICATION NO. : 15/194825
DATED : October 30, 2018
INVENTOR(S) : Jef DeBrabander and Luis Parada Page 1 of 1

It is certified that error appears in the above-identified patent and that said Letters Patent is hereby corrected as shown below:

In the Claims

In Claim 1, Column 218, Lines 36-44, delete first two chemical structures and insert

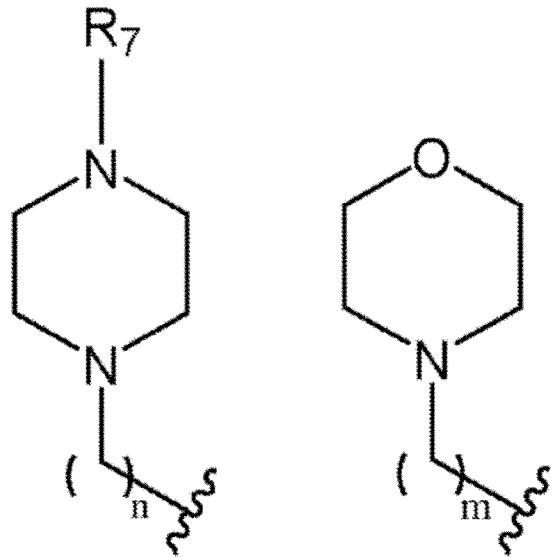

-- therefor.

Signed and Sealed this
Fifth Day of February, 2019

Andrei Iancu
*Director of the United States Patent and Trademark Office*